US009067955B2

(12) United States Patent
Buchwald et al.

(10) Patent No.: US 9,067,955 B2
(45) Date of Patent: Jun. 30, 2015

(54) COPPER-CATALYZED FORMATION OF CARBON-HETEROATOM AND CARBON—CARBON BONDS

(75) Inventors: Stephen L. Buchwald, Newton, MA (US); Artis Klapars, Edison, NJ (US); Jon C. Antilla, Tampa, FL (US); Gabriel E. Job, Ithaca, NY (US); Martina Uhlenbrock, Berlin (DE); Fuk Y. Kwong, Cambridge, MA (US); Gero Nordmann, Boston, MA (US); Edward J. Hennessy, Roslindale, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1319 days.

(21) Appl. No.: 11/431,154

(22) Filed: May 9, 2006

(65) Prior Publication Data
US 2006/0264673 A1 Nov. 23, 2006

Related U.S. Application Data

(62) Division of application No. 11/028,500, filed on Jan. 4, 2005, now Pat. No. 7,115,784, which is a division of application No. 10/435,719, filed on May 8, 2003, now Pat. No. 6,867,298, which is a division of application No. 10/128,981, filed on Apr. 24, 2001, now Pat. No. 6,759,554.

(60) Provisional application No. 60/286,268, filed on Apr. 24, 2001, provisional application No. 60/344,208, filed on Dec. 21, 2001, provisional application No. 60/348,014, filed on Oct. 24, 2001.

(51) Int. Cl.
C07F 5/02 (2006.01)
C07C 47/00 (2006.01)
(Continued)

(52) U.S. Cl.
CPC ............... C07F 9/4056 (2013.01); C07B 37/04 (2013.01); C07B 41/04 (2013.01); C07B 43/04 (2013.01); C07C 41/16 (2013.01); C07C 45/68 (2013.01); C07C 45/71 (2013.01); C07C 51/353 (2013.01); C07C 67/343 (2013.01); C07C 209/10 (2013.01); C07C 213/08 (2013.01); C07C 221/00 (2013.01); C07C 227/18 (2013.01); C07C 231/12 (2013.01); C07C 241/04 (2013.01); C07C 249/02 (2013.01); C07C 249/16 (2013.01); C07C 253/14 (2013.01); C07C 253/30 (2013.01); C07C 269/06 (2013.01); C07C 273/1854 (2013.01); C07C 277/08 (2013.01); C07C 281/02 (2013.01); C07C 303/38 (2013.01); C07C 319/20 (2013.01); C07C 2101/14 (2013.01); C07D 205/08 (2013.01); C07D 207/16 (2013.01); C07D 207/267 (2013.01); C07D 207/27 (2013.01); C07D 207/323 (2013.01); C07D 209/08 (2013.01); C07D 209/14 (2013.01); C07D 209/16 (2013.01); C07D 209/48 (2013.01); C07D 211/26 (2013.01); C07D 211/76 (2013.01); C07D 213/30 (2013.01); C07D 213/64 (2013.01); C07D 213/74 (2013.01); C07D 231/12 (2013.01); C07D 231/56 (2013.01); C07D 233/32 (2013.01); C07D 233/56 (2013.01); C07D 235/06 (2013.01); C07D 237/32 (2013.01); C07D 239/42 (2013.01); C07D 245/06 (2013.01); C07D 249/08 (2013.01); C07D 249/18 (2013.01); C07D 263/22 (2013.01); C07D 295/023 (2013.01); C07D 295/033 (2013.01); C07D 295/073 (2013.01); C07D 307/79 (2013.01); C07D 333/36 (2013.01); C07D 333/66 (2013.01); C07D 401/04 (2013.01);
(Continued)

(58) Field of Classification Search
USPC .......... 560/38, 82, 103; 558/87; 586/323, 332
See application file for complete search history.

(56) References Cited

U.S. PATENT DOCUMENTS 2,490,813 A 12/1949 Hughes et al.
4,259,519 A 3/1981 Stille
(Continued)

FOREIGN PATENT DOCUMENTS

GB 1420211 A 1/1976
JP H03-215448 9/1991
(Continued)

OTHER PUBLICATIONS

Setsune et. al. (Chemistry Letters, 1981, (3), pp. 267-370).*
(Continued)

Primary Examiner — Clinton Brooks
(74) Attorney, Agent, or Firm — Dana M. Gordon; Foley Hoag LLP

(57) ABSTRACT

The present invention relates to copper-catalyzed carbon-heteroatom and carbon-carbon bond-forming methods, such as the reaction of Z-X with C(L)(R)(R')$_2$ in the present of a catalyst and a base, thereby forming C(Z)(R)(R')$_2$; wherein X represents I, Cl, alkylsulfonate, or arylsulfonate; Z represents optionally substituted aryl, heteroaryl or alkenyl; L represents H or a negative charge; catalyst comprises a copper atom or ion, and a ligand, wherein the ligand is an optionally substituted aryl alcohol, alkyl amine, 1,2-diamine, 1,2-aminoalcohol, 1,2-diol, imidazolium carbene, pyridine, or 1,10-phenanthroline; the ligand is a chelating ligand; and the base represents a Bronsted base; R represents H, optionally substituted alkyl, cycloalkyl, aralkyl, aryl, or heteroaryl; R' represents independently for each occurrence H, alkyl, cycloalkyl, aralkyl, aryl, or heteroaryl, formyl, acyl, —CO$_2$R", —C(O)N(R)$_2$, sulfonyl, —P(O)(OR")$_2$, —CN, or —NO$_2$; R" represents independently for each occurrence optionally substituted alkyl, cycloalkyl, aralkyl, aryl, or heteroaryl; and C(R')$_2$(R) taken together may represent nitrile.

21 Claims, 32 Drawing Sheets

| (51) | Int. Cl. | |
|---|---|---|
| | C07C 201/00 | (2006.01) |
| | C07C 205/00 | (2006.01) |
| | C07B 41/00 | (2006.01) |
| | C07C 27/10 | (2006.01) |
| | C07F 9/40 | (2006.01) |
| | C07B 37/04 | (2006.01) |
| | C07B 41/04 | (2006.01) |
| | C07B 43/04 | (2006.01) |
| | C07C 41/16 | (2006.01) |
| | C07C 45/68 | (2006.01) |
| | C07C 45/71 | (2006.01) |
| | C07C 51/353 | (2006.01) |
| | C07C 67/343 | (2006.01) |
| | C07C 209/10 | (2006.01) |
| | C07C 213/08 | (2006.01) |
| | C07C 221/00 | (2006.01) |
| | C07C 227/18 | (2006.01) |
| | C07C 231/12 | (2006.01) |
| | C07C 241/04 | (2006.01) |
| | C07C 249/02 | (2006.01) |
| | C07C 249/16 | (2006.01) |
| | C07C 253/14 | (2006.01) |
| | C07C 253/30 | (2006.01) |
| | C07C 269/06 | (2006.01) |
| | C07C 273/18 | (2006.01) |
| | C07C 277/08 | (2006.01) |
| | C07C 281/02 | (2006.01) |
| | C07C 303/38 | (2006.01) |
| | C07C 319/20 | (2006.01) |
| | C07D 205/08 | (2006.01) |
| | C07D 207/16 | (2006.01) |
| | C07D 207/267 | (2006.01) |
| | C07D 207/27 | (2006.01) |
| | C07D 207/323 | (2006.01) |
| | C07D 209/08 | (2006.01) |
| | C07D 209/14 | (2006.01) |
| | C07D 209/16 | (2006.01) |
| | C07D 209/48 | (2006.01) |
| | C07D 209/86 | (2006.01) |
| | C07D 211/26 | (2006.01) |
| | C07D 211/76 | (2006.01) |
| | C07D 213/30 | (2006.01) |
| | C07D 213/64 | (2006.01) |
| | C07D 213/74 | (2006.01) |
| | C07D 231/12 | (2006.01) |
| | C07D 231/56 | (2006.01) |
| | C07D 233/32 | (2006.01) |
| | C07D 233/56 | (2006.01) |
| | C07D 235/06 | (2006.01) |
| | C07D 237/32 | (2006.01) |
| | C07D 239/42 | (2006.01) |
| | C07D 245/06 | (2006.01) |
| | C07D 249/08 | (2006.01) |
| | C07D 249/18 | (2006.01) |
| | C07D 263/22 | (2006.01) |
| | C07D 295/023 | (2006.01) |
| | C07D 295/033 | (2006.01) |
| | C07D 295/073 | (2006.01) |
| | C07D 307/79 | (2006.01) |
| | C07D 333/36 | (2006.01) |
| | C07D 333/66 | (2006.01) |
| | C07D 401/04 | (2006.01) |
| | C07D 405/12 | (2006.01) |
| | C07D 407/12 | (2006.01) |
| | C07D 409/04 | (2006.01) |
| | C07D 471/04 | (2006.01) |
| | C07D 473/00 | (2006.01) |
| | C07C 231/08 | (2006.01) |

(52) U.S. Cl.
CPC .......... *C07D 405/12* (2013.01); *C07D 407/12* (2013.01); *C07D 409/04* (2013.01); *C07D 471/04* (2013.01); *C07D 473/00* (2013.01); *C07C 2101/16* (2013.01); *C07C 231/08* (2013.01); *C07C 2101/08* (2013.01)

(56) References Cited

U.S. PATENT DOCUMENTS

| 4,423,234 | A | 12/1983 | Plummer et al. |
|---|---|---|---|
| 4,642,374 | A | 2/1987 | Lucy et al. |
| 4,659,803 | A | 4/1987 | Bartmann et al. |
| 4,734,521 | A | 3/1988 | Frazier |
| 4,764,625 | A | 8/1988 | Turner et al. |
| 4,983,774 | A | 1/1991 | Cahiez et al. |
| 5,159,115 | A | 10/1992 | Pappas et al. |
| 5,300,675 | A | 4/1994 | Elango |
| 5,405,981 | A | 4/1995 | Lipshutz |
| 5,648,539 | A | 7/1997 | Goodbrand et al. |
| 5,648,542 | A | 7/1997 | Goodbrand et al. |
| 5,705,697 | A | 1/1998 | Goodbrand et al. |
| 5,723,669 | A | 3/1998 | Goodbrand et al. |
| 5,723,671 | A | 3/1998 | Goodbrand et al. |
| 5,808,055 | A | 9/1998 | Nakajima et al. |
| 5,908,939 | A | 6/1999 | Baak et al. |
| 6,156,925 | A * | 12/2000 | Meyer et al. ............ 560/82 |
| 6,180,836 | B1 | 1/2001 | Cheng et al. |
| 6,242,648 | B1 | 6/2001 | Yamasaki et al. |
| 6,395,921 | B1 * | 5/2002 | Marhold et al. ......... 560/82 |
| 6,541,639 | B2 | 4/2003 | Zhou et al. |
| 2001/0047013 | A1 | 11/2001 | Lang et al. |
| 2002/0010347 | A1 | 1/2002 | Bonrath et al. |

FOREIGN PATENT DOCUMENTS

| JP | H10-139742 | 5/1998 |
|---|---|---|
| JP | H11-130738 | 5/1999 |
| RU | 2148613 | 5/2000 |

OTHER PUBLICATIONS

Goodbrand et al. J. Org. Chem. 1999, 670-674.*
Gujadhur, R. K. et al., "Formation of Aryl-Nitrogen, Aryl-Oxygen, and Aryl-Carbon Bonds Using Well-Defined Copper(I)-Based Catalysts", *Organic Letters*, 3(26):4315-4317 (2001).
Kalinin, A. V. et al., "The Directed Ortho Metalation-Ullmann Connection. A New Cu(I)-Catalyzed Variant for the Synthesis of Substituted Diaryl Ethers", *J. Org. Chem.*, 64:2986-2987 (1999).
Kang, S-K et al., "Copper-Catalyzed N-Arylation of Aryl Iodides with Benzamines or Nitrogen Heterocycles in the Presence of Ethylenediamine", *Synlett.*, 3:427-430 (Thieme Stuttgart)(2002).
Klapars, A. et al., "A General and Efficient Copper Catalyst for the Amidation of Aryl Halides and the N-Arylation of Nitrogen Heterocycles", *J. Am. Chem. Soc.*, 123:7727-7729 (ACS)(2001).
Kwong, F. Y. et al., "Copper-Catalyzed Coupling of Alkylamines and Aryl Iodides: An Efficient System Even in an Air Atmosphere", *Organic Letters*, 4(4):581-584 (2002).
Bacon RGR et al., "Copper-promoted reactions in aromatic chemistry", Quarterly Reviews, Chemical Society, 19(2): 95-125 (1965).
Bacon RGR et al., "Metal ions and complexes in organic reactions. Part XX. Copper-catalysed reactions of aromatic bromocarboxylates with carbanions, giving oxo-acids, isocoumarins, and related products", Journal of the Chemical Society, Perkin Transactions 1: Organic and Bioorganic Chemistry, No. 13, pp. 1267-1272 (1975).
Extended European Search Report dated Dec. 23, 2011, in related European patent application No. EP10168790.

(56) References Cited

OTHER PUBLICATIONS

Communication Pursuant to Article 94(3) EPC dated Apr. 26, 2013, in related European patent application No. EP10168790.
Third Party Observations, filed May 3, 2013, in related European patent application No. EP10168790.
Communication Pursuant to Article 94(3) EPC dated May 16, 2013, in related European patent application No. EP10168790.
Okuro, K. et al., "Copper-Catalyzed Reaction of Aryl Iodides with Active Methylene Compounds", J. Org. Chem., 58:7606-7607 (American Chemical Society, USA, 1993).
Examination Report from corresponding European application EP 10168790.3 dated Dec. 17, 2013.
Arai et al., "The Ullmann Condensation Reaction of Haloanthraquinone Derivatives with Amines in Aprotic Solvents, IV. Kinetic Studies of the Condensation with Ethylenediamine," Bulletin of the Chemical Society of Japan, 52(6):1731-1734 (1979).
Avendano et al., "The Problem of the Existence of C(Ar)-H . . . N Intramolecular Hydrogen Bonds in a Family of 9-azaphenyl-9H-carbazoles," J. Chem. Soc. Perkin Trans. 2, pp. 1547-1555 (1993).
Bacon and Rennison, "Metal Ions and Complexes in Organic Reactins. Part IX. Copper(I)-catalysed Conversion of Aryl Halides into Alkyl Ethers," Journal of Chemical Society (C), pp. 312-315 (1969).
Beletskaya et al., "Pd- and Cu-catalyzed selective Arylation of Benzotriazole," Tetrahedron Letters, 39:5617-5620 (1989).
Campbell et al., "Structural Studies in the 1:1 Copper(I) Halide-Pyridine Base System," Australian Journal of Chemistry 30(9):1937-1945 (1977).
Duplantier et al., "7-Oxo-4,5,6,7-tetrahydro-1 H-pyrazolo [3,4-c] pyridines as Novel Inhibitors of Human Eosinophil Phosphodiesterase," J. Med. Chem., 41:2268-2277 (1998).
Fabian, "Kinetics and Mechanism of Complex-formation Reactions of Ammonia and Methylamine with Copper(II) Complexes in Aqueous Solution," J. Chem. Soc. Dalton Trans. 9:1355-1358 (1994).
Faith, Keyes and Clark's Industrial Chemicals, 4th ed., pp. 674-678, John Wiley & Sons (1975).
Gauthier and Frechet, "Phase-Transfer Catalysis in the Ullmann Synthesis of Substituted Triphenylamines," Synthesis, 4:383-385 (Apr. 1987).
Goodbrand and Hui, "Ligand-Accerlated Catalysis of the Ullmann Condensation: application to Hole Conducting Triarylarnines," J. Org. Chem. 64:670-674 (1999).
Greiner, Alfred, "An Improvement of the N-Arylation of Amides; Application to the Synthesis of Substituted 3-(N-Acetyl-N-phenylabino) Pyridmes," Synthesis No. 4:312-313 (Apr. 1989).
Gujadhur et al., "Formation of Aryl-nitrogen Bonds Using a Soluble Copper (I) Catalyst," Tetrahedron Letters 42:4791-4793 (2001).
Ito et al., "Synthesis of Oligo (m-aniline)," Tetrahedron Letters, 36(48):8809-8812 (1995).
Joyeau et al., "Synthesis of Benzocarbacephem and Benzocarbacephem Derivatives by Copper-Promoted Intramolecular Aromatic Substitution," J. Chem. Soc. Perkin Trans. I., pp. 1899-1907 (1987).
Kametani et al., "Studies on the Syntheses of Heterocyclic Compounds. Part. 865.1/7 a Novel Synthesis of Indole Derivatives by Intramolecular Nucleophilic Aromatic Substitution," J.C. S. Perkin I, pp. 290-294 (1981).
Kang et al., "Copper-Catalyzed N-Arylation of Amines with Hypervalent Iodonium Salts," Synlett No. 7:1022-1024 (2000).
Kato et al., "Water-Soluble Receptors for Cyclic-AMP and Their Use for Evaluation Phosphate-Guanidinium Interactions," J. Am. Chem. Soc. 116:3279-3284 (1994).
Keegstra, M.A., "Copper Catalysed Preparation of Vinyl Ethers from Unactivated Vinylic Halides," Tetrahedron 48(13):2681-2690 (1992).
Kiyomori et al., "An Efficient Copper-Catalyzed Coupling of Aryl Halides with Imidazoles," Tetrahedron Letters, 40:2657-2660 (1999).
Kondratov, S.A. and Shein, S.M., "Nucleophilic substitution in the aromatic series, LV. Reaction of o-nitrochlorobenzene with ammonia in the presence of copper compounds," Zhrnal Organicheskoi Khimii, 15(11):2387-2390 (1979) (As Abstracted by CAPLUS).
Lexy and Kauffmann, "Synthese, Lithiierung und Oxidative Kupplung von 1,3,5-Tri(I-Pyrazolyl) benzol," Chem. Ber. 113:2755-2759 (1980).
Lindley James, "Copper Assisted Nucleophilic Substitution of Aryl Halogen," Tetrahedron, 40(9):1433-1456 (1984).
Murakami et al., Fisher Indolization of Ethyl Pyruvate 2-[2-Trifluoromethyl) Phenyl]-Phenylhydrazone and New Insight Into the Mechanism of the Goldberg Reaction. (Fisher Indolization and Its Related Compounds. XXVI), Chem. Pharm. Bull. 43(8):1281-1286 (1995).
Palkowitz et al., "Discovery and Synthesis of [6-Hdroxy-3-[4-[2-(1-piperidinyl)ethoxy]phenoxyl]-2-(4-Hydroxyphenyl)] benzo[b]thiophene: A Novel, Highly Potent, Selective Estrogen Receptor Modulator," Journal od Medicinal Chemistry 40(10):1407-1416 (May 9, 1997).
Ragan et al., "2,5-Dimethylpyrrole Protection Facilitates Copper(I)-Mediated Methoxylations of Aryl Iodides in the Presence of Anilines," Synthesis, pp. 1599-1603 (1998).
Renger Bernd, "Direkte N-Arylierung von Amiden: Eine Verbesserung der Goldberg-Reaktion," Synthesis, 9:856-860 (1985).
Sawyer et al., "Synthesis of Diaryl Ethers, Diaryl Thioethers, and Diarylamines Mediated by Potassium Fluoride-Alumina and 18-Crown-6: Expansion of Scope and Utility," J. Org. Chem., 63:6338-6343 (1998).
Smith III and Sawyer, "A Novel and Selective Method for the N-Arylation of Indoles Mediated by KF/Al$_2$O$_3$," Tetrahedron Letters 37(3):299-302 (1996).
Smith III and Sawyer, "An S NAr-Based Preparation of 1-(2-, 3-, and 4-Pyridyl) Indoles Using Potassium Fluoride/Alumina," Heterocycles 51(1): 157-160 (1999).
Steglich and Hoefle, "Hypernucleophilic acylation catalysts. II. Simple preparation of acy-5-oxazolinones from 5-acyloxyoxazoles," Tetrahedron Letters. 54:4727-4730 (1970) CAPLUS Abstract.
Straumanis and Circulus, "New complex compounds of mercury and copper halides with aliphatic amines," Z. Anorg. Allgem. Chem., 230:65-87 (1936) CAPLUS Abstract.
Sugahara and Ukita, "A Facile Copper-Catalyzed Ullmann Condensation: N-Arylation of Heterocyclic Compounds Containing an -NHCO-Moiety," Chem. Pharm. Bull., 45(4):719-721 (1977).
Tokmakov and Grandorg, "Rearrangement of 1-Arylindoles to 5H-Dibenz[b, f]azepines," Tetrahedron 51(7):2091-2098 (1995).
Uangst et al., "Synthesis of Novel 1-Phenyl-1H-Indole-2-Carboxylic Acids. I Utilization of Ullmann and Dieckmann Reactions for the Preparation of 3-Hydroxy, 3-Alkoxy, and 3-Alkyl Derivatives," Journal of Heterocyclic Chemistry, 24(3):811-815 (May-Jun. 1987).
Vainshtein, F.M. and Tomilenko, E.I., "Exchange of halogens in halobenzenes in a reaction with ammonia with participation of copper (I)," Zhrnal Vsesoyuznogo Khimicheskogo Obshchestva im. D.I. Mendeleeva, 13(6):709-710 (1968) (As Abstracted by CAPLUS).
Vedejs E., "Substituted Isoquinolines by Noyori Transfer Hydrogenation: Enantioselective Synthesis of Chiral Diamines Containing an aniline Subunit," J. Org. Chem. 64:6724-6729 (1999).
Yamamoto and Kurata, "Ullmann Condensation Using Copper or Copper Oxide as the Reactant. Arylation of Active Hydrogen Compounds (imides, amides, phenol, benzoic acid, and phenylacetylene)," Can. J. Chem. 61:86-91 (1983).

* cited by examiner

| | | | |
|---|---|---|---|
| 17 | (S)-proline structure | 24 | 70 |
| 18 | aniline (H₂N-Ph) | 36[c] (90°C) | 41 |
| 19 | neopentylamine (H₂N-C(CH₃)₃-type) | 12 (90°C) | O-arylated ethylene glycol was observed. |
| 20 | di-tert-butylamine (HN(tBu)₂-type) | 12 (90°C) | O-arylated ethylene glycol was observed. |
| 21 | 2-pyrrolidinone | 36 (90°C) | 50 |

[a] Isolated yield was reported in average of 2 run. [b] 1 mol% CuI. [c] 10mol% CuI. [d] The reaction was conducted under air. [e] 10%CuI, ⁿBuOH solvent at 90 °C.

FIG. 2C

Amination of aryl iodides with amines

Ar—R + HN(R)(R') —[5 mol% CuI, K₃PO₄, 2 equiv. ethylene glycol, isopropanol, 80 °C]→ Ar-N(R)(R') — R' (3)

1.0 mmol + 1.2 mmol

| Entry | Arl | Amines | Products | Time/h | %Yield[a] |
|---|---|---|---|---|---|
| 1 | 4-MeO-C₆H₄-I | cyclohexyl-NH₂ | 4-MeO-C₆H₄-NH-cyclohexyl | 14[b] | 70 |
| 2 | 4-MeO-C₆H₄-I | H₂N-(CH₂)₄-OH | 4-MeO-C₆H₄-NH-(CH₂)₄-OH | 14[b] | 85 |
| 3 | 3-Me-C₆H₄-I | H₂N-CH₂-CH₂-cyclohexenyl | 3-Me-C₆H₄-NH-CH₂-CH₂-cyclohexenyl | 22 | 87 |

FIG. 3A

| FIG. 3A |
| FIG. 3B |

Table 4. Amination of Bromobenzene in the Presence of Substituted Phenols.

| Entry | ArOH | % Conv. | GC yield% |
|---|---|---|---|
| 1 | 2,6-dimethylphenol | 57 | 56% GC yield |
| 2 | 2-(1-methylethyl)phenol with additional HO | 99 | 45% GC yield |
| 3 | 1-naphthol | 75 | 61% GCyield |

| Entry | Cu Complex | % Conv.[a] | % Yield[b] |
|---|---|---|---|
| 1 | CuI | 68 | 67 |
| 2 | CuCl | 83 (100)[c] | 83 (>99)[c] |
| 3 | CuBr | 82 (99)[c] | 82 (99)[c] |
| 4 | CuOAc | 89 (>99)[c] | 89 (99)[c] |
| 5 | CuCl$_2$•H$_2$O | 49 | 42 |
| 6 | CuBr$_2$ | 53 | 47 |
| 7 | CuF$_2$ | 24 | 6 |
| 8 | Cu(OAc)$_2$ | 57 (99)[c] | 53 (98)[c] |
| 9 | Cu(acac)$_2$ | 60 | 56 |
| 10 | Cu(OTf)$_2$ | 55 | 50 |
| 11 | CuSO$_4$•5H$_2$O | 44 | 35 |

[a]Calibrated GC conversion. [b]Calibrated GC yield. [c]Yields in parentheses were obtained for reactions performed at 90 °C for 20 h.

| | | CuI:L = 1:1 | | CuI:L = 1:4 | |
|---|---|---|---|---|---|
| Entry | Solvent | %Conv.ᵃ | % Yieldᵇ | %Conv.ᵃ | % Yieldᵇ |
| 1 | Neat | 91 | 88 | 88 | 80 |
| 2 | DMF | 70 | 66 | 94 | 90 |
| 3 | NMP | 13 | Trace | 77 | 69 |
| 4 | Et₃N | 9 | Trace | 39 | 33 |
| 5 | ⁱPr₂NH | 10 | 4 | 25 | 28 |
| 6 | Toluene | 56 | 50 | 59 | 53 |
| 7 | DME | 68 | 63 | 76 | 69 |
| 8 | Dioxane | 65 | 60 | 83 | 79 |
| 9 | DMF:Tol = 1:1 | / | / | 95 | 92 |
| 10 | DMF:Tol = 1:4 | / | / | 89 | 83 |
| 11 | DMF:Tol = 1:9 | / | / | 78 | 73 |

ᵃCalibrated GC conversion. ᵇCalibrated GC yield.

| Entry | Ligand | % Conv.[a] | % yield[b] |
|---|---|---|---|
| 1 | 1 | 90 | 27 |
| 2 | 2 | 94 | 64 |
| 3 | 3 | 95 | 79 |
| 4 | 4 | 46 | 38 |
| 5 | 5 | 70 | 64 |
| 6[c] | 6 | 55 | 47 |
| 7[c] | 7 | 60 | 35 |
| 8[c] | 8 | 41 | 36 |
| 9[c] | 9 | 99 | 99 |
| 10[c] | 10 | 99 | 99 |
| 11[c] | 11 | 99 | 99 |
| 12[c] | 12 | 67 | 64 |

[a]Calibrated GC conversion. [b]Calibrated GC yield. [c]5-Bromo-*m*-xylene was used instead of bromobenzene; 5 mol% CuI was used.

| Entry | Ligand | % Conv.[a] | % yield[b] |
|-------|--------|-----------|-----------|
| 1 | 1 | 71 | 66 |
| 2 | 2 | 11 | 8 |
| 3 | 3 | 93 | 90 |
| 4 | 4 | 83 | 79 |
| 5 | 5 | 93 | 92 |
| 6 | 6 | 65 | 65 |

[a]Calibrated GC conversion. [b]Calibrated GC yield.

| Entry | CuI and L | Temp./ °C | Time/ h | % Conv.[a] | % Yield[b] |
|---|---|---|---|---|---|
| 1 | 2% CuI, 8% L | 100 | 24 | 87 | 86 |
| 2 | 2% CuI, 8% L | 100 | 42 | 98 | 96 (90 iso.) |
| 3 | 1% CuI, 5% L | 90 | 54 | 85 | 83 |
| 4 (control) | 5% CuI, 20% L | 100 | 18 | 97 | 95 |

[a]Calibrated GC conversion. [b]Calibrated GC yield.

| Entry | ArBr | Amine | Product | %Conv. | % yield[a] |
|---|---|---|---|---|---|
| 1 | 2-Br-anisole | H₂N-(CH₂)₅-Me | 2-MeO-C₆H₄-NH-(CH₂)₅-Me | 95 | 89 @ 100°C |
| 2 | 2-Br-benzyl alcohol | H₂N-(CH₂)₅-Me | 2-(HOCH₂)-C₆H₄-NH-(CH₂)₅-Me | >99 | 81 |
| 3 | 2-Br-1,4-dimethylbenzene | H₂N-CH₂CH₂-cyclohexenyl | 2,5-Me₂-C₆H₃-NH-CH₂CH₂-cyclohexenyl | 96 | 79 @ 100°C |
| 4[b] | 1,4-dibromobenzene | H₂N-(CH₂)₅-Me | 4-Br-C₆H₄-NH-(CH₂)₅-Me | >99 | 83 |
| 5[c] | 1,4-dibromobenzene | H₂N-(CH₂)₅-Me | Hex-NH-C₆H₄-NH-Hex | >99 | 81 @ 100°C |
| 6 | 3-bromopyridine | 3-pyridyl-CH₂-NH₂ | 3-pyridyl-CH₂-NH-(3-pyridyl) | >99 | 83 |
| 7 | 3-bromobenzothiophene | H₂N-CH₂CH₂-cyclohexenyl | 3-(cyclohexenyl-CH₂CH₂-NH)-benzothiophene | 99 | 82 |
| 8 | 5-bromopyrimidine | 4-MeO-C₆H₄-CH₂-NH₂ | 5-(4-MeO-benzyl-NH)-pyrimidine | 95 | 85 |

[a] Isolated yield. [b] 1.2 mmol of amine was used. [c] 4.0 mmol of amine was used, 42 hours.

Figure 12

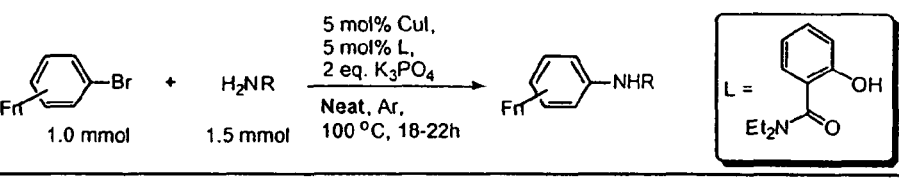

| Entry | ArBr | Amine | Product | %Conv. | %yield[a] |
|---|---|---|---|---|---|
| 1 | 3,5-Me₂C₆H₃Br | H₂N-pentyl | 3,5-Me₂C₆H₃-NH-pentyl | 95 | 90 |
| 2 | 3,5-Me₂C₆H₃Br | 4-MeC₆H₄NH₂ | 3,5-Me₂C₆H₃-NH-C₆H₄-4-Me | 22 / 11 | 9[b] / 0 (NaOtBu) |
| 3 | 3,5-Me₂C₆H₃Br | indole | N-(3,5-dimethylphenyl)indole | 90 | 89[c] |
| 4 | 3-O₂N-C₆H₄Br | H₂N-pentyl | 3-O₂N-C₆H₄-NH-pentyl | 96 | 59 |
| 5 | 3-H₂N-C₆H₄Br | H₂N-pentyl | 3-H₂N-C₆H₄-NH-pentyl | 98 | 71 |
| 6 | 4-Me-C₆H₄Br | cyclohexenyl-CH₂CH₂-NH₂ | 4-Me-C₆H₄-NH-CH₂CH₂-cyclohexenyl | 99 | 92 |
| 7 | 4-Cl-C₆H₄Br | 4-(aminomethyl)piperidine | 4-Cl-C₆H₄-NH-CH₂-piperidine | >99 | 60 |
| 8 | 3-Br-pyridine | H₂N-pentyl | 3-(pentylamino)pyridine | >99 | 82 @ 90°C |

[a] Isolated yield was reported. [b] GC yield was reported. [c] average of 2 run.

Figure 14
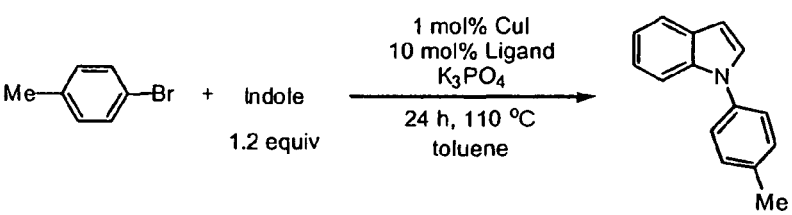
| Ligand | % GC Yield | Ligand | % GC Yield |
| --- | --- | --- | --- |
| 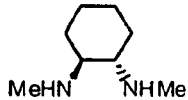 | 98 | 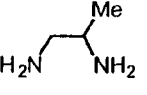 | 12 |
| 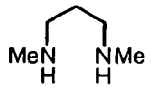 | 9 | 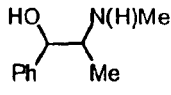 | 37 |
| 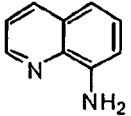 | 5 | 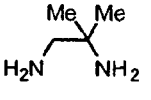 | 50 |
| 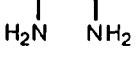 | 5 | 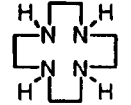 | 71 |
| 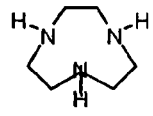 | 6 | 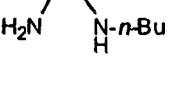 | 60 |
| | | 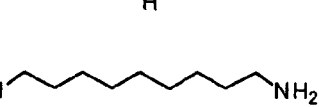 | 11 |

| Ligand | % GC Yield | Ligand | % GC Yield |
|---|---|---|---|
| MeHN-CH(CH2Ph)-CH2-NHMe | 58 (4h) | tris(2-aminoethyl)amine · X H2O | 25 |
| MeNH-C(=O)-NHMe | 6 | 2-pyridinealdoxime | 1 |
| MeNH-C(=O)-C(=O)-NHMe | 1 | ethyl 2-pyridinecarboxylate | 4 |
| 2-(2-pyridyl)ethyl-NHMe | 8 | 1-(2-pyridyl)-3-methyl-imidazolidin-2-one | 3 |
| di(2-pyridyl) ketoxime | 7 | 2-(2-hydroxyphenyl)-4,5-dihydrooxazole | 4 |
| 1-methyl-3-(1-methylimidazol-2-yl)imidazolidin-2-one | 3 | N,N-diethyl-2-hydroxy-5-methylbenzamide | 42 |

| Entry | Ligand | Amount of ligand (mol%) | GC yield |
|---|---|---|---|
| 1 | pyridine-2-COOH | 22 | 76%[a] |
| 2 | MeS~SMe | 11 | 22% |
| 3 | phenanthrene bis(methoxyimine) | 12 | 36% |
| 4 | bis(N-methylimidazol-2-yl) ketone | 10 | 77% |
| 5 | bis(4-Me2N-benzylidene) ethylenediamine | 10 | 47% |
| 6 | N,N'-dibenzyl piperazine-2,3-dione | 10 | 52%[b] |

[a] 1.7 mmol of Cs$_2$CO$_3$ was used. [b] 2.1 mmol K$_3$PO$_4$ was used instead of Cs$_2$CO$_3$.

| Entry | Ligand | GC yield (%) |
|---|---|---|
| 1 | Me, H₂N⌃NH₂ | 50% |
| 2 | CH₃(CH₂)₁₀, H₂N⌃NH₂ | 51% |
| 3 | Ph, H₂N⌃NHMe | 95% |

Figure 19

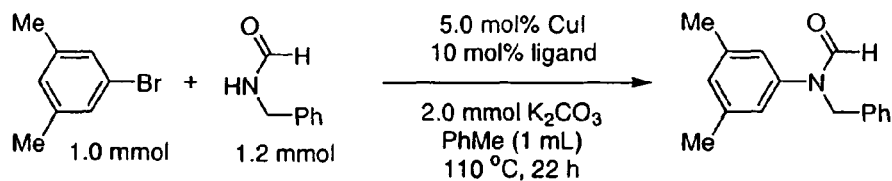

| Entry | Ligand | GC yield | Entry | Ligand | GC yield |
|---|---|---|---|---|---|
| 1 | H₂N⌒NH₂ | 26% | 7[b] | H₂N/\NH₂ (cis cyclohexane) | 52% |
| 2 | H₂N⌒NHMe | 84% | | | |
| 3 | MeHN⌒NHMe | 92% | 8[c] | H₂N/\NH₂ (cyclohexane) | 39% |
| 4 | H₂N⌒NHnBu | 84% | | | |
| 5 | MeHN⌒NMe₂ | 12% | 9[d] | MeHN/\NHMe (cyclohexane) | 93% |
| 6[a] | H₂N/\NH₂ (cyclohexane) | 33% | 10[e] | EtHN/\NHEt (cyclohexane) | 39% |

[a] Racemic *trans*-isomer of the ligand. [b] *cis*-Isomer of the ligand. [c] The commercial mixture of the *cis*- and *trans*-isomers of the ligand. [d] Racemic *trans*-isomer of the ligand. [e] Racemic *trans*-isomer of the ligand.

| Entry | Ligand | GC yield |
|-------|--------|----------|
| 1 | $Ph_3P$ | 39% |
| 2 | $(MeO)_3P$ | 55% |
| 3 | $Ph_3As$ | 37% |
| 4 | Me(CO)CH₂(CO)Me | 75% |
| 5 | Ph(CO)CH₂(CO)Ph | 74% |
| 6 | MeHN-CH₂CH₂-OH | 56% |

| Entry | Copper Compound | GC yield |
|---|---|---|
| 1 | Cu powder | 86% |
| 2 | CuI | 97% |
| 3 | CuCl | 93% |
| 4 | CuSCN | 85% |
| 5 | $Cu_2O$ | 91% |
| 6 | $CuCl_2$ | 55% |
| 7 | $CuSO_4\ 5H_2O$ | 79% |
| 8 | Cu(II) acetate | 71% |
| 9 | Cu(II) acetylacetonate | 83% |

| Entry | Base | %Conv.[a] | %Yield[b] |
|---|---|---|---|
| 1 | $K_3PO_4$ | 98 | 96 |
| 2 | $K_3PO_4 \cdot H_2O$ | 36 | 28 |
| 3 | $Na_3PO_4$ | 28 | 8 |
| 4 | $Li_3PO_4$ | 30 | 2 |
| 5 | $Cs_2CO_3$ | 85 | 83 |
| 6 | $K_2CO_3$ | 74 | 71 |
| 7 | $Na_2CO_3$ | 31 | 4 |
| 8 | $Li_2CO_3$ | 30 | 2 |
| 9 | NaOH | 17 | 1 |
| 10 | KOH | 20 | 1 |
| 11 | $K_4P_2O_7$ | 31 | 3 |
| 12 | KOAc | 41 | 14 |
| 13 | DBU | 25 | 1 |

[a]Conversion of 5-bromo-*m*-xylene based on GC integration. [b]Calibrated GC yield.

| Entry | Base | %Conv.[a] | %Yield[b] |
|-------|------|-----------|-----------|
| 1 | K$_3$PO$_4$ | 98 | 93 |
| 2 | K$_2$CO$_3$ | 34 | 10 |
| 3 | Cs$_2$CO$_3$ | 99 | 77 |
| 4 | NaO$^t$Bu | 77 | 43 |
| 5 | NaOH | 72 | 26 |
| 6 | KOH | 58 | 29 |

[a]Conversion of iodobenzene based on GC integration. [b]Calibrated GC yield.

Figure 25

PhI + H₂NBn →(10 mol% CuI, diol, 2.0 eq. K₃PO₄, isopropanol, 18 h, 80 °C)→ Ph-N(H)Bn

| entry | diol | equiv of diol | conv, % | yield, %[b] |
|---|---|---|---|---|
| 1 |  | 0.1 | 27 | 5 |
| 2 |  | 0.2 | 34 | 10 |
| 3 | HO~~OH (ethylene glycol) | 0.5 | 52 | 42 |
| 4 |  | 1.0 | 80 | 77 |
| 5 |  | 2.0 | 98 | 93 (87[c]) |
| 6 | HO~~~OH (1,3-propanediol) | 2.0 | 20 | trace |
| 7 | HO~~~~OH (1,4-butanediol) | 2.0 | 21 | trace |
| 8 | HO-CH(OH)-CH₂-CH₂-Me | 2.0 | 53 | 34 |
| 9 | Me₂C(OH)-C(OH)Me₂ | 2.0 | 29 | trace (42[c]) |
| 10 | cis-cyclohexane-1,2-diol | 2.0 | 44 | 31 |
| 11 | trans-cyclohexane-1,2-diol | 2.0 | 49 | 33 |
| 12 | Ph-CH(OH)-CH(OH)-Ph | 2.0 | 52 | 27 |
| 13 | HO~~OMe | 2.0 | 20 | 7 (38[c]) |
| 14 | HO~~O~~OH | 2.0 | 32 | 17 (31[c]) |
| 15 | HO-CH₂-CH(OH)-CH₂-OH (glycerol) | 2.0 | 29 | 18 (14[c]) |
| 16 | sucrose | 2.0 | 5 | trace |

[a] Reaction conditions: 1.0 mmol iodobenzene, 1.2 mmol benzylamine, 10 mol% CuI, 2.0 mmol diol, 2.0 mmol K₃PO₄, i-PrOH (1 mL), 80 °C under Ar. [b] Calibrated GC yield. [c] Diol used as solvent.

| Entry | Ligand | Amount of ligand (mmol) | GC yield |
|---|---|---|---|
| 1 | HO-CH₂CH₂-N(Me)-CH₂CH₂-OH | 2.0 | 63% |
| 2 | HO~~NMe₂ | 0.50 | 48% |
| 3 | pyridine-2-COOH | 0.50 | 7% |
| 4 | H₂N-CH₂-COOH | 0.50 | 11% |
| 5 | 8-hydroxyquinoline | 0.50 | 16% |

COPPER-CATALYZED FORMATION OF CARBON-HETEROATOM AND CARBON—CARBON BONDS

RELATED APPLICATIONS

This application is a divisional of U.S. patent application Ser. No. 11/028,500, filed Jan. 4, 2005, now U.S. Pat. No. 7,115,784; which is a divisional of U.S. patent application Ser. No. 10/435,719, filed May 8, 2003, now U.S. Pat. No. 6,867,298; which is a divisional of U.S. patent application Ser. No. 10/128,981, filed Apr. 24, 2002, now U.S. Pat. No. 6,759,554; which claims the benefit of priority to U.S. Provisional Patent Application Ser. No. 60/286,268, filed Apr. 24, 2001; U.S. Provisional Patent Application Ser. No. 60/348,014, filed Oct. 24, 2001; and U.S. Provisional Patent Application Ser. No. 60/344,208, filed Dec. 21, 2001; the specifications of all of which are hereby incorporated by reference.

GOVERNMENT SUPPORT

This invention was made with government support under grant number R01 GM058160 awarded by the National Institutes of Health. The government has certain rights in this invention.

BACKGROUND OF THE INVENTION

N-Aryl amines and amides are important substructures in natural products and industrial chemicals, such as pharmaceuticals, dyes, and agricultural products. Palladium-catalyzed methods for the N-arylation of amines and amides are now widely-exploited for the synthesis of arylamine and N-arylamide moieties in pharmaceuticals, materials with important electronic properties, and ligands for early metal catalysts. Likewise, the palladium-catalyzed coupling to form carbon-carbon bonds between an aryl or vinyl halide and a carbon nucleophile is widely used. See, e.g., Stille, J. K. Angew. Chem., Int. Ed. Engl., 25:508-524 (1986); Miyaura, N. et al., Chem. Rev., 95:2457-2483 (1995); Negishi, E. Acc. Chem. Res., 15:340-348 (1982).

However, the ever-increasing cost of palladium detracts from the allure of these powerful methods. Consequently, a need exists for a general and efficient catalytic method for synthesizing N-aryl amines and amides, from aryl halides and the corresponding amines and amides, based on a catalyst that does not comprise a rare, costly transition metal, such as palladium. Likewise, a need also exists for a general and efficient catalytic method for forming carbon-carbon bonds between an aryl or vinyl halide and a carbon nucleophile, based on a catalyst that does not comprise a rare, costly transition metal, such as palladium.

In 1998, bulk palladium sold on the international metal market for roughly five-thousand-times the cost of bulk copper. Therefore, based on catalyst cost, the aforementioned transformations would be orders of magnitude more appealing if they could be achieved with catalysts comprising copper in place of palladium.

SUMMARY OF THE INVENTION

The present invention relates to copper-catalyzed carbon-heteroatom and carbon-carbon bond-forming methods. In certain embodiments, the present invention relates to copper-catalyzed methods of forming a carbon-nitrogen bond between the nitrogen atom of an amide or amine moiety and the activated carbon of an aryl, heteroaryl, or vinyl halide or sulfonate. In additional embodiments, the present invention relates to copper-catalyzed methods of forming a carbon-nitrogen bond between a nitrogen atom of an acyl hydrazine and the activated carbon of an aryl, heteroaryl, or vinyl halide or sulfonate. In other embodiments, the present invention relates to copper-catalyzed methods of forming a carbon-nitrogen bond between the nitrogen atom of a nitrogen-containing heteroaromatic, e.g., indole, pyrazole, and indazole, and the activated carbon of an aryl, heteroaryl, or vinyl halide or sulfonate. In certain embodiments, the present invention relates to copper-catalyzed methods of forming a carbon-oxygen bond between the oxygen atom of an alcohol and the activated carbon of an aryl, heteroaryl, or vinyl halide or sulfonate. The present invention also relates to copper-catalyzed methods of forming a carbon-carbon bond between a reactant comprising a nucleophilic carbon atom, e.g., an enolate or malonate anion, and the activated carbon of an aryl, heteroaryl, or vinyl halide or sulfonate. Importantly, all the methods of the present invention are relatively inexpensive to practice due to the low cost of the copper comprised by the catalysts.

BRIEF DESCRIPTION OF THE FIGURES

FIG. 4 tabulates copper-catalyzed aminations of bromobenzene using n-hexyl amine and various substituted phenols as ligands.

FIG. 10 tabulates copper-catalyzed aminations of various functionalized aryl bromides.

FIG. 11 tabulates copper-catalyzed aminations of various ortho-substituted, dibromo-substituted and heterocyclic aryl bromides.

FIG. 12 tabulates copper-catalyzed aminations of various functionalized aryl bromides using various amines without solvent.

FIG. 14 tabulates copper-catalyzed arylations of indole in toluene using 4-bromotoluene and various ligands.

FIG. 19 tabulates copper-catalyzed arylations of N-benzyl formamide in toluene using 3,5-dimethylphenyl bromide and various ligands.

FIG. 25 tabulates copper-catalyzed arylations of benzyl amine in isopropanol using various diols as the ligand.

DETAILED DESCRIPTION OF THE INVENTION

Figure 1A:
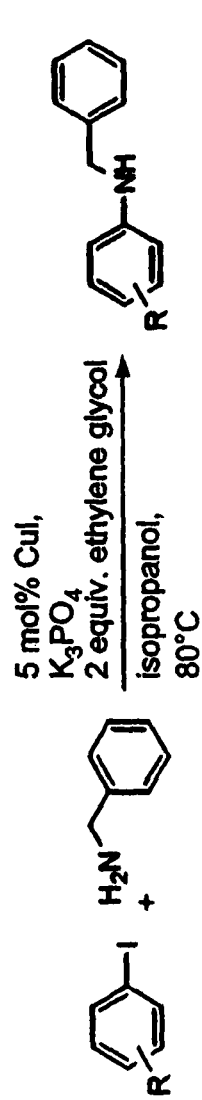
FIG. 1 tabulates the results of various copper-catalyzed arylations of benzylamine using aryl iodides, and the reaction conditions employed.
Figure 1B:
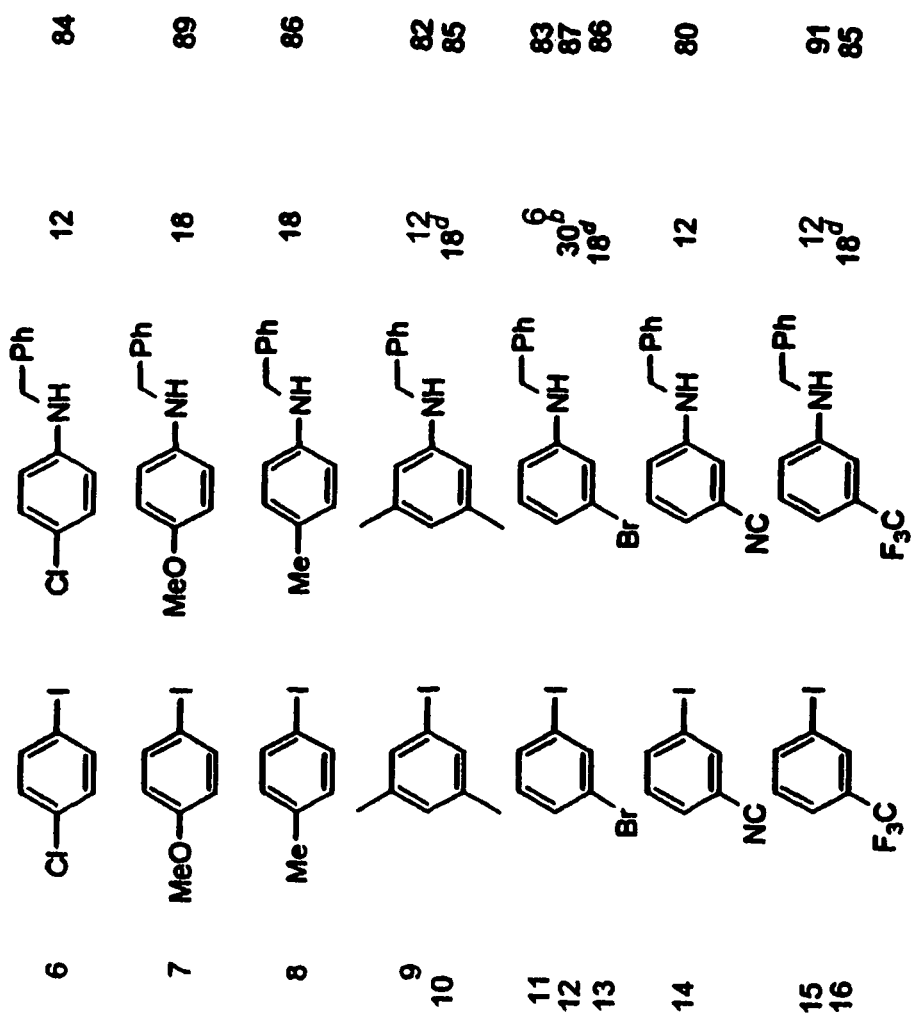
Figure 1C:
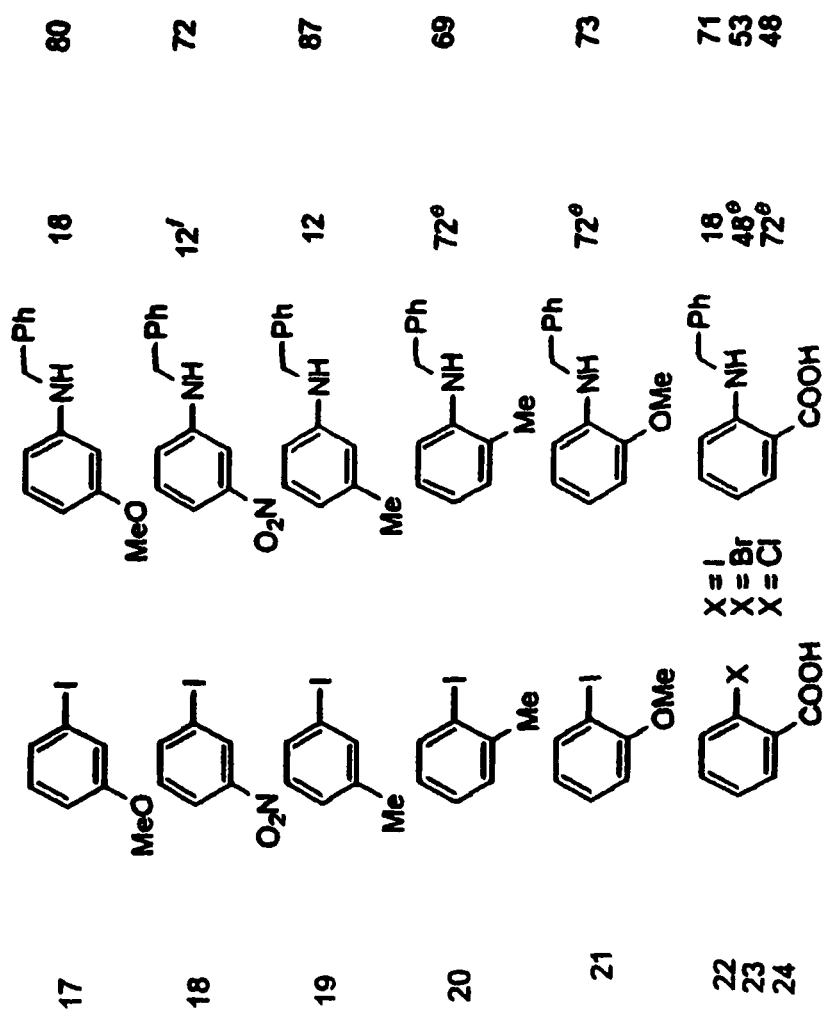
Figure 1D:
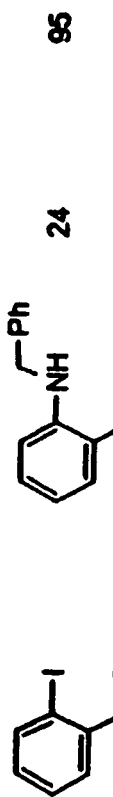

The present invention relates to copper-catalyzed carbon-heteroatom and carbon-carbon bond-forming methods. In certain embodiments, the present invention relates to copper-catalyzed methods of forming a carbon-nitrogen bond between the nitrogen atom of an amide or amine moiety and the activated carbon of an aryl, heteroaryl, or vinyl halide or sulfonate. In additional embodiments, the present invention relates to copper-catalyzed methods of forming a carbon-nitrogen bond between a nitrogen atom of an acyl hydrazine and the activated carbon of an aryl, heteroaryl, or vinyl halide or sulfonate. In other embodiments, the present invention relates to copper-catalyzed methods of forming a carbon-nitrogen bond between the nitrogen atom of a nitrogen-containing heteroaromatic, e.g., indole, pyrazole, and indazole, and the activated carbon of an aryl, heteroaryl, or vinyl halide or sulfonate. In certain embodiments, the present invention relates to copper-catalyzed methods of forming a carbon-oxygen bond between the oxygen atom of an alcohol and the activated carbon of an aryl, heteroaryl, or vinyl halide or sulfonate. The present invention also relates to copper-catalyzed methods of forming a carbon-carbon bond between a reactant comprising a nucleophilic carbon atom, e.g., an enolate or malonate anion, and the activated carbon of an aryl, heteroaryl, or vinyl halide or sulfonate. Importantly, all the methods of the present invention are relatively inexpensive to practice due to the low cost of the copper comprised by the catalysts.

Cu-Catalyzed N-Arylation of Amides

The coupling of aryl iodides and bromides with amides, the so-called Goldberg reaction, is not very general in terms of substrate scope, often requiring stoichiometric quantities of copper complexes. Moreover, as with the related Ullmann reaction, the reaction conditions for the Goldberg reaction are often quite harsh, with required temperatures as high as 210° C. Nevertheless, the methods of the present invention effect these reactions using only 1 mol % CuI and have successfully used as little as 0.2 mol % CuI. In many instances, a system derived from 1% CuI, 10% (racemic)-trans-cyclohexane-1,2-diamine, and $K_3PO_4$ or $Cs_2CO_3$ provides an outstanding catalyst for the amidation of aryl iodides. Importantly, CuI is an air-stable Cu(I) source. As can been seen in the Exemplification, the process enjoys broad substrate scope with respect to the aryl iodide component. Notably, the arylation of a 2° amide-containing substrate and of 4-iodoaniline are possible; Pd-catalyzed C—N bond-forming processes with substrates that contain these functional groups are not successful. We have also been able to N-arylate N-BOC hydrazine. Further, this process provides a convenient entry into the synthesis of hydrazines, and, therefore, a means to access Fischer indole substrates and other heterocycle synthons.

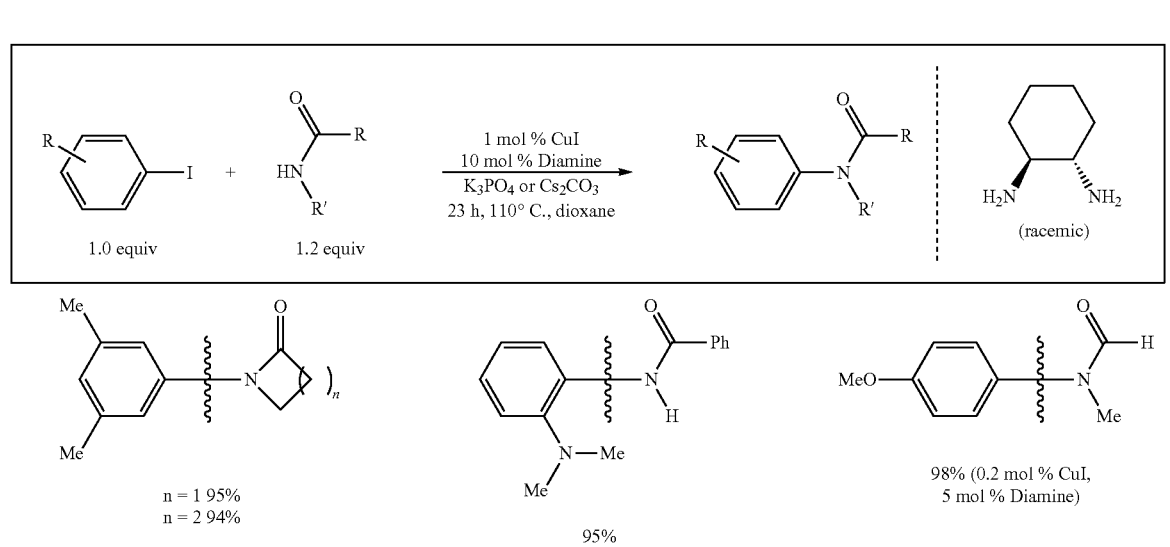

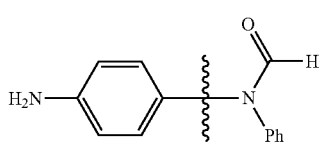
87%

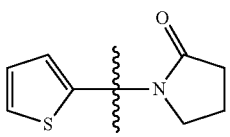
100%

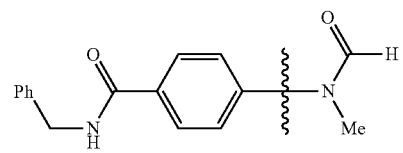
98%

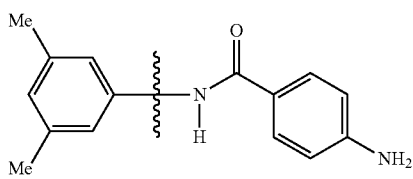
92%

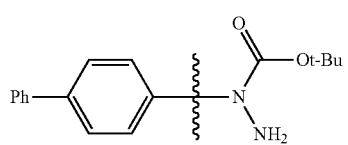
88% (5 mol % CuI, 10 mol % phen)

The copper-catalyzed methods of the present invention allow the amidation of aryl bromides. These reactions typically use 1-20 mol % CuI; for example, in one embodiment, 1 mol % CuI was used, yielding the product in 90% yield. Additionally, the coupling of an unactivated aryl chloride with an amide has also been achieved using the methods of the present invention.

The methods of the present invention also work well for the coupling of aryl iodides with primary amides; in fact, there appear to be no limitations on the nature of the acyl substituent (R in RC(O)NH$_2$). With respect to 2° amides, N-acyl anilines and lactams are preferred substrates. N-formyl amides derived from alkyl amines are satisfactory substrates. Consequently, we believe that steric hindrance influences the outcome of the methods. In embodiments wherein ligand arylation competes with substrate arylation, the use of a 1,10-phenanthroline or an N,N'-dimethyl-1,2-diamine gives improved results.

In preferred embodiments, the pK$_a$ of the amide is in the particular range of 20-25, as measured in DMSO. Generally, strong bases are less effective than weak bases in the methods of the present invention; for example, Cs$_2$CO$_3$ and K$_3$PO$_4$ are efficient bases in many embodiments. For the coupling of aryl bromides at low catalyst loadings, and for the coupling of aryl chlorides, the use of K$_2$CO$_3$ is preferred. These results are consistent with the notion that it is important to keep the concentration of the deprotonated amide low in order to prevent deactivation of the catalyst. Interestingly, to a certain extent, decreasing the catalyst loading does not appear to compromise the reaction efficiency.

Cu-Catalyzed N-Arylation of Heterocycles

In terms of the desirability of the products, some of the most important substrates for the catalyzed N-arylation are nitrogen-containing heterocycles, e.g., pyrrole, and indole. Previous reports of copper-mediated heterocycle N-arylations suffer from limitations similar to those of the Ullmann reaction. Likewise, the Cu-promoted or catalyzed coupling of heterocycles with aryl boronic acids is of limited scope. Moreover, boronic acids are much less attractive as precursors than aryl halides. Accordingly, a general solution to the arylation of heterocycles has been sought for years.

The methods of the present invention allow N-arylation of nitrogen-containing heteroaromatics using 2-haloanisole or 2-methyl indole as one of the coupling partners; in these embodiments, the methods of the present invention afford the desired products nearly quantitatively, whereas the same transformations are very difficult using Pd catalysts. Further, the methods of the present invention enable N-arylation of pyrazole and indazole. Accordingly, the methods of the present invention enable the arylation of a variety of nitrogen heterocycles.

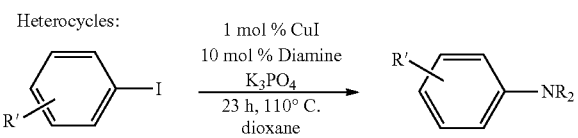

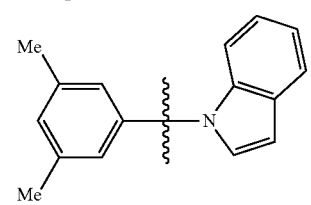
100%

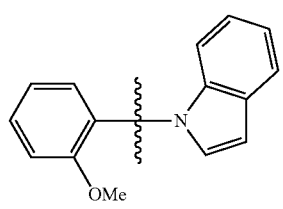
100%

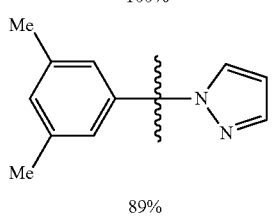
89%

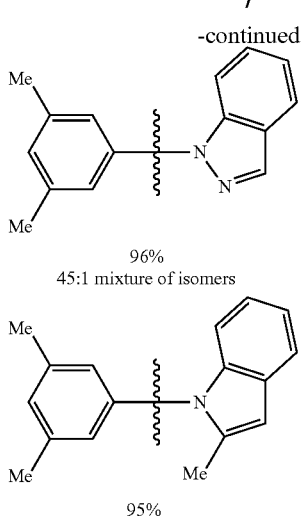

96%
45:1 mixture of isomers

95%

Mild, inexpensive bases, such as $K_3PO_4$ and $K_2CO_3$, are effective in these transformations. These reactions are usually very clean, and arene reduction is typically less problematic than in corresponding Pd systems. The methods of the present invention are often able to effect the desired coupling with as little as 1 mol % CuI; however, elevated temperatures, e.g., 110° C., are normally required for the reaction. Nevertheless, in certain embodiments, a method of the present invention provides an N-aryl heteroaromatic in good yield when performed at room temperature.

Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The term "Bronsted base" is art-recognized and refers to an uncharged or charged atom or molecule, e.g., an oxide, amine, alkoxide, or carbonate, that is a proton acceptor.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane, or point, of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderance of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

%Enantiomeric Excess $A(ee)$=(%Enantiomer $A$)−(%Enantiomer $B$)

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantimerically-enriched unreacted substrate. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 of fewer. Likewise, preferred cycloalkyls have from 4-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "alkenyl" and "alkynyl" refer to unsaturated aliphatic groups analogous in length and possible substitution to the alkyls described above, but which contain at least one double or triple carbon-carbon bond, respectively.

The term "organometallic" refers to compounds comprising a metallic atom (such as mercury, zinc, lead, magnesium or lithium) or a metalloid atom (such as silicon, or tin) that is bonded directly to a carbon atom, such as methyl magnesium bromide, phenyl lithium, and phenyl-trimethyl-tin.

The terms "amine" and "amino" are art-recognized and refer to both unsubstituted and substituted amines, e.g., a moiety that can be represented by the general formula:

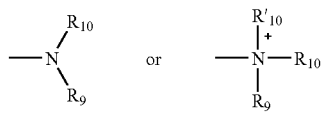

wherein $R_9$, $R_{10}$ and $R'_{10}$ each independently represent a group permitted by the rules of valence.

The abbreviation "DBU" refers to 1,8-diazabicyclo[5.4.0]undec-7-ene, which has the following structure:

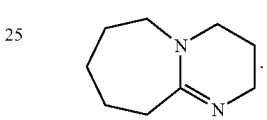

The term "acylamino" is art-recognized and refers to a moiety that can be represented by the general formula:

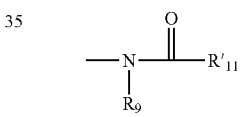

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

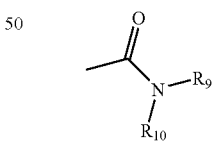

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

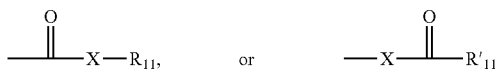

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

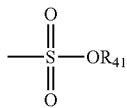

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfonylamino" is art recognized and includes a moiety that can be represented by the general formula:

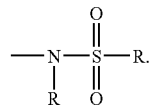

The term "sulfamoyl" is the art-recognized and includes a moiety that can be represented by the general formula:

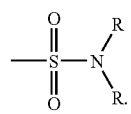

The term "sulfonyl", as used herein, refers to a moiety that can be represented by the general formula:

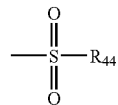

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

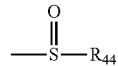

in which $R_{44}$ is selected from the group consisting of hydrogen, alkyl, alkenyl, alkynyl, cycloalkyl, heterocyclyl, aralkyl, or aryl.

The term "sulfate", as used herein, means a sulfonyl group, as defined above, attached to two hydroxy or alkoxy groups. Thus, in a preferred embodiment, a sulfate has the structure:

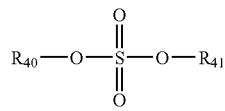

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The term "heteroatom" as used herein means an atom of any element other than carbon or hydrogen. Preferred heteroatoms are nitrogen, oxygen, sulfur, phosphorus and selenium.

For purposes of this invention, the chemical elements are identified in accordance with the Periodic Table of the Elements, CAS version, Handbook of Chemistry and Physics, 67th Ed., 1986-87, inside cover.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms, represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Methods of the Invention

In certain embodiments, a method of the present invention is represented by Scheme 1:

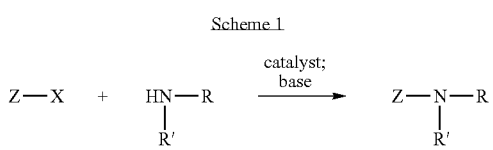

wherein

X represents I, Br, Cl, alkylsulfonate, or arylsulfonate;

Z represents optionally substituted aryl, heteroaryl or alkenyl;

catalyst comprises a copper atom or ion, and a ligand;

base represents a Bronsted base;

R represents alkyl, cycloalkyl, aralkyl, aryl, heteroaryl, formyl, acyl, alkylO$_2$C—, arylO$_2$C—, heteroarylO$_2$C—, aralkylO$_2$C—, heteroaralkylO$_2$C—, acyl(R')N—, alkylOC(O)N(R')—, arylOC(O)N(R')—, aralkylOC(O)N(R')—, heteroaralkylOC(O)N(R')—, —N=C(alkyl)$_2$, or —N=C(aryl)$_2$;

R' represents H, alkyl, cycloalkyl, aralkyl, heteroaralkyl, aryl, heteroaryl, formyl, acyl, amino, or —C(NR")N(R")$_2$;

R" represents independently for each occurrence H, alkyl, cycloalkyl, aryl, heteroaryl, aralkyl or heteroaralkyl;

R and R' taken together may represent =C(alkyl)$_2$, or =C(aryl)$_2$; and

R and R' are optionally connected by a covalent bond;

provided that when R is aryl or heteroaryl, R' is not formyl or acyl;

further provided that when R is formyl or acyl, R' is not aryl or heteroaryl.

In certain embodiments, the methods of the present invention are represented by Scheme 1 and the attendant definitions, wherein X represents I.

In certain embodiments, the methods of the present invention are represented by Scheme 1 and the attendant definitions, wherein X represents Br.

In certain embodiments, the methods of the present invention are represented by Scheme 1 and the attendant definitions, wherein X represents Cl.

In certain embodiments, the methods of the present invention are represented by Scheme 1 and the attendant definitions, wherein the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 1 and the attendant definitions, wherein the ligand comprised by the catalyst is an optionally substituted phenol, 1,2-diaminocyclohexane, or 1,2-diaminoalkane.

In certain embodiments, the methods of the present invention are represented by Scheme 1 and the attendant definitions, wherein the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 1 and the attendant definitions, wherein the ligand comprised by the catalyst is a chelating ligand.

In certain embodiments, the methods of the present invention are represented by Scheme 1 and the attendant definitions, wherein the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 1 and the attendant definitions, wherein the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 1 and the attendant definitions, wherein the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 1 and the attendant definitions, wherein the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein the base is potassium phosphate, potassium carbonate, cesium carbonate, sodium tert-butoxide, or sodium hydroxide.

In certain embodiments, the methods of the present invention are represented by Scheme 1 and the attendant definitions, wherein the catalyst is present in less than or equal to about 10 mol % relative to Z-X.

In certain embodiments, the methods of the present invention are represented by Scheme 1 and the attendant definitions, wherein the catalyst is present in less than or equal to about 5 mol % relative to Z-X.

In certain embodiments, the methods of the present invention are represented by Scheme 1 and the attendant definitions, wherein the catalyst is present in less than or equal to about 1 mol % relative to Z-X.

In certain embodiments, the methods of the present invention are represented by Scheme 1 and the attendant definitions, wherein the catalyst is present in less than or equal to about 0.1 mol % relative to Z-X.

In certain embodiments, the methods of the present invention are represented by Scheme 1 and the attendant definitions, wherein the method is conducted at a temperature less than about 150 C.

In certain embodiments, the methods of the present invention are represented by Scheme 1 and the attendant definitions, wherein the method is conducted at a temperature less than about 140 C.

In certain embodiments, the methods of the present invention are represented by Scheme 1 and the attendant definitions, wherein the method is conducted at a temperature less than about 110 C.

In certain embodiments, the methods of the present invention are represented by Scheme 1 and the attendant definitions, wherein the method is conducted at a temperature less than about 100 C.

In certain embodiments, the methods of the present invention are represented by Scheme 1 and the attendant definitions, wherein the method is conducted at a temperature less than about 90 C.

In certain embodiments, the methods of the present invention are represented by Scheme 1 and the attendant definitions, wherein the method is conducted at a temperature less than about 50 C.

In certain embodiments, the methods of the present invention are represented by Scheme 1 and the attendant definitions, wherein the method is conducted at a temperature less than about 40 C.

In certain embodiments, the methods of the present invention are represented by Scheme 1 and the attendant definitions, wherein the method is conducted at ambient temperature.

In certain embodiments, the methods of the present invention are represented by Scheme 1 and the attendant definitions, wherein Z represents optionally substituted aryl.

In certain embodiments, the methods of the present invention are represented by Scheme 1 and the attendant definitions, wherein Z represents optionally substituted phenyl.

In certain embodiments, the methods of the present invention are represented by Scheme 1 and the attendant definitions, wherein R' represents H, or alkyl.

In certain embodiments, the methods of the present invention are represented by Scheme 1 and the attendant definitions, wherein X represents I; and the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 1 and the attendant definitions, wherein X represents I; and the ligand comprised by the catalyst is an optionally substituted phenol, 1,2-diaminocyclohexane, or 1,2-diaminoalkane.

In certain embodiments, the methods of the present invention are represented by Scheme 1 and the attendant definitions, wherein X represents I; and the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 1 and the attendant definitions, wherein X represents I; and the ligand comprised by the catalyst is a chelating ligand.

In certain embodiments, the methods of the present invention are represented by Scheme 1 and the attendant definitions, wherein X represents I; and the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 1 and the attendant definitions, wherein X represents I; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 1 and the attendant definitions, wherein X represents I; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 1 and the attendant definitions, wherein X represents I; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents I; the ligand comprised by the catalyst is an optionally substituted phenol, 1,2-diaminocyclohexane, or 1,2-diaminoalkane; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents I; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents I; the ligand comprised by the catalyst is a chelating ligand; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents I; the ligand comprised by the catalyst is an optionally substituted 1,2-diaminocyclohexane, 1,10-phenanthroline, 2-hydroxyethyl amine, or 1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents 1; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents I; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents 1; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents I; the ligand comprised by the catalyst is an optionally substituted phenol, 1,2-diaminocyclohexane, or 1,2-diaminoalkane; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents I; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents I; the ligand comprised by the catalyst is a chelating ligand; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents I; the ligand comprised by the catalyst is an optionally substituted 1,2-diaminocyclohexane, 1,10-phenanthroline, 2-hydroxyethyl amine, or 1,2-diaminoethane; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents I; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents I; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents Br; and the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 1 and the attendant definitions, wherein X represents Br; and the ligand comprised by the catalyst is an optionally substituted phenol, 1,2-diaminocyclohexane, or 1,2-diaminoalkane.

In certain embodiments, the methods of the present invention are represented by Scheme 1 and the attendant definitions, wherein X represents Br; and the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 1 and the attendant definitions, wherein X represents Br; and the ligand comprised by the catalyst is a chelating ligand.

In certain embodiments, the methods of the present invention are represented by Scheme 1 and the attendant definitions, wherein X represents Br; and the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 1 and the attendant definitions, wherein X represents Br; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 1 and the attendant definitions, wherein X represents Br; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 1 and the attendant definitions, wherein X represents Br; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Br; the ligand comprised by the catalyst is an optionally substituted phenol, 1,2-diaminocyclohexane, or 1,2-diaminoalkane; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Br; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Br; the ligand comprised by the catalyst is a chelating ligand; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Br; the ligand comprised by the catalyst is an optionally substituted 1,2-diaminocyclohexane, 1,10-phenanthroline, 2-hydroxyethyl amine, or 1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Br; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents Br; the ligand comprised by the catalyst is an optionally substituted phenol, 1,2-diaminocyclohexane, or 1,2-diaminoalkane; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents Br; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents Br; the ligand comprised by the catalyst is a chelating ligand; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents Br; the ligand comprised by the catalyst is an optionally substituted 1,2-diaminocyclohexane, 1,10-phenanthroline, 2-hydroxyethyl amine, or 1,2-diaminoethane; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents Cl; and the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 1 and the attendant definitions, wherein X represents Cl; and the ligand comprised by the catalyst is an optionally substituted phenol, 1,2-diaminocyclohexane, or 1,2-diaminoalkane.

In certain embodiments, the methods of the present invention are represented by Scheme 1 and the attendant definitions, wherein X represents Cl; and the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 1 and the attendant definitions, wherein X represents Cl; and the ligand comprised by the catalyst is a chelating ligand.

In certain embodiments, the methods of the present invention are represented by Scheme 1 and the attendant definitions, wherein X represents Cl; and the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 1 and the attendant definitions, wherein X represents Cl; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 1 and the attendant definitions, wherein X represents Cl; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 1 and the attendant definitions, wherein X represents Cl; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Cl, the ligand comprised by the catalyst is an optionally substituted phenol, 1,2-diaminocyclohexane, or 1,2-diaminoalkane; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Cl; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Cl; the ligand comprised by the catalyst is a chelating ligand; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Cl; the ligand comprised by the catalyst is an optionally substituted 1,2-diaminocyclohexane, 1,10-phenanthroline, 2-hydroxyethyl amine, or 1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Cl; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents Cl; the ligand comprised by the catalyst is an optionally substituted phenol, 1,2-diaminocyclohexane, or 1,2-diaminoalkane; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents Cl; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10- phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents Cl; the ligand comprised by the catalyst is a chelating ligand; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents Cl; the ligand comprised by the catalyst is an optionally substituted 1,2-diaminocyclohexane, 1,10-phenanthroline, 2-hydroxyethyl amine, or 1,2-diaminoethane; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 1 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is potassium phosphate, potassium carbonate, cesium carbonate, sodium tert-butoxide, or sodium hydroxide.

In certain embodiments, a method of the present invention is represented by Scheme 2:

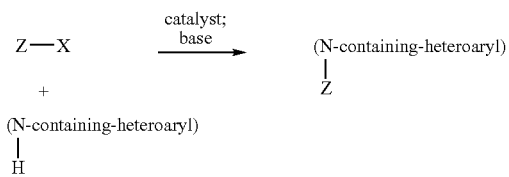

wherein
X represents I, Br, Cl, alkylsulfonate, or arylsulfonate;
Z represents optionally substituted aryl, heteroaryl or alkenyl;
(N-containing-heteroaryl)-H represents optionally substituted pyrazole, pyrrole, tetrazole, imidazole, indazole, 1,2,3-triazole, 1,2,4-trizole, indole, carbazole, benzotriazole, benzimidazole, guanine, purine, adenine, xanthine, 8-azaadenine, 8-azoapoxanthine, uracil, 6-azauracil, cytocine, thymine, 6-azathymine, uric acid, benzoylene urea, 4-(3H)-pyrimidone, pyridone, 1(2H)-phthalazinone, 1,2,3-benzotriazine-4(3H)-one, benzimidazolinone, 2-benzoxazolinone, thymidine, uridine, (−)-inosine, 1H-1,2,3,5-diazadiphosphole, 1H-1,2,3-azadiphosphole, 1H-1,2,4-azadiphosphole, 1H-1,2,4-diazaphosphole, 1H-1,2,3-diazaphosphole, 1H-1,3,2-diazaphosphole, 1H-1,2-azadiphosphole, 1H-1,3-azadiphosphole, 1H-1,2,3,4-triazaphosphole, 1H-1,2,3,5-dithiadiazolidene, 1H-1,3,2,4-dithiadiazolidene, 1,3,2-oxathiazole, 3H-1,2,3-oxathiazole, 1,3,2-dithiazole, 1H-1,2-azaborole, pentazole, 3H-1,2,3-dioxazole, 2H-1,2,3-oxadiazine, 2H-1,2,4-oxadiazine, 2H-1,2,5-oxadiazine, 2H-1,2,6-oxadiazine, 2H-1,2,3-thiadiazine, 2H-1,2,4-thiadiazine, 2H-1,2,5-thiadiazine, 2H-1,2,6-thiadiazine, 2H-1,2-thiazine, 1,3,5,2,4,6-trithiatriazine, 2H-1,2,4,5-oxatriazine, 4H-1,3,2,4-dithiadiazine, 2H, 4H-1,3,2,5-dioxadiazine, 2H-1,5,2,4-dioxadiazine, 2H-1,2,4,6-thiatriazine, 2H-1,2,4,5-thiatriazine, 4H-1,3,2-dithiazane, 4H-1,3,2-dioxazine, 2H-1,5,2-dioxazine, 1,3,4-dithiazane, 4H-1,3,2-oxathiazine, 2H,4H-1,3,2-oxathiazine, 2H, 4H-1,5,2-oxathiazine, 2H-1,2-diazepine, 2H-1,3-diazepine, 2H-1,4-diazepine, 2H-1,2,5-triazepine, 2H-1,3,5-triazepine, 2H-1,2,4-triazepine, 1H-azepine, 2H-1,2,3,5-tetrazepine, 2H-1,2,4,6-tetrazepine, 2H-1,2,4,5-tetrazepine, 2H-1,5,2,4-dithiadiazepine, 1,3,5,2,4,7-trithiatriazepine, 1,3,5,2,4-trithiadiazepine, pentahydro-1,3,5,2,4,6,8-trithiatetrazocine, 2H,6H-1,5,2,4,6,8-dithiatetrazocine, 2H-1,2,5-oxadiazocine, 2H-1,2,6-oxadiazocine, 2H-1,2-oxazocine, 2H-1,2-thiazocine, 4H-1,2,5-thiadiazocine, 4H-1,2,6-thiadiazocine, 5H-[1,2,4]-thiadiazolo[1,5-b][1,2,4]oxathiazole, triazolothiadiazole, thienothiadiazole, 1H-imidazo[1,2-a]imidazole, 4H-furo[3,2-b]pyrrole[3,4-b],1H-pyrrolopyrazole, 1H-[2,3-d]thienopyrazole, 1H-[3,4-d]thienopyrazole, 1H-[2,3-c]thienopyrazole, 1H-[3,4-c]thienopyrazole, 1H-1,3-benzazaphole, 1H-benzazepine, 2H-2-benzazepine, 1H-1,3-benzodiazepine, 1H-1,4-benzodiazepine, 1H-1,5-benzodiazepine, 1H-1,2,4-benzotriazepine, 1H-1,2,5-benzotriazepine, 1H-1,3,4-benzotriazepine, or 3H-3-benzazepine;
catalyst comprises a copper atom or ion, and a ligand; and
base represents a Bronsted base.

In certain embodiments, the methods of the present invention are represented by Scheme 2 and the attendant definitions, wherein (N-containing-heteroaryl)-H represents optionally substituted pyrrole, pyrazole, indole, indazole, azaindole, carbazole, imidazole, purine, or benzimidazole.

In certain embodiments, the methods of the present invention are represented by Scheme 2 and the attendant definitions, wherein X represents I.

In certain embodiments, the methods of the present invention are represented by Scheme 2 and the attendant definitions, wherein X represents Br.

In certain embodiments, the methods of the present invention are represented by Scheme 2 and the attendant definitions, wherein X represents Cl.

In certain embodiments, the methods of the present invention are represented by Scheme 2 and the attendant definitions, wherein the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 2 and the attendant definitions, wherein the ligand comprised by the catalyst is an optionally substituted phenol, 1,2-diaminocyclohexane, or 1,2-diaminoalkane.

In certain embodiments, the methods of the present invention are represented by Scheme 2 and the attendant definitions, wherein the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl) pyridine, and (methylimino)diacetic acid.

In certain embodiments, the methods of the present invention are represented by Scheme 2 and the attendant definitions, wherein the ligand comprised by the catalyst is a chelating ligand.

In certain embodiments, the methods of the present invention are represented by Scheme 2 and the attendant definitions, wherein the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 2 and the attendant definitions, wherein the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 2 and the attendant definitions, wherein the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 2 and the attendant definitions, wherein the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein the base is potassium phosphate, potassium carbonate, cesium carbonate, sodium tert-butoxide, or sodium hydroxide.

In certain embodiments, the methods of the present invention are represented by Scheme 2 and the attendant definitions, wherein the catalyst is present in less than or equal to about 10 mol % relative to Z-X.

In certain embodiments, the methods of the present invention are represented by Scheme 2 and the attendant definitions, wherein the catalyst is present in less than or equal to about 5 mol % relative to Z-X.

In certain embodiments, the methods of the present invention are represented by Scheme 2 and the attendant definitions, wherein the catalyst is present in less than or equal to about 1 mol % relative to Z-X.

In certain embodiments, the methods of the present invention are represented by Scheme 2 and the attendant definitions, wherein the catalyst is present in less than or equal to about 0.1 mol % relative to Z-X.

In certain embodiments, the methods of the present invention are represented by Scheme 2 and the attendant definitions, wherein the method is conducted at a temperature less than about 150 C.

In certain embodiments, the methods of the present invention are represented by Scheme 2 and the attendant definitions, wherein the method is conducted at a temperature less than about 140 C.

In certain embodiments, the methods of the present invention are represented by Scheme 2 and the attendant definitions, wherein the method is conducted at a temperature less than about 110 C.

In certain embodiments, the methods of the present invention are represented by Scheme 2 and the attendant definitions, wherein the method is conducted at a temperature less than about 100 C.

In certain embodiments, the methods of the present invention are represented by Scheme 2 and the attendant definitions, wherein the method is conducted at a temperature less than about 90 C.

In certain embodiments, the methods of the present invention are represented by Scheme 2 and the attendant definitions, wherein the method is conducted at a temperature less than about 50 C.

In certain embodiments, the methods of the present invention are represented by Scheme 2 and the attendant definitions, wherein the method is conducted at a temperature less than about 40 C.

In certain embodiments, the methods of the present invention are represented by Scheme 2 and the attendant definitions, wherein the method is conducted at ambient temperature.

In certain embodiments, the methods of the present invention are represented by Scheme 2 and the attendant definitions, wherein Z represents optionally substituted aryl.

In certain embodiments, the methods of the present invention are represented by Scheme 2 and the attendant definitions, wherein Z represents optionally substituted phenyl.

In certain embodiments, the methods of the present invention are represented by Scheme 2 and the attendant definitions, wherein X represents I; and the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 2 and the attendant definitions, wherein X represents I; and the ligand comprised by the catalyst is an optionally substituted phenol, 1,2-diaminocyclohexane, or 1,2-diaminoalkane.

In certain embodiments, the methods of the present invention are represented by Scheme 2 and the attendant definitions, wherein X represents 1; and the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1, 10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 2 and the attendant definitions, wherein X represents I; and the ligand comprised by the catalyst is a chelating ligand.

In certain embodiments, the methods of the present invention are represented by Scheme 2 and the attendant definitions, wherein X represents 1; and the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 2 and the attendant definitions, wherein X represents I; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 2 and the attendant definitions, wherein X represents I; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 2 and the attendant definitions, wherein X represents I; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents 1; the ligand comprised by the catalyst is an optionally substituted phenol, 1,2-diaminocyclohexane, or 1,2-diaminoalkane; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents I; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents I; the ligand comprised by the catalyst is a chelating ligand; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents I; the ligand comprised by the catalyst is an optionally substituted 1,2-diaminocyclohexane, 1,10-phenanthroline, 2-hydroxyethyl amine, or 1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents I; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents I; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents I; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents 1; the ligand comprised by the catalyst is an optionally substituted phenol, 1,2-diaminocyclohexane, or 1,2-diaminoalkane; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents I; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid;

and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents I; the ligand comprised by the catalyst is a chelating ligand; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents I; the ligand comprised by the catalyst is an optionally substituted 1,2-diaminocyclohexane, 1,10-phenanthroline, 2-hydroxyethyl amine, or 1,2-diaminoethane; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents I; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents I; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents Br; and the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 2 and the attendant definitions, wherein X represents Br; and the ligand comprised by the catalyst is an optionally substituted phenol, 1,2-diaminocyclohexane, or 1,2-diaminoalkane.

In certain embodiments, the methods of the present invention are represented by Scheme 2 and the attendant definitions, wherein X represents Br; and the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 2 and the attendant definitions, wherein X represents Br; and the ligand comprised by the catalyst is a chelating ligand.

In certain embodiments, the methods of the present invention are represented by Scheme 2 and the attendant definitions, wherein X represents Br; and the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 2 and the attendant definitions, wherein X represents Br; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 2 and the attendant definitions, wherein X represents Br; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 2 and the attendant definitions, wherein X represents Br; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents Br; the ligand comprised by the catalyst is an optionally substituted phenol, 1,2-diaminocyclohexane, or 1,2-diaminoalkane; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents Br; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents Br; the ligand comprised by the catalyst is a chelating ligand; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents Br; the ligand comprised by the catalyst is an optionally substituted 1,2-diaminocyclohexane, 1,10-phenanthroline, 2-hydroxyethyl amine, or 1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents Br; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents Br; the ligand comprised by the catalyst is an optionally substituted phenol, 1,2-diaminocyclohexane, or 1,2-diaminoalkane; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents Br; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents Br; the ligand comprised by the catalyst is a chelating ligand; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents Br; the ligand comprised by the catalyst is an optionally substituted 1,2-diaminocyclohexane, 1,10-phenanthroline, 2-hydroxyethyl amine, or 1,2-diaminoethane; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents Cl; and the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 2 and the attendant definitions, wherein X represents Cl; and the ligand comprised by the catalyst is an optionally substituted phenol, 1,2-diaminocyclohexane, or 1,2-diaminoalkane.

In certain embodiments, the methods of the present invention are represented by Scheme 2 and the attendant definitions, wherein X represents Cl; and the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 2 and the attendant definitions, wherein X represents Cl; and the ligand comprised by the catalyst is a chelating ligand.

In certain embodiments, the methods of the present invention are represented by Scheme 2 and the attendant definitions, wherein X represents Cl; and the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 2 and the attendant definitions, wherein X represents Cl; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 2 and the attendant definitions, wherein X represents Cl; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 2 and the attendant definitions, wherein X represents Cl; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is a carbonate, phosphate oxide, hydroxide, alkoxide, aryloxide, amine, metal amide, fluoride, or guanidine.

In certain embodiments, the methods of the present invention are represented by Scheme 2 and the attendant definitions, wherein X represents Cl; the ligand comprised by the catalyst is an optionally substituted phenol, 1,2-diaminocyclohexane, or 1,2-diaminoalkane; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents Cl; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents Cl; the ligand comprised by the catalyst is a chelating ligand; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents Cl; the ligand comprised by the catalyst is an optionally substituted 1,2-diaminocyclohexane, 1,10-phenanthroline, 2-hydroxyethyl amine, or 1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 2 and the attendant definitions, wherein X represents Cl; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents Cl; the ligand comprised by the catalyst is an optionally substituted phenol, 1,2-diaminocyclohexane, or 1,2-diaminoalkane; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents Cl; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents Cl; the ligand comprised by the catalyst is a chelating ligand; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents Cl; the ligand comprised by the catalyst is an optionally substituted 1,2-diaminocyclohexane, 1,10-phenanthroline, 2-hydroxyethyl amine, or 1,2-diaminoethane; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 2 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is potassium phosphate, potassium carbonate, cesium carbonate, sodium tert-butoxide, or sodium hydroxide.

In certain embodiments, a method of the present invention is represented by Scheme 3:

Scheme 3

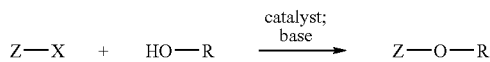

wherein

X represents I, Br, Cl, alkylsulfonate, or arylsulfonate;

Z represents optionally substituted aryl, heteroaryl, or alkenyl;

catalyst comprises a copper atom or ion, and a ligand;

base represents a Bronsted base; and

R represents optionally substituted alkyl, cycloalkyl, aralkyl, heteroaralkyl, alkenylalkyl, or alkynylalkyl.

In certain embodiments, the methods of the present invention are represented by Scheme 3 and the attendant definitions, wherein X represents I.

In certain embodiments, the methods of the present invention are represented by Scheme 3 and the attendant definitions, wherein X represents Br.

In certain embodiments, the methods of the present invention are represented by Scheme 3 and the attendant definitions, wherein X represents Cl.

In certain embodiments, the methods of the present invention are represented by Scheme 3 and the attendant definitions, wherein the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 3 and the attendant definitions, wherein the ligand comprised by the catalyst is an optionally substituted phenol, 1,2-diaminocyclohexane, or 1,2-diaminoalkane.

In certain embodiments, the methods of the present invention are represented by Scheme 3 and the attendant definitions, wherein the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 3 and the attendant definitions, wherein the ligand comprised by the catalyst is a chelating ligand.

In certain embodiments, the methods of the present invention are represented by Scheme 3 and the attendant definitions, wherein the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 3 and the attendant definitions, wherein the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 3 and the attendant definitions, wherein the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 3 and the attendant definitions, wherein the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein the base is potassium phosphate, potassium carbonate, cesium carbonate, sodium tert-butoxide, or sodium hydroxide.

In certain embodiments, the methods of the present invention are represented by Scheme 3 and the attendant definitions, wherein the catalyst is present in less than or equal to about 10 mol % relative to Z-X.

In certain embodiments, the methods of the present invention are represented by Scheme 3 and the attendant definitions, wherein the catalyst is present in less than or equal to about 5 mol % relative to Z-X.

In certain embodiments, the methods of the present invention are represented by Scheme 3 and the attendant definitions, wherein the catalyst is present in less than or equal to about 1 mol % relative to Z-X.

In certain embodiments, the methods of the present invention are represented by Scheme 3 and the attendant definitions, wherein the catalyst is present in less than or equal to about 0.1 mol % relative to Z-X.

In certain embodiments, the methods of the present invention are represented by Scheme 3 and the attendant definitions, wherein the method is conducted at a temperature less than about 150 C.

In certain embodiments, the methods of the present invention are represented by Scheme 3 and the attendant definitions, wherein the method is conducted at a temperature less than about 140 C.

In certain embodiments, the methods of the present invention are represented by Scheme 3 and the attendant definitions, wherein the method is conducted at a temperature less than about 110 C.

In certain embodiments, the methods of the present invention are represented by Scheme 3 and the attendant definitions, wherein the method is conducted at a temperature less than about 100 C.

In certain embodiments, the methods of the present invention are represented by Scheme 3 and the attendant definitions, wherein the method is conducted at a temperature less than about 90 C.

In certain embodiments, the methods of the present invention are represented by Scheme 3 and the attendant definitions, wherein the method is conducted at a temperature less than about 50 C.

In certain embodiments, the methods of the present invention are represented by Scheme 3 and the attendant definitions, wherein the method is conducted at a temperature less than about 40 C.

In certain embodiments, the methods of the present invention are represented by Scheme 3 and the attendant definitions, wherein the method is conducted at ambient temperature.

In certain embodiments, the methods of the present invention are represented by Scheme 3 and the attendant definitions, wherein Z represents optionally substituted aryl.

In certain embodiments, the methods of the present invention are represented by Scheme 3 and the attendant definitions, wherein Z represents optionally substituted phenyl.

In certain embodiments, the methods of the present invention are represented by Scheme 3 and the attendant definitions, wherein X represents I; and the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 3 and the attendant definitions, wherein X represents I; and the ligand comprised by the catalyst is an optionally substituted phenol, 1,2-diaminocyclohexane, or 1,2-diaminoalkane.

In certain embodiments, the methods of the present invention are represented by Scheme 3 and the attendant definitions, wherein X represents I; and the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,1-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 3 and the attendant definitions, wherein X represents I; and the ligand comprised by the catalyst is a chelating ligand.

In certain embodiments, the methods of the present invention are represented by Scheme 3 and the attendant definitions, wherein X represents I; and the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 3 and the attendant definitions, wherein X represents I; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 3 and the attendant definitions, wherein X represents I; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 3 and the attendant definitions, wherein X represents I; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents I; the ligand comprised by the catalyst is an optionally substituted phenol, 1,2-diaminocyclohexane, or 1,2-diaminoalkane; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents I; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid;

and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents I; the ligand comprised by the catalyst is a chelating ligand; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents 1; the ligand comprised by the catalyst is an optionally substituted 1,2-diaminocyclohexane, 1,10-phenanthroline, 2-hydroxyethyl amine, or 1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents I; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents I; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents I; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents I; the ligand comprised by the catalyst is an optionally substituted phenol, 1,2-diaminocyclohexane, or 1,2-diaminoalkane; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents I; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents I; the ligand comprised by the catalyst is a chelating ligand; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents I; the ligand comprised by the catalyst is an optionally substituted 1,2-diaminocyclohexane, 1,10-phenanthroline, 2-hydroxyethyl amine, or 1,2-diaminoethane; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents 1; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents I; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents Br; and the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 3 and the attendant definitions, wherein X represents Br; and the ligand comprised by the catalyst is an optionally substituted phenol, 1,2-diaminocyclohexane, or 1,2-diaminoalkane.

In certain embodiments, the methods of the present invention are represented by Scheme 3 and the attendant definitions, wherein X represents Br; and the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1, 10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 3 and the attendant definitions, wherein X represents Br; and the ligand comprised by the catalyst is a chelating ligand.

In certain embodiments, the methods of the present invention are represented by Scheme 3 and the attendant definitions, wherein X represents Br; and the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 3 and the attendant definitions, wherein X represents Br; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 3 and the attendant definitions, wherein X represents Br; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 3 and the attendant definitions, wherein X represents Br; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents Br; the ligand comprised by the catalyst is an optionally substituted phenol, 1,2-diaminocyclohexane, or 1,2-diaminoalkane; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents Br; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents Br; the ligand comprised by the catalyst is a chelating ligand; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents Br; the ligand comprised by the catalyst is an optionally substituted 1,2-diaminocyclohexane, 1,10-phenanthroline, 2-hydroxyethyl amine, or 1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane, and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents Br; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents Br; the ligand comprised by the catalyst is an optionally substituted phenol, 1,2-diaminocyclohexane, or 1,2-diaminoalkane; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents Br; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid;

and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents Br; the ligand comprised by the catalyst is a chelating ligand; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents Br; the ligand comprised by the catalyst is an optionally substituted 1,2-diaminocyclohexane, 1,10-phenanthroline, 2-hydroxyethyl amine, or 1,2-diaminoethane; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents Cl; and the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 3 and the attendant definitions, wherein X represents Cl; and the ligand comprised by the catalyst is an optionally substituted phenol, 1,2-diaminocyclohexane, or 1,2-diaminoalkane.

In certain embodiments, the methods of the present invention are represented by Scheme 3 and the attendant definitions, wherein X represents Cl; and the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 3 and the attendant definitions, wherein X represents Cl; and the ligand comprised by the catalyst is a chelating ligand.

In certain embodiments, the methods of the present invention are represented by Scheme 3 and the attendant definitions, wherein X represents Cl; and the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 3 and the attendant definitions, wherein X represents Cl; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 3 and the attendant definitions, wherein X represents Cl; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 3 and the attendant definitions, wherein X represents Cl; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents Cl; the ligand comprised by the catalyst is an optionally substituted phenol, 1,2-diaminocyclohexane, or 1,2-diaminoalkane; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents Cl; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents Cl; the ligand comprised by the catalyst is a chelating ligand; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents Cl; the ligand comprised by the catalyst is an optionally substituted 1,2-diaminocyclohexane, 1,10-phenanthroline, 2-hydroxyethyl amine, or 1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 3 and the attendant definitions, wherein X represents Cl; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents Cl; the ligand comprised by the catalyst is an optionally substituted phenol, 1,2-diaminocyclohexane, or 1,2-diaminoalkane; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents Cl; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents Cl; the ligand comprised by the catalyst is a chelating ligand; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents Cl; the ligand comprised by the catalyst is an optionally substituted 1,2-diaminocyclohexane, 1,10-phenanthroline, 2-hydroxyethyl amine, or 1,2-diaminoethane; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 3 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is potassium phosphate, potassium carbonate, cesium carbonate, sodium tert-butoxide, or sodium hydroxide.

In certain embodiments, a method of the present invention is represented by Scheme 4:

Scheme 4

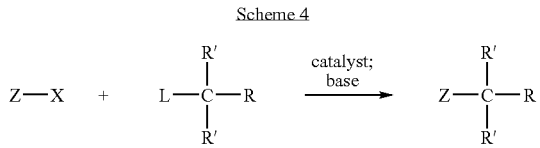

wherein
X represents I, Br, Cl, alkylsulfonate, or arylsulfonate;
Z represents optionally substituted aryl, heteroaryl or alkenyl;
L represents H or a negative charge;
catalyst comprises a copper atom or ion, and a ligand;
base represents a Bronsted base;
R represents H, optionally substituted alkyl, cycloalkyl, aralkyl, aryl, or heteroaryl;
R' represents independently for each occurrence H, alkyl, cycloalkyl, aralkyl, aryl, or heteroaryl, formyl, acyl, —CO$_2$R", —C(O)N(R)$_2$, sulfonyl, —P(O)(OR")$_2$, —CN, or —NO$_2$;
R" represents independently for each occurrence optionally substituted alkyl, cycloalkyl, aralkyl, aryl, or heteroaryl; and
C(R')$_2$(R) taken together may represent nitrile.

In certain embodiments, the methods of the present invention are represented by Scheme 4 and the attendant definitions, wherein X represents I.

In certain embodiments, the methods of the present invention are represented by Scheme 4 and the attendant definitions, wherein X represents Br.

In certain embodiments, the methods of the present invention are represented by Scheme 4 and the attendant definitions, wherein X represents Cl.

In certain embodiments, the methods of the present invention are represented by Scheme 4 and the attendant definitions, wherein the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 4 and the attendant definitions, wherein the ligand comprised by the catalyst is an optionally substituted phenol, 1,2-diaminocyclohexane, or 1,2-diaminoalkane.

In certain embodiments, the methods of the present invention are represented by Scheme 4 and the attendant definitions, wherein the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 4 and the attendant definitions, wherein the ligand comprised by the catalyst is a chelating ligand.

In certain embodiments, the methods of the present invention are represented by Scheme 4 and the attendant definitions, wherein the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 4 and the attendant definitions, wherein the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 4 and the attendant definitions, wherein the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 4 and the attendant definitions, wherein the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein the base is potassium phosphate, potassium carbonate, cesium carbonate, sodium tert-butoxide, or sodium hydroxide.

In certain embodiments, the methods of the present invention are represented by Scheme 4 and the attendant definitions, wherein the catalyst is present in less than or equal to about 10 mol % relative to Z-X.

In certain embodiments, the methods of the present invention are represented by Scheme 4 and the attendant definitions, wherein the catalyst is present in less than or equal to about 5 mol % relative to Z-X.

In certain embodiments, the methods of the present invention are represented by Scheme 4 and the attendant definitions, wherein the catalyst is present in less than or equal to about 1 mol % relative to Z-X.

In certain embodiments, the methods of the present invention are represented by Scheme 4 and the attendant definitions, wherein the catalyst is present in less than or equal to about 0.1 mol % relative to Z-X.

In certain embodiments, the methods of the present invention are represented by Scheme 4 and the attendant definitions, wherein the method is conducted at a temperature less than about 150 C.

In certain embodiments, the methods of the present invention are represented by Scheme 4 and the attendant definitions, wherein the method is conducted at a temperature less than about 140 C.

In certain embodiments, the methods of the present invention are represented by Scheme 4 and the attendant definitions, wherein the method is conducted at a temperature less than about 110 C.

In certain embodiments, the methods of the present invention are represented by Scheme 4 and the attendant definitions, wherein the method is conducted at a temperature less than about 100 C.

In certain embodiments, the methods of the present invention are represented by Scheme 4 and the attendant definitions, wherein the method is conducted at a temperature less than about 90 C.

In certain embodiments, the methods of the present invention are represented by Scheme 4 and the attendant definitions, wherein the method is conducted at a temperature less than about 50 C.

In certain embodiments, the methods of the present invention are represented by Scheme 4 and the attendant definitions, wherein the method is conducted at a temperature less than about 40 C.

In certain embodiments, the methods of the present invention are represented by Scheme 4 and the attendant definitions, wherein the method is conducted at ambient temperature.

In certain embodiments, the methods of the present invention are represented by Scheme 4 and the attendant definitions, wherein Z represents optionally substituted aryl.

In certain embodiments, the methods of the present invention are represented by Scheme 4 and the attendant definitions, wherein Z represents optionally substituted phenyl.

In certain embodiments, the methods of the present invention are represented by Scheme 4 and the attendant definitions, wherein R represents H.

In certain embodiments, the methods of the present invention are represented by Scheme 4 and the attendant definitions, wherein R' represents independently for each occurrence acyl, or —CO$_2$R".

In certain embodiments, the methods of the present invention are represented by Scheme 4 and the attendant definitions, wherein R" represents independently for each occurrence alkyl, cycloalkyl, or aralkyl.

In certain embodiments, the methods of the present invention are represented by Scheme 4 and the attendant definitions, wherein X represents I; and the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 4 and the attendant definitions, wherein X represents I; and the ligand comprised by the catalyst is an optionally substituted phenol, 1,2-diaminocyclohexane, or 1,2-diaminoalkane.

In certain embodiments, the methods of the present invention are represented by Scheme 4 and the attendant definitions, wherein X represents I; and the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 4 and the attendant definitions, wherein X represents I; and the ligand comprised by the catalyst is a chelating ligand.

In certain embodiments, the methods of the present invention are represented by Scheme 4 and the attendant definitions, wherein X represents I; and the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 4 and the attendant definitions, wherein X represents I; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 4 and the attendant definitions, wherein X represents I; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane;

In certain embodiments, the methods of the present invention are represented by Scheme 4 and the attendant definitions, wherein X represents I; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents I; the ligand comprised by the catalyst is an optionally substituted phenol, 1,2-diaminocyclohexane, or 1,2-diaminoalkane; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents I; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents I; the ligand comprised by the catalyst is a chelating ligand; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents I; the ligand comprised by the catalyst is an optionally substituted 1,2-diaminocyclohexane, 1,10-phenanthroline, 2-hydroxyethyl amine, or 1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents I; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents I; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents I; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents 1; the ligand comprised by the catalyst is an optionally substituted phenol, 1,2-diaminocyclohexane, or 1,2-diaminoalkane; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents I; the ligand comprised by the catalyst is selected from the group consisting of 2-phenylphenol, 2,6-dimethylphenol, 2-isopropylphenol, I-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents I; the ligand comprised by the catalyst is a chelating ligand; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents I; the ligand comprised by the catalyst is an optionally substituted 1,2-diaminocyclohexane, 1,10-phenanthroline, 2-hydroxyethyl amine, or 1,2-diaminoethane; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents I; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents I; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents Br; and the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 4 and the attendant definitions, wherein X represents Br; and the ligand comprised by the catalyst is an optionally substituted phenol, 1,2-diaminocyclohexane, or 1,2-diaminoalkane.

In certain embodiments, the methods of the present invention are represented by Scheme 4 and the attendant definitions, wherein X represents Br; and the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 4 and the attendant definitions, wherein X represents Br; and the ligand comprised by the catalyst is a chelating ligand.

In certain embodiments, the methods of the present invention are represented by Scheme 4 and the attendant definitions, wherein X represents Br; and the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 4 and the attendant definitions, wherein X represents Br; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 4 and the attendant definitions, wherein X represents Br; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 4 and the attendant definitions, wherein X represents Br; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents Br; the ligand comprised by the catalyst is an optionally substituted phenol, 1,2-diaminocyclohexane, or 1,2-diaminoalkane; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents Br; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents Br; the ligand comprised by the catalyst is a chelating ligand; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents Br; the ligand comprised by the catalyst is an optionally substituted 1,2-diaminocyclohexane, 1,10-phenanthroline, 2-hydroxyethyl amine, or 1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents Br; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents Br; the ligand comprised by the catalyst is an optionally substituted phenol, 1,2-diaminocyclohexane, or 1,2-diaminoalkane; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents Br; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents Br; the ligand comprised by the catalyst is a chelating ligand; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents Br; the ligand comprised by the catalyst is an optionally substituted 1,2-diaminocyclohexane, 1,10-phenanthroline, 2-hydroxyethyl amine, or 1,2-diaminoethane; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents Br; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents Cl; and the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline.

In certain embodiments, the methods of the present invention are represented by Scheme 4 and the attendant definitions, wherein X represents Cl; and the ligand comprised by the catalyst is an optionally substituted phenol, 1,2-diaminocyclohexane, or 1,2-diaminoalkane.

In certain embodiments, the methods of the present invention are represented by Scheme 4 and the attendant definitions, wherein X represents Cl; and the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid.

In certain embodiments, the methods of the present invention are represented by Scheme 4 and the attendant definitions, wherein X represents Cl; and the ligand comprised by the catalyst is a chelating ligand.

In certain embodiments, the methods of the present invention are represented by Scheme 4 and the attendant definitions, wherein X represents Cl; and the ligand comprised by the catalyst is an optionally substituted 1,2-diaminocyclohexane, 1,10-phenanthroline, 2-hydroxyethyl amine, or 1,2-diaminoethane.

In certain embodiments, the methods of the present invention are represented by Scheme 4 and the attendant definitions, wherein X represents Cl; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane.

In certain embodiments, the methods of the present invention are represented by Scheme 4 and the attendant definitions, wherein X represents Cl; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane.

In certain embodiments, the methods of the present invention are represented by Scheme 4 and the attendant definitions, wherein X represents Cl; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents Cl; the ligand comprised by the catalyst is an optionally substituted phenol, 1,2-diaminocyclohexane, or 1,2-diaminoalkane; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents Cl; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents Cl; the ligand comprised by the catalyst is a chelating ligand; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents Cl; the ligand comprised by the catalyst is an optionally substituted 1,2-diaminocyclohexane, 1,10-phenanthroline, 2-hydroxyethyl amine, or 1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is a carbonate, phosphate, oxide, hydroxide, alkoxide, aryloxide, amine, metal amide, fluoride, or guanidine.

In certain embodiments, the methods of the present invention are represented by Scheme 4 and the attendant definitions, wherein X represents Cl; the ligand comprised by the catalyst is an optionally substituted aryl alcohol, alkyl amine, 1,2-diamine, 1,2-aminoalcohol, 1,2-diol, imidazolium carbene, pyridine, or 1,10-phenanthroline; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents Cl; the ligand comprised by the catalyst is an optionally substituted phenol, 1,2-diaminocyclohexane, or 1,2-diaminoalkane; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents Cl; the ligand comprised by the catalyst is selected from the group consisting of 2-phenylphenol, 2,6-dimethylphenol, 2-isopropylphenol, 1-naphthol, 8-hydroxyquinoline, 8-aminoquinoline, DBU, 2-(dimethylamino)ethanol, ethylene glycol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, and (methylimino)diacetic acid; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents Cl; the ligand comprised by the catalyst is a chelating ligand; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents Cl; the ligand comprised by the catalyst is an optionally substituted 1,2-diaminocyclohexane, 1,10-phenanthroline, 2-hydroxyethyl amine, or 1,2-diaminoethane; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, or N,N'-dimethyl-1,2-diaminoethane; and the base is potassium phosphate, potassium carbonate, cesium carbonate, sodium tert-butoxide, or sodium hydroxide.

In certain embodiments, the methods of the present invention are represented by Scheme 4 and the attendant definitions, wherein X represents Cl; the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, or N,N'-dimethyl-1,2-diaminoethane; and the base is potassium phosphate, potassium carbonate, cesium carbonate, sodium tert-butoxide, or sodium hydroxide.

Catalysts of the Invention

In general, the catalysts used in the methods of the present invention comprise a copper atom or ion, and a ligand. The copper atom or ion of the catalyst may be derived from any commercially available copper salt, e.g., a copper (I) or copper (II) salt. In certain embodiments, the copper atom or ion is provided as copper (I) iodide.

The ligand of a catalyst comprises a Lewis basic atom, e.g., selected from nitrogen, oxygen, sulfur, phosphorus, and arsenic, such that the Lewis basic atom is capable of interacting with the aforementioned copper atom or ion. The ligand of a catalyst may be a chelating ligand, i.e., a ligand comprising two Lewis basic atoms, e.g., selected from nitrogen, oxygen, phosphorus, and arsenic, with a spatial relationship therebetween, such that the Lewis basic atoms are capable of interacting simultaneously with the aforementioned copper atom or ion. For example, a chelating ligand may be a diamine, aminoalcohol, or a bis-phosphine. In certain embodiments, a chelating ligand is a 1,2-diamine, or 1,3-diamine. In certain embodiments, a chelating ligand is a 1,2-diaminocyclohexane, a 1,10-phenanthroline, a 2-hydroxyethyl amine, or a 1,2-diaminoethane. In certain embodiments, a chelating ligand is 1,2-diaminocyclohexane, N,N'-dimethyl-1,2-diaminocyclohexane, N-tolyl-1,2-diaminocyclohexane, 1,10-phenanthroline, ethanolamine, 1,2-diaminoethane, or N,N'-dimethyl-1,2-diaminoethane. In certain embodiments, a chelating ligand is cis-1,2-diaminocyclohexane, trans-1,2-diaminocyclohexane, or a mixture of cis- and trans-1,2-diaminocyclohexane. Additionally, with respect to asymmetric chelating ligands, the ligand may be provided as a single enantiomer, a mixture of stereoisomers, or a racemic mixture. In certain embodiments, the ligand serves as the solvent for a method of the present invention. For example, in an embodiment wherein the ligand comprised by the catalyst is an amine that is a liquid under the conditions for practicing a method of the present invention, the method may be practiced using said amine as the solvent.

The copper atom or ion and the ligand of the catalyst of the methods of the present invention may be added to the reaction mixture separately or simultaneously, or they may be added in the form of preformed catalyst complex. Although the methods of the present invention do not require the formation of a copper-chelating ligand complex, such complexes are likely present. Moreover, the identity of the ligand effects various characteristics of the methods of the present invention.

In certain embodiments, the catalyst of a method of the present invention is covalently tethered to a solid support, e.g., a polymer bead or a resin. For example, the ligand of a catalyst of the present invention may be covalently tethered to a solid support, e.g., a Wang resin. Additionally, one or more of the substrates of a method of the present invention may be covalently tethered to a solid support, e.g., a polymer bead or a resin. For example, the Z-X substrate of a method of the present invention may be covalently tethered to a solid support, e.g., a Wang resin. Alternatively, the nucleophilic substrate, i.e., the substrate that effectively replaces X in Z-X, of a method of the present invention may be covalently tethered to a solid support, e.g., a Wang resin. Further, in certain embodiments, both substrates may be covalently tethered to a solid support. In certain embodiments, one or more of the substrates or the catalyst or any of them are isolated in a semi-permeable membrane, e.g., a dialysis bag.

Suitable Bases

A wide range of Bronsted bases may be used in the methods of the present invention. Generally, any Bronsted base may be used in the methods of the present invention. For example, suitable bases include $K_3PO_4$, $K_2CO_3$, $Na_2CO_3$, $Tl_2CO_3$, $Cs_2CO_3$, K(OtBu), Li(OtBu), Na(OtBu), K(OPh), and Na(OPh), or mixtures thereof. In certain embodiments, the Bronsted base used will be selected from the group consisting of phosphates, carbonates, and alkoxides. In certain embodiments, the base is selected from the group consisting of potassium phosphate, potassium carbonate, cesium carbonate, and sodium tert-butoxide.

Typically, there is no need to use large excesses of base in the methods of the present invention. In certain embodiments, no more than four equivalents of base are used, relative to the nucleophilic reactant. In other embodiments, no more than two equivalents of base are used, relative to the nucleophilic reactant. Further, in reactions using the corresponding anion of the nucleophilic reactant in place of its conjugate base, there may be no need for additional base.

Nucleophiles

Nucleophiles which are useful in the methods of the present invention may be selected by the skilled artisan according to several criteria. In general, a suitable nucleophile will have one or more of the following properties: 1) It will be capable of reaction with the substrate at the desired electrophilic site; 2) It will yield a useful product upon reaction with the substrate; 3) It will not react with the substrate at functionalities other than the desired electrophilic site; 4) It will react with the substrate at least partly through a mechanism catalyzed by the chiral catalyst; 5) It will not substantially undergo further undesired reaction after reacting with the substrate in the desired sense; and 6) It will not substantially react with or degrade the catalyst. It will be understood that while undesirable side reactions (such as catalyst degradation) may occur, the rates of such reactions can be rendered slow—through the selection of reactants and conditions—in comparison with the rate of the desired reaction(s).

Routine experimentation may be necessary to determine the preferred nucleophile for a given transformation. For example, if a nitrogen-containing nucleophile is desired, in order to form a carbon-nitrogen bond, it may be selected from the group comprising amines, amides, and imides. Further, heteroaromatics may also be used as the nucleophilic reactant. For example, a carbon-nitrogen bond may be formed comprising the nitrogen of an optionally substituted indole, pyrrole, or carbazole. Moreover, numerous other nitrogen-containing functional groups serve as substrates in the instant methods of forming carbon-nitrogen bonds. For example, hydrazines, acylhydrazines, hydrazones, imines, and alkoxy-carbonylhydrazines are suitable substrates for the carbon-nitrogen bond-forming methods of the present invention.

Similarly, an oxygen-containing nucleophile, such as an alcohol, alkoxide, or siloxane, may be used to form an oxygen-carbon bond; and a sulfur-containing nucleophile, such as a mercaptan, may be used to form a carbon-sulfur bond. Likewise, a carbon nucleophile, e.g., a malonate or a beta-keto ester, may be used to form a carbon-carbon bond. Additional suitable nucleophiles will be apparent to those of ordinary skill in the art of organic chemistry. A nucleophile introduced in the reaction mixture as an anion may comprise a conventional counterion, e.g., an alkali metal cation, alkaline earth cation, or ammonium ion. In certain embodiments, the nucleophilic moiety may be part of the substrate, resulting in an intramolecular bond-forming reaction.

In certain embodiments, the nucleophile is selected from the group consisting of primary amides, secondary amides, lactams, hydrazines, imines, hydrazones, carbazates, primary amines, secondary amines, NH-containing heteroaromatics (e.g., pyrroles, indoles, and imidazoles), malonates, carbamates, imides, and alcohols.

Aryl, Heteroaryl or Vinyl Halides or Sulfonates

The methods of the present invention may be used to form a bond between the halogen-bearing or sulfonate-bearing carbon atom of an aryl halide or sulfonate, heteroaryl halide or sulfonate, or vinyl halide or sulfonate, and a nucleophilic nitrogen or carbon or oxygen atom of a second molecule. Of course, as mentioned supra, the halogen-bearing carbon of the aryl halide, heteroaryl halide, or vinyl halide, or the sulfonate-bearing carbon of the aryl sulfonate, heteroaryl sulfonate, or vinyl sulfonate, and the nucleophilic nitrogen or carbon may be part of a single molecule, rendering the bond-formation intramolecular.

In certain embodiments, an aryl halide or sulfonate is used, wherein its aryl moiety is a radical of an aromatic hydrocarbon (single or polycyclic), such as benzene, naphthalene, anthracene and phenanthrene. In certain embodiments, the aryl halide may be selected from the group consisting of optionally-substituted phenyl halides.

In certain embodiments, a heteroaryl halide or sulfonate is used, wherein its heteroaryl moiety is a radical of an heteroaromatic (single or polycyclic), such as pyrrole, thiophene, thianthrene, furan, pyran, isobenzofuran, chromene, xanthene, phenoxathiin, pyrrole, imidazole, pyrazole, thiazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine.

In general, suitable aromatic compounds have the formula $Z_p ArX$, wherein Ar is aryl or heteroaryl; and X is a sulfonate or a halogen selected from the group consisting of chlorine, bromine, and iodine. In certain embodiments, X is a halide selected from the group consisting of chlorine, bromine, and iodine. In certain embodiments, X represents a sulfonate moiety. Further, Z represents one or more optional substituents on the aromatic ring, though each occurence of Z (p>1) is independently selected. By way of example only, each incidence of substitution independently can be, as valence and stability permit, a halogen, a lower alkyl, a lower alkenyl, a lower alkynyl, a carbonyl (e.g., an ester, a carboxylate, or a formate), a thiocarbonyl (e.g., a thiolester, a thiolcarboxylate, or a thiolformate), an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, $-(CH_2)_m-R_8$, $-(CH_2)_m-OH$, $-(CH_2)_m-O$-lower alkyl, $-(CH_2)_m-O$-lower alkenyl, $-(CH_2)_m-O-(CH_2)_n-R_8$, $-(CH_2)_m-SH$, $-(CH_2)_m-S$-lower alkyl, $-(CH_2)_m-S$-lower alkenyl, $-(CH_2)_m-S-(CH_2)_n-R_8$, or protecting groups of the above or a solid or polymeric support; $R_8$ represents a substituted or unsubstituted aryl, aralkyl, cycloalkyl, cycloalkenyl, or heterocycle; and n and m are independently for each occurrence zero or an integer in the range of 1 to 6. When the aryl moiety is phenyl, p is in the range of 0 to 5. For fused rings, where the number of potential substitution sites on the aryl moiety is greater than five, the range defined for p must be adjusted appropriately.

Reaction Conditions

The methods of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants, products and catalyst.

In certain embodiments, the methods of the present invention are conducted at a temperature less than about 150 C. In certain embodiments, the methods of the present invention are conducted at a temperature less than about 140 C. In certain embodiments, the methods of the present invention are conducted at a temperature less than about 110 C. In certain embodiments, the methods of the present invention are conducted at a temperature less than about 100 C. In certain embodiments, the methods of the present invention are conducted at a temperature less than about 90 C. In certain embodiments, the methods of the present invention are conducted at a temperature less than about 50 C. In certain embodiments, the methods of the present invention are conducted at a temperature less than about 40 C. In certain embodiments, the methods of the present invention are conducted at ambient temperature.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants or the catalyst can be immobilized by attachment to or incorporation into a polymer or other insoluble matrix.

Subsequent Transformations

A product synthesized by a method of the present invention may be either an end-product or an intermediate in a synthesis scheme. In cases where the product synthesized by a method of the present invention is an intermediate, the product may be subjected to one or more additional transformations to yield the desired end-product. The set of additional transformations contemplated comprises isomerizations, hydrolyses, oxidations, reductions, additions, eliminations, olefinations, functional group interconversions, transition metal-mediated reactions, transition metal-catalyzed reactions, bond-forming reactions, cleavage reactions, fragmentation reactions, thermal reactions, photochemical reactions, cycloadditions, sigmatropic rearrangements, electrocyclic reactions, chemoselective reactions, regioselective reactions, stereoselective reactions, diastereoselective reactions, enantioselective reactions, and kinetic resolutions. The invention expressly comprises use of a method of the present invention as a step—either initial, intermediate or final—in the synthesis of known or new pharmaceuticals, e.g., antivirals, antibiotics, and analgesics.

Combinatorial Libraries

The subject methods of the present invention readily lend themselves to the creation of combinatorial libraries of compounds for the screening of pharmaceutical, agrochemical or other biological or medical activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116: 2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay.

EXEMPLIFICATION

The invention now being generally described, it will be more readily understood by reference to the following examples which are included merely for purposes of illustration of certain aspects and embodiments of the present invention, and are not intended to limit the invention.

Example 1

General Procedure A—Arylations Using Aryl or Heteroaryl Iodides

An oven-dried resealable Schlenk tube was charged with CuI (2.0 mg, 0.0105 mmol, 1.0 mol %), amide (1.2 mmol) and $K_3PO_4$ (2.1 mmol), evacuated and backfilled with argon. trans-1,2-Cyclohexanediamine (13 μL, 0.108 mmol, 11 mol %), dodecane (235 μL), aryl iodide (1.0 mmol) and dioxane (1.0 mL) were added under argon. The Schlenk tube was sealed and the reaction mixture was stirred magnetically at 110° C. for 23 h. The resulting suspension was cooled to room temperature and filtered through a 0.5×1 cm pad of silica gel eluting with 10 mL of ethyl acetate. The filtrate was concentrated and the residue was purified by flash chromatography to afford pure product.

Example 2

General Procedure B—Arylations Using Aryl or Heteroaryl Iodides

To a flame-dried resealable Schlenk tube was added CuI (2.0 mg, 0.0105 mmol, 1.0 mol %), the heterocycle (1.2 mmol) and $K_3PO_4$ (2.1 mmol), evacuated twice and backfilled with argon. Dodecane (45 μL, 0.20 mmol), 5-iodo-m-xylene (144 μL, 1.0 mmol), trans-1,2-cyclohexanediamine (12 μL, 0.10 mmol, 10 mol %) and dioxane (1.0 mL) were added under argon. The Schlenk tube was sealed and the reaction was stirred with heating via an oil bath at 110° C. for 20 hours. The reaction mixture was cooled to ambient temperature, diluted with 2-3 mL ethyl acetate, and filtered through a plug of silica gel eluting with 10-20 mL of ethyl acetate. The filtrate was concentrated and the resulting residue was purified by column chromatography to provide the purified product.

Example 3

General Procedure C—Arylations Using Aryl or Heteroaryl Bromides

An oven-dried resealable Schlenk tube containing a stirbar was charged with CuI (20 mg, 0.1 mmol, 10 mol %), amide (1.2 mmol) and $K_3PO_4$ (425 mg, 2 mmol), evacuated and backfilled with argon. trans-1,2-Diaminocyclohexane (11.5 mg, 6.1 mmol), heteroaryl bromide (1.0 mmol) and dioxane (1 ml) were injected, and under a flow of argon, the septum was replaced by a Teflon screw cap. The tube was sealed, and the mixture was stirred and heated in an oil bath at 110° C. for the time specified. The resulting mixture was cooled to room temperature and filtered through Celite with dichloromethane. The filtrate was concentrated under reduced pressure and the residue chromatographed on silica gel.

Example 4

N-(4-Allyloxycarbonylphenyl)benzamide

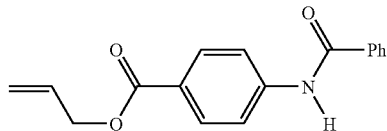 [SMILES: C=CCOC(=O)c1ccc(NC(=O)c2ccccc2)cc1]

Using general procedure A, benzamide (150 mg, 1.24 mmol) was coupled with allyl 4-iodobenzoate (300 mg, 1.04 mmol). The crude product was purified by flash chromatography on silica gel (2×15 cm; hexane-ethyl acetate 3:1, 10 mL fractions). Fractions 8-15 provided 266 mg (91% yield) of the product as white crystals. $^1$H NMR (400 MHz, CDCl$_3$): δ 8.14-8.09 (m, 2H), 8.00 (br s, 1H), 7.93-7.88 (m, 2H), 7.80-7.75 (m, 2H), 7.63-7.58 (m, 1H), 7.56-7.51 (m, 2H), 6.07 (ddt, J=17.2, 11.7, 5.6 Hz, 1H), 5.45 (dq, J=17.2, 1.4 Hz, 1H), 5.32 (dq, J=11.7, 1.4 Hz, 1H), 4.85 (dt, J=5.6, 1.4 Hz, 2H).

Example 5

N-Benzyl-N-(3,5-dimethylphenyl)formamide

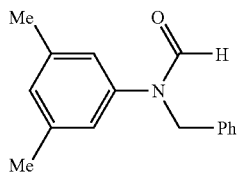 [SMILES: Cc1cc(C)cc(N(C=O)Cc2ccccc2)c1]

Using general procedure A, N-benzylformamide (170 mg, 1.26 mmol) was coupled with 5-iodo-m-xylene (150 μL, 1.04 mmol). The crude product was purified by flash chromatography on silica gel (2×15 cm; hexane-ethyl acetate 3:1; 15 mL fractions). Fractions 7-13 provided 247 mg (99% yield) of the product as a colorless oil. $^1$H NMR (400 MHz, CDCl$_3$): δ 8.55 (s, 1H), 7.39-7.22 (m, 5H), 6.91 (s, 1H), 6.75 (s, 2H), 5.00 (s, 2H), 2.30 (s, 6H).

Example 6

N-(2-Dimethylaminophenyl)benzamide

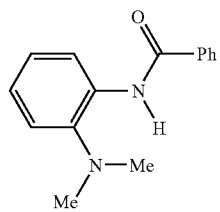

Using general procedure A, benzamide (150 mg, 1.24 mmol) was coupled with N,N-dimethyl-2-iodoaniline (160 μL, 1.05 mmol). The crude product was purified by flash chromatography on silica gel (2×15 cm; hexane-ethyl acetate 7:1; 15 mL fractions). Fractions 8-15 provided 239 mg (95% yield) of the product as a pale yellow oil. ¹H NMR (400 MHz, CDCl₃): δ9.42 (br s, 1H), 8.57 (dd, J=7.8, 1.4 Hz, 1H), 7.98-7.92 (m, 2H), 7.62-7.51 (m, 3H), 7.26 (dd, J=7.8, 1.4 Hz, 1H), 7.22 (td, J=7.8, 1.4 Hz, 1H), 7.12 (td, J=7.8, 1.4 Hz, 1H), 2.74 (s, 6H).

Example 7

N-(2-Nitrophenyl)benzamide

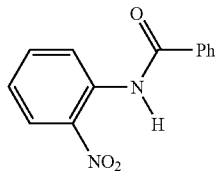 [SMILES: O=C(Nc1ccccc1[N+](=O)[O-])c1ccccc1]

Using general procedure A, benzamide (150 mg, 1.24 mmol) was coupled with 1-iodo-2-nitrobenzene (260 mg, 1.04 mmol). The crude product was purified by flash chromatography on silica gel (2×15 cm; hexane-ethyl acetate 8:1; 15 mL fractions). Fractions 8-14 provided 177 mg (70% yield) of the product as bright yellow needles. The ¹H NMR spectrum was in accord with that reported by Murphy et al. Murphy, J. A.; Rasheed, F.; Gastaldi, S.; Ravishanker, T.; Lewis, N. J. Chem. Soc., Perkin Trans 1 1997, 1549.

Example 8

N-(4-Aminophenyl)-N-phenylacetamide

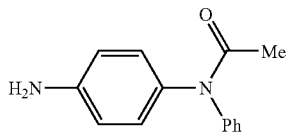 [SMILES: CC(=O)N(c1ccccc1)c1ccc(N)cc1]

Using general procedure A, acetanilide (165 mg, 1.22 mmol) was coupled with 4-iodoaniline (228 mg, 1.04 mmol). The crude product was purified by flash chromatography on silica gel (2×20 cm; hexane-ethyl acetate 1:4; 20 mL factions). Fractions 10-20 provided 192 mg (82% yield) of the product as a pale yellow solid. ¹H NMR (400 MHz, CDCl₃): δ 7.50-7.10 (m, 5H), 7.09-7.04 (m, 2H), 6.74-6.61 (m, 2H), 3.90-3.50 (br s, 2H), 2.07 (s, 3H).

Example 9

4-Amino-N-(3,5-dimethylphenyl)benzamide

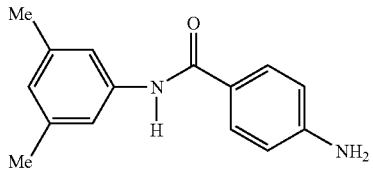 [SMILES: Cc1cc(C)cc(NC(=O)c2ccc(N)cc2)c1]

Using general procedure A, 4-aminobenzamide (170 mg, 1.25 mmol) was coupled with 5-iodo-m-xylene (150 µL, 1.04 mmol). The crude product was purified by flash chromatography on silica gel (2×20 cm; hexane-ethyl acetate 2:3; 15 mL fractions). Fractions 9-18 provided 246 mg (98% yield) of the product as a white solid. ¹H NMR (400 MHz, CDCl₃): δ 7.74-7.69 (m, 2H), 7.66 (br s, 1H), 7.28 (s, 2H), 6.78 (s, 1H), 6.74-6.69 (m, 2H), 4.05 (br s, 2H), 2.33 (s, 6H). ¹³C NMR (100 MHz, CDCl₃): δ 165.7, 150.3, 139.1, 138.6, 129.2, 126.2, 124.8, 118.2, 114.6, 21.8.

Example 10

N-(4-Benzylaminocarbonylphenyl)-N-methylformamide

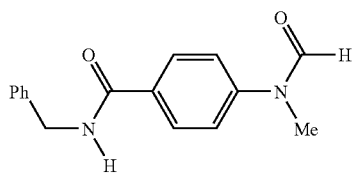 [SMILES: CN(C=O)c1ccc(C(=O)NCc2ccccc2)cc1]

An oven-dried resealable Schlenk tube was charged with CuI (2.0 mg, 0.0105 mmol, 1.0 mol %), 4-iodo-N-benzylbenzamide (350 mg, 1.04 mmol), K₃PO₄ (450 mg, 2.12 mmol), evacuated and backfilled with argon. trans-1,2-Cyclohexanediamine (13 µL, 0.108 mmol, 11 mol %), dodecane (235 µL), N-methylformamide (74 µL, 1.27 mmol) and dioxane (1.0 mL) were added under argon. The Schlenk tube was sealed and the reaction mixture was stirred magnetically at 110° C. for 23 h. The resulting suspension was cooled to room temperature and filtered through a 0.5×1 cm pad of silica gel eluting with 10 mL of ethyl acetate. The filtrate was concentrated and the residue was purified by flash chromatography on silica gel (2×15 cm; ethyl acetate-dichloromethane 2:1; 20 mL fractions). Fractions 7-18 provided 273 mg (98% yield) of the product as white crystals. ¹H NMR (400 MHz, CDCl₃): δ 8.57 (s, 1H), 7.90-7.86 (m, 2H), 7.40-7.29 (m, 5H), 7.25-7.20 (m, 2H), 6.62 (br s, 1H), 4.66 (d, J=5.7 Hz, 2H), 3.35 (s, 3H). ¹³C NMR (100 MHz, CDCl₃): δ 166.6, 162.3, 145.2, 138.4, 132.2, 129.2, 129.0, 128.3, 128.1, 121.5, 44.6, 32.0.

Example 11

N-(3,5-Dimethylphenyl)-2-azetidinone

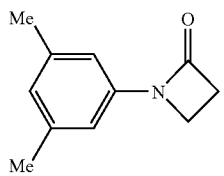

Using general procedure A, 2-azetidinone (88 mg, 1.24 mmol) was coupled with 5-iodo-m-xylene (150 µL, 1.04 mmol). The crude product was purified by flash chromatography on silica gel (2×15 cm; hexane-ethyl acetate 1:1; 15 mL fractions). Fractions 5-10 provided 173 mg (95% yield) of the product as a white solid. $^1$H NMR (400 MHz, CDCl$_3$): δ 7.01 (s, 2H), 6.76 (s, 1H), 3.61 (t, J=4.5 Hz, 2H), 3.10 (t, J=4.5 Hz, 2H), 2.32 (s, 6H).

Example 12

N-(2-Thiophenyl)-2-pyrrolidinone

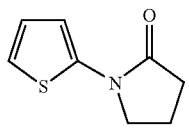 [SMILES: O=C1CCCN1c1cccs1]

An oven-dried resealable Schlenk tube was charged with CuI (2.0 mg, 0.0105 mmol, 1.0 mol %) and K$_3$PO$_4$ (450 mg, 2.12 mmol), evacuated and backfilled with argon. trans-1,2-Cyclohexanediamine (13 μL, 0.108 mmol, 11 mol %), dodecane (235 μL), 2-iodothiophene (115 μL, 1.04 mmol), 2-pyrrolidinone (94 μL, 1.24 mmol) and dioxane (1.0 mL) were added under argon. The Schlenk tube was sealed and the reaction mixture was stirred magnetically at 110° C. for 23 h. The resulting suspension was cooled to room temperature and filtered through a 0.5×1 cm pad of silica gel eluting with 10 mL of ethyl acetate. The filtrate was concentrated and the residue was purified by flash chromatography on silica gel (2×15 cm; hexane-ethyl acetate 1:1; 20 mL fractions). Fractions 9-15 provided 174 mg (100% yield) of the product as white crystals. $^1$H NMR (400 MHz, CDCl$_3$): δ6.95 (dd, J=5.5, 1.3 Hz, 1H), 6.90 (dd, J=5.5, 3.7 Hz, 1H), 6.55 (dd, J=3.7, 1.3 Hz, 1H), 3.92 (t, J=7.4 Hz, 2H), 2.66 (t, J=7.4 Hz, 2H), 2.27 (p, J=7.4 Hz, 2H). $^{13}$C NMR (100 MHz, CDCl$_3$): δ 172.4, 140.9, 124.2, 118.4, 110.9, 49.2, 31.7, 18.3.

Example 13

Preparation of N-(4-methoxyphenyl)-N-methylformamide using 0.2 mol % CuI

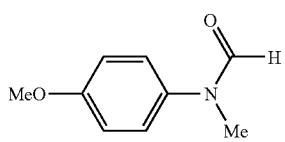 [SMILES: COc1ccc(N(C)C=O)cc1]

An oven-dried resealable Schlenk tube was charged with CuI (2.0 mg, 0.0105 mmol, 0.2 mol %) and K$_3$PO$_4$ (2.25 g, 10.6 mmol), evacuated and backfilled with argon. trans-1,2-Cyclohexanediamine (33 μL, 0.269 mmol, 5.2 mol %), dodecane (1.20 mL), 4-iodoanisole (1.22 g, 5.21 mmol), N-methylformamide (360 μL, 6.15 mmol) and dioxane (5.0 mL) were added under argon. The Schlenk tube was sealed and the reaction mixture was stirred magnetically at 110° C. for 23 h. The resulting suspension was cooled to room temperature and filtered through a 1.5×10 cm pad of silica gel eluting with 50 mL of ethyl acetate. The light green filtrate was concentrated and the residue was purified by flash chromatography on silica gel (2×15 cm; hexane-ethyl acetate 1:1; 20 mL fractions). Fractions 8-17 provided 840 mg (98% yield) of the product as a colorless oil. The $^1$H NMR spectrum was in accord with that reported by Hoffman et al. Hoffman, R. V.; Salvador, J. M. *J. Org. Chem.* 1992, 57, 4487.

Example 14

Preparation of N-(2-methoxyphenyl)benzamide at 40° C.

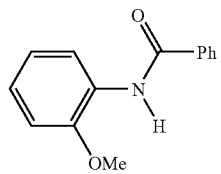 [SMILES: COc1ccccc1NC(=O)c1ccccc1]

Using general procedure A, benzamide (150 mg, 1.24 mmol) was coupled with 2-iodoanisole (135 μL, 1.04 mmol) at 40° C. for 18 h. The crude product was purified by flash chromatography on silica gel (2×15 cm; hexane-ethyl acetate 3:1; 15 mL fractions). Fractions 8-12 provided 49 mg (21% yield) of the product as a colorless oil. The $^1$H NMR spectrum was in accord with that reported by Narasaka et al. Tsutsi, H.; Ichikawa, T.; Narasaka, K. *Bull. Chem. Soc. Jpn.* 1999, 72, 1869.

Example 15

1-Benzoyl-2-(3,5-dimethylphenyl)hydrazine

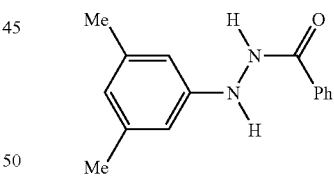

An oven-dried resealable Schlenk tube was charged with CuI (2.0 mg, 0.0105 mmol, 1.0 mol %), benzoic hydrazide (170 mg, 1.25 mmol), K$_2$CO$_3$ (290 mg, 2.10 mmol), evacuated and backfilled with argon. trans-1,2-Cyclohexanediamine (13 μL, 0.108 mmol, 11 mol %), dodecane (235 μL), 5-iodo-m-xylene (150 μL, 1.04 mmol) and dioxane (1.0 mL) were added under argon. The Schlenk tube was sealed and the reaction mixture was stirred magnetically at 110° C. for 23 h. The resulting suspension was cooled to room temperature and filtered through a 0.5×1 cm pad of silica gel eluting with 10 mL of ethyl acetate. The filtrate was concentrated and the residue was purified by flash chromatography on silica gel (2×15 cm; hexane-ethyl acetate 2:1; 15 mL fractions). Fractions 9-13 provided 159 mg (64% yield) of the product as a pale tan solid. $^1$H NMR (300 MHz, CDCl$_3$): δ 8.06 (br s, 1H), 7.87-7.82 (m, 2H), 7.60-7.44 (m, 3H), 6.58 (s, 1H), 6.54 (s, 2H), 6.32 (br s, 1H), 2.25 (s, 6H).

Example 16

1-tert-Butoxycarbonyl-1-(4-phenylphenyl)hydrazine

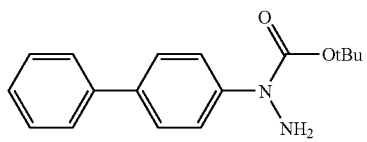

An oven-dried resealable Schlenk tube was charged with CuI (50 mg, 0.263 mmol, 5.1 mol %), 1,10-phenanthroline (100 mg, 0.555 mmol, 11 mol %), 4-iodobiphenyl (1.45 g, 5.18 mmol), Cs$_2$CO$_3$ (2.30 g, 7.06 mmol), evacuated and backfilled with argon. tert-Butyl carbazate (825 mg, 6.24 mmol) and dioxane (1.0 mL) were added under argon. The Schlenk tube was sealed and the reaction mixture was stirred magnetically at 110° C. for 23 h. The resulting suspension was cooled to room temperature and filtered through a 1×1 cm pad of silica gel eluting with 50 mL of ethyl acetate. The filtrate was concentrated and the residue was purified by flash chromatography on silica gel (2×20 cm; hexane-ethyl acetate 4:1; 20 mL fractions). Fractions 9-20 provided 1.29 g (88% yield) of the product as a light yellow solid. $^1$H NMR (400 MHz, CDCl$_3$): δ 7.64-7.59 (m, 2H), 7.57 (s, 4H), 7.48-7.43 (m, 2H), 7.38-7.33 (m, 1H), 4.50 (s, 2H), 1.56 (s, 9H).

Example 17

N-(3,5-Dimethylphenyl)benzophenone imine

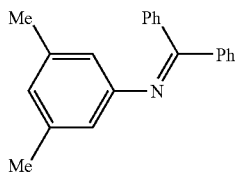 [SMILES: Cc1cc(C)cc(N=C(c2ccccc2)c2ccccc2)c1]

An oven-dried resealable Schlenk tube was charged with CuI (2.0 mg, 0.0105 mmol, 1.0 mmol %), sodium tert-butoxide (150 mg, 1.56 mmol), evacuated and backfilled with argon. trans-1,2-Cyclohexanediamine (13 µL, 0.108 mmol, 11 mol %), dodecane (235 µL), 5-iodo-m-xylene (150 µL, 1.04 mmol), benzophenone imine (210 µL, 1.25 mmol) and dioxane (1.0 mL) were added under argon. The Schlenk tube was sealed and the reaction mixture was stirred magnetically at 110° C. for 36 h. The resulting dark brown suspension was cooled to room temperature and filtered through a 0.5×1 cm pad of silica gel eluting with 10 mL of ethyl acetate. The filtrate was concentrated and the residue was purified by flash chromatography on silica gel (2×15 cm; hexane-ethyl acetate 30:1; 15 mL fractions). Fractions 6-11 provided 46 mg (15% yield) of the product as a pale tan solid. $^1$H NMR (300 MHz, CDCl$_3$): δ 7.79-7.75 (m, 2H), 7.52-7.40 (m, 3H), 7.34-7.26 (m, 3H), 7.20-7.15 (m, 2H), 6.60 (s, 1H), 6.39 (s, 2H) 2.19 (s, 6H).

Example 18

N-(3,5-Dimethylphenyl)benzophenone hydrazone

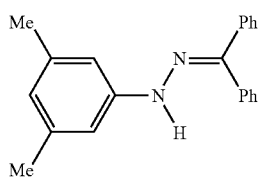 [SMILES: Cc1cc(C)cc(NN=C(c2ccccc2)c2ccccc2)c1]

An oven-dried resealable Schlenk tube was charged with CuI (2.0 mg, 0.0105 mmol, 1.0 mol %), benzophenone hydrazone (245 mg, 1.25 mmol), sodium tert-butoxide (145 mg, 1.51 mmol), evacuated and backfilled with argon. trans-1,2-Cyclohexanediamine (13 µL, 0.108 mmol, 11 mol %), dodecane (235 µL), 5-iodo-m-xylene (150 µL, 1.04 mmol) and dioxane (1.0 mL) were added under argon. The Schlenk tube was sealed and the reaction mixture was stirred magnetically at 110° C. for 23 h. The resulting dark brown suspension was cooled to room temperature and filtered through a 0.5×1 cm pad of silica gel eluting with 10 mL of hexane-ethyl acetate 5:1. The filtrate was concentrated and the residue was purified by flash chromatography on silica gel (2×20 cm; hexane-ethyl acetate 40:1; 15 mL fractions). Fractions 10-12 provided 251 mg (80% yield) of the product as a bright yellow solid. The $^1$H NMR spectrum was in accord with that reported by Buchwald et al. Wagaw, S.; Yang, B. H.; Buchwald, S. L. *J. Am. Chem. Soc.* 1999, 44, 10251.

Example 19

N-(3,5-Dimethylphenyl)-N,N-diphenylamine

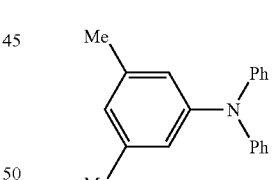

An oven-dried resealable Schlenk tube was charged with CuI (2.0 mg, 0.0105 mmol, 1.0 mol %), diphenylamine (210 mg, 1.24 mmol), sodium tert-butoxide (145 mg, 1.51 mmol), evacuated and backfilled with argon. trans-1,2-Cyclohexanediamine (13 µL, 0.108 mmol, 11 mol %), dodecane (235 µL), 5-iodo-m-xylene (150 µL, 1.04 mmol) and dioxane (1.0 mL) were added under argon. The Schlenk tube was sealed and the reaction mixture was stirred magnetically at 110° C. for 24 h. The resulting pale brown suspension was cooled to room temperature and filtered through a 0.5×1 cm pad of silica gel eluting with 10 mL of hexane-ethyl acetate 5:1. The filtrate was concentrated and the residue was purified by flash chromatography on silica gel (2×25 cm; hexane-ethyl acetate 40:1; 15 mL fractions). Fractions 9-13 provided 211 mg (74% yield) of the product as white crystals. The $^1$H NMR spectrum

Example 20

1-(3,5-Dimethylphenyl)indazole

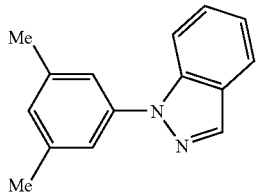 [SMILES: Cc1cc(C)cc(-n2ncc3ccccc32)c1]

Using general procedure A, indazole (148 mg, 1.25 mmol) was coupled with 5-iodo-m-xylene (150 μL, 1.04 mmol). The crude product was purified by flash chromatography on silica gel (2×15 cm; hexane-ethyl acetate 10:1; 10 mL fractions). Fractions 4-10 provided 222 mg (96% yield) of the product as a pale yellow oil. $^1$H NMR (300 MHz, CDCl$_3$): δ 8.20 (d, J=1.0 Hz, 1H), 7.83-7.74 (m, 2H), 7.46-7.40 (m, 1H), 7.36 (s, 2H), 7.25-7.19 (m, 1H), 7.01 (s, 1H), 2.43 (s, 6H).

Example 21

N-(3,5-Dimethylphenyl)-2-methylindole

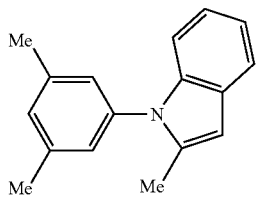 [SMILES: Cc1cc(C)cc(-n2c(C)cc3ccccc32)c1]

Using general procedure A, 2-methylindole (165 mg, 1.26 mmol)) was coupled with 5-iodo-m-xylene (150 μL, 1.04 mmol). The crude product was purified by flash chromatography on silica gel (2×15 cm; hexane-ether 40:1; 15 mL fractions). Fractions 4-9 provided 232 mg (95% yield) of the product as a colorless oil. $^1$H NMR (300 MHz, CDCl$_3$): δ 7.62-7.53 (m, 1H), 7.15-7.05 (m, 4H), 6.98 (s, 2H), 6.39 (s, 1H), 2.41 (s, 6H), 2.31 (d, J=1.0 Hz, 3H).

Example 22

N-(2-Methoxyphenyl)indole

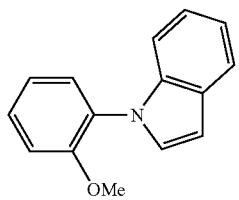 [SMILES: COc1ccccc1-n1ccc2ccccc21]

Using general procedure A, indole (146 mg, 1.25 mmol)) was coupled with 2-iodoanisole (135 μL, 1.04 mmol). The crude product was purified by flash chromatography on silica gel (2×15 cm; hexane-ether 15:1; 15 mL fractions). Fractions 6-10 provided 232 mg (100% yield) of the product as a colorless oil. The $^1$H NMR spectrum was in accord with that reported by Maiorana et al. Maiorana, S.; Baldoli, C.; Del Buttero, P.; Di Ciolo, M.; Papagni, A. *Synthesis* 1998, 735.

Example 23

1-(3,5-Dimethylphenyl)pyrrole

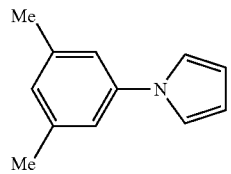 [SMILES: Cc1cc(C)cc(-n2cccc2)c1]

Using general procedure B, pyrrole (83 μL, 1.2 mmol) was coupled with 5-iodo-m-xylene to give the crude product. Column chromatography (2×15 cm, hexane:ethyl acetate 9:1) provided 0.170 g (99% yield) of the product as a colorless oil. $^1$H NMR (400 MHz, CDCl$_3$): δ 7.07 (t, J=7.0 Hz, 2H), 7.02 (s, 2H), 6.89 (s, 1H), 6.33 (t, J=7.0 Hz, 2H), 2.37 (s, 6H).

Example 24

1-(3,5-Dimethylphenyl)-1-pyrazole

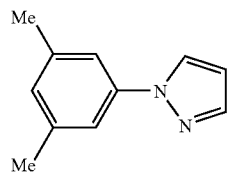 [SMILES: Cc1cc(C)cc(-n2cccn2)c1]

Using general procedure B, pyrazole (0.082 g, 1.2 mmol) was coupled with 5-iodo-m-xylene using K$_2$CO$_3$ (2.1 mmol) as the base to give the crude product. Column chromatography (2×15 cm, hexane:ethyl acetate 9:1) provided 0.153 g (89% yield) of the product as a colorless oil. $^1$H NMR (400 MHz, CDCl$_3$): δ7.90 (d, J=2.2 Hz, 1H), 7.71 (d, J=1.5 Hz, 1H), 7.32 (s, 2H), 6.93 (s, 1H), 6.44 (t, J=2.2 Hz, 1H), 2.38 (s, 6H).

Example 25

1-(3,5-Dimethylphenyl)-1-(7-azaindole)

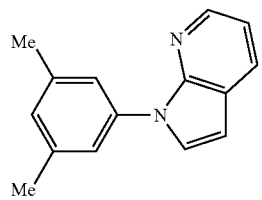 [SMILES: Cc1cc(C)cc(-n2ccc3cccnc32)c1]

Using general procedure B, 7-azaindole (0.142 g, 1.2 mmol) was coupled with 5-iodo-m-xylene to give the crude product. Column chromatography (2×15 cm, hexane:ethyl acetate 5:1) provided 0.220 g (99% yield) of the product as a white solid. $^1$H NMR (400 MHz, CDCl$_3$): δ 8.38 (dd, J=1.5 Hz and J=4.7 Hz, 1H), 7.97 (dd, J=1.5 Hz and J=7.8 Hz, 1H), 7.48 (d, J=3.6 Hz, 1H), 7.33 (s, 2H), 7.12 (dd, J=4.7 Hz and J=7.8 Hz, 1H) 6.99 (s, 1H), 6.60 (d, J=3.6 Hz, 1H), 2.41 (s, 6H).

Example 26

1-(3,5-Dimethylphenyl)carbazole

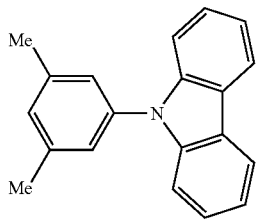

Using general procedure B, pyrrole (83 µL, 1.2 mmol) was coupled with 5-iodo-m-xylene to give the crude product. Column chromatography (2×15 cm, hexane:ethyl acetate 50:1) provided 0.268 g (99% yield) of the product as a white solid. $^1$H NMR (400 MHz, CDCl$_3$): δ 8.15 (d, J=7.8 Hz, 2H), 7.41 (m, 4H), 7.28 (m, 2H), 7.18 (s, 2H), 7.11 (s, 1H), 2.43 (s, 6H).

Example 27

1-(3,5-Dimethylphenyl)-1-purine

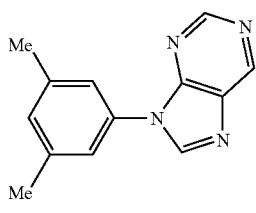 [SMILES: Cc1cc(C)cc(-n2cnc3cncnc32)c1]

Using general procedure B, purine (0.144 g, 1.2 mmol) was coupled with 5-iodo-m-xylene using CuI (9.5 mg, 0.050 mmol, 5.0 mol %), Cs$_2$CO$_3$ (2.1 mmol), trans-1,2-cyclohexanediamine (24 µL, 0.20 mmol, 20 mol %) and dimethylformamide (1.0 mL) to give the crude product. Column chromatography (2×15 cm, hexane:ethyl acetate 1:1) provided 0.073 g (33% yield) of the product as a white solid. $^1$H NMR (400 MHz, CDCl$_3$): δ 9.24 (s, 1H), 9.06 (s, 1H), 8.34 (s, 1H), 7.31 (s, 2H), 7.13 (s, 1H), 2.44 (s, 6H).

Example 28

1-(3,5-Dimethylphenyl)-1-imidazole

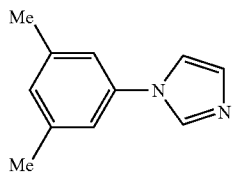 [SMILES: Cc1cc(C)cc(-n2ccnc2)c1]

Using general procedure B, imidazole (0.102 g, 1.2 mmol) was coupled with 5-iodo-m-xylene using CuI (9.5 mg, 0.050 mmol, 5.0 mol %), Cs$_2$CO$_3$ (2.1 mmol), trans-1,2-cyclohexanediamine (24 µL, 0.20 mmol, 20 mol %) and dioxane (1.0 mL) to give the crude product. Column chromatography (2×15 cm, hexane:ethyl acetate 1:4) provided 0.142 g (82% yield) of the product as a clear viscous oil. $^1$H NMR (400 MHz, CDCl$_3$): δ 7.84 (s, 1H), 7.25 (d, J=1 Hz, 1H), 7.19 (d, J=1 Hz, 1H), 7.00 (s, 3H), 2.37 (s, 6H).

Example 29

1-(3,5-Dimethylphenyl)-1-benzimidazole

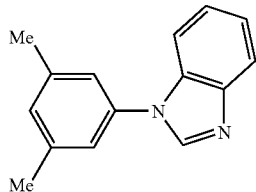 [SMILES: Cc1cc(C)cc(-n2cnc3ccccc32)c1]

Using general procedure B, benzimidazole (0.144 g, 1.2 mmol) was coupled with 5-iodo-m-xylene using CuI (0.019 g, 0.10 mmol, 10 mol %), Cs$_2$CO$_3$ (2.1 mmol), 1,10-phenanthroline (0.036 g, 0.20 mmol, 20 mol %) and dimethylformamide (0.5 mL) to give the crude product. Column chromatography (2×15 cm, hexane:ethyl acetate 1:1) provided 0.205 g (92% yield) of the product as a white solid. $^1$H NMR (400 MHz, CDCl$_3$): δ 8.10 (s, 1H), 7.87 (m, 1H), 7.55 (m, 1H), 7.33 (m, 2H), 7.13 (s, 2H), 7.10 (s, 1H), 2.43 (s, 6H).

Example 30

1-(3,5-Dimethylphenyl)-1-indazole

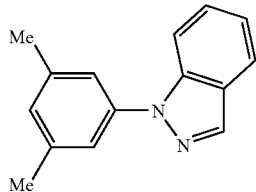 [SMILES: Cc1cc(C)cc(-n2ncc3ccccc32)c1]

Using general procedure B, indazole (0.142 g, 1.2 mmol) was coupled with 5-iodo-m-xylene however the reaction was run at room temperature. Gas chromatographic analysis of the crude reaction mixture after filtration as per the general procedure it was determined that 52% of the 5-iodo-m-xylene was consumed. The ratio of the title compound to 1-(3,5-dimethylphenyl)-2-indazole was determined to be greater than 25 to 1 by GC analysis.

Example 31

N-(3,5-Dimethylphenyl)benzamide

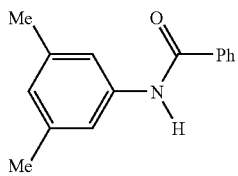 [SMILES: Cc1cc(C)cc(NC(=O)c2ccccc2)c1]

An oven-dried resealable Schlenk tube was charged with CuI (4.0 mg, 0.0210 mmol, 1.0 mol %), benzamide (300 mg, 2.48 mmol), $K_2CO_3$ (600 mg, 4.38 mmol), evacuated and backfilled with argon. trans-1,2-Cyclohexanediamine (26 µL, 0.216 mmol, 11 mol %), 5-bromo-m-xylene (280 µL, 2.06 mmol) and dioxane (1.0 mL) were added under argon. The Schlenk tube was sealed and the reaction mixture was stirred magnetically at 110° C. for 23 h. The resulting suspension was cooled to room temperature and filtered through a 0.5×1 cm pad of silica gel eluting with 10 mL of ethyl acetate. The filtrate was concentrated and the residue was purified by flash chromatography on silica gel (2×20 cm; hexane-ethyl acetate 3:1; 15 mL fractions). Fractions 10-15 provided 419 mg (90% yield) of the product as white crystals. $^1$H NMR (400 MHz, $CDCl_3$): δ 7.92-7.85 (m, 3H), 7.59-7.75 (m, 3H), 7.31 (s, 2H), 6.82 (s, 1H), 2.34 (s, 6H). $^{13}$C NMR (100 MHz, $CDCl_3$): δ 165.6, 138.7, 137.7, 135.1, 131.7, 128.7, 126.9, 126.3, 117.9, 21.3. IR (neat, cm$^{-1}$): 3300, 1649, 1614, 1547.

Example 32

N-(2-Methoxyphenyl)benzamide

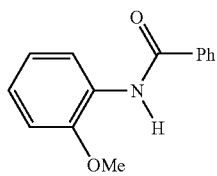

An oven-dried resealable Schlenk tube was charged with CuI (6.0 mg, 0.0315 mmol, 1.0 mol %), benzamide (460 mg, 3.80 mmol), $K_2CO_3$ (850 mg, 6.15 mmol), evacuated and backfilled with argon. trans-1,2-Cyclohexanediamine (40 µL, 0.333 mmol, 11 mol %), 2-bromoanisole (0.38 mL, 3.05 mmol) and dioxane (0.50 mL) were added under argon. The Schlenk tube was sealed and the reaction mixture was stirred magnetically at 110° C. for 23 h. The resulting suspension was cooled to room temperature and filtered through a 0.5×1 cm pad of silica gel eluting with 10 mL of ethyl acetate. The filtrate was concentrated and the residue was purified by flash chromatography on silica gel (2×20 cm; hexane-ethyl acetate 5:1; 20 mL fractions). Fractions 10-15 provided 573 mg (83% yield) of the product as a colorless oil. The $^1$H NMR spectrum was in accord with that reported by Narasaka et al. Tsutsi, H.; Ichikawa, T.; Narasaka, K. *Bull. Chem. Soc. Jpn.* 1999, 72, 1869.

Example 33

N-(4-Methoxyphenyl)-2-azetidinone

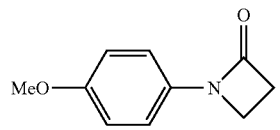

An oven-dried resealable Schlenk tube was charged with CuI (6.0 mg, 0.0315 mmol, 1.0 mol %), 2-azetidinone (300 mg, 4.22 mmol), $K_2CO_3$ (850 mg, 6.15 mmol), evacuated and backfilled with argon. trans-1,2-Cyclohexanediamine (40 µL, 0.333 mmol, 11 mol %), 4-bromoanisole (0.38 mL, 3.04 mmol) and dioxane (0.50 mL) were added under argon. The Schlenk tube was sealed and the reaction mixture was stirred magnetically at 110° C. for 23 h. The resulting suspension was cooled to room temperature and filtered through a 0.5×1 cm pad of silica gel eluting with 10 mL of ethyl acetate. The filtrate was concentrated and the residue was purified by flash chromatography on silica gel (2×20 cm; hexane-ethyl acetate 1:1; 20 mL fractions). Fractions 10-22 provided 320 mg (59% yield) of the product as white crystals. $^1$H NMR (400 MHz, $CDCl_3$): δ 7.35-7.29 (m, 2H), 6.91-6.86 (m, 2H), 3.81 (s, 3H), 3.60 (t, J=4.4 Hz, 2H), 3.11 (t, J=4.4 Hz, 2H).

Example 34

N-Thiophen-3-yl-benzamide

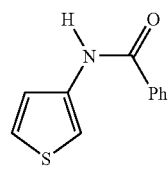 [SMILES: O=C(Nc1ccsc1)c1ccccc1]

Using general procedure C, 3-bromothiophene was coupled with benzamide with the reaction time of 21 h. Chromatography gave 198.9 mg (98%) of the title compound as a solid. $^1$H NMR ($CDCl_3$, 300 MHz): δ 8.34 (br s, 1H), 7.85 (dd, 2H, J=1.2, 8.1 Hz), 7.72 (dd, 1H, J=1.2, 3.0 Hz), 7.55-7.41 (m, 3H), 7.26 (dd, 1H, J=3.3, 4.8 Hz), 7.14 (dd, 1H, J=1.5, 5.4 Hz).

Example 35

N-Methyl-N-thiophen-3-yl-formamide

Using general procedure C with the exception that CuI (10 mg, 0.05 mmol, 5 mol %) was used, 3-bromothiophene was coupled with N-methylformamide with the reaction time of 24 h. Chromatography gave 114 mg (81%) of the title compound as an oil. $^1$H NMR (CDCl$_3$, 300 MHz): δ 8.36 (s, 0.8H), 7.71 (s, 0.2H), 7.49 (dd, 0.2H, J=1.5, 5.4 Hz), 7.08 (dd, 0.2H, J=1.2, 3.0 Hz), 6.80 (dd, 0.2H, J=3.3, 5.4 Hz), 6.64 (dd, 0.8H, J=3.3, 5.1 Hz), 6.30 (dd, 0.8H, J=1.8, 5.4 Hz), 5.98 (dd, 0.8H, J=1.2, 3.0 Hz), 2.79 (s, 2.4H), 2.21 (s, 0.6H).

Example 36

1-Thiophen-2-yl-pyrrolidin-2-one

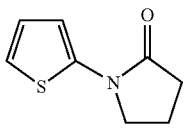

Using general procedure C, 2-bromothiophene was coupled with 2-pyrrolidinone with the reaction time of 16 h. Chromatography gave 158 mg (95%) of the title compound as a solid. $^1$H NMR (CDCl$_3$, 300 MHz): δ 6.94-6.86 (m, 2H), 6.53 (br s, 1H), 3.89 (t, 2H, J=7.2 Hz), 2.63 (t, 2H, J=8.1 Hz), 2.24 (p, 2H, J=7.5 Hz).

Example 37

N-Phenyl-N-thiophen-3-yl-acetamide

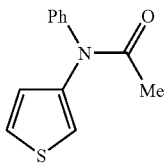 [SMILES: CC(=O)N(c1ccccc1)c1ccsc1]

Using general procedure C, 3-bromothiophene was coupled with acetanilide with the reaction time of 15 h. Chromatography gave 178 mg (82%) of the title compound as an oil. $^1$H NMR (CDCl$_3$, 300 MHz): δ 7.44 (br s, 3H), 7.28 (s, 2H), 7.18 (s, 2H), 6.94 (d, 1H, J=4.8 Hz), 1.99 (br s, 3H).

Example 38

1-Quinolin-3-yl-pyrrolidin-2-one

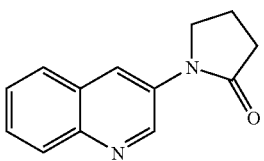 [SMILES: O=C1CCCN1c1cnc2ccccc2c1]

Using general procedure C, 3-bromoquinoline was coupled with 2-pyrrolidinone with the reaction time of 15 h. Chromatography gave 210 mg (99%) of the title compound as a solid. $^1$H NMR (CDCl$_3$, 300 MHz): δ 9.24 (d, 1H, J=2.7 Hz), 8.45 (d, 1H, J=2.4 Hz), 8.08 (d, 1H, J=8.4 Hz), 7.82 (d, 1H, J=8.1 Hz), 7.66 (t, 1H, J=7.7 Hz), 7.55 (t, 1H, J=7.5 Hz), 4.04 (t, 2H, J=7.2 Hz), 2.69 (t, 2H, J=8.1 Hz), 2.28 (p, 2H, J=7.8 Hz).

Example 39

Cyclohexanecarboxylic acid pyrimidin-5-yl-amide

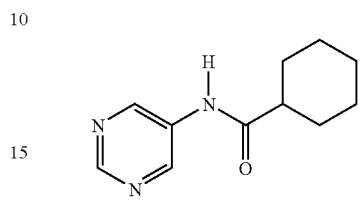

An oven-dried resealable Schlenk tube containing a stirbar was charged with CuI (20 mg, 0.1 mmol, 10 mol %), cyclohexanecarboxamide (153 mg, 1.2 mmol), 5-bromopyrimidine (160 mg, 1 mmol), and K$_3$PO$_4$ (425 mg, 2 mmol), evacuated and backfilled with argon. N,N'-Dimethylethylenediamine (8.9 mg, 0.1 mmol) and dioxane (1 ml) were injected, and under a flow of argon, the septum was replaced by a Teflon screw cap. The tube was sealed, and the mixture was stirred and heated in an oil bath at 110° C. for 16 h. The contents of the tube were then partitioned between water and dichloromethane. The aqueous layer was separated, and extracted two times with additional dichloromethane. The organics were then combined, dried over Na$_2$SO$_4$, filtered, concentrated under reduced pressure. The residue was chromatographed on silica gel followed by recrystallization from dichloromethane/hexane to give 154 mg (75%) of the title compound as a solid. $^1$H NMR (CDCl$_3$, 300 MHz): δ 9.02 (s, 2H), 8.97 (s, 1H), 7.40 (br s, 1H), 2.32 (tt, 1H, J=3.6, 11.4 Hz), 2.10-1.20 (m, 10H).

Example 40

N-(4-Methylphenyl)benzamide

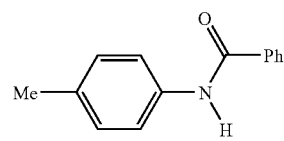 [SMILES: Cc1ccc(NC(=O)c2ccccc2)cc1]

An oven-dried resealable Schlenk tube was charged with CuI (20 mg, 0.105 mmol, 5.1 mol %), benzamide (250 mg, 2.06 mmol), K$_2$CO$_3$ (600 mg, 4.34 mmol), evacuated and backfilled with argon. trans-1,2-Cyclohexanediamine (26 μL, 0.217 mmol, 10.5 mol %) and 4-chlorotoluene (1.0 mL, 8.44 mmol) were added under argon. The Schlenk tube was sealed and the reaction mixture was stirred magnetically at 140° C. for 46 h. The resulting black suspension was cooled to room temperature and filtered through a 0.5×1 cm pad of silica gel eluting with 10 mL of ethyl acetate. The filtrate was concentrated and the residue was purified by flash chromatography on silica gel (2×20 cm; hexane-ethyl acetate 2:1; 15 mL fractions). Fractions 5-15 were concentrated, the solid residue was suspended in 10 mL of hexane and filtered to provide 413 mg (95% yield) of the product as white crystals. The $^1$H NMR spectrum was in accord with that reported by Erdik et al. Erdik, E.; Daskapan, T. *J. Chem. Soc., Perkin Trans. 1* 1999, 3139.

Example 41

N-(4-Methylphenyl)-2-pyrrolidinone

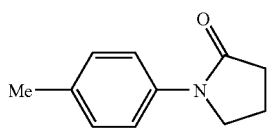 [SMILES: Cc1ccc(N2CCCC2=O)cc1]

An oven-dried resealable Schlenk tube was charged with CuI (20 mg, 0.105 mmol, 5.1 mol %), K$_2$CO$_3$ (600 mg, 4.34 mmol), evacuated and backfilled with argon. trans-1,2-Cyclohexanediamine (26 µL, 0.217 mmol, 11 mol %), 2-pyrrolidinone (155 µL, 2.04 mmol) and 4-chlorotoluene (1.0 mL, 8.44 mmol) were added under argon. The Schlenk tube was sealed and the reaction mixture was stirred magnetically at 140° C. for 42 h. The resulting suspension was cooled to room temperature and filtered through a 0.5×1 cm pad of silica gel eluting with 10 mL of ethyl acetate. The filtrate was concentrated and the residue was purified by flash chromatography on silica gel (2×20 cm; hexane-ethyl acetate 3:7; 20 mL fractions). Fractions 10-20 provided 223 mg (62% yield) of the product as white crystals. The $^1$H NMR spectrum was in accord with that reported by Boeyens et al. Billing, D. G.; Boeyens, J. C. A.; Denner, L.; Du Plooy, K. E.; Long, G. C.; Michael, J. P. *Acta Cryst. (B)* 1991, B47, 284.

Example 42

N-(3,5-Dimethylphenyl)phthalimide

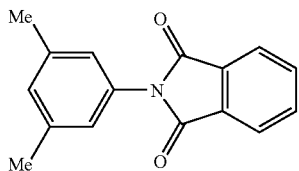 [SMILES: Cc1cc(C)cc(N2C(=O)c3ccccc3C2=O)c1]

An oven-dried resealable Schlenk tube was charged with CuI (200 mg, 1.05 mmol), phthalimide (185 mg, 1.26 mmol), K$_2$CO$_3$ (290 mg, 2.10 mmol), evacuated and backfilled with argon. trans-1,2-Cyclohexanediamine (130 µL, 1.06 mmol), dodecane (235 µL), 5-iodo-m-xylene (150 µL, 1.04 mmol) and dioxane (1.0 mL) were added under argon. The Schlenk tube was sealed and the reaction mixture was stirred magnetically at 110° C. for 23 h. The resulting brown suspension was cooled to room temperature and filtered through a 0.5×1 cm pad of silica gel eluting with 10 mL of ethyl acetate. The filtrate was concentrated and the residue was purified by flash chromatography on silica gel (2×15 cm; hexane-ethyl acetate 3:1; 15 mL fractions). Fractions 8-11 provided 34 mg (13% yield) of the product as a tan solid. The $^1$H NMR spectrum was in accord with that reported by Hashimoto et al. Shibata, Y.; Sasaki, K.; Hashimoto, Y.; Iwasaki, S. *Chem. Pharm. Bull.* 1996, 44, 156.

Example 43

N-(3,5-Dimethylphenyl)-4-cyanoaniline

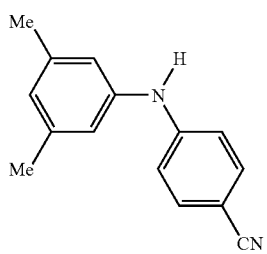 [SMILES: Cc1cc(C)cc(Nc2ccc(C#N)cc2)c1]

An oven-dried resealable Schlenk tube was charged with CuI (10 mg, 0.0525 mmol, 5.0 mol %), 1,10-phenanthroline (20 mg, 0.111 mmol), 4-cyanoaniline (146 mg, 1.24 mg), sodium tert-butoxide (145 mg, 1.51 mmol), evacuated and backfilled with argon. Dodecane (235 µL), 5-iodo-m-xylene (150 µL, 1.04 mmol) and dioxane (1.0 mL) were added under argon. The Schlenk tube was sealed and the reaction mixture was stirred magnetically at 110° C. for 23 h. The resulting brown suspension was cooled to room temperature and filtered through a 0.5×1 cm pad of silica gel eluting with 10 mL of ethyl acetate. The filtrate was concentrated and the residue was purified by flash chromatography on silica gel (2×15 cm; hexane-ethyl acetate 5:1; 10 mL fractions). Fractions 7-16 provided 159 mg (69% yield) of the product as white crystals. $^1$H NMR (400 MHz, CDCl$_3$): δ 7.51-7.47 (m, 2H), 6.91-6.95 (m, 2H), 6.83-6.80 (m, 2H), 6.80-6.78 (m, 1H), 6.02 (br s, 1H), 2.33 (q, J=0.5 Hz, 6H).

Example 44

N-(3,5-Dimethylphenyl)-N-methylaniline

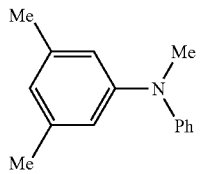

An oven-dried resealable Schlenk tube was charged with CuI (10 mg, 0.0525 mmol, 5.0 mol %), 1,10-phenanthroline (20 mg, 0.111 mmol), sodium tert-butoxide (145 mg, 1.51 mmol), evacuated and backfilled with argon. Dodecane (235 µL), 5-iodo-m-xylene (150 µL, 1.04 mmol), N-methylaniline (135 µL, 1.25 mmol) and dioxane (1.0 mL) were added under argon. The Schlenk tube was sealed and the reaction mixture was stirred magnetically at 110° C. for 24 h. The resulting brown suspension was cooled to room temperature and filtered through a 0.5×1 cm pad of silica gel eluting with 10 mL of ethyl acetate. The filtrate was concentrated and the residue was purified by flash chromatography on silica gel (2×15 cm; hexane-ether 50:1; 10 mL fractions). Fractions 7-11 provided 110 mg (50% yield) of the product as a colorless oil. $^1$H NMR (400 MHz, CDCl₃): δ 7.33-7.27 (m, 2H), 7.05-6.94 (m, 3H), 6.72 (s, 2H), 6.68 (s, 1H), 3.33 (s, 3H), 2.31 (s, 6H).

Example 45

N-(3,5-Dimethylphenyl)-1,2-trans-cyclohexanediamine

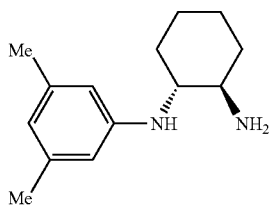 [SMILES: Cc1cc(C)cc(N[C@@H]2CCCC[C@H]2N)c1]

An oven-dried resealable Schlenk tube was charged with CuI (40 mg, 0.210 mmol), K₂CO₃ (850 mg, 6.15 mmol), evacuated and backfilled with argon. trans-1,2-Cyclohexanediamine (240 μL, 2.00 mmol) and 5-iodo-m-xylene (900 μL, 6.24 mmol) were added under argon. The Schlenk tube was sealed and the reaction mixture was stirred magnetically at 100° C. for 23 h. The resulting purple-blue suspension was cooled to room temperature and filtered through a 2×1 cm pad of Celite eluting with 50 mL of dichloromethane. The filtrate was concentrated and the residue was purified by flash chromatography on silica gel (2×20 cm; dichloromethane saturated with aq NH₃-methanol 40:1; 15 mL fractions). Fractions 9-13 provided 178 mg (41% yield) of the product as a tan solid. ¹H NMR (400 MHz, CDCl₃): δ 6.39 (s, 1H), 6.34 (s, 2H), 3.36 (br s, 1H), 3.03-2.92 (m, 1H), 2.56-2.46 (m, 1H), 2.25 (s, 6H), 2.20-2.10 (m, 1H), 2.08-1.95 (m, 1H), 1.83-1.70 (n, 2H), 1.55-1.20 (m, 5H), 1.10-1.00 (m, 1H).

Example 46

N,N-bis-(3,5-Dimethylphenyl)-1,2-trans-cyclohexanediamine

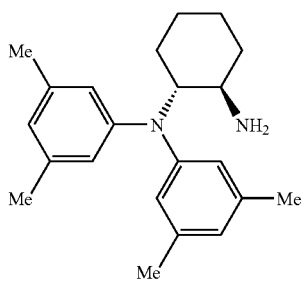 [SMILES: Cc1cc(C)cc(N(c2cc(C)cc(C)c2)[C@@H]2CCCC[C@H]2N)c1]

An oven-dried resealable Schlenk tube was charged with CuI (40 mg, 0.210 mmol), K₃PO₄ (1.30 g, 6.12 mmol), evacuated and backfilled with argon. trans-1,2-Cyclohexanediamine (240 μL, 2.00 mmol), 5-iodo-m-xylene (900 μL, 6.24 mmol) and 2-methoxyethyl ether (1.0 mL) were added under argon. The Schlenk tube was sealed and the reaction mixture was stirred magnetically at 140° C. for 24 h. The resulting dark brown suspension was cooled to room temperature and filtered through a 2×1 cm pad of Celite eluting with 50 mL of dichloromethane. The filtrate was concentrated and the residue was purified by flash chromatography on silica gel (2×20 cm; chloroform-chloroform saturated with aq NH₃-methanol 40:40:1; 15 mL fractions). Fractions 7-14 provided 465 mg (72% yield) of the product as a tan solid. ¹H NMR (400 MHz, CDCl₃): δ 6.67 (s, 1H), 6.57 (s, 2H), 3.65-3.55 (m, 1H), 2.68-2.58 (m, 1H), 2.28 (s, 12H), 2.08-1.92 (m, 2H), 1.83-1.64 (m, 2H), 1.58-1.10 (m, 6H).

Example 47

N-(4-Dimethylaminophenyl)-1,2-trans-cyclohexanediamine

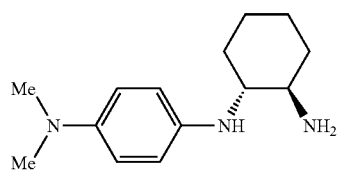 [SMILES: CN(C)c1ccc(N[C@@H]2CCCC[C@H]2N)cc1]

An oven-dried resealable Schlenk tube was charged with CuI (190 mg, 0.998 mmol), K₃PO₄ (2.10 g, 9.89 mmol), 4-bromo-N,N-dimethylaniline (1.00 g, 5.00 mmol), evacuated and backfilled with argon. trans-1,2-Cyclohexanediamine (0.60 L, 5.00 mmol) and dioxane (3.0 mL) were added under argon. The Schlenk tube was sealed and the reaction mixture was stirred magnetically at 110° C. for 70 h. The resulting dark brown suspension was cooled to room temperature and filtered through a 2×1 cm pad of Celite eluting with 50 mL of dichloromethane. The filtrate was concentrated and the residue was purified by flash chromatography on silica gel (2×20 cm; dichloromethane saturated with aq NH₃-methanol 40:1; 20 mL fractions). Fractions 12-16 provided 692 mg (59% yield) of the product as a brown solid. ¹H NMR (400 MHz, CDCl₃): δ 6.75-6.63 (m, 4H), 3.00 (br s, 1H), 2.87-2.77 (m, 7H), 2.53-2.45 (m, 1H), 2.17-2.04 (m, 1H), 2.02-1.94 (m, 1H), 1.78-1.16 (m, 7H), 1.04-0.92 (m, 1H). ¹³C NMR (100 MHz, CDCl₃) δ 144.7, 140.9, 116.2, 116.1, 62.0, 56.5, 42.6, 35.7, 33.0, 25.8, 25.5.

Example 48

Preparation of dimethyl 3,5-dimethylphenylmalonate using 1,10-phenanthroline as ligand for Cu

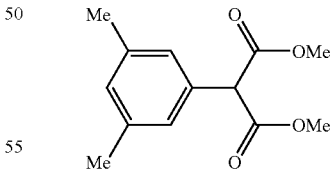

An oven-dried resealable Schlenk tube was charged with CuI (10 mg, 0.0525 mmol, 5.0 mol %), 1,10-phenanthroline (20 mg, 0.111 mmol), Cs₂CO₃ (460 mg, 1.41 mmol), evacuated and backfilled with argon. Dodecane (235 μL), 5-iodo-m-xylene (150 μL, 1:04 mmol), dimethyl malonate (145 μL, 1.27 mmol) and dioxane (1.0 mL) were added under argon. The Schlenk tube was sealed and the reaction mixture was stirred magnetically at 110° C. for 23 h. The resulting gray suspension was cooled to room temperature and filtered through a 0.5×1 cm pad of silica gel eluting with 10 mL of ethyl acetate. The filtrate was concentrated and the residue was purified by flash chromatography on silica gel (2×15 cm; hexane-ethyl acetate 6:1; 10 mL fractions). Fractions 9-15 provided 216 mg (88% yield) of the product as a colorless oil. ¹H NMR (400 MHz, CDCl₃): δ 7.03 (s, 2H), 7.00 (s, 1H), 4.61 (s, 1H), 3.77 (s, 6H), 2.35 (s, 6H). ¹³C NMR (100 MHz, CDCl₃) δ 169.2, 138.7, 132.7, 130.5, 127.3, 57.8, 53.2, 21.7.

Example 49

Preparation of dimethyl 3,5-dimethylphenylmalonate using trans-1,2-cyclohexanediamine as ligand for Cu

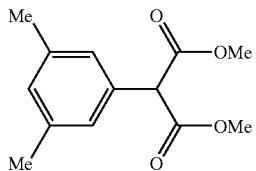 [SMILES: COC(=O)C(C(=O)OC)c1cc(C)cc(C)c1]

An oven-dried resealable Schlenk tube was charged with CuI (2.0 mg, 0.0105 mmol, 1.0 mol %), K₃PO₄ (450 mg, 2.12 mmol), evacuated and backfilled with argon. Dodecane (235 µL), trans-1,2-cyclohexanediamine (13 µL, 0.108 mmol, 10 mol %), 5-iodo-m-xylene (150 µL, 1.04 mmol), dimethyl malonate (145 µL, 1.27 mmol) and dioxane (1.0 mL) were added under argon. The Schlenk tube was sealed and the reaction mixture was stirred magnetically at 110° C. for 23 h. The resulting pale yellow suspension was cooled to room temperature and filtered through a 0.5×1 cm pad of silica gel eluting with 10 mL of ethyl acetate. The filtrate was concentrated and the residue was purified by flash chromatography on silica gel (2×20 cm; hexane-ethyl acetate 5:1; 20 mL fractions). Fractions 10-16 provided 135 mg (55% yield) of the product as a colorless oil.

Example 50

(S)—O-(3,5-Dimethylphenyl)mandelic acid

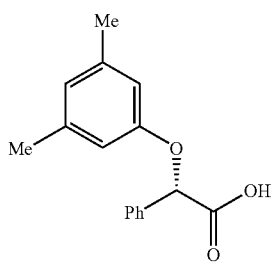 [SMILES: Cc1cc(C)cc(O[C@H](C(=O)O)c2ccccc2)c1]

An oven-dried resealable Schlenk tube was charged with CuI (20 mg, 0.105 mmol, 10 mol %), (S)-mandelic acid (190 mg, 1.25 mmol), K₂CO₃ (430 mg, 3.11 mmol), evacuated and backfilled with argon. Dodecane (235 µL), 5-iodo-m-xylene (150 µL, 1.04 mmol), and N,N-dimethylacetamide (1.0 mL) were added under argon. The Schlenk tube was sealed and the reaction mixture was stirred magnetically at 110° C. for 23 h. The resulting pale yellow suspension was poured into 20 mL of 10% aq HCl and extracted with 3×20 mL of dichloromethane. The combined organic phase was dried (Na₂SO₄), concentrated, and the residue was purified by flash chromatography on silica gel (2×15 cm; hexane-ethyl acetate-acetic acid 40:20:1; 15 mL fractions). Fractions 7-13 provided 91 mg (34% yield) of the product as a white solid. ¹H NMR (400 MHz, CDCl₃): δ 10.65 (br s, 1H), 7.64-7.57 (m, 2H), 7.47-7.36 (m, 3H), 6.67 (s, 1H), 6.61 (s, 2H), 5.65 (s, 1H), 2.28 (s, 6H).

Example 51

N-(4-Methylphenyl)-trans-1,2-cyclohexanediamine

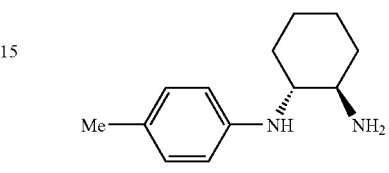

An oven-dried resealable Schlenk tube was charged with CuI (190 mg, 0.998 mmol), K₃PO₄ (2.10 g, 9.89 mmol), evacuated and backfilled with argon. trans-1,2-Cyclohexanediamine (0.60 mL, 5.00 mmol), 4-bromotoluene (0.70 mL, 5.69 mmol) and dioxane (3.0 mL) were added under argon. The Schlenk tube was sealed and the reaction mixture was stirred magnetically at 110° C. for 70 h. The resulting dark brown suspension was cooled to room temperature and filtered through a 2×1 cm pad of Celite eluting with 50 mL of dichloromethane. The black filtrate was concentrated and the residue was purified by flash chromatography on silica gel (2×20 cm; dichloromethane saturated with aq NH₃-methanol 50:1; 15 mL fractions). Fractions 9-11 provided 650 mg (64% yield) of the product as a brown solid. ¹H NMR (400 MHz, CDCl₃): δ 7.00-6.95 (m, 2H), 6.62-6.57 (m, 2H), 3.30 (br s, 1H), 2.96-2.86 (br m, 1H), 2.49 (td, J=10.4, 3.6, 1H), 2.23 (s, 3H), 2.17-2.08 (m, 1H), 2.02-1.94 (m, 1H), 1.79-1.66 (m, 2H), 1.44 (br s, 2H), 1.38-1.17 (m, 314), 1.07-0.95 (m, 1H). ¹³C NMR (100 MHz, CDCl₃) δ 145.9, 129.7, 126.6, 113.9, 60.5, 56.1, 35.2, 32.4, 25.3, 25.0, 20.3.

Example 52

Preparation of N-(3,5-dimethylphenyl)benzamide at room temperature using N-(4-methylphenyl)-trans-1,2-cyclohexanediamine

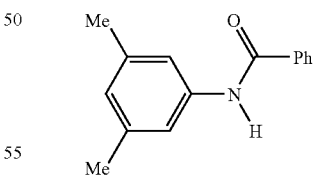

An oven-dried resealable Schlenk tube was charged with CuI (10 mg, 0.0525 mmol, 5.0 mol %), trans-N-(4-methylphenyl)-1,2-cyclohexanediamine (22 mg, 0.108 mmol, 10 mol %), benzamide (150 mg, 1.24 mmol), Cs₂CO₃ (650 mg, 1.99 mmol), evacuated and backfilled with argon. Dioxane (1.0 mL) and 5-iodo-m-xylene (150 µL, 1.04 mmol) were added under argon. The Schlenk tube was sealed and the reaction mixture was stirred magnetically at room temperature for 46 h. The resulting suspension was filtered through a 0.5×1 cm pad of silica gel eluting with 10 mL of ethyl acetate.

The filtrate was concentrated and the residue was purified by flash chromatography on silica gel (2×20 cm; hexane-ethyl acetate 3:1; 15 mL fractions). Fractions 8-15 provided 214 mg (91% yield) of the product as white crystals.

Example 53

Preparation of N-(3,5-dimethylphenyl)benzamide at 50° C. using N-(4-methylphenyl)-trans-1,2-cyclohexanediamine An oven-dried resealable Schlenk tube was charged with CuI (2.0 mg, 0.0105 mmol, 1.0 mol %), N-(4-methyl-phenyl)-trans-1,2-cyclohexanediamine (22 mg, 0.108 mmol, 10 mol %), benzamide (150 mg, 1.24 mmol), $Cs_2CO_3$ (650 mg, 1.99 mmol), evacuated and backfilled with argon. Dioxane (1.0 mL) and 5-iodo-m-xylene (150 μL, 1.04 mmol) were added under argon. The Schlenk tube was sealed and the reaction mixture was stirred magnetically at 50° C. for 23 h. The resulting light brown suspension was filtered through a 0.5×1 cm pad of silica gel eluting with 10 mL of ethyl acetate. The filtrate was concentrated and the residue was purified by flash chromatography on silica gel (2×20 cm; hexane-ethyl acetate 3:1; 15 mL fractions). Fractions 9-14 provided 228 mg (97% yield) of the product as a pale pink solid.

Example 54

Preparation of N-(3,5-dimethylphenyl)benzamide using 1,3-bis(2,4,6-trimethylphenyl)-imidazolium chloride A 10 mL pear-shape flask was charged with CuI (20 mg, 0.105 mmol, 5.0 mol %), 1,3-bis(2,4,6-trimethylphenyl)-imidazolium chloride (36 mg, 0.106 mmol, 5.1 mol %), evacuated and backfilled with argon. The flask was transferred into a glovebox, and NaOtBu (11 mg, 0.114 mmol, 5.5 mol %) was added under nitrogen. The flask was capped with a septum and removed from the glovebox. Dioxane (2.0 mL) was added and the resulting light brown suspension was stirred at room temperature for 15 min. Meanwhile, an oven-dried resealable Schlenk tube was charged with benzamide (300 mg, 2.48 mmol), $K_3PO_4$ (900 mg, 4.24 mmol), evacuated and backfilled with argon. The Schlenk tube was capped with a rubber septum, and 5-iodo-m-xylene (300 μL, 2.08 mmol) was added under argon. The catalyst suspension prepared above was transferred via a thick cannula to the reaction mixture in the Schlenk tube. The Schlenk tube was sealed with a Teflon valve and the reaction mixture was stirred magnetically at 110° C. for 23 h. The resulting brown suspension was cooled to room temperature, dodecane (470 μL, GC standard) was added, and the mixture was filtered through a Celite pad eluting with ethyl acetate. The GC analysis of the filtrate indicated a 27% yield of the product.

Example 55

Preparation of N-(3,5-dimethylphenyl)benzamide using 1,3-bis(2,6-diisopropylphenyl)-imidazolinium chloride A 10 mL pear-shape flask was charged with CuI (20 mg, 0.105 mmol, 5.0 mol %), 1,3-bis(2,6-diisopropylphenyl)imidazolinium chloride (45 mg, 0.105 mmol, 5.0 mol %), evacuated and backfilled with argon. The flask was transferred into a glovebox, and NaOtBu (11 mg, 0.114 mmol, 5.5 mol %) was added under nitrogen. The flask was capped with a septum and removed from the glovebox. Dioxane (2.0 mL) was added and the resulting light brown suspension was stirred at room temperature for 15 min. Meanwhile, an oven-dried resealable Schlenk tube was charged with benzamide (300 mg, 2.48 mmol), $K_3PO_4$ (900 mg, 4.24 mmol), evacuated and backfilled with argon. The Schlenk tube was capped with a rubber septum, and 5-iodo-m-xylene (300 μL, 2.08 mmol) was added under argon. The catalyst suspension prepared above was transferred via a thick cannula to the reaction mixture in the Schlenk tube. The Schlenk tube was sealed with a Teflon valve and the reaction mixture was stirred magnetically at 110° C. for 23 h. The resulting light brown suspension was cooled to room temperature, dodectne (470 μL, GC standard) was added, and the mixture was filtered through a Celite pad eluting with ethyl acetate. The GC analysis of the filtrate indicated a 38% yield of the product.

Example 56

Preparation of N-(4-methylphenyl)benzamide using 4-chlorotoluene and N,N'-dimethyl-trans-1,2-cyclohexanediamine at 110° C.

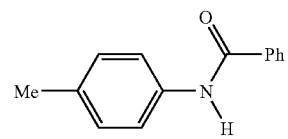 [SMILES: Cc1ccc(NC(=O)c2ccccc2)cc1]

An oven-dried resealable Schlenk tube was charged with CuI (20 mg, 0.105 mmol, 5.1 mol %), benzamide (250 mg, 2.06 mmol), $K_2CO_3$ (600 mg, 4.34 mmol), evacuated and backfilled with argon. N,N'-Dimethyl-trans-1,2-cyclohexanediamine (35 μL, 0.222 mmol, 11 mol %) and 4-chlorotoluene (1.0 mL, 8.44 mmol) were added under argon. The Schlenk tube was sealed and the reaction mixture was stirred magnetically at 110° C. for 23 h. The resulting dark blue-green suspension was cooled to room temperature and filtered through a 0.5×1 cm pad of silica gel eluting with 10 mL of ethyl acetate. The light brown filtrate was concentrated and the residue was purified by flash chromatography on silica gel (2×20 cm; hexane-ethyl acetate 2:1; 15 mL fractions). Fractions 4-10 were concentrated, the solid residue was suspended in 10 mL of hexane and filtered to provide 392 mg (90% yield) of the product as fine white needles.

Example 57

N-(2-Methoxyphenyl)acetamide

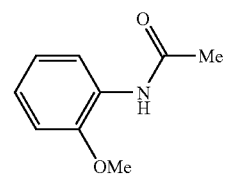 [SMILES: COc1ccccc1NC(C)=O]

An oven-dried resealable Schlenk tube was charged with CuI (2.0 mg, 0.0105 mmol, 1.0 mol %), acetamide (180 mg, 3.05 mmol), $K_3PO_4$ (450 mg, 2.12 mmol), evacuated and backfilled with argon. trans-1,2-Cyclohexanediamine (13 μL, 0.108 mmol, 10 mol %), 2-iodoanisole (135 µL, 1.04 mmol) and dioxane (1.0 mL) were added under argon. The Schlenk tube was sealed and the reaction mixture was stirred magnetically at 90° C. for 23 h. The resulting light green suspension was cooled to room temperature and filtered through a 0.5×1 cm pad of silica gel eluting with 10 mL of ethyl acetate. The filtrate was concentrated and the residue was purified by flash chromatography on silica gel (2×15 cm; hexane-ethyl acetate 2:3; 20 mL fractions). Fractions 10-16 provided 162 mg (94% yield) of the product as white crystals. The $^1$H NMR spectrum was in accord with that reported. Hibbert, F.; Mills, J. F.; Nyburg, S. C.; Parkins, A. W. *J. Chem. Soc., Perkin Trans. 1* 1998, 629.

Example 58

N-(3,5-Dimethylphenyl)-2-pyrrolidinone

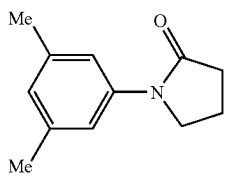

An oven-dried resealable Schlenk tube was charged with CuI (2.0 mg, 0.0105 mmol, 1.0 mol %), K$_3$PO$_4$ (450 mg, 2.12 mmol), evacuated and backfilled with argon. trans-1,2-Cyclohexanediamine (13 µL, 0.108 mmol, 10 mol %), 5-iodo-m-xylene (150 µL, 1.04 mmol), 2-pyrrolidinone (94 µL, 1.24 mmol) and dioxane (1.0 mL) were added under argon. The Schlenk tube was sealed and the reaction mixture was stirred magnetically at 110° C. for 24 h. The resulting pale yellow suspension was cooled to room temperature and filtered through a 0.5×1 cm pad of silica gel eluting with 10 mL of ethyl acetate. The filtrate was concentrated and the residue was purified by flash chromatography on silica gel (2×20 cm; hexane-ethyl acetate 3:2; 20 mL fractions). Fractions 12-23 provided 193 mg (98% yield) of the product as white crystals. $^1$H NMR (400 MHz, CDCl$_3$): δ 7.23 (s, 2H), 6.82 (s, 1H), 3.85 (t, J=7.1 Hz, 2H), 2.61 (t, J=8.1 Hz, 2H), 2.34 (s, 6H), 2.16 (tt, J=8.1, 7.1 Hz, 2H). $^{13}$C NMR (100 MHz, CDCl$_3$): δ 174.1, 139.2, 138.4, 126.3, 118.0, 49.1, 32.8, 21.5, 18.1. IR (neat, cm$^{-1}$): 1692, 1596, 1480, 1393, 1333, 1247, 852. Anal. Calcd for C$_{12}$H$_{15}$NO: C, 76.16; H, 7.99. Found: C, 76.06; 8.06.

Example 59

Preparation of
N-(3,5-dimethylphenyl)-2-pyrrolidinone using copper(II) chloride

An oven-dried resealable Schlenk tube was charged with CuCl$_2$ (1.5 mg, 0.0112 mmol, 1.1 mol %), K$_3$PO$_4$ (450 mg, 2.12 mmol), evacuated and backfilled with argon. trans-1,2-Cyclohexanediamine (13 µL, 0.108 mmol, 10 mol %), 5-iodo-m-xylene (150 µL, 1.04 mmol), 2-pyrrolidinone (94 µL, 1.24 mmol) and dioxane (1.0 mL) were added under argon. The Schlenk tube was sealed and the reaction mixture was stirred magnetically at 110° C. for 23 h. The resulting pale brown suspension was cooled to room temperature and filtered through a 0.5×1 cm pad of silica gel eluting with 10 mL of ethyl acetate. The filtrate was concentrated and the residue was purified by flash chromatography on silica gel (2×20 cm; hexane-ethyl acetate 2:3; 15 mL fractions). Fractions 9-18 provided 194 mg (99% yield) of the product as white crystals.

Example 60

Preparation of
N-(3,5-dimethylphenyl)-2-pyrrolidinone using copper powder

An oven-dried resealable Schlenk tube was charged with copper powder (1.5 mg, 0.0236 mmol, 1.1 mol %), K$_3$PO$_4$ (900 mg, 4.24 mmol), evacuated and backfilled with argon. trans-1,2-Cyclohexanediamine (26 µL, 0.217 mmol, 10 mol %), 5-iodo-m-xylene (300 µL, 2.08 mmol), 2-pyrrolidinone (190 µL, 2.50 mmol) and dioxane (2.0 mL) were added under argon. The Schlenk tube was sealed and the reaction mixture was stirred magnetically at 110° C. for 23 h. The resulting light brown suspension was cooled to room temperature, dodecane (235 µL, GC standard) was added, and the mixture was filtered through a Celite pad eluting with ethyl acetate. The GC analysis of the filtrate indicated a 99% yield of the product.

Example 61

Preparation of
N-(3,5-dimethylphenyl)-2-pyrrolidinone under nitrogen

An oven-dried resealable Schlenk tube was charged with CuI (2.0 mg, 0.0105 mmol, 1.0 mol %), K$_3$PO$_4$ (450 mg, 2.12 mmol), evacuated and backfilled with nitrogen. trans-1,2-Cyclohexanediamine (13 µL, 0.108 mmol, 10 mol %), 5-iodo-m-xylene (150 µL, 1.04 mmol), 2-pyrrolidinone (94 µL, 1.24 mmol) and dioxane (1.0 mL) were added under nitrogen. The Schlenk tube was sealed and the reaction mixture was stirred magnetically at 110° C. for 23 h. The resulting pale brown suspension was cooled to room temperature, dodecane (235 µL, GC standard) was added, and the mixture was filtered through a Celite pad eluting with ethyl acetate. The GC analysis of the filtrate indicated a 99% yield of the product.

Example 62

Preparation of
N-(3,5-dimethylphenyl)-2-pyrrolidinone under air

An oven-dried resealable Schlenk tube was charged with CuI (2.0 mg, 0.0105 mmol, 1.0 mol %) and K$_3$PO$_4$ (450 mg, 2.12 mmol) under air. trans-1,2-Cyclohexanediamine (13 µL, 0.108 mmol, 10 mol %), 5-iodo-m-xylene (150 µL, 1.04 mmol), 2-pyrrolidinone (94 µL, 1.24 mmol) and dioxane (1.0 mL) were added under air. The Schlenk tube was sealed and the reaction mixture was stirred magnetically at 110° C. for 23 h. The resulting brown suspension was cooled to room temperature, dodecane (235 µL, GC standard) was added, and the mixture was filtered through a Celite pad eluting with ethyl acetate. The GC analysis of the filtrate indicated a 95% yield of the product.

Example 63

General Procedure for the Arylation of N—H Heterocycles

To a flame-dried resealable Schlenk tube was added CuI, the heterocycle (1.2 mmol) and base (2.1 mmol), was evacuated twice and back-filled with argon. Dodecane (45 μL, 0.20 mmol), the aryl halide, trans-1,2-cyclohexanediamine and dioxane were then added successively under argon. The Schlenk tube was sealed and the reaction was stirred with heating via an oil bath at 110° C. for 20 hours. The reaction mixture was cooled to ambient temperature, diluted with 2-3 mL ethyl acetate, and filtered through a plug of silica gel eluting with 10-20 mL of ethyl acetate. The filtrate was concentrated and the resulting residue was purified by column chromatography to provide the purified product.

Example 64

2-(3,5-dimethylphenyl)]-1-phthalazinone

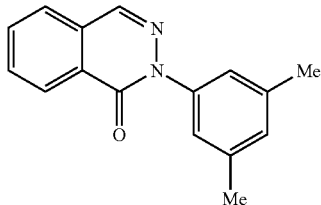 [SMILES: Cc1cc(C)cc(-n2ncc3ccccc3c2=O)c1]

Using the general procedure outlined in Example 63, phthalazinone (0.175 g, 1.2 mmol) was coupled with 5-iodo-m-xylene (144 μL, 1.00 mmol) using CuI (5.7 mg, 0.030 mmol, 3.0 mol %), $Cs_2CO_3$ (2.1 mmol), trans-1,2-cyclohexanediamine (24 μL, 0.20 mmol, 20 mol %) and dioxane (0.5 mL) to give the crude product. Column chromatography (2×15 cm, hexane:ethyl acetate 10:1) provided 0.225 g (90% yield) of the product as a white solid. $^1$H NMR (400 MHz, $CDCl_3$): δ 8.52 (d, J=7.3 Hz, 1H), 8.28 (s, 1H), 7.79-7.87 (m, 2H), 7.74-7.47 (m, 1H), 7.25 (bs, 2H), 7.04 (s, 1H), 2.40 (s, 6H).

Example 65

1-(4-methylphenyl)-indole

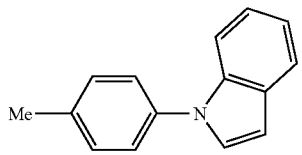 [SMILES: Cc1ccc(-n2ccc3ccccc32)cc1]

Using the general procedure outlined in Example 63, indole (0.117 g, 1.00 mmol) was coupled with 4-bromotoluene (185 μL, 1.50 mmol) using CuI (9.5 mg, 0.050 mmol, 5.0 mol %), $K_3PO_4$ (2.1 mmol), trans-1,2-cyclohexanediamine (24 μL, 0.20 mmol, 20 mol %) and dioxane (1.0 mL) to give the crude product. Column chromatography (2×15 cm, hexane:ethyl acetate 50:1) provided 0.197 g (95% yield) of the product as a white solid. This product was pure by $^1$H NMR when compared to the known spectra.

Example 66

Alternative preparation of 1-(4-methylphenyl)-indole

Using the general procedure outlined in Example 63, indole (0.117 g, 1.00 mmol) was coupled with 4-chlorotoluene (1 mL, 8.45 mmol) using CuI (9.5 mg, 0.050 mmol, 5.0 mol %), $K_3PO_4$ (2.1 mmol) and trans-1,2-cyclohexanediamine (24 μL, 0.20 mmol, 20 mol %) to give the crude product. Column chromatography (2×15 cm, hexane:ethyl acetate 50:1) provided 0.066 g (32% GC yield) of the product as a white solid. This product was pure by $^1$H NMR when compared to the known spectra.

Example 67

1-(4-methylphenyl)-2-phenylindole

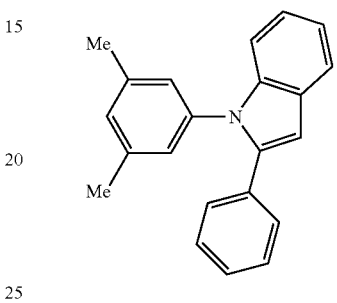

Using the general procedure outlined in Example 63, 2-phenylindole (0.232 g, 1.20 mmol) was coupled with 5-iodo-m-xylene (144 μL, 1.00 mmol) using CuI (9.5 mg, 0.050 mmol, 5.0 mol %), $K_3PO_4$ (2.1 mmol), trans-1,2-cyclohexanediamine (24 μL, 0.20 mmol, 20 mol %) and dioxane (0.5 mL) to give the crude product. Column chromatography (2×15 cm, hexane:ethyl acetate 10:1) provided 0.220 g (74% yield) of the product as a white solid. $^1$H NMR (400 MHz, $CDCl_3$): δ 7.92 (m, 1H), 7.55 (m, 3H), 7.47 (m, 3H), 7.41 (m, 2H), 7.20 (bs, 1H), 7.13 (bs, 2H), 7.05 (d, 1H, J=0.6 Hz), 2.52 (s, 6H). $^3$C NMR (100 MHz, $CDCl_3$): δ 140.63, 139.10, 138.82, 138.29, 132.60, 128.90, 128.70, 128.14, 128.03, 127.12, 125.66, 122.09, 120.48, 120.39, 21.19.

Example 68

1-(3,5-Dimethylphenyl)-5-methoxyindole

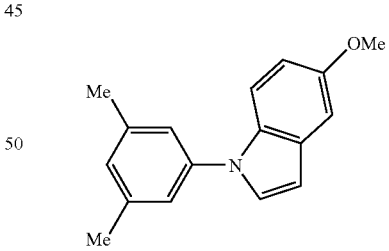

Using the general procedure outlined in Example 63, 5-methoxyindole (0.177 g, 1.20 mmol) was coupled with 5-iodo-m-xylene (144 μL, 1.00 mmol) using CuI (2.0 mg, 0.010 mmol, 1.0 mol %), $K_3PO_4$ (2.1 mmol), trans-1,2-cyclohexanediamine (12 μL, 0.10 mmol, 10 mol %) and dioxane (1.0 mL) to give the crude product. Column chromatography (2×15 cm, hexane:ethyl acetate 50:1) provided 0.250 g (100% yield) of the product as a white solid. $^1$H NMR (400 MHz, $CDCl_3$): δ 7.66 (d, 1H, J=8.9 Hz), 7.43 (d, 1H, J=3.2 Hz), 7.32 (d, 1H, J=3.3 Hz), 7.27 (bs, 2H), 7.12 (bs, 1H), 7.07 (dd, 1H, J=2.4 Hz and J=9.0 Hz), 6.75 (d, 1H, J=2.2 Hz), 4.02 (s, 3H), 2.54 (s, 6H). $^{13}$C NMR (100 MHz, $CDCl_3$): δ 154.33, 139.68, 139.20, 130.93, 129.71, 128.26, 127.78, 121.58, 112.20, 111.37, 102.80, 102.45, 55.58, 21.20.

Example 69

Preparation of N-(4-methoxyphenyl)-N-methylformamide using a mixture of cis- and trans-1,2-cyclohexanediamine

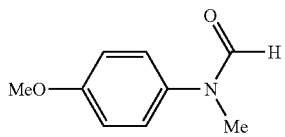 [SMILES: COc1ccc(N(C)C=O)cc1]

An oven-dried resealable Schlenk tube was charged with CuI (10 mg, 0.0525 mmol, 5.0 mol %), Cs$_2$CO$_3$ (460 mg, 1.41 mmol), evacuated and backfilled with argon. 1,2-Cyclohexanediamine (a mixture of cis and trans isomers, 13 μL, 0.106 mmol, 10 mol %), N-methylformamide (72 μL, 1.23 mmol), 4-iodoanisole (245 mg, 1.05 mmol) and dioxane (1.0 mL) were added under argon. The Schlenk tube was sealed with a Teflon valve and the reaction mixture was stirred magnetically at 110° C. for 22 h. The resulting pale brown suspension was cooled to room temperature and filtered through a 0.5×1 cm pad of silica gel eluting with 10 mL of ethyl acetate. The filtrate was concentrated and the residue was purified by flash chromatography on silica gel (2×10 cm; hexane-ethyl acetate 3:2; 15 mL fractions). Fractions 16-29 provided 158 mg (91% yield) of the product as a colorless oil. The $^1$H NMR spectrum was in accord with that reported by Hoffman. Hoffman et al. *J. Org. Chem.* 1992, 57, 4487.

Example 70

N-tert-Butoxycarbonyl-N-(3,5-dimethylphenyl) aniline

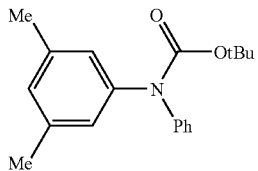 [SMILES: Cc1cc(C)cc(N(C(=O)OC(C)(C)C)c2ccccc2)c1]

An oven-dried resealable Schlenk tube was charged with CuI (2.0 mg, 0.0105 mmol, 1.0 mol %), N-tert-butoxycarbonylaniline (200 mg, 1.04 mmol), K$_3$PO$_4$ (450 mg, 2.12 mmol), evacuated and backfilled with argon. trans-1,2-Cyclohexanediamine (13 μL, 0.108 mmol, 10 mol %), 5-iodo-m-xylene (190 μL, 1.32 mmol) and dioxane (1.0 mL) were added under argon. The Schlenk tube was sealed with a Teflon valve and the reaction mixture was stirred magnetically at 110° C. for 23 h. The resulting pale yellow suspension was cooled to room temperature and filtered through a 0.5×1 cm pad of silica gel eluting with 10 mL of ethyl acetate. The filtrate was concentrated and the residue was purified by flash chromatography on silica gel (2×20 cm; hexane-ethyl acetate 20:1; 20 mL fractions). Fractions 12-20 provided 299 mg (97% yield) of the product as white crystals. $^1$H NMR (400 MHz, CDCl$_3$): δ 7.36-7.30 (m, 2H), 7.27-7.16 (m, 3H), 6.87 (s, 2H), 6.85 (s, 1H), 2.30 (s, 6H), 1.48 (s, 9H). $^{13}$C NMR (100 MHz, CDCl$_3$): δ 153.9, 143.2, 142.7, 138.3, 128.6, 127.5, 126.9, 125.4, 124.8, 80.9, 28.2, 21.2. Anal. Calcd for C$_{19}$H$_{23}$NO$_2$: C, 76.74; H, 7.79. Found: C, 76.61; 7.87.

Example 71

Preparation of N-(3,5-dimethylphenyl)benzamide at room temperature using N-(4-dimethylaminophenyl)-trans-1,2-cyclohexane-diamine

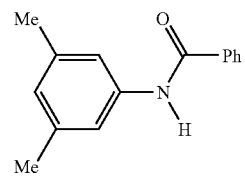 [SMILES: Cc1cc(C)cc(NC(=O)c2ccccc2)c1]

An oven-dried resealable Schlenk tube was charged with CuI (10 mg, 0.0525 mmol, 5.0 mol %), N-(4-dimethylaminophenyl)-trans-1,2-cyclohexanediamine (25 mg, 0.107 mmol, 10 mol %), benzamide (150 mg, 1.24 mmol), Cs$_2$CO$_3$ (650 mg, 1.99 mmol), evacuated and backfilled with argon. Dioxane (1.0 mL) and 5-iodo-m-xylene (150 μL, 1.04 mmol) were added under argon. The Schlenk tube was sealed with a Teflon valve and the reaction mixture was stirred magnetically at room temperature for 23 h. The resulting light brown suspension was filtered through a 0.5×1 cm pad of silica gel eluting with 10 mL of ethyl acetate. The dark purple-brown filtrate was concentrated and the residue was purified by flash chromatography on silica gel (2×15 cm; hexane-ethyl acetate 3:1; 15 mL fractions). Fractions 7-15 provided 208 mg (89% yield) of the product as a pale yellow solid.

Example 72

Preparation of N-(3,5-dimethylphenyl)-2-pyrrolidinone using ethylenediamine

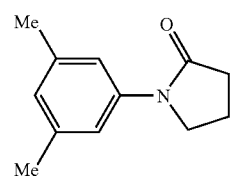

An oven-dried resealable Schlenk tube was charged with CuI (2.0 mg, 0.0105 mmol, 1.0 mol %), K$_3$PO$_4$ (450 mg, 2.12 mmol), evacuated and backfilled with argon. Ethylenediamine (15 μL, 0.224 mmol, 22 mol %), 5-iodo-m-xylene (150 μL, 1.04 mmol), 2-pyrrolidinone (94 μL, 1.24 mmol) and dioxane (1.0 mL) were added under argon. The Schlenk tube was sealed with a Teflon valve and the reaction mixture was stirred magnetically at 110° C. for 23 h. The resulting pale brown suspension was cooled to room temperature and filtered through a 0.5×1 cm pad of silica gel eluting with 10 mL of ethyl acetate. The filtrate was concentrated and the residue was purified by flash chromatography on silica gel (2×15 cm; hexane-ethyl acetate 2:3; 15 mL fractions). Fractions 9-18 provided 191 mg (97% yield) of the product as white crystals.

Example 73

Preparation of N-(3,5-dimethylphenyl)-2-pyrrolidinone using ethanolamine

An oven-dried resealable Schlenk tube was charged with CuI (2.0 mg, 0.0105 mmol, 1.0 mol %), $K_3PO_4$ (450 mg, 2.12 mmol), evacuated and backfilled with argon. Ethanolamine (12 μL, 0.199 mmol, 19 mol %), 5-iodo-m-xylene (150 μL, 1.04 mmol), 2-pyrrolidinone (94 μL, 1.24 mmol) and dioxane (1.0 mL) were added under argon. The Schlenk tube was sealed with a Teflon valve and the reaction mixture was stirred magnetically at 110° C. for 23 h. The resulting light brown suspension was cooled to room temperature and filtered through a 0.5×1-cm pad of silica gel eluting with 10 mL of ethyl acetate. The filtrate was concentrated and the residue was purified by flash chromatography on silica gel (2×20 cm; hexane-ethyl acetate 2:3; 15 mL fractions). Fractions 10-18 provided 136 mg (69% yield) of the product as white crystals. The $^1H$ NMR spectrum was in accord with that reported above.

Example 74

Preparation of N-(3,5-dimethylphenyl)-2-pyrrolidinone at 110° C. for 60 min

An oven-dried resealable Schlenk tube was charged with CuI (2.0 mg, 0.0105 mmol, 1.0 mol %), $K_3PO_4$ (450 mg, 2.12 mmol), evacuated and backfilled with argon. trans-1,2-Cyclohexanediamine (13 μL, 0.108 mmol, 10 mol %), 5-iodo-m-xylene (150 μL, 1.04 mmol), 2-pyrrolidinone (94 μL, 1.24 mmol) and dioxane (1.0 mL) were added under argon. The Schlenk tube was sealed with a Teflon valve and the reaction mixture was stirred magnetically at 110° C. for 60 min. The resulting pale blue suspension was cooled to room temperature and filtered through a 0.5×1 cm pad of silica gel eluting with 10 mL of ethyl acetate. The filtrate was concentrated and the residue was purified by flash chromatography on silica gel (2×20 cm; hexane-ethyl acetate 2:3; 15 mL fractions). Fractions 10-20 provided 176 mg (89% yield) of the product as white crystals. The $^1H$ NMR spectrum was in accord with that reported above.

Example 75

Preparation of N-(4-methylphenyl)-2-pyrrolidinone using 4-chlorotoluene and N,N'-dimethyl-trans-1,2-cyclohexanediamine at 130° C.

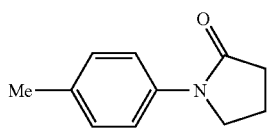

An oven-dried resealable Schlenk tube was charged with CuI (20 mg, 0.105 mmol, 5.1 mol %), $K_2CO_3$ (600 mg, 4.34 mmol), evacuated and backfilled with argon. N,N'-Dimethyl-trans-1,2-cyclohexanediamine (35 μL, 0.222 mmol, 11 mol %), 2-pyrrolidinone (155 μL, 2.04 mmol) and 4-chlorotoluene (1.0 mL, 8.44 mmol) were added under argon. The Schlenk tube was sealed with a Teflon valve and the reaction mixture was stirred magnetically at 130° C. for 23 h. The resulting dark brown suspension was cooled to room temperature and filtered through a 0.5×1 cm pad of silica gel eluting with 10 mL of ethyl acetate. The filtrate was concentrated and the residue was purified by flash chromatography on silica gel (2×20 cm; hexane-ethyl acetate 1:4; 15 mL fractions). Fractions 7-15 provided 336 mg (94% yield) of the product as white crystals.

Example 76

Preparation of N-(4-methoxyphenyl)-2-pyrrolidinone using 4-chloroanisole and N,N'-dimethyl-trans-1,2-cyclohexanediamine at 130° C.

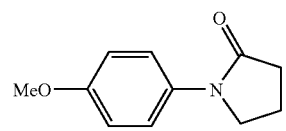 [SMILES: COc1ccc(N2CCCC2=O)cc1]

An oven-dried resealable Schlenk tube was charged with CuI (20 mg, 0.105 mmol, 5.1 mol %), $K_2CO_3$ (600 mg, 4.34 mmol), evacuated and backfilled with argon. N,N'-Dimethyl-trans-1,2-cyclohexanediamine (35 μL, 0.222 mmol, 11 mol %), 2-pyrrolidinone (155 μL, 2.04 mmol) and 4-chloroanisole (1.0 mL, 8.16 mmol) were added under argon. The Schlenk tube was sealed with a Teflon valve and the reaction mixture was stirred magnetically at 130° C. for 23 h. The resulting dark brown suspension was cooled to room temperature and filtered through a 0.5×1 cm pad of silica gel eluting with 10 mL of ethyl acetate. The filtrate was concentrated and the residue was purified by flash chromatography on silica gel (2×15 cm; ethyl acetate; 20 mL fractions). Fractions 7-15 provided 188 mg (48% yield) of the product as a white solid. The $^1H$ NMR spectrum was in accord with that reported by Easton et al. Easton, C. J.; Pitt, M. J.; Ward, C. M. Tetrahedron 1995, 51, 12781.

Example 77

Preparation of N-(4-methoxycarbonylphenyl)-2-pyrrolidinone using methyl 4-chlorobenzoate and N,N'-dimethyl-trans-1,2-cyclohexanediamine at 110° C.

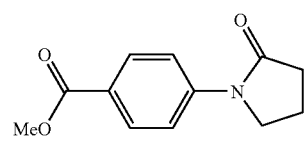 [SMILES: COC(=O)c1ccc(N2CCCC2=O)cc1]

An oven-dried resealable Schlenk tube was charged with CuI (20 mg, 0.105 mmol, 5.1 mol %), methyl 4-chlorobenzoate (1.40 g, 8.21 mmol), $K_2CO_3$ (600 mg, 4.34 mmol), briefly evacuated and backfilled with argon. N,N'-Dimethyl-trans-1,2-cyclohexanediamine (35 μL, 0.222 mmol, 11 mol %) and 2-pyrrolidinone (155 μL, 2.04 mmol) were added under argon. The Schlenk tube was sealed with a Teflon valve and the reaction mixture was stirred magnetically at 110° C. for 23 h. The resulting light green-brown suspension was cooled to room temperature and filtered through a 2×0.5 cm pad of silica gel eluting with 30 mL of ethyl acetate. The filtrate was concentrated and the residue was purified by flash chromatography on silica gel (2×20 cm; hexane-ethyl acetate 1:4; 15 mL fractions). Fractions 10-19 provided 266 mg (59% yield) of the product as white crystals. The $^1$H NMR spectrum was in accord with that reported by Atigadda et al. Atigadda, V. R.; Brouillette, W. J.; Duarte, F.; Ali, S. M.; Babu, Y. S.; Bantia, S.; Chand, P.; Chu, N.; Montgomery, J. A.; Walsh, D. A.; Sudbeck, E. A.; Finley, J.; Luo, M.; Air, G. M.; Layer, G. W. *J. Med. Chem.* 1999, 42, 2332.

Example 78

Copper Catalyzed Amination (Ethylene Glycol System)

General Procedure for Cu-Catalyzed Amination Under Argon Atmosphere (5 Mol % CuI Catalyst)

Copper(I) iodide (10 mg, 0.05 mmol) and anhydrous fine powder potassium phosphate (425 mg, 2.00 mmol) were put into a Telfon septum screw-capped test tube. The tube was evacuated and back filled with argon. 2-Propanol (1.0 mL), ethylene glycol (111 μL, 2.00 mmol), benzylamine (131 μL, 1.20 mmol) and iodobenzene (112 μL, 1.00 mmol) were added successively by micro-syringe at room temperature. The reaction was heated to 80° C. to give a pale yellow suspension. The reaction was heated to a specified time and then allowed to room temperature. Diethyl ether (2 mL) and water (2 mL) were added to the reaction mixture. The organic layer was analyzed by GC. The reaction mixture was further extracted by diethyl ether (4×10 mL). The combined organic phase was washed by water, brine and dried over sodium sulfate or magnesium sulfate. The solvent was removed by rotary evaporation to give the brown residue which was purified by column chromatography on silica gel using a solvent mixture (hexane/ethyl acetate=20/1) to afford a light yellow liquid as the product.

General Procedure for Amination Under an Argon Atmosphere (1 Mol % CuI Catalyst)

Copper(I) iodide (2.0 mg, 0.01 mmol) and anhydrous fine powder potassium phosphate (425 mg, 2.00 mmol) were put into a screw-capped test tube with a Teflon septum. The tube was evacuated and back filled with argon three times. 2-Propanol (1.0 mL), ethylene glycol (111 μL, 2.00 mmol), amine (1.20 mmol) and aryl iodide (1.00 mmol) were added successively by micro-syringe at room temperature. The reaction mixture was heated at 80° C. for the specified time and then allowed to reach room temperature. Diethyl ether (2 mL) and water (2 mL) were added to the reaction mixture. The organic layer was analyzed by GC. The reaction mixture was further extracted by diethyl ether (4×10 mL). The combined organic phases were washed by water, brine and dried over sodium sulfate. The solvent was removed by rotary evaporation to give a residue which was purified by column chromatography on silica gel using hexane/ethyl acetate as the eluent to afford the desired product.

General Procedure for Cu-Catalyzed Amination Under Air Conditions

Copper(I) iodide (10 mg, 0.05 mmol) and anhydrous fine powder potassium phosphate (425 mg, 2.00 mmol) were put into a Teflon septum screw-capped test tube followed by the addition of 2-propanol (1.0 mL), ethylene glycol (111 μL, 2.00 mmol), benzylamine (131 μL, 1.20 mmol) and iodobenzene (112 μL, 1.00 mmol) by micro-syringe at room temperature. The tube was capped and the reaction was heated to 80° C. to give a yellow suspension. The reaction was heated to a specified time and then allowed to room temperature. Diethyl ether (2 mL) and water (2 mL) were added to the reaction mixture. The organic layer was analyzed by GC. The reaction mixture was further extracted by diethyl ether (4×10 mL). The combined organic phase was washed by water, brine and dried over sodium sulfate or magnesium sulfate. The solvent was removed by rotary evaporation to give the brown residue which was purified by column chromatography on silica gel using a solvent mixture (hexane/ethyl acetate=20/1) to afford a light yellow liquid as the product.

N-(Phenyl)benzylamine (FIG. 1, Entries 1 and 2)

The general procedure under argon or air was followed using copper(I) iodide (10 mg, 0.05 mmol), $K_3PO_4$ (425 mg, 2.00 mmol), benzylamine (131 μL, 1.20 mmol), iodobenzene (112 μL, 1.00 mmol), ethylene glycol (111 μL, 2.00 mmol) and 2-propanol (1.0 mL). Column chromatography using a solvent mixture (hexane/ethyl acetate=20/1, $R_f$=0.6) afforded N-(phenyl)benzylamine (166 mg, 91% isolated yield) as colorless liquid. Spectral data ($^1$H NMR) matched with the literature references and GC analysis indicated >95% purity. See Apodaca, R.; Xiao, W. *Org. Lett.* 2001, 3, 1745-1748.

4-(N-benzyl)aminoacetophenone (FIG. 1, Entries 3 and 4)

The general procedure under argon was followed using copper(I) iodide (2.0 mg, 0.01 mmol), $K_3PO_4$ (425 mg, 2.00 mmol), benzylamine (131 μL, 1.20 mmol), 4-iodoacetophenone (246 mg, 1.00 mmol), ethylene glycol (111 μL, 2.00 mmol) and 2-propanol (1.0 mL). Column chromatography using a solvent mixture (hexane/ethyl acetate=5/1, $R_f$=0.2) afforded 4-(N-benzyl)aminoacetophenone (203 mg, 90% isolated yield) as yellow solid. Spectral data ($^1$H NMR) matched with the literature references and GC analysis indicated >95% purity. See Nose, A.; Kudo, T. *Chem. Pharm. Bull.* 1986, 34, 4817-4820.

4-(N-Benzyl)aminobenzonitrile (FIG. 1, Entry 5)

The general procedure under argon was followed using copper(I) iodide (10 mg, 0.05 mmol), $K_3PO_4$ (425 mg, 2.00 mmol), benzylamine (131 μl, 1.20 mmol), 4-iodobenzonitrile (229 mg, 1.00 mmol), ethylene glycol (111 μl, 2.00 mmol) and 2-propanol (1.0 mL). Column chromatography using a solvent mixture (hexane/ethyl acetate=5/1, $R_f$=0.4) afforded 4-(N-benzyl)aminobenzonitrile (164 mg, 79% isolated yield) as light yellow solid. Spectral data ($^1$H NMR) matched with the literature references and GC analysis indicated >95% purity. See Wolfe, J. P.; Tomori, H.; Sadighi, J. P.; Yin, J.; Buchwald, S. L. *J. Org. Chem.* 2000, 65, 1158-1174.

N-(4-Chlorophenyl)benzylamine (FIG. 1, Entry 6)

The general procedure under argon was followed using copper(I) iodide (10 mg, 0.05 mmol), $K_3PO_4$ (425 mg, 2.00 mmol), benzylamine (131 μL, 1.20 mmol), 4-chloroiodobenzene (239 mg, 1.00 mmol), ethylene glycol (111 μL, 2.00 mmol) and 2-propanol (1.0 mL). Column chromatography using a solvent mixture (hexane/ethyl acetate=10/1, $R_f$=0.4) afforded N-(4-chlorophenyl)benzylamine (182 mg, 84% isolated yield) as light yellow liquid. The spectral data ($^1$H NMR) matched with the literature references and GC analysis indicated >95% purity. See Burton, R. D.; Bartberger, M. D.; Zhang, Y.; Eyler, J. R.; Schanze, K. S. *J. Am. Chem. Soc.* 1996, 118, 5655-5664.

N-Benzyl-4-methoxyaniline (FIG. 1, Entry 7)

The general procedure under argon was followed using copper(I) iodide (10 mg, 0.05 mmol), $K_3PO_4$ (425 mg, 2.00 mmol), benzylamine (131 µL, 1.20 mmol), 4-iodoanisole (234 mg, 1.00 mmol), ethylene glycol (111 µL, 2.00 mmol) and 2-propanol (1.0 mL). Column chromatography using a solvent mixture (hexane/ethyl acetate=10/1, $R_f$=0.4) afforded N-benzyl-4-methoxyaniline (192 mg, 90% isolated yield) as light yellow solid. The spectral data ($^1$H NMR) matched with the literature references and GC analysis indicated >95% purity.

N-(4-Tolyl)benzylamine (FIG. 1, Entry 8)

The general procedure under argon was followed using copper(I) iodide (10 mg, 0.05 mmol), $K_3PO_4$ (425 mg, 2.00 mmol), benzylamine (131 µL, 1.20 mmol), 4-iodotoluene (218 mg, 1.00 mmol), ethylene glycol (111 µL, 2.00 mmol) and 2-propanol (1.0 mL). Column chromatography using a solvent mixture (hexane/ethyl acetate=20/1, $R_f$=0.5) afforded N-(4-tolyl)benzylamine (169 mg, 86% isolated yield) as colorless liquid. The spectral data ($^1$H NMR) matched with the literature references and GC analysis indicated >95% purity.

5-(N-Benzyl)amino-m-xylene (FIG. 1, Entries 9 and 10)

The general procedure under argon or air was followed using copper(I) iodide (10 mg, 0.05 mmol), $K_3PO_4$ (425 mg, 2.00 mmol), benzylamine (131 µL, 1.20 mmol), 5-iodo-m-xylene (144 µl, 1.00 mmol), ethylene glycol (111 µL, 2.00 mmol) and 2-propanol (1.0 mL). Column chromatography using a solvent mixture (hexane/ethyl acetate=20/1, $R_f$=0.5) afforded 5-(N-benzyl)amino-m-xylene (177 mg, 84% isolated yield) as colorless liquid. The spectral data ($^1$H NMR) matched with the literature references and GC analysis indicated >95% purity. See Wolfe, J. P.; Buchwald, S. L. *J. Org. Chem.* 2000, 65, 1144-1157.

N-(3-Bromophenyl)benzylamine (FIG. 1, Entries 11-13)

The general procedure under argon or air was followed using copper(I) iodide (10 mg, 0.05 mmol or 2.0 mg, 0.01 mmol), $K_3PO_4$ (425 mg, 2.00 mmol), benzylamine (131 µl, 1.20 mmol), 3-bromoiodobenzene (128 µL, 1.00 mmol), ethylene glycol (111 µL, 2.00 mmol) and 2-propanol (1.0 mL). Column chromatography using a solvent mixture (hexane/ethyl acetate=20/1, $R_f$=0.4) afforded N-(3-bromophenyl)benzylamine (217 mg, 83% isolated yield) as colorless liquid. The spectral data ($^1$H NMR) matched with the literature references and GC analysis indicated >95% purity. See Beletskaya, I. P.; Bessmertnykh, A. G.; Guilard, R. *Synlett* 1999, 1459-1461.

N-(3-Cyanophenyl)benzylamine (FIG. 1, Entry 14)

The general procedure under argon was followed using copper(I) iodide (10 mg, 0.05 mmol), $K_3PO_4$ (425 mg, 2.00 mmol), benzylamine (131 µL, 1.20 mmol), 3-iodobenzonitrile (229 mg, 1.00 mmol), ethylene glycol (111 µL, 2.00 mmol) and 2-propanol (1.0 mL). Column chromatography using a solvent mixture (hexane/ethyl acetate=5/1, $R_f$=0.5) afforded N-(3-cyanophenyl)benzylamine (165 mg, 80% isolated yield) as light yellow solid. The spectral data ($^1$H NMR) matched with the literature references and GC analysis indicated >95% purity.

N-(3-Trifluoromethylphenyl)benzylamine (FIG. 1, Entries 15 and 16)

The general procedure under argon or air was followed using copper(I) iodide (10 mg, 0.05 mmol), $K_3PO_4$ (425 mg, 2.00 mmol), benzylamine (131 µL, 1.20 mmol), 3-iodobenzonitrile (144 µl, 1.00 mmol), ethylene glycol (111 µl, 2.00 mmol) and 2-propanol (1.0 mL). Column chromatography using a solvent mixture (hexane/ethyl acetate=20/1, f=0.4) afforded N-(3-trifluoromethylphenyl)benzylamine (229 mg, 91% isolated yield) as colorless liquid. The spectral data ($^1$H NMR) matched with the literature references and GC analysis indicated >95% purity. See Desmurs, J. R.; Lecouve, J. P.; Kempf, H.; Betremieux, I.; Ratton, S. *New J. Chem.* 1992, 16, 99-106.

N-(3-Methoxyphenyl)benzylamine (FIG. 1, Entry 17)

The general procedure under argon was followed using copper(I) iodide (10 mg, 0.05 mmol), $K_3PO_4$ (425 mg, 2.00 mmol), benzylamine (131 µL, 1.20 mmol), 3-iodoanisole (119 µl, 1.00 mmol), ethylene glycol (111 µL, 2.00 mmol) and 2-propanol (1.0 mL). Column chromatography using a solvent mixture (hexane/ethyl acetate=10/1, $R_f$=0.4) afforded N-(3-methoxyphenyl)benzylamine (171 mg, 80% isolated yield) as white solid. The spectral data ($^1$H NMR) matched with the literature references and GC analysis indicated >95% purity. See Ali, M. H.; Buchwald, S. L. *J. Org. Chem.* 2001, 66, 2560-2565.

N-(3-Nitrophenyl)benzylamine (FIG. 1, Entry 18)

The general procedure under argon was followed using copper(I) iodide (10 mg, 0.05 mmol), $K_3PO_4$ (425 mg, 2.00 mmol), benzylamine (109 µL, 1.00 mmol), 3-iodonitrobenzene (349 mg, 1.40 mmol), ethylene glycol (111 µL, 2.00 mmol) and 2-propanol (1.0 mL). Column chromatography using a solvent mixture (hexane/ethyl acetate=5/1, $R_f$=0.4) afforded N-(3-nitrophenyl)benzylamine (164 mg, 72% isolated yield) as orange solid. The spectral data ($^1$H NMR) matched with the literature references and GC analysis indicated >95% purity. See Leardini, R.; Nanni, D.; Tundo, A.; Zanardi, G.; Ruggieri, F. *J. Org. Chem.* 1992, 57, 1842-1848.

N-(3-Tolyl)benzylamine (FIG. 1, Entry 19)

The general procedure under argon was followed using copper(I) iodide (10 mg, 0.05 mmol), $K_3PO_4$ (425 mg, 2.00 mmol), benzylamine (131 µL, 1.20 mmol), 3-iodotoluene (128 µl, 1.00 mmol), ethylene glycol (111 µL, 2.00 mmol) and 2-propanol (1.0 mL). Column chromatography using a solvent mixture (hexane/ethyl acetate=20/1, $R_f$=0.5) afforded N-(3-tolyl)benzylamine (171 mg, 87% isolated yield) as colorless liquid. The spectral data ($^1$H NMR) matched with the literature references and GC analysis indicated >95% purity. See Spagnolo, P.; Zanirato, P. *Tetrahedron Lett.* 1987, 28, 961-964.

N-(2-Tolyl)benzylamine (FIG. 1, Entry 20)

The general procedure under argon was followed using copper(I) iodide (19 mg, 0.10 mmol), $K_3PO_4$ (425 mg, 2.00 mmol), benzylamine (131 μL, 1.20 mmol), 2-Iodotoluene (127 μl, 1.00 mmol), ethylene glycol (111 mL, 2.00 mmol) and 1-butanol (1.0 mL) at 100° C. Column chromatography using a solvent mixture (hexane/ethyl acetate=20/1, $R_f$=0.5) afforded N-(2-tolyl)benzylamine (136 mg, 69% isolated yield) as colorless liquid. The spectral data ($^1$H NMR) matched with the literature references and GC analysis indicated >95% purity. See Maccarone, E.; Mamo, A.; Torre, M. *J. Org. Chem.* 1979, 44, 1143-1146.

N-(2-Methoxyphenyl)benzylamine (FIG. 1, Entry 21)

The general procedure under argon was followed using copper(I) iodide (19 mg, 0.10 mmol), $K_3PO_4$ (425 mg, 2.00 mmol), benzylamine (131 μl, 1.20 mmol), 2-iodoanisole (130 μl, 1.00 mmol), ethylene glycol (111 μl, 2.00 mmol) and 1-butanol (1.0 mL) at 100° C. Column chromatography using a solvent mixture (hexane/ethyl acetate=10/1, $R_f$=0.4) afforded N-(2-methoxyphenyl)benzylamine (149 mg, 70% isolated yield) as colorless liquid. The spectral data ($^1$H NMR) matched with the literature references and GC analysis indicated >95% purity.

2-(N-Benzyl)aminobenzoic acid (FIG. 1, Entries 22-24)

The general procedure under argon was followed using copper(I) iodide (10 mg, 0.05 mmol), $K_3PO_4$ (636 mg, 3.00 mmol), benzylamine (131 μL, 1.20 mmol), 2-iodobenzoic acid (248 mg, 1.00 mmol), ethylene glycol (111 μL, 2.00 mmol) and 2-propanol (1.0 mL). After heated for a specified duration, the reaction was allowed to reach room temperature. Water and diluted HCl (10%) was added until ~pH 3. Diethyl ether (2 mL) was added and the organic layer was analyzed by tlc. The reaction mixture was further extracted by diethyl ether (4×10 mL) and the combined organic phase was washed with brine and dried over $Na_2SO_4$. The solvent was rotary evaporated and the yellowish-brown residue was purified by column chromatography using a solvent mixture (diethyl ether/ethylacetate=1/1, $R_f$=0.3) to afford 2-(N-benzyl)aminobenzoic acid (161 mg, 71% isolated yield) as light yellow solid. For aryl bromide substrate: copper(I) iodide (19 mg, 0.101 mmol), $K_3PO_4$ (636 mg, 3.00 mmol), benzylamine (131 μl, 1.20 mmol), 2-bromobenzoic acid (201 mg, 1.00 mmol), ethylene glycol (111 μl, 2.00 mmol) and 1-butanol (1.0 mL) was used and heated to 100° C. The above workup procedures was followed and obtained 2-(N-benzyl)aminobenzoic acid (120 mg, 53% isolated yield) as light yellow solid. For aryl chloride substrate: copper(I) iodide (19 mg, 0.10 mmol), $K_3PO_4$ (636 mg, 3.00 mmol), benzylamine (131 μl, 1.20 mmol), 2-chlorobenzoic acid (157 mg, 1.00 mmol), ethylene glycol (111 μl, 2.00 mmol) and 1-butanol (1.0 mL) was used and heated to 100° C. The above workup procedures was followed and obtained 2-(N-benzyl)aminobenzoic acid (109 mg, 48% isolated yield) as light yellow solid. The spectral data ($^1$H NMR) matched with the literature references and indicated >95% purity. See Chang, M. R.; Takeuchi, Y.; Hashigaki, K.; Yamato, M. *Heterocycles* 1992, 33, 147-152. Moore, J. A.; Sutherland, G. J.; Sowerby, R.; Kelly, E. G.; Palermo, S.; Webster, W. *J. Org. Chem.* 1969, 34, 887-892.

2-(N-Benzyl)aminobenzylalcohol (FIG. 1, Entry 25)

The general procedure under argon was followed using copper(I) iodide (10 mg, 0.5 mmol), $K_3PO_4$ (425 mg, 2.00 mmol), benzylamine (131 μL, 1.20 mmol), 2-iodobenzylalcohol (234 mg, 1.00 mmol), ethylene glycol (111 μL, 2.00 mmol) and 2-propanol (1.0 mL). Column chromatography using a solvent mixture (hexane/ethyl acetate=4/1, $R_f$=0.3) afforded 2-(N-benzyl)aminobenzylalcohol (203 mg, 95% isolated yield) as off-white solid. The spectral data ($^1$H NMR) matched with the literature references and GC analysis indicated >95% purity. See Coppola, G. A. *J Herterocyl. Chem.* 1986, 23, 223-224.

4-(N-Benzyl)aminoaniline (FIG. 1, Entry 26)

The general procedure under argon was followed using copper(I) iodide (19 mg, 0.10 mmol), $K_3PO_4$ (425 mg, 2.00 mmol), benzylamine (218 μL, 2.0 mmol), 4-iodoaniline (219 mg, 1.00 mmol), ethylene glycol (111 μL, 2.00 mmol) and 2-propanol (1.0 mL) at 90° C. Column chromatography using a solvent gradient (hexane/ethyl acetate=2/1 to 1/1, $R_f$=0.2) afforded 4-(N-benzyl)aminoaniline (101 mg, 51% isolated yield) as brown solid. The spectral data ($^1$H NMR) matched with the literature references and GC analysis indicated >95% purity. See Araki, T.; Tsukube, H. *J. Polym. Sci., Polym. Lett. Ed.* 1979, 17, 501-505.

Ethyl 4-(N-benzyl)aminobenzoate (FIG. 1, Entry 27)

The general procedure under argon was followed using copper(I) iodide (10 mg, 0.05 mmol), $K_3PO_4$ (425 mg, 2.00 mmol), benzylamine (131 μL, 1.20 mmol), ethyl 4-iodobenzoate (167 μl, 1.00 mmol), ethylene glycol (111 μL, 2.00 mmol) and ethanol (1.0 mL). Column chromatography using a solvent mixture (hexane/ethyl acetate=5/1, $R_f$=0.4) afforded ethyl 4-(N-benzyl)aminobenzoate (113 mg, 50% isolated yield) as light yellow solid. The spectral data ($^1$H NMR) matched with the literature references and GC analysis indicated >95% purity. See Albright, J. D.; DeVries, V. G.; Largis, E. E.; Miner, T. G. Reich, M. F.; Schaffer, S.; Shepherd, R. G.; Upeslacis, J. *J. Med. Chem.* 1983, 26, 1378-1393; and Onaka, M.; Umezono, A.; Kawai, M.; Izumi, Y. *J. Chem. Soc., Chem. Commun.* 1985, 1202-1203.

N-(1-Naphthyl)benzylamine (FIG. 1, Entry 28)

The general procedure under argon was followed using copper(I) iodide (10 mg, 0.05 mmol), $K_3PO_4$ (425 mg, 2.00 mmol), benzylamine (131 μL, 1.20 mmol), 1-iodonaphthlene (146 μl, 1.00 mmol), ethylene glycol (111 μL, 2.00 mmol) and 2-propanol (1.0 mL). Column chromatography using a solvent mixture (hexane/ethyl acetate=20/1, $R_f$=0.4) afforded N-(1-naphthyl)benzylamine (163 mg, 70% isolated yield) as light yellow solid. The spectral data ($^1$H NMR) matched with the literature references and GC analysis indicated >95% purity. See Janin, Y. L.; Bisagni, E. *Synthesis* 1993, 57-59.

Figure 2A:
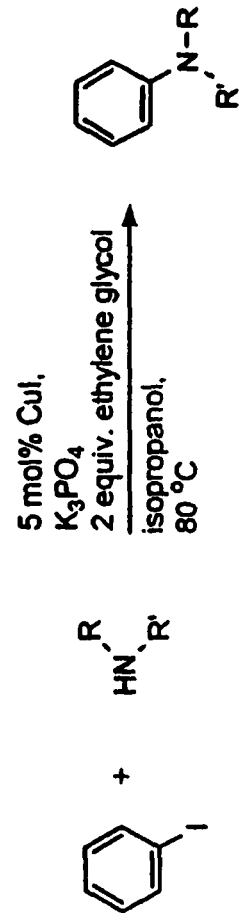
FIG. 2 tabulates the results of copper-catalyzed arylations of various amines using iodobenzene, and the reaction conditions employed.
Figure 2B:
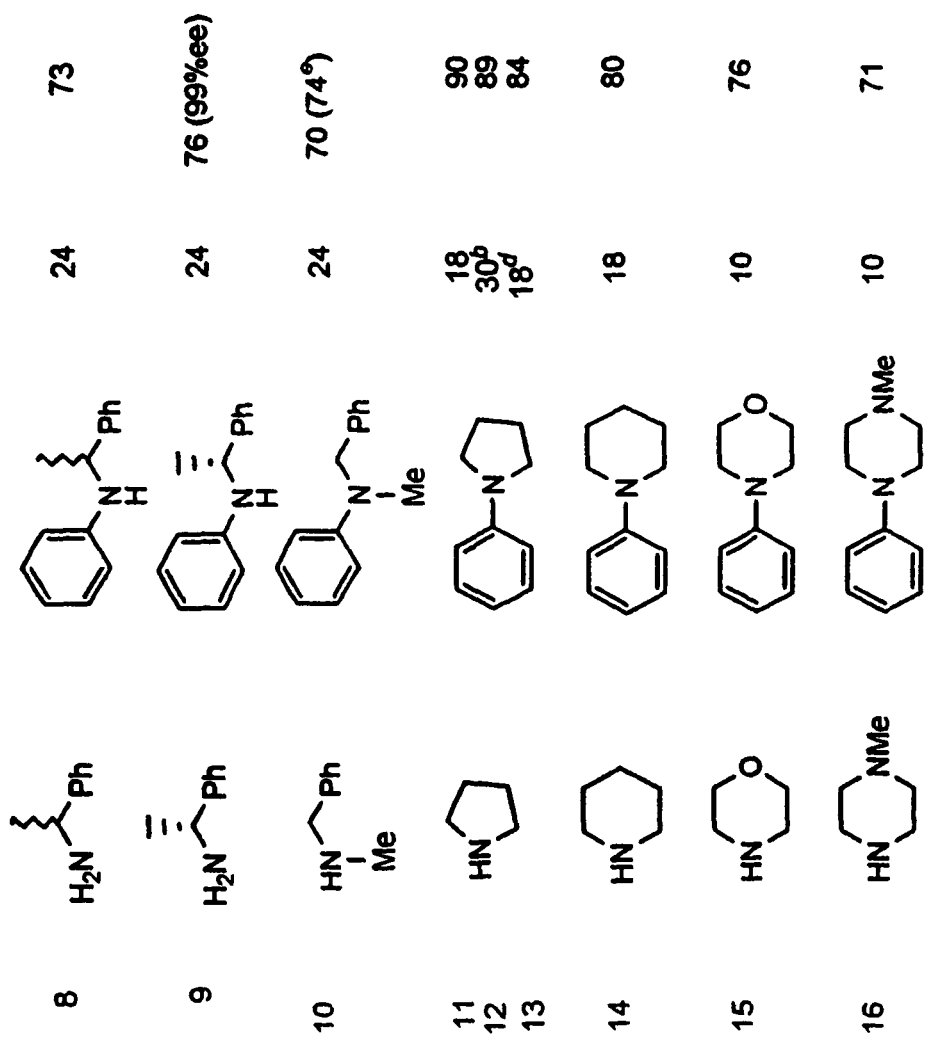

N-(Phenyl)hexylamine (FIG. 2, Entries 2-4)

The general procedure under argon or air was followed using copper(I) iodide (10 mg, 0.05 mmol or 2.0 mg, 0.01 mmol), $K_3PO_4$ (425 mg, 2.00 mmol), hexylamine (159 μL, 1.20 mmol), iodobenzene (112 μL, 1.00 mmol), ethylene glycol (111 μL, 2.00 mmol) and 2-propanol (1.0 mL). Column chromatography using a solvent mixture (hexane/ethyl acetate=20/1, $R_f$=0.5) afforded N-(phenyl)hexylamine (152 mg, 86% isolated yield) as colorless liquid. The spectral data ($^1$H NMR) matched with the literature references and GC analysis indicated >95% purity. See Bomann, M. D.; Guch, I. C.; DiMare, M. *J. Org. Chem.* 1995, 60, 5995-5996.

N-(2-Methoxyethyl)aniline (FIG. 2, Entries 5-7)

The general procedure under argon or air was followed using copper(I) iodide (10 mg, 0.05 mmol or 2.0 mg, 0.01 mmol), $K_3PO_4$ (425 mg, 2.00 mmol), 2-methoxyethylamine (104 μL, 1.20 mmol), iodobenzene (112 μL, 1.00 mmol), ethylene glycol (111 μL, 2.00 mmol) and 2-propanol (1.0 mL). Column chromatography using a solvent mixture (hexane/ethyl acetate=10/1, $R_f$=0.2) afforded N-(2-methoxyethyl)aniline (138 mg, 91% isolated yield) as colorless liquid. The spectral data ($^1$H NMR) matched with the literature references and GC analysis indicated >95% purity. See Fancher, L. W.; Gless, R. D., Jr.; Wong, R. Y. *Tetrahedron Lett.* 1988, 29, 5095-5098.

N-(Phenyl)-α-methylbenzylamine (FIG. 2, Entry 8)

The general procedure under argon was followed using copper(I) iodide (10 mg, 0.05 mmol), $K_3PO_4$ (425 mg, 2.00 mmol), α-methylbenzylamine (155 μL, 1.20 mmol), iodobenzene (112 μL, 1.00 mmol), ethylene glycol (111 μL, 2.00 mmol) and 2-propanol (1.0 mL). Column chromatography using a solvent mixture (hexane/ethyl acetate=20/1, $R_f$=0.5) afforded N-(phenyl)-α-methylbenzylamine (144 mg, 73% isolated yield) as colorless liquid. HPLC conditions: (column: Daicel OD-H; solvent: 10% $^i$PrOH in hexane; flow rate: 0.7 mL/min; UV lamp: 254 nm; retention time: 6.01, 6.78 min). The spectral data ($^1$H NMR) matched with the literature references and GC analysis indicated >95% purity. See Kainz, S.; Brinkmann, A.; Leitner, W.; Pfaltz, A. *J. Am. Chem. Soc.* 1999, 121, 6421-6429.

(R)—N-(Phenyl)-α-methylbenzylamine (FIG. 2, Entry 9)

The general procedure under argon was followed using copper(I) iodide (10 mg, 0.05 mmol), $K_3PO_4$ (425 mg, 2.00 mmol), (R)-α-methylbenzylamine (155 μL, 1.20 mmol), iodobenzene (112 μL, 1.00 mmol), ethylene glycol (111 μL, 2.00 mmol) and 2-propanol (1.0 mL). Column chromatography using a solvent mixture (hexane/ethyl acetate=20/1, $R_f$=0.5) afforded (R)—N-(phenyl)-α-methylbenzylamine (150 mg, 76% isolated yield, 99% ee) as colorless liquid. HPLC conditions: (column: Daicel OD-H; solvent: 10% $^i$ProH in hexane; flow rate: 0.7 mL/min; UV lamp: 254 nm; retention time: 6.74 min). The spectral data ($^1$H NMR) matched with the literature references and GC analysis indicated >95% purity.

N-Methyl-N-phenylbenzylamine (FIG. 2, Entry 10)

The general procedure under argon was followed using copper(I) iodide (19 mg, 0.10 mmol), $K_3PO_4$ (425 mg, 2.00 mmol), N-methylbenzylamine (155 μL, 1.20 mmol), iodobenzene (112 μL, 1.00 mmol), ethylene glycol (111 μL, 2.00 mmol) and 1-butanol (1.0 mL) at 90° C. Column chromatography using a solvent mixture (hexane/ethyl acetate=20/1, $R_f$=0.5) afforded N-methyl-N-phenylbenzylamine (146 mg, 74% isolated yield) as colorless liquid. The spectral data ($^1$H NMR) matched with the literature references and GC analysis indicated >95% purity. See Brenner, E.; Schneider, R.; Fort, Y. *Tetrahedron* 1999, 55, 12829-12842.

N-(Phenyl)pyrrolidine (FIG. 2, Entries 11-13)

The general procedure under argon or air was followed using copper(I) iodide (10 mg, 0.05 mmol or 2.0 mg, 0.01 mmol), $K_3PO_4$ (425 mg, 2.00 mmol), pyrrolidine (100 μL, 1.20 mmol), iodobenzene (112 μL, 1.00 mmol), ethylene glycol (111 μL, 2.00 mmol) and 2-propanol (1.0 mL). Column chromatography using a solvent mixture (hexane/ethyl acetate=20/1, $R_f$=0.4) afforded N-(phenyl)pyrrolidine (133 mg, 90% isolated yield) as colorless liquid. The spectral data ($^1$H NMR) matched with the literature references and GC analysis indicated >95% purity. See Ishikawa, T.; Uedo, E.; Tani, R.; Saito, S. *J. Org. Chem.* 2001, 66, 186-191.

N-(Phenyl)piperidine (FIG. 2, Entry 14)

The general procedure under argon was followed using copper(I) iodide (10 mg, 0.05 mmol), $K_3PO_4$ (425 mg, 2.00 mmol), piperidine (119 μL, 1.20 mmol), iodobenzene (112 μL, 1.00 mmol), ethylene glycol (111 μL, 2.00 mmol) and 2-propanol (1.0 mL). Column chromatography using a solvent mixture (hexane/ethyl acetate=20/1, $R_f$=0.4) afforded N-(phenyl)piperidine (129 mg, 80% isolated yield) as colorless liquid. The spectral data ($^1$H NMR) matched with the literature references and GC analysis indicated >95% purity. See Beller, M.; Breindl, C.; Riermeier, T. H.; Tillack, A. *J. Org. Chem.* 2001, 66, 1403-1412; and Li, G. Y. *Angew. Chem., Int. Ed.* 2001, 40, 1513-1516.

N-(Phenyl)morpholine (FIG. 2, Entry 15)

The general procedure under argon was followed using copper(I) iodide (10 mg, 0.05 mmol), $K_3PO_4$ (425 mg, 2.00 mmol), morpholine (130 μL, 1.50 mmol), iodobenzene (112 μL, 1.00 mmol), ethylene glycol (111 μL, 2.00 mmol) and 2-propanol (1.0 mL). Column chromatography using a solvent mixture (hexane/ethyl acetate=20/1, $R_f$=0.2) afforded N-(phenyl)morpholine (124 mg, 76% isolated yield) as colorless liquid. The spectral data ($^1$H NMR) matched with the literature references and GC analysis indicated >95% purity. See Desmarets, C.; Schneider, R.; Fort, Y. *Tetrahedron Lett.* 2000, 41, 2875-2879.

N-phenyl-N'-(methyl)piperazine (FIG. 2, Entry 16)

The general procedure under argon was followed using copper(I) iodide (10 mg, 0.05 mmol), $K_3PO_4$ (425 mg, 2.00 mmol), N-(methyl)piperazine (166 μL, 1.50 mmol), iodobenzene (112 μL, 1.00 mmol), ethylene glycol (111 μL, 2.00 mmol) and 2-propanol (1.0 mL). Column chromatography using a solvent mixture (hexane/ethyl acetate=20/1, $R_f$=0.1) afforded N-phenyl-N'-(methyl)piperazine (125 mg, 71% isolated yield) as colorless liquid. The spectral data ($^1$H NMR) matched with the literature references and GC analysis indicated >95% purity.

N-Phenyl-L-proline (FIG. 2, Entry 17)

The general procedure under argon was followed using copper(I) iodide (10 mg, 0.05 mmol), $K_3PO_4$ (425 mg, 2.00 mmol), L-proline (138 mg, 1.20 mmol), iodobenzene (112 μL, 1.00 mmol), ethylene glycol (111 μL, 2.00 mmol) and 2-propanol (1.0 mL). After heated for a specified duration, the reaction was allowed to reach room temperature. Water and diluted HCl (10%) was added until ~pH 3. Diethyl ether (2 mL) was added and the organic layer was analyzed by tlc. The reaction mixture was further extracted by diethyl ether (4×10 mL) and the combined organic phase was washed with brine and dried over $Na_2SO_4$. The solvent was rotary evaporated and the yellowish-brown residue was purified by column chromatography using a solvent mixture (diethyl ether/ethyl acetate=1/1, R=0.2) to afford N-phenyl-L-proline (134 mg, 70% isolated yield) as light yellow solid. The spectral data ($^1$H NMR) matched with the literature references and indicated >95% purity. See Ma, D.; Zhang, Y.; Yao, J.; Wu, S.; Tao, F. *J. Am. Chem. Soc.* 1998, 120, 12459-12467.

N-(Phenyl)aniline (FIG. 2, Entry 18)

The general procedure under argon was followed using copper(I) iodide (10 mg, 0.05 mmol), $K_3PO_4$ (425 mg, 2.00 mmol), aniline (109 μL, 1.20 mmol), iodobenzene (112 μL, 1.00 mmol), ethylene glycol (111 μL, 2.00 mmol) and 2-propanol (1.0 mL) at 90° C. Column chromatography using a solvent mixture (hexane/ethyl acetate=5/1, $R_f$=0.4) afforded N-(phenyl)aniline (69 mg, 41% isolated yield) as light yellow solid. The spectral data ($^1$H NMR) matched with the literature references and GC analysis indicated >95% purity.

N-(Phenyl)-2-pyrrolidinone (FIG. 2, Entry 21)

The general procedure under argon was followed using copper(I) iodide (10 mg, 0.05 mmol), $K_3PO_4$ (425 mg, 2.00 mmol), 2-pyrrolidinone (91 μL, 1.20 mmol), Iodobenzene (112 μL, 1.00 mmol), ethylene glycol (111 μL, 2.00 mmol) and 2-propanol (1.0 mL) at 90° C. Column chromatography using a solvent mixture (hexane/ethyl acetate=1/1) afforded N-(phenyl)-2-pyrrolidinone (80 mg, 50% isolated yield) as white solid. The spectral data ($^1$H NMR) matched with the literature references and GC analysis indicated >95% purity. See Yin, J.; Buchwald, S. L. *Org. Lett.* 2000, 2, 1101-1104; and Kang, S.-K.; Lee, S.-H.; Lee, D. *Synlett* 2000, 1022-1024.

Figure 3B:
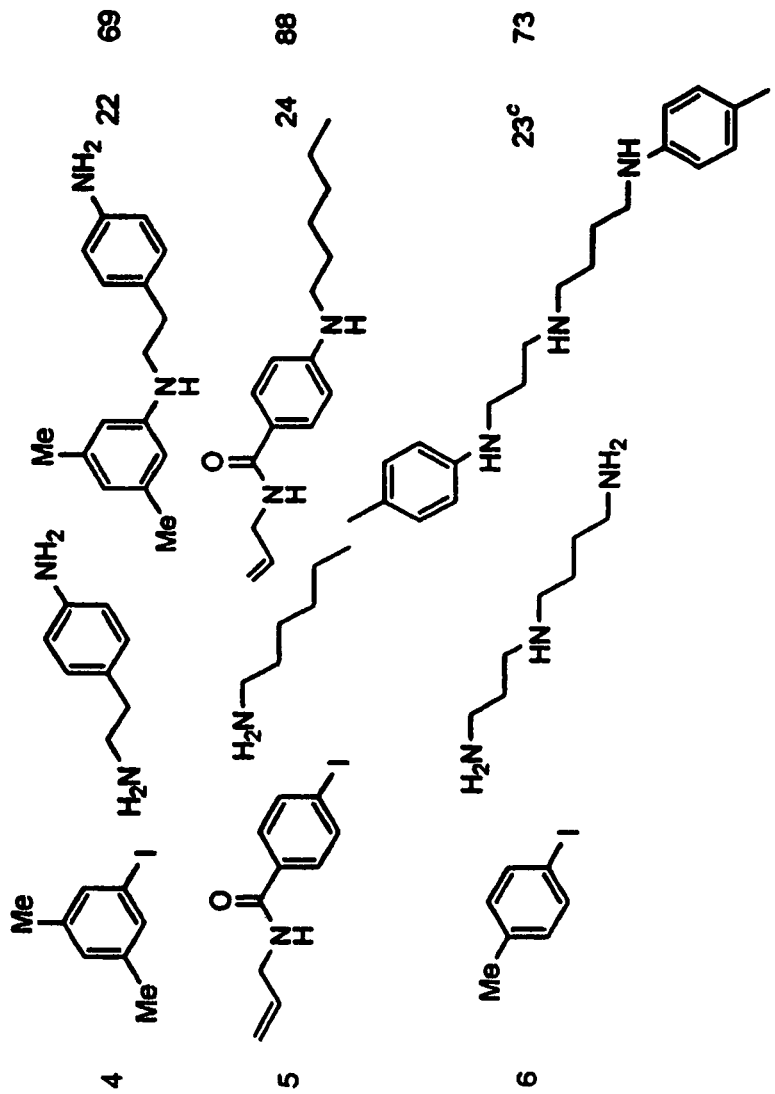
FIG. 3 tabulates copper-catalyzed arylations of various amines using various aryl iodides, and the reaction conditions employed.

N-(4-Methoxyphenyl)cyclohexylamine (FIG. 3, Entry 1)

An oven-dried resealable 15 mL Schlenk tube was charged with CuI (9.5 mg, 0.0499 mmol, 5.0 mol %), $K_3PO_4$ (440 mg, 2.07 mmol), evacuated and backfilled with argon. Cyclohexylamine (144 μL, 1.26 mmol), ethylene glycol (0.11 mL, 1.97 mmol), and a solution of 4-iodoanisole (235 mg, 1.00 mmol) in 1-butanol (1.0 mL) were added under argon. The Schlenk tube was sealed with a Teflon valve and the reaction mixture was stirred magnetically at 100° C. for 14 h. The resulting thick, green-brown suspension was allowed to reach room temperature, poured into a solution of 30% aq ammonia (1 mL) in water (20 mL), and extracted with 3×15 mL of $CH_2Cl_2$. The colorless organic phase was dried ($Na_2SO_4$), concentrated, and the residue was purified by flash chromatography on silica gel (2×15 cm; hexane-ethyl acetate 5:1; 15 mL fractions). Fractions 9-17 provided 143 mg (70% yield) of the product as white crystals. $^1$H NMR (400 MHz, $CDCl_3$): δ 6.79-6.72 (m, 2H), 6.60-6.53 (m, 2H), 3.74 (s, 3H), 3.22 (br s, 1H), 3.16 (tt, J=10.2, 3.6 Hz, 1H), 2.10-1.98 (m, 2H), 1.80-1.69 (m, 2H), 1.68-1.58 (m, 1H), 1.40-1.04 (m, 5H). $^{13}$C NMR (100 MHz, $CDCl_3$): δ 151.8, 141.6, 114.8, 114.7, 55.8, 52.7, 33.6, 25.9, 25.0. IR (neat, cm$^{-1}$): 3388, 1509, 1239, 1038, 818. Anal. Calcd. for $C_{13}H_{19}NO$: C, 76.06; H, 9.33. Found: C, 76.00; H, 9.32.

5-(4-Methoxyphenylamino)-1-pentanol (FIG. 3, Entry 2)

An oven-dried resealable 15 mL Schlenk tube was charged with CuI (9.5 mg, 0.0499 mmol, 5.0 mol %), $K_3PO_4$ (440 mg, 2.07 mmol), evacuated and backfilled with argon. 5-Amino-1-pentanol (135 μL, 1.24 mmol), ethylene glycol (0.11 mL, 1.97 mmol), and a solution of 4-iodoanisole (235 mg, 1.00 mmol) in 1-butanol (1.0 mL) were added under argon. The Schlenk tube was sealed with a Teflon valve and the reaction mixture was stirred magnetically at 100° C. for 14 h. The resulting thick, yellow-brown suspension was allowed to reach room temperature, poured into a solution of 30% aq ammonia (1 mL) in water (20 mL), and extracted with 3×15 mL of $CH_2Cl_2$. The organic phase was dried ($Na_2SO_4$), concentrated, and the residue was purified by flash chromatography on silica gel (2×15 cm; ethyl acetate; 15 mL fractions). Fractions 6-15 provided 177 mg (85% yield) of the product as a pale tan oil. $^1$H NMR (400 MHz, $CDCl_3$): δ 6.80-6.74 (m, 2H), 6.60-6.54 (m, 2H), 3.74 (s, 3H), 3.65 (t, J=6.4 Hz, 2H), 3.07 (t, J=7.0 Hz, 2H), 2.5 (br s, 2H), 1.68-1.55 (m, 4H), 1.52-1.41 (m, 2H). $^{13}$C NMR (100 MHz, $CDCl_3$): δ 151.9, 142.6, 114.8, 114.0, 62.7, 55.8, 44.9, 32.4, 29.4, 23.3. IR (neat, cm$^{-1}$): 3350, 1511, 1233, 1036, 820. Anal. Calcd. for $C_{12}H_{19}NO_2$: C, 68.87; H, 9.15. Found: C, 68.93; H, 9.12.

N-(3-Methylphenyl)-2-(1-cyclohexenyl)ethylamine (FIG. 3, Entry 3)

An oven-dried resealable 15 mL Schlenk tube was charged with CuI (9.6 mg, 0.0504 mmol, 5.0 mol %), $K_3PO_4$ (440 mg, 2.07 mmol), evacuated and backfilled with argon. 3-Iodotoluene (130 μL, 1.01 mmol), 2-(1-cyclohexenyl)ethylamine (170 μL, 1.22 mmol), ethylene glycol (115 μL, 1.97 mmol), and isopropyl alcohol (1.0 mL) were added under argon. The Schlenk tube was sealed with a Teflon valve and the reaction mixture was stirred magnetically at 80° C. for 22 h. The resulting thick, green-brown suspension was allowed to reach room temperature, poured into a solution of 30% aq ammonia (1 mL) in water (20 mL), and extracted with 3×15 mL of $CH_2Cl_2$. The organic phase was dried ($Na_2SO_4$), concentrated, and the residue was purified by flash chromatography on silica gel (2×15 cm; hexane-ethyl acetate 50:1; 15 mL fractions). Fractions 12-17 provided 189 mg (87% yield) of the product as a colorless oil. $^1$H NMR (400 MHz, $CDCl_3$): δ 7.06 (t, J=7.4 Hz, 1H), 6.52 (d, J=7.4 Hz, 1H), 6.46-6.39 (m, 2H), 5.53 (m, 1H), 3.57 (br s, 1H), 3.14 (t, J=6.8 Hz, 2H), 2.30-2.22 (m, 5H), 2.07-1.98 (m, 2H), 1.97-1.90 (m, 2H), 1.67-1.52 (m, 4H). $^{13}$C NMR (100 MHz, $CDCl_3$): δ 148.5, 138.9, 134.9, 129.1, 123.5, 118.1, 113.6, 109.9, 41.4, 37.6, 27.8, 25.2, 22.8, 22.4, 21.6. IR (neat, cm$^{-1}$): 3406, 1603, 1590, 1509, 1492, 1478, 1328, 766, 691. Anal. Calcd. for $C_{15}H_{21}N$: C, 83.67; H, 9.83. Found: C, 83.82; H, 9.84.

2-(4-Aminophenyl)-N-(3,5-dimethylphenyl)ethylamine (FIG. 3, Entry 4)

An oven-dried resealable 15 mL Schlenk tube was charged with CuI (9.6 mg, 0.0504 mmol, 5.0 mol %), $K_3PO_4$ (440 mg, 2.07 mmol), evacuated and backfilled with argon. 5-Iodo-m-xylene (145 μL, 1.00 mmol), 2-(4-aminophenyl)ethylamine (160 μL, 1.21 mmol), ethylene glycol (115 μL, 2.06 mmol), and isopropyl alcohol (1.0 mL) were added under argon. The Schlenk tube was sealed with a Teflon valve and the reaction mixture was stirred magnetically at 80° C. for 22 h. The resulting thick, gray-brown suspension was allowed to reach room temperature, poured into a solution of 30% aq ammonia (1 mL) in water (20 mL), and extracted with 3×15 mL of $CH_2Cl_2$. The yellow-brown organic phase was dried ($Na_2SO_4$), concentrated, and the residue was purified by flash chromatography on silica gel (2×20 cm; hexane-ethyl acetate 3:2; 15 mL fractions). Fractions 9-18 were concentrated and the residue was recrystallized from hexanes (5 mL) to give 167 mg (69% yield) of the desired product as large white needles. $^1$H NMR (400 MHz, CDCl$_3$): δ 7.04-6.97 (m, 2H), 6.67-6.61 (m, 2H), 6.36 (s, 1H), 6.24 (s, 2H), 3.65-3.50 (br m, 3H), 3.30 (t, J=6.8 Hz, 2H), 2.79 (t, J=7.0 Hz, 2H), 2.23 (s, 6H). $^{13}$C NMR (100 MHz, CDCl$_3$): δ 148.2, 144.7, 138.8, 129.5, 129.2, 119.3, 115.3, 110.9, 45.3, 34.6, 21.5. IR (neat, cm$^{-1}$): 3361, 3215, 1600, 1515, 1472, 1337, 1273, 1181, 820.

N-(4-Methylphenyl)-N'-[3-(4-methylphenylamino) propyl]-1,4-butanediamine (FIG. 3, Entry 6)

An oven-dried resealable 15 mL Schlenk tube was charged with CuI (9.6 mg, 0.0504 mmol), 4-iodotoluene (260 mg, 1.19 mmol), K$_3$PO$_4$ (440 mg, 2.07 mmol), evacuated and backfilled with argon. N-(3-Aminopropyl)-1,4-butanediamine (79 μL, 0.503 mmol), ethylene glycol (115 μL, 2.06 mmol), and isopropyl alcohol (1.0 mL) were added under argon. The Schlenk tube was sealed with a Teflon valve and the reaction mixture was stirred magnetically at 80° C. for 23 h. The resulting thick, gray-brown suspension was allowed to reach room temperature, poured into a solution of 30% aq ammonia (1 mL) in water (20 mL), and extracted with 3×1 5 mL of CH$_2$Cl$_2$. The organic phase was dried (Na$_2$SO$_4$), concentrated, and the residue was purified by flash chromatography on silica gel (2×15 cm; dichloromethane-dichloromethane saturated with 30% aq ammonia-methanol 30:20: 2; 15 mL fractions). Fractions 12-24 were concentrated and the residue was recrystallized from hexanes (2 mL) to give 119 mg (73% yield) of the desired product as fine white crystals. $^1$H NMR (400 MHz, CDCl$_3$): δ 6.98 (d, J=8.4 Hz, 4H), 6.56-6.50 (m, 4H), 4.04 (br s, 1H), 3.56 (br s, 1H), 3.17 (t, J=6.6 Hz, 2H), 3.11 (t, J=6.6 Hz, 2H), 2.74 (t, J=6.6 Hz, 2H), 2.64 (t, J=6.9 Hz, 2H), 2.23 (s, 6H), 1.79 (quintet, J=6.6 Hz, 2H), 1.70-1.54 (m, 4H), 0.95 (br s, 1H). $^{13}$C NMR (100 MHz, CDCl$_3$): δ 146.3, 146.1, 129.7, 126.3, 112.89, 112.85, 49.8, 48.5, 44.2, 43.3, 29.6, 27.8, 27.3, 20.4.

Example 79

Preparation of N-Phenylhexylamine Using 2-phenylphenol as the Ligand and Toluene as the Solvent

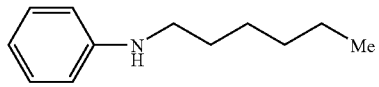 [SMILES: CCCCCCNc1ccccc1]

A screw cap test tube was purged with nitrogen and charged with CuI (9.5 mg, 0.0499 mmol, 5.0 mol %), 2-phenylphenol (34 mg, 0.200 mmol, 20 mol %), and K$_3$PO$_4$ (440 mg, 2.07 mmol). The test tube was capped and brought into a nitrogen filled glovebox, the cap being removed immediately before evacuating the antechamber. The test tube was sealed with an open top screw cap lined with a Teflon-faced silicone rubber septum and then removed from the glovebox. Bromobenzene (105 μL, 1.00 mmol), n-hexylamine (160 μL, 1.21 mmol), and toluene (1.0 mL) were added using syringes. After the reaction mixture was stirred magnetically at 100° C. for 23 h, the resulting dark brown suspension was allowed to reach room temperature, poured into a solution of 30% aq ammonia (1 mL) in water (20 mL), and extracted with 3×15 mL of CH$_2$Cl$_2$. The light brown organic phase was dried (Na$_2$SO$_4$), concentrated, and the residue was purified by flash chromatography on silica gel (2×15 cm; hexane-dichloromethane 2:1; 15 mL fractions). Fractions 14-25 provided 112 mg (63% yield) of the desired product as a colorless liquid. The $^1$H NMR spectrum matched the one reported. Barluenga, J.; Fananas, F. J.; Villamana, J.; Yus, M. J. Org. Chem. 1982, 47, 1560.

Example 80

Preparation of N-phenylhexylamine Using 2-phenylphenol as the Ligand and Dioxane as the Solvent A screw cap test tube was purged with nitrogen and charged with CuI (9.5 mg, 0.0499 mmol, 5.0 mol %), 2-phenylphenol (34 mg, 0.200 mmol, 20 mol %), and K$_3$PO$_4$ (440 mg, 2.07 mmol). The test tube was capped and brought into a nitrogen filled glovebox, the cap being removed immediately before evacuating the antechamber. The test tube was sealed with an open top screw cap lined with a Teflon-faced silicone rubber septum and then removed from the glovebox. Bromobenzene (105 μL, 1.00 mmol), n-hexylamine (160 μL, 1.21 mmol), and dioxane (1.0 mL) were added using syringes. After the reaction mixture was stirred magnetically at 100° C. for 23 h, the resulting brown suspension was allowed to reach room temperature and was then diluted with ether (2 mL) and water (1 mL). Dodecane (230 μL; internal GC standard) was added and a sample of the top (organic) layer was analyzed by GC revealing 74% conversion of bromobenzene and 60% yield of the desired product.

Example 81

Preparation of N-phenylhexylamine Using 2-phenylphenol as the Ligand and No Solvent A screw cap test tube was purged with nitrogen and charged with CuI (9.5 mg, 0.0499 mmol, 5.0 mol %), 2-phenylphenol (34 mg, 0.200 mmol, 20 mol %), and K$_3$PO$_4$ (440 mg, 2.07 mmol). The test tube was capped and brought into a nitrogen filled glovebox, the cap being removed immediately before evacuating the antechamber. The test tube was sealed with an open top screw cap lined with a Teflon-faced silicone rubber septum and then removed from the glovebox. Bromobenzene (105 μL, 1.00 mmol) and n-hexylamine (0.94 mL, 7.12 mmol) were added using syringes. After the reaction mixture was stirred magnetically at 100° C. for 23 h, the resulting brown suspension was allowed to reach room temperature, poured into a solution of 30% aq ammonia (1 mL) in water (20 mL), and extracted with 3×15 mL of CH$_2$Cl$_2$. The light brown organic phase was dried (Na$_2$SO$_4$), concentrated, and the residue was purified by flash chromatography on silica gel (2×20 cm; hexane-dichloromethane 2:1; 15 mL fractions). Fractions 13-25 provided 161 mg (91% yield) of the desired product as a colorless liquid. The $^1$H NMR spectrum matched the one reported. Barluenga, J.; Fananas, F. J.; Villamana, J.; Yus, M. J. Org. Chem. 1982, 47, 1560.

Example 82

Preparation of N-phenylhexylamine from Phenyl Trifluoromethanesulfonate

An oven-dried resealable 15 mL Schlenk tube was charged with CuI (19.5 mg, 0.102 mmol, 10 mol %), 2-phenylphenol (86 mg, 0.505 mmol, 50 mol %), K$_3$PO$_4$ (440 mg, 2.07 mmol), evacuated and backfilled with argon. n-Hexylamine (135 μL, 1.02 mmol) and phenyl trifluoromethanesulfonate (0.98 mL, 6.05 mmol) were added under argon. The Schlenk tube was sealed with a Teflon valve and the reaction mixture was stirred magnetically at 120° C. for 23 h. The resulting thick, brown suspension was allowed to reach room temperature and was then diluted with ethyl acetate (2 mL). Dodecane (230 μL; internal GC standard) was added and a sample of the supernatant solution was analyzed by GC revealing 1% yield of the desired product. The identity of the product was confirmed by GC-MS (signal at 177 m/z).

Example 83

Preparation of N-(4-methylphenyl)hexylamine from 4-chlorotoluene

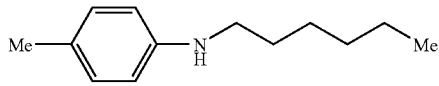

An oven-dried resealable 15 mL Schlenk tube was charged with CuI (19.5 mg, 0.102 mmol, 10 mol %), 2-phenylphenol (86 mg, 0.505 mmol, 50 mol %), $K_3PO_4$ (440 mg, 2.07 mmol), evacuated and backfilled with argon. n-Hexylamine (135 μL, 1.02 mmol) and 4-chlorotoluene (0.95 mL, 8.01 mmol) were added under argon. The Schlenk tube was sealed with a Teflon valve and the reaction mixture was stirred magnetically at 120° C. for 23 h. The resulting brown suspension was allowed to reach room temperature and filtered through a 0.5×1 cm silica plug eluting with dichloromethane (10 mL). The filtrate was concentrated and the residue was purified by flash chromatography on silica gel (2×20 cm; hexane-dichloromethane 2:1; 15 mL fractions). Fractions 12-23 were concentrated and the residue was further purified by flash chromatography on silica gel (2×15 cm; hexane-ethyl acetate 20:1; 15 mL fractions). Fractions 9-15 provided 85 mg (44% yield) of the pure desired product as large colorless crystals. The $^1H$ and $^{13}C$ NMR spectra were in accord with those reported. Wolfe, J. P.; Buchwald, S. L. *J. Org. Chem.* 1996, 61, 1133.

Example 84

Preparation of N-phenyl-N',N',N'',N''-tetramethylguanidine using 2-phenylphenol as the ligand in toluene

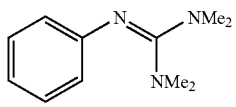

A 15 mL Schlenk tube was charged with CuI (9.6 mg, 0.0504 mmol, 5.0 mol %), 2-phenylphenol (34 mg, 0.200 mmol, 20 mol %), $K_3PO_4$ (430 mg, 2.03 mmol), evacuated and backfilled with argon. Iodobenzene (112 μL, 1.00 mmol), N,N,N',N'-tetramethylguanidine (190 μL, 1.51 mmol) and toluene (1.0 mL) were added under argon. The Schlenk tube was sealed with a Teflon valve and stirred at 110° C. for 23 h. The resulting pale brown suspension was allowed to reach room temperature and then filtered through a Celite plug eluting with dichloromethane. The filtrate was concentrated and the residue was purified by flash chromatography on silica gel (2×15 cm; methanol-dichloromethane (saturated with 30% aq $NH_3$) 1:5, 20 mL fractions). Fractions 26-43 provided 159 mg (83% yield) of the desired product.

Example 85

2-(N-Benzyl)aminobenzoic acid

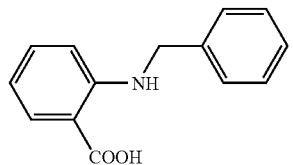 [SMILES: O=C(O)c1ccccc1NCc1ccccc1]

Aryl Bromide Substrate

Copper(I) iodide (19 mg, 0.10 mmol), $K_3PO_4$ (636 mg, 3.00 mmol) and 2-bromobenzoic acid (201 mg, 1.00 mmol) were put into a screw-capped test tube with a Teflon septum. The tube was evacuated and back-filled with argon three times. 1-Butanol (1.0 mL), ethylene glycol (111 μL, 2.00 mmol) and benzylamine (131 μL, 1.20 mmol) were added by micro-syringes. The reaction was heated at 100° C. for 48 hours to give a pale blue suspension. After the reaction mixture was allowed to reach room temperature, water and diluted HCl (10%) were added until ~pH 3. Diethyl ether (2 mL) was added and the organic layer was analyzed by tlc. The reaction mixture was further extracted by diethyl ether (4×10 mL) and the combined organic phases were washed with brine and dried over $Na_2SO_4$. Column chromatography on silica gel eluting with diethyl ether/ethyl acetate=1/1 provided 2-(N-benzyl)aminobenzoic acid (120 mg, 53% isolated yield) as a light yellow solid.

Aryl Chloride Substrate

Copper(I) iodide (19 mg, 0.10 mmol), $K_3PO_4$ (636 mg, 3.00 mmol), benzylamine (131 μL, 1.20 mmol), 2-chlorobenzoic acid (157 mg, 1.00 mmol), ethylene glycol (111 μL, 2.00 mmol) and 1-butanol (1.0 mL) were used and heated to 100° C. for 72 hours. The above workup procedure was followed and gave 2-(N-benzyl)aminobenzoic acid (109 mg, 48% isolated yield) as a light yellow solid.

Aryl Iodide Substrate

Copper(I) iodide (10 mg, 0.05 mmol), $K_3PO_4$ (636 mg, 3.00 mmol), benzylamine (131 μL, 1.20 mmol), 2-iodobenzoic acid (248 mg, 1.00 mmol), ethylene glycol (111 μL, 2.00 mmol) and 2-propanol (1.0 mL) were used and heated at 80° C. for 18 hours. The above workup procedure was followed and gave 2-(N-benzyl)aminobenzoic acid (161 mg, 71% isolated yield) as a light yellow solid.

Example 86

General Procedure for Amination of Bromobenzene in Toluene Under an Ar Atmosphere Copper (I) iodide (10 mg, 0.05 mmol, 5 mol %), anhydrous fine powder potassium phosphate (425 mg, 2.0 mmol) and the substituted phenol (0.2 mmol, 20 mol %) were put into a screw-capped test tube with a Teflon septum. The tube was evacuated and back-filled with argon (3 cycles). Anhydrous toluene (1.0 mL), bromobenzene (105 μL, 1.0 mmol) and n-hexylamine (158 μL, 1.2 mmol) were added by micro-syringe at room temperature. The reaction mixture was heated at 100° C. for 18 hours. The reaction mixture was then allowed to reach room temperature. Diethyl ether (2 mL), water (2 mL) and dodecane (internal standard, 227 μL) were added. The organic layer was analyzed by GC to determine the yield of N-phenylhexylamine. Examples using the above procedure are tabulated in FIG. 4.

Example 87

Preparation of N-phenylhexylamine Using 2,6-dimethylphenol as the Ligand and DMF as the Solvent Copper (I) iodide (10 mg, 0.05 mmol, 5 mol %), anhydrous fine powder potassium phosphate (425 mg, 2.0 mmol) and 2,6-dimethylphenol (24 mg, 0.2 mmol, 20 mol %) were put into a screw-capped test tube with a Teflon septum. The tube was evacuated and back-filled with argon (3 cycles). Anhydrous DMF (1.0 mL), bromobenzene (105 μL, 1.0 mmol) and n-hexylamine (158 μL, 1.2 mmol) were added by micro-syringe at room temperature. The reaction mixture was heated at 100° C. for 18 hours. The reaction mixture was then allowed to reach room temperature. Diethyl ether (2 mL), water (2 mL) and dodecane (internal standard, 227 μL) were added. The organic layer was analyzed by PC to give 48% GC yield of N-phenylhexylamine.

Example 88

Preparation of N-phenylhexylamine Using 2,6-dimethylphenol as the Ligand and No Solvent Copper (I) iodide (10 mg, 0.05 mmol, 5 mol %), anhydrous fine powder potassium phosphate (425 mg, 2.0 mmol) and 2,6-dimethylphenol (24 mg, 0.2 mmol, 20 mol %) were put into a screw-capped test tube with a Teflon septum. The tube was evacuated and back-filled with argon (3 cycles). Bromobenzene (105 μL, 1.0 mmol) and n-hexylamine (1.05 mL, 8.0 mmol) were added by micro-syringe at room temperature. The reaction mixture was heated at 100° C. for 18 hours. The reaction mixture was then allowed to reach room temperature. Diethyl ether (2 mL), water (2 mL) and dodecane (internal standard, 227 μL) were added. The organic layer was analyzed by GC to give 100% conversion of bromobenzene. The aqueous phase was further extracted with diethyl ether (4×10 mL). The combined organic phases were washed with water, brine and dried over sodium sulfate. The solvent was removed by rotary evaporation and the residue was purified by column chromatography on silica gel eluting with hexane/ethyl acetate=20/1 to afford N-phenylhexylamine a colorless oil (152 mg, 86% isolated yield).

Example 89

Procedure for Amination of Bromobenzene Under an Air Atmosphere

Copper (I) iodide (10 mg, 0.05 mmol, 5 mol %), anhydrous fine powder potassium phosphate (425 mg, 2.0 mmol) and 2-phenylphenol (34 mg, 0.2 mmol, 20 mol %) were put into a screw-capped test tube with a Teflon septum. Anhydrous toluene (1.0 mL), bromobenzene (105 μL, 1.0 mmol) and n-hexylamine (158 μL, 1.2 mmol) were added by micro-syringe at room temperature under air atmosphere. The reaction mixture was heated at 100° C. for 22 hours. The reaction mixture was then allowed to reach room temperature. Diethyl ether (2 mL), water (2 mL) and dodecane (internal standard, 227 μL) were added. The organic layer was analyzed by GC to give 33% GC yield of N-phenylhexylamine.

Example 90

Procedures for Amination of Aryl Iodides in Toluene Under an Argon Atmosphere

Iodobenzene Substrate

Copper (I) iodide (10 mg, 0.05 mmol, 5 mol %), anhydrous fine powder potassium phosphate (425 mg, 2.0 mmol) and 2,6-dimethylphenol (24 mg, 0.2 mmol, 20 mol %) were put into a screw-capped test tube with a Teflon septum. The tube was evacuated and back-filled with argon (3 cycles). Iodobenzene (112 μL, 1.0 mmol) and n-hexylamine (158 μL, 1.0 mmol) were added by micro-syringe at room temperature. The reaction mixture was heated at 80° C. for 18 hours. The reaction mixture was then allowed to reach room temperature. Diethyl ether (2 mL), water (2 mL) and dodecane (internal standard, 227 μL) were added. The organic layer was analyzed by GC to give 41% GC yield of N-phenylhexylamine.

2-Iodoanisole Substrate

Copper (1) iodide (10 mg, 0.05 mmol, 5 mol %), anhydrous fine powder potassium phosphate (425 mg, 2.0 mmol) and 2,6-dimethylphenol (24 mg, 0.2 mmol, 20 mol %) were put into a screw-capped test tube with a Teflon septum. The tube was evacuated and back-filled with argon (3 cycles). 2-Iodoanisole (130 μL, 1.0 mmol) and n-hexylamine (158 μL, 1.0 mmol) were added by micro-syringe at room temperature. The reaction mixture was heated at 80° C. for 18 hours. The reaction mixture was then allowed to reach room temperature. Diethyl ether (2 mL), water (2 mL) and dodecane (internal standard, 227 μL) were added. The organic layer was analyzed by GC to give 41% GC yield of N-(2-methoxyphenyl)hexylamine.

Example 91

1-Phenyl-2-(2-tolylamino)ethanol

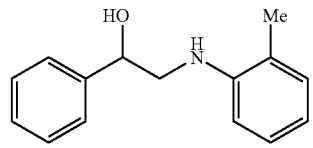 [SMILES: Cc1ccccc1NCC(O)c1ccccc1]

A 15 mL screw top test tube fitted with a PTFE septum cap was purged with argon before addition of CuI (5.0 mg, 0.026 mmol, 2.6 mol %), NaOH (83.0 mg, 2.08 mmol), and rac-2-amino-1-phenylethanol (143 mg, 1.04 mmol). 2-Iodotoluene (159 μL, 1.25 mmol) and isopropyl alcohol (1.0 mL) were added, via syringe, under argon. The septum cap was replaced with a solid, Teflon-lined cap and the reaction was stirred magnetically at 90° C. for 48 h. The resulting homogeneous solution was allowed to cool before dilution with 10 mL brine. The reaction mixture was transferred to a separatory funnel and extracted with methylene chloride (3×10 mL). The organics were washed with 0.1 M NaOH (2×10 mL), washed with brine (1×15 mL), dried over MgSO$_4$ and concentrated. The crude material was purified by silica gel chromatography

Example 92 trans-2-Phenylamino cyclohexanol

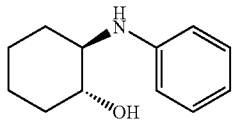 [SMILES: O[C@@H]1CCCC[C@H]1Nc1ccccc1]

A 15 mL screw top test tube fitted with a PTFE septum cap was purged with argon before addition of CuI (5.0 mg, 0.026 mmol, 2.6 mol %), NaOH (83.0 mg, 2.08 mmol) and rac-2-amino-1-cyclohexanol HCl (158 mg, 1.04 mmol). Iodobenzene (139 μL, 1.25 mmol), dimethyl sulfoxide (670 μL), and a stock solution of 9.45 M NaOH (330 μL, 3.12 mmol) were added, via syringe, under argon. The septum cap was replaced with a solid, Teflon-lined cap and the reaction was stirred magnetically at 90° C. for 48 h. The resulting homogeneous solution was allowed to cool before dilution with 10 mL brine. The reaction mixture was transferred to a separatory funnel and extracted with diethyl ether (3×10 mL). The organic extracts were washed with 3 M HCl (3×10 mL). The acid extracts were then cooled in an ice bath and the solution was basified using a saturated NaOH solution. When the pH of the solution became basic, as indicated by pH paper, the solution became opaque. The mixture was transferred to a separatory funnel and extracted with methylene chloride (3×10 mL). The organic extract was washed with brine, dried over $MgSO_4$ and concentrated. A pale yellow oil was obtained and placed under high vacuum overnight. While under vacuum the oil solidified to give 182.5 mg (92% yield) of an off-white solid, mp 57-58° C.

Example 93 trans-2-(2-Chlorophenylamino)cyclohexanol

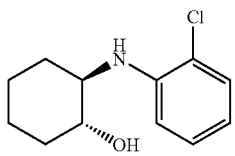 [SMILES: O[C@@H]1CCCC[C@H]1Nc1ccccc1Cl]

A 15 mL screw top test tube fitted with a PTFE septum cap was purged with argon before addition of CuI (5.0 mg, 0.026 mmol, 2.6 mol %), NaOH (125 mg, 3.12 mmol) and rac-2-amino-1-cyclohexanol HCl (158 mg, 1.04 mmol). 2-Chloro-1-iodobenzene (152 μL, 1.25 mmol) and isopropyl alcohol (1.0 mL) were added, via syringe, under argon. The septum cap was replaced with a solid, Teflon-lined cap and the reaction was stirred magnetically at 90° C. for 48 h. The resulting homogeneous solution was allowed to cool before dilution with 10 mL brine. The reaction mixture was transferred to a separatory funnel and extracted with methylene chloride (3×10 mL). The organics were washed with brine, dried over $MgSO_4$ and concentrated. The crude material was purified by silica gel chromatography using hexanes/ethyl acetate (60:40). The product was obtained as a yellow oil in 91% yield (212.7 mg).

Example 94

2-[Ethyl-(2-methoxyphenyl)amino]ethanol

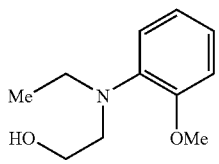

A 15 mL screw top test tube fitted with a PTFE septum cap was purged with argon before addition of CuI (5.0 mg, 0.026 mmol, 2.6 mol %) and NaOH (83.0 mg, 2.08 mmol). 2-(aminoethyl)-ethanol (101 μL, 1.04 mmol), 2-iodoanisole (162 μL, 1.25 mmol) and isopropyl alcohol (1.0 mL) were added, via syringe, under argon. The septum cap was replaced with a solid, Teflon-lined cap and the reaction was stirred magnetically at 90° C. for 48 h. The resulting homogeneous solution was allowed to cool before dilution with 10 mL brine. The reaction mixture was transferred to a separatory funnel and extracted with methylene chloride (3×10 mL). The organics were washed with 0.1 M NaOH (2×10 mL), washed with brine (1×15 mL), dried over $MgSO_4$ and concentrated. The crude material was purified by silica gel chromatography using methylene chloride/ethyl acetate (70:30). The product was obtained as a pale yellow, viscous oil in 72% yield (145.8 mg).

Example 95

2-(3-Nitrophenylamino)-1-phenylethanol

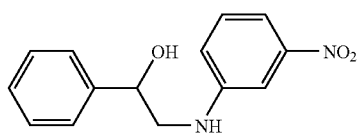

A 15 mL screw top test tube fitted with a PTFE septum cap was purged with argon before addition of CuI (5.0 mg, 0.026 mmol, 2.6 mol %), $K_3PO_4$ (425 mg, 2.0 mmol), rac-2-amino-1-phenylethanol (140 mg, 1.02 mmol) and 1-iodo-3-nitrobenzene (302 mg, 1.25 mmol). Ethylene glycol (56 μL, 1.02 mmol) and isopropyl alcohol (1.0 mL) were added, via syringe, under argon. The septum cap was replaced with a solid, Teflon-lined cap and the reaction was stirred magnetically at 75° C. for 48 h. The reaction mixture was allowed to cool before dilution with 10 mL brine and extraction with methylene chloride (3×10 mL). The organic extracts were washed with 0.1 M NaOH (2×10 mL), washed with brine (1×15 mL), dried over $MgSO_4$ and concentrated. The crude material was purified by silica gel chromatography using methylene chloride/ethyl acetate (96:4). The product was obtained as an orange, viscous oil in 66% yield (172.8 mg).

Example 96

N-Phenylephedrine

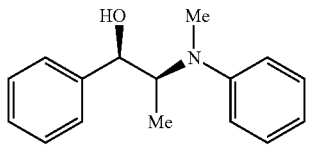 [SMILES: C[C@@H]([C@H](O)c1ccccc1)N(C)c1ccccc1]

A 15 mL screw top test tube fitted with a PTFE septum cap was purged with argon before addition of CuI (10.0 mg, 0.052 mmol, 5.2 mol %), NaOtBu (288 mg, 3.0 mmol) and (1R,2S)-ephedrine HCl (202 mg, 1.0 mmol). Iodobenzene (168 µL, 1.5 mmol) and dimethyl sulfoxide (1.25 mL) were added, via syringe, under argon. The septum cap was replaced with a solid, Teflon-lined cap and the reaction was stirred magnetically at 100° C. for 22 h. The resulting solution was allowed to cool before dilution with 10 mL brine. The reaction mixture was transferred to a separatory funnel and extracted with methylene chloride (3×10 mL). The organics were washed with 0.1 M NaOH (2×10 mL), washed with brine (1×15 mL), dried over MgSO$_4$ and concentrated. The crude material was purified by silica gel chromatography using methylene chloride. The product was obtained as a pale yellow, viscous oil in 72% yield (175 mg). $^1$H NMR (500 MHz, CDCl$_3$): ∂ 1.16 (d, J=6.9 Hz, 3H), ∂ 2.39 (broad s, 1H), a 2.70 (s, 3H), ∂ 4.01 (dq, J=6.9, 5.5 Hz, 1H), ∂ 4.74 (d, J=5.2 Hz, 1H), ∂ 6.68 (m, 3H), ∂ 7.20 (m, 7H). $^{13}$C NMR (125 MHz, CDCl$_3$): ∂ 12.1, 32.4, 59.5, 75.9, 113.3, 116.8, 125.9, 127.3, 128.1, 129.0, 142.5, 150.0.

Example 97

Preparation of O-phenylephedrine

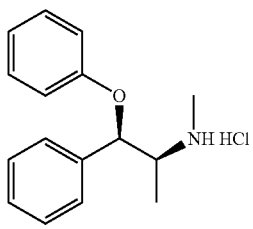

A 15 mL screw top test tube fitted with a PTFE septum cap was charged with CuI (10.0 mg, 0.05 mmol, 5 mol %), Cs$_2$CO$_3$ (652 mg, 2.00 mmol), and (1R,2S)-ephedrine (165 mg, 1.00 mmol). Iodobenzene (168 µL, 1.50 mmol) and butyronitrile (1 mL) were added, via syringe, while purging with nitrogen. The septum cap was replaced with a solid, Teflon-lined cap and the reaction was stirred magnetically at 125° C. for 25.5 h. The resulting heterogeneous solution was allowed to cool before dilution with 5 mL ethyl acetate. The reaction mixture was filtered and the solvent was removed to yield a dark oil; this oil was taken up in a small volume of ether and then added to dilute HCl. The resulting white precipitate was collected by vacuum filtration and washed well with hexanes. After drying in vacuo, a 67% yield (187.1 mg) of the HCl salt was obtained. All characterization data are for the free base. $^1$H NMR (300 MHz, CDCl$_3$): δ 1.12 (d, J=6.3 Hz, 3H), 1.34 (broad s, 1H), 2.43 (s, 3H), 2.92 (dq, J=6.6, 4.4 Hz, 1H), 5.17 (d, 1H), 6.83 (m, 3H), 7.22 (m, 7H). $^{13}$C NMR (75.5 MHz, CDCl$_3$): 14.8, 34.0, 60.3, 81.3, 115.6, 120.6, 126.4, 127.4, 128.3, 129.1, 139.2, 158.0.

Example 98

Benzyl Phenylamine Using Sodium Hydroxide as Base in DMSO

A 15 mL screw top test tube fitted with a PTFE septum cap was purged with argon before addition of CuI (10.0 mg, 0.052 mmol, 5 mol %). Iodobenzene (116 µL, 1.04 mmol), benzylamine (114 µL, 1.04 mmol), dimethylsulfoxide (660 µL) and 6.33 M NaOH (330 µL, 2.08 mmol) were added via syringe. The test tube was purged with argon before replacing the septum cap with a solid, Teflon-lined cap. The reaction was stirred magnetically at 110° C. for 4.25 h. The reaction mixture was allowed to cool before dilution with 10 mL water and extraction with diethyl ether (3×10 mL). The organic extracts were washed with 3.0 M HCl (3×10 mL). The acid extracts were cooled in an ice bath and the solution was basified using a saturated NaOH solution. When the pH of the solution became basic, as indicated by pH paper, the solution became opaque. The mixture was transferred to a separatory funnel and extracted with methylene chloride (3×10 mL). The organic extract was washed with brine, dried over MgSO$_4$ and concentrated. The product was obtained as a pale yellow, viscous oil in 19% yield (35.9 mg).

Example 99

N-Phenylbenzylamine, N-phenyl-N-methylbenzylamine, N-phenyl-(1-phenylethyl)amine and N-phenylpiperidine using sodium hydroxide as base in DMSO A 15 mL screw top test tube fitted with a PTFE septum cap was purged with argon before addition of CuI (10.0 mg, 0.052 mmol, 5 mol %). Iodobenzene (116 µL, 1.04 mmol), amine (1.04 mmol), dimethylsulfoxide (660 µL) and 6.33 M NaOH (330 µL, 2.08 mmol) were added via syringe. The test tube was purged with argon before replacing the septum cap with a solid, Teflon-lined cap. The reaction was stirred magnetically at 95° C. for 20.5 h. The reaction mixture was allowed to cool before dilution with 5 mL water and 5 mL diethyl ether. An aliquot was removed for GC analysis; GC yields were 26%, 6%, 12%, and 13%, respectively.

Example 100

N-Arylation of 5-amino-1-pentanol and 4-amino-1-butanol using sodium hydroxide as base in DMSO A 15 mL screw top test tube fitted with a PTFE septum cap was purged with argon before addition of CuI (10.0 mg, 0.052 mmol, 5 mol %). Iodobenzene (116 µL, 1.04 mmol), aminoalcohol (1.04 mmol), dimethylsulfoxide (660 µL) and 6.33 M NaOH (330 µL, 2.08 mmol) were added via syringe. The test tube was purged with argon before replacing the septum cap with a solid, Teflon-lined cap. The reaction was stirred magnetically at 90° C. for 24 h. The reaction mixture was allowed to cool before dilution with 10 mL water and extraction with diethyl ether (3×10 mL). The organic extracts were washed with 3.0 M HCl (3×10 mL). The acid extracts were cooled in an ice bath and the solution was basified using a saturated NaOH solution. When the pH of the solution became basic, as indicated by pH paper, the solution became opaque. The mixture was transferred to a separatory funnel and extracted with methylene chloride (3×10 mL). The organic extract was washed with brine, dried over MgSO$_4$ and concentrated. A pale yellow oil was obtained and placed under high vacuum overnight. The products were obtained as light yellow, viscous oils; the isolated yields were 49% and 47%, respectively.

Example 101

2-phenylamino Ethanol Using Sodium Hydride as Base in THF

An oven-dried 15 mL screw top test tube fitted with a PTFE septum cap was purged with argon before addition of CuI (10.0 mg, 0.052 mmol, 5 mol %), NaH (60% dispersion in mineral oil, 25 mg, 1.04 mmol), ethanolamine (63 μL, 1.04 mmol) and tetrahydrofuran (1 mL). The reaction was stirred until bubbling subsided. Iodobenzene (116 μL, 1.04 mmol) was added via syringe and the test tube was purged with argon before replacing the septum cap with a solid, Teflon-lined cap. The reaction was stirred magnetically at 65° C. for 24 h. The reaction mixture was allowed to cool before dilution with 10 mL water and extraction with diethyl ether (3×10 mL). The organic extracts were washed with brine, dried over MgSO$_4$ and concentrated. The crude material was purified by column chromatography using hexane/ethyl acetate (25:75). The product was obtained as an oil in 52% yield $^1$H NMR (500 MHz, CDCl$_3$): ∂2.54 (broad s, 1H), ∂ 3.24 (t, J=5.2 Hz, 2H), ∂ 3.76 (t, J=5.2 Hz, 2H), ∂ 4.00 (broad s, 1H), ∂ 6.62 (m, 2H), ∂ 6.73 (m, 1H), ∂ 7.17 (m, 2H). $^{13}$C NMR (125 MHz, CDCl$_3$): ∂ 46.0, 61.0, 113.2, 117.8, 129.2, 148.0.

Example 102

Preparation of 1-butoxy-3,5-dimethylbenzene without solvent using 2-phenylphenol as ligand and cesium carbonate as base

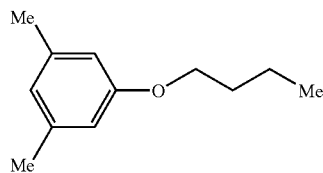

A screw cap test tube was charged with n-butanol (1.37 mL, 15.0 mmol), 3,5-dimethyliodobenzene (150 μL, 1.04 mmol), CuI (19.8 mg, 0.104 mmol), Cs$_2$CO$_3$ (977 mg, 3.00 mmol) and 2-phenylphenol (88.5 mg, 0.520 mmol). The test tube was sealed with a screw cap. The reaction mixture was stirred magnetically and heated at 105° C. for 40 hours. The reaction mixture was allowed to reach room temperature. Dodecane (237 μL, 1.04 mmol; internal standard) was added and a GC sample was filtered through Celite and eluted with CH$_2$Cl$_2$. GC analysis revealed 64% yield of the desired product. The identity of the product was confirmed by $^1$H NMR and GC-MS (signal at 178 m/z). $^1$H NMR (400 MHz, CDCl$_3$): δ 6.52 (s, 1H), 6.47 (s, 2H), 3.88 (t, J=6.5 Hz, 2H), 2.21 (s, 6H), 1.72-1.63 (m, 2H), 1.47-1.32 (m, 2H), 0.90 (t, J=7.4 Hz, 3H).

Example 103

Preparation of 1-butoxy-3,5-dimethylbenzene without solvent using 2-phenylphenol as ligand and potassium phosphate as base A screw cap test tube was charged with n-butanol (1.37 mL, 15.0 mmol), 3,5-dimethyliodobenzene (150 μL, 1.04 mmol), CuI (19.8 mg, 0.104 mmol), K$_3$PO$_4$ (571 mg, 2.69 mmol) and 2-phenylphenol (88.5 mg, 0.520 mmol). The test tube was sealed with a screw cap. The reaction mixture was stirred magnetically and heated at 105° C. for 40 hours. The reaction mixture was allowed to reach room temperature. Dodecane (237 μL, 1.04 mmol; internal standard) was added and a GC sample was filtered through Celite and eluted with CH$_2$Cl$_2$. GC analysis revealed 5% yield of the desired product.

Example 104

Preparation of 1-butoxy-3,5-dimethylbenzene using various ligands

A screw cap test tube was charged with n-butanol (573 μL, 6.26 mmol), 3,5-dimethyliodobenzene (144 μL, 1.00 mmol), CuI (19.0 mg, 0.100 mmol), Cs$_2$CO$_3$ (977 mg, 3.00 mmol), the ligand (0.500 mmol) and toluene (1 mL). The test tube was sealed with a screw cap. The reaction mixture was stirred magnetically and heated at 105° C. for 36 hours. The reaction mixture was allowed to reach room temperature. Dodecane (227 μL, 1.00 mmol; internal standard) was added and a GC sample was filtered through Celite and eluted with CH$_2$Cl$_2$. The yield of the desired product was determined using GC analysis; the results are tabulated below.

| Ligand | GC yield |
| --- | --- |
| 2-Phenylphenol | 81% |
| 2,6-Dimethylphenol | 75% |
| 2-Isopropylphenol | 65% |
| 1-Naphthol | 43% |
| 2-(Dimethylamino)ethanol | 46% |
| N,N-Dimethylglycine | 73% |
| Methyliminodiacetic acid | 28% |
| N,N,N',N'-Tetramethylethylenediamine | 20% |

Example 105

Preparation of 1-butoxy-3,5-dimethylbenzene using various solvents

A screw cap test tube was charged with n-butanol (573 μL, 6.26 mmol), 3,5-dimethyliodobenzene (144 μL, 1.00 mmol), CuI (19.0 mg, 0.100 mmol), Cs$_2$CO$_3$ (977 mg, 3.00 mmol), 2-phenylphenol (85.1 mg, 0.500 mmol) and the solvent (1 mL). The test tube was sealed with a screw cap. The reaction mixture was stirred magnetically and heated at 90° C. for 36 hours. The reaction mixture was allowed to reach room temperature. Dodecane (227 μL, 1.00 mmol; internal standard) was added and a GC sample was filtered through Celite and eluted with CH$_2$Cl$_2$. The yield of the desired product was determined using GC analysis; the results are tabulated below.

| Solvent | GC yield |
|---|---|
| 1,4-Dioxane | 46% |
| 1,2-Dimethoxyethane | 42% |
| Triethylamine | 55% |

Example 106

Preparation of 1-butoxy-3,5-dimethylbenzene without ligand using cesium carbonate as base and toluene as solvent A screw cap test tube was charged with n-butanol (1.25 mL, 13.7 mmol), 3,5-dimethyliodobenzene (144 µL, 1.00 mmol), CuI (19.0 mg, 0.100 mmol), $Cs_2CO_3$ (977 mg, 3.00 mmol) and toluene (1 mL). The test tube was sealed with a screw cap. The reaction mixture was stirred magnetically and heated at 105° C. for 42 hours. The reaction mixture was allowed to reach room temperature. Dodecane (227 µL, 1.00 mmol; internal standard) was added and a GC sample was filtered through Celite and eluted with $CH_2Cl_2$. GC analysis revealed 50% yield of the desired product.

Example 107

Preparation of 1-butoxy-3,5-dimethylbenzene using 1,10-phenanthroline as ligand, cesium carbonate as base and toluene as solvent A screw cap test tube was charged with n-butanol (183 µl, 2.00 mmol), 3,5-dimethyliodobenzene (144 µL, 1.00 mmol), CuI (19.0 mg, 0.100 mmol), $Cs_2CO_3$ (977 mg, 3.00 mmol), 1,10-phenanthroline (90.1 mg, 0.500 mmol) and toluene (1 mL). The test tube was sealed with a screw cap. The reaction mixture was stirred magnetically and heated at 110° C. for 40 hours. The reaction mixture was allowed to reach room temperature. Dodecane (227 µL, 1.00 mmol; internal standard) was added and a GC sample was filtered through Celite and eluted with $CH_2Cl_2$. GC analysis revealed 83% yield of the desired product.

Example 108

4-Butoxyaniline

A test tube was charged with CuI (20 mg, 0.10 mmol, 10 mol %), 1,10-phenanthroline (36 mg, 0.20 mmol, 20 mol %), $Cs_2CO_3$ (456 mg, 1.4 mmol), 4-iodoaniline (219 mg, 1.0 mmol) and n-butanol (1.0 mL). The test tube was sealed and the reaction mixture was stirred at 110° C. for 23 h. The resulting suspension was cooled to room temperature and filtered through a 0.5×1 cm pad of silica gel eluting with ethyl acetate. The filtrate was concentrated. Purification of the residue by flash chromatography on silica gel (2×20 cm; hexane/ethyl acetate 10:1) provided 66 mg (40% yield) of the title compound as a red-brown oil.

Example 109

2-Butoxytoluene

A test tube was charged with CuI (20 mg, 0.10 mmol, 10 mol %), 1,10-phenanthroline (36 mg, 0.20 mmol, 20 mol %), $Cs_2CO_3$ (456 mg, 1.4 mmol), 2-iodotoluene (127 µL, 1.0 mmol) and n-butanol (1.0 mL). The test tube was sealed and the reaction mixture was stirred at 110° C. for 23 h. The resulting suspension was cooled to room temperature and filtered through a 0.5×1 cm pad of silica gel eluting with ethyl acetate. The filtrate was concentrated. Purification of the residue by flash chromatography on silica gel (2×20 cm; hexane) provided 159 mg (97% yield) of the title compound as a colorless oil.

Example 110

Preparation of 3-butoxyanisole using 5 mol % CuI

A test tube was charged with CuI (10 mg, 0.050 mmol, 5 mol %), 1,10-phenanthroline (36 mg, 0.20 mmol, 20 mol %), $Cs_2CO_3$ (456 mg, 1.4 mmol), 3-iodoanisole (119 µL, 1.0 mmol) and n-butanol (1.0 mL). The test tube was sealed and the reaction mixture was stirred at 110° C. for 20 h. The resulting suspension was cooled to room temperature and filtered through a 0.5×1 cm pad of silica gel eluting with ethyl acetate. The filtrate was concentrated. Purification of the residue by flash chromatography on silica gel (2×20 cm; hexane) provided 177 mg (98% yield) of the title compound as a pale yellow oil.

Example 111

3-Butoxypyridine

A test tube was charged with CuI (20 mg, 0.10 mmol, 10 mol %), 1,10-phenanthroline (36 mg, 0.20 mmol, 20 mol %), $Cs_2CO_3$ (652 mg, 2.0 mmol), 3-iodopyridine (205 mg, 1.0 mmol) and n-butanol (1.0 mL). The test tube was sealed and the reaction mixture was stirred at 110° C. for 23 h. The resulting suspension was cooled to room temperature and filtered through a 0.5×1 cm pad of silica gel eluting with ethyl acetate. The filtrate was concentrated. Purification of the residue by flash chromatography on silica gel (2×20 cm; hexane/ethyl acetate 8:1) provided 125 mg (83% yield) of the title compound as a light yellow oil.

Example 112

4-Isopropoxyanisole

A test tube was charged with CuI (20 mg, 0.10 mmol, 10 mol %), 1,10-phenanthroline (36 mg, 0.20 mmol, 20 mol %), $Cs_2CO_3$ (456 mg, 1.4 mmol), 4-iodoanisole (234 mg, 1.0 mmol) and isopropanol (1.0 mL). The test tube was sealed and the reaction mixture was stirred at 110° C. for 23 h. The resulting suspension was cooled to room temperature and filtered through a 0.5×1 cm pad of silica gel eluting with ethyl acetate. The filtrate was concentrated. Purification of the residue by flash chromatography on silica gel (2×20 cm; hexane/ethyl acetate 20:1) provided 138 mg (83% yield) of the title compound as a colorless oil.

Example 113

4-Cyclopentoxyanisole

A test tube was charged with CuI (20 mg, 0.10 mmol, 10 mol %), 5-methyl-1,10-phenanthroline (39 mg, 0.20 mmol, 20 mol %), $Cs_2CO_3$ (652 mg, 2.0 mmol), 4-iodoanisole (234 mg, 1.0 mmol) and cyclopentanol (1.0 mL). The test tube was sealed and the reaction mixture was stirred at 110° C. for 24 h. The resulting suspension was cooled to room temperature and filtered through a 0.5×1 cm pad of silica gel eluting with diethyl ether. The filtrate was concentrated. Purification of the residue by flash chromatography on silica gel (2×20 cm; pentane/diethyl ether 30:1) provided 128 mg (67% yield) of the title compound as a colorless oil.

Example 114

3-Ethoxyanisole

A test tube was charged with CuI (20 mg, 0.10 mmol, 10 mol %), 1,10-phenanthroline (36 mg, 0.20 mmol, 20 mol %), $Cs_2CO_3$ (456 mg, 1.4 mmol), 3-iodoanisole (119 μL, 1.0 mmol) and ethanol (1.0 mL). The test tube was sealed and the reaction mixture was stirred at 110° C. for 20 h. The resulting suspension was cooled to room temperature and filtered through a 0.5×1 cm pad of silica gel eluting with diethyl ether. The filtrate was concentrated. Purification of the residue by flash chromatography on silica gel (2×20 cm; pentane/diethyl ether 30:1) provided 142 mg (93% yield) of the title compound as a colorless oil.

Example 115

2-Methoxybenzyl Alcohol

A test tube was charged with CuI (20 mg, 0.10 mmol, 10 mol %), 1,10-phenanthroline (36 mg, 0.20 mmol, 20 mol %), $Cs_2CO_3$ (456 mg, 1.4 mmol), 2-iodobenzylalcohol (234 mg, 1.0 mmol) and methanol (1.0 mL). The test tube was sealed and the reaction mixture was stirred at 80° C. for 24 h. The resulting suspension was cooled to room temperature and filtered through a 0.5×1 cm pad of silica gel eluting with diethyl ether. The filtrate was concentrated. Purification of the residue by flash chromatography on silica gel (2×20 cm; pentane/diethyl ether 2:1) provided 122 mg (88% yield) of the title compound as a colorless oil.

Example 116

3-Butoxybenzonitrile

A test tube was charged with CuI (20 mg, 0.10 mmol, 10 mol %), 5-methyl-1,10-phenanthroline (39 mg, 0.20 mmol, 20 mol %), $Cs_2CO_3$ (652 mg, 2.0 mmol), 3-iodobenzonitrile (229 mg, 1.0 mmol), n-butanol (366 μL, 4.0 mmol) and toluene (1 mL). The test tube was sealed and the reaction mixture was stirred at 110° C. for 28 h. The resulting suspension was cooled to room temperature and filtered through a 0.5×1 cm pad of silica gel eluting with ethyl acetate. The filtrate was concentrated. Purification of the residue by flash chromatography on silica gel (2×20 cm; hexane/ethyl acetate 30:1) provided 152 mg (87% yield) of the title compound as a colorless oil.

Example 117

3-Methoxybenzonitrile

A test tube was charged with CuI (20 mg, 0.10 mmol, 10 mol %), 1,10-phenanthroline (36 mg, 0.20 mmol, 20 mol %), $Cs_2CO_3$ (652 mg, 2.0 mmol), 3-iodobenzonitrile (229 mg, 1.0 mmol), methanol (162 μL, 4.0 mmol) and toluene (1 mL). The test tube was sealed and the reaction mixture was stirred at 110° C. for 23 h. The resulting suspension was cooled to room temperature and filtered through a 0.5×1 cm pad of silica gel eluting with diethyl ether. The filtrate was concentrated. Purification of the residue by flash chromatography on silica gel (2×20 cm; pentane/diethyl ether 5:1) provided 111 mg (84% yield) of the title compound as a colorless oil.

Example 118

Regioselective preparation of 4-phenoxy-2-butanol from 1,3-butanediol

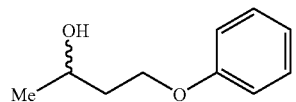 [SMILES: CC(O)CCOc1ccccc1]

A screw cap test tube was charged with 1,3-butanediol (178 μL, 2.00 mmol), iodobenzene (112 μL, 1.00 mmol), CuI (19.4 mg, 0.100 mmol), 5-methyl-1,10-phenanthroline (38.8 mg, 0.200 mmol), $Cs_2CO_3$ (652 mg, 2.00 mmol) and toluene (1.0 mL). The test tube was sealed with a screw cap. The reaction mixture was stirred magnetically and heated at 110° C. for 44 hours. The reaction mixture was allowed to reach room temperature. The reaction mixture was filtered over a short silica gel plug eluting with $CH_2Cl_2$. The solvent was removed under reduced pressure. Chromatography on silica gel (35 g, pentane/EtOAc 5:1) afforded the desired product in 55% yield.

Example 119

(R)-3-(1-phenylethoxy)anisole

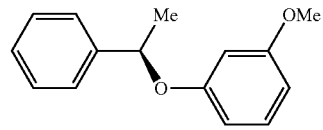 [SMILES: COc1cccc(O[C@H](C)c2ccccc2)c1]

A test tube was charged with CuI (20 mg, 0.10 mmol, 10 mol %), 5-methyl-1,10-phenanthroline (39 mg, 0.20 mmol, 20 mol %), $Cs_2CO_3$ (652 mg, 2.0 mmol), 3-iodoanisole (119 μL, 1.0 mmol), (R)-(+)-1-phenylethanol (205 μL, 1.7 mmol, >99% ee) and toluene (1 mL). The test tube was sealed and the reaction mixture was stirred at 110° C. for 32 h. The resulting suspension was cooled to room temperature and filtered through a 0.5×1 cm pad of silica gel eluting with ethyl acetate. The filtrate was concentrated. Purification of the residue by flash chromatography on silica gel (2×20 cm; hexane/ethyl acetate 30:1) provided 173 mg (76% yield, 98% ee) of the title compound as a colorless oil.

Example 120

Preparation of 1-heptoxy-3,5-dimethylbenzene using low catalyst loading

A screw cap test tube was charged with n-heptanol (283 μL, 2.00 mmol), 3,5-dimethyliodobenzene (144 μL, 1.00 mmol), CuI (4.75 mg, 0.025 mmol), 1,10-phenanthroline (1.80 mg, 0.01 mmol), $Cs_2CO_3$ (977 mg, 3.00 mmol) and o-xylene (1 mL). The test tube was sealed with a screw cap. The reaction mixture was stirred magnetically and heated at 120° C. for 19 hours. The reaction mixture was allowed to reach room temperature. Dodecane (227 μL, 1.00 mmol; internal standard)

Example 121

General procedure for the preparation of
1-heptoxy-3,5-dimethylbenzene using various
solvents A screw cap test tube was charged with n-heptanol (283 µL, 2.00 mmol), 3,5-dimethyliodobenzene (144 µL, 1.00 mmol), CuI (19.0 mg, 0.100 mmol), 1,10-phenanthroline (90.1 mg, 0.500 mmol), $Cs_2CO_3$ (977 mg, 3.00 mmol) and solvent (1 mL). The test tube was sealed with a screw cap. The reaction mixture was stirred magnetically and heated at 120° C. for 40 hours. The reaction mixture was allowed to reach room temperature. Dodecane (227 µL, 1.00 mmol; internal standard) was added and a GC sample was filtered through Celite and eluted with $CH_2Cl_2$. The yield of the desired product was determined using GC analysis; the results are tabulated below.

| Solvent | GC yield |
| --- | --- |
| DMF | 52% |
| tri-n-propylamine | 40% |
| n-butyronitrile | 62% |
| DMSO | 41% |

Example 122

General procedure for the preparation of
1-heptoxy-3,5-dimethylbenzene using various
nitrogen ligands A screw cap test tube was charged with n-heptanol (283 µL, 2.00 mmol), 3,5-dimethyliodobenzene (144 µL, 1.00 mmol), CuI (19.0 mg, 0.100 mmol), ligand (0.200 mmol), $Cs_2CO_3$ (977 mg, 3.00 mmol) and o-xylene (1 mL). The test tube was sealed with a screw cap. The reaction mixture was stirred magnetically and heated at 120° C. for 19 hours. The reaction mixture was allowed to reach room temperature. Dodecane (227 µL, 1.00 mmol; internal standard) was added and a GC sample was filtered through Celite and eluted with $CH_2Cl_2$. The yield of the desired product was determined using GC analysis; the results are tabulated below.

| Ligand | GC yield |
| --- | --- |
| 8-Hydroxyquinoline | 30% |
| 2-(Aminomethyl)pyridine | 28% |
| 8-Aminoquinoline | 6% |

Example 123

Preparation of 1-heptoxy-3,5-dimethylbenzene using
trans-N,N'-dimethyl-1,2-diaminocyclohexane as
ligand A screw cap test tube was charged with n-heptanol (283 µL, 2.00 mmol), 3,5-dimethyliodobenzene (144 µL, 1.00 mmol), CuI (19.0 mg, 0.100 mmol), trans-N,N'-dimethyl-1,2-diaminocyclohexane (71.1 mg, 0.500 mmol), $Cs_2CO_3$ (977 mg, 3.00 mmol) and o-xylene (1 mL). The test tube was sealed with a screw cap. The reaction mixture was stirred magnetically and heated at 140° C. for 17 hours. The reaction mixture was allowed to reach room temperature. Dodecane (227 µL, 1.00 mmol; internal standard) was added and a GC sample was filtered through Celite and eluted with $CH_2Cl_2$. GC analysis revealed 67% yield of the desired product.

Example 124

General procedure for the preparation of
1-heptoxy-3,5-dimethylbenzene using various
1,10-phenanthroline type ligands A screw cap test tube was charged with n-heptanol (283 µL, 2.00 mmol), 3,5-dimethyliodobenzene (144 µL, 1.00 mmol), CuI (19.0 mg, 0.100 mmol), ligand (0.200 mmol), $Cs_2CO_3$ (977 mg, 3.00 mmol) and toluene (1 mL). The test tube was sealed with a screw cap. The reaction mixture was stirred magnetically and heated at 110° C. for 39 hours. The reaction mixture was allowed to reach room temperature. Dodecane (227 µL, 1.00 mmol; internal standard) was added and a GC sample was filtered through Celite and eluted with $CH_2Cl_2$. The yield of the desired product was determined using GC analysis; the results are tabulated below.

| Ligand | GC yield |
| --- | --- |
| 1,10-Phenanthroline | 81% |
| 4,7-Diphenyl-1,10-phenanthroline | 91% |
| 4,7-Dimethyl-1,10-phenanthroline | 85% |
| 5-Methyl-1,10-phenanthroline | 95% |
| 5-Chloro-1,10-phenanthroline | 90% |
| 5-Nitro-1,10-phenanthroline | 41% |

Example 125

Preparation of 1-heptoxy-3,5-dimethylbenzene at
70° C.

A screw cap test tube was charged with n-heptanol (283 µl, 2.00 mmol), 3,5-dimethyliodobenzene (144 µL, 1.00 mmol), CuI (19.0 mg, 0.100 mmol), 5-methyl-1,10-phenanthroline (38.8 mg, 0.200 mmol), $Cs_2CO_3$ (977 mg, 3.00 mmol) and toluene (0.5 mL). The test tube was sealed with a screw cap. The reaction mixture was stirred magnetically and heated at 70° C. for 23 hours. The reaction mixture was allowed to reach room temperature. Dodecane (227 µL, 1.00 mmol; internal standard) was added and a GC sample was filtered through Celite and eluted with $CH_2Cl_2$. GC analysis revealed 68% yield of the desired product.

Example 126

Preparation of 1-heptoxy-3,5-dimethylbenzene at
70° C. in n-heptanol as solvent

A screw cap test tube was charged with n-heptanol (1.00 mL), 3,5-dimethyliodobenzene (144 µL, 1.00 mmol), CuI (19.0 mg, 0.100 mmol), 5-methyl-1,10-phenanthroline (38.8 mg, 0.200 mmol) and $Cs_2CO_3$ (977 mg, 3.00 mmol). The test tube was sealed with a screw cap. The reaction mixture was stirred magnetically and heated at 70° C. for 48 hours. The reaction mixture was allowed to reach room temperature. Dodecane (227 µL, 1.00 mmol; internal standard) was added and a GC sample was filtered through Celite eluting with CH$_2$Cl$_2$. GC analysis revealed 100% yield of the desired product.

Example 127

Preparation of 1-heptoxy-3,5-dimethylbenzene at room temperature in n-heptanol as solvent A screw cap test tube was charged with n-heptanol (1.00 mL), 3,5-dimethyliodobenzene (144 μL, 1.00 mmol), CuI (19.0 mg, 0.100 mmol), 5-methyl-1,10-phenanthroline (38.8 mg, 0.200 mmol) and Cs$_2$CO$_3$ (977 mg, 3.00 mmol). The test tube was sealed with a screw cap. The reaction mixture was stirred magnetically at room temperature for 29 hours. Dodecane (227 μL, 1.00 mmol; internal standard) was added and a GC sample was filtered through Celite eluting with CH$_2$Cl$_2$. GC analysis revealed 18% yield of the desired product.

Example 128

Preparation of 1-heptoxy-3,5-methylbenzene from 3,5-dimethylbromobenzene

A screw cap test tube was charged with n-heptanol (283 μL, 2.00 mmol), 3,5-dimethylbromobenzene (136 μL, 1.00 mmol), CuI (19.0 mg, 0.100 mmol), 1,10-phenanthroline (90.1 mg, 0.500 mmol), Cs$_2$CO$_3$ (977 mg, 3.00 mmol) and o-xylene (1 mL). The test tube was sealed with a screw cap. The reaction mixture was stirred magnetically and heated at 140° C. for 44 hours. The reaction mixture was allowed to reach room temperature. Dodecane (227 μL, 1.00 mmol; internal standard) was added and a GC sample was filtered through Celite and eluted with CH$_2$Cl$_2$. GC analysis revealed 16% yield of the desired product.

Example 129

Preparation of 2,3-dihydrobenzofuran from 2-bromophenethyl alcohol using 5-methyl-1,10-phenanthroline as the ligand

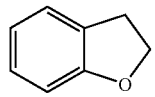

A screw cap test tube was charged with 2-bromophenethyl alcohol (136 μL, 1.00 mmol), CuI (19.0 mg, 0.100 mmol), 5-methyl-1,10-phenanthroline (38.8 mg, 0.200 mmol), Cs$_2$CO$_3$ (977 mg, 3.00 mmol) and toluene (1 mL). The test tube was sealed with a screw cap. The reaction mixture was stirred magnetically and heated at 110° C. for 43 hours. The reaction mixture was allowed to reach room temperature. Dodecane (227 μL, 1.00 mmol; internal standard) was added and a GC sample was filtered through Celite and eluted with CH$_2$Cl$_2$. GC analysis revealed 72% yield of the desired product.

Example 130

(R)-4-Benzyl-3-phenyl-2-oxazolidinone

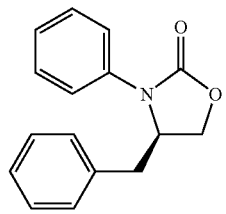 [SMILES: O=C1OC[C@@H](Cc2ccccc2)N1c1ccccc1]

A 15 mL resealable Schlenk tube was charged with CuI (9.6 mg, 0.0504 mmol, 5.0 mol %), (R)-4-benzyl-2-oxazolidinone (215 mg, 1.21 mmol), K$_2$CO$_3$ (280 mg, 2.03 mmol), evacuated and backfilled with argon. Racemic trans-N,N'-dimethyl-1,2-cyclohexanediamine (16 μL, 0.102 mmol, 10 mol %), iodobenzene (106 μL, 0.947 mmol) and toluene (1.0 mL) were added under argon. The Schlenk tube was sealed with a Teflon valve and the reaction mixture was stirred at 80° C. for 24 h. The resulting pale blue suspension was allowed to reach room temperature and then filtered through a 0.5×1 cm pad of silica gel eluting with 10 mL of ethyl acetate. The filtrate was concentrated and the residue was purified by flash chromatography on silica gel (2×15 cm, hexane-ethyl acetate 2:1, 15 mL fractions). Fractions 11-19 provided 238 mg (99% yield) of the desired product as a pale tan solid. HPLC analysis on a Daicel OD column (hexane-isopropanol 85:15, 0.7 mL/min, t$_r$(R)=23.3 min, t$_r$(S)=26.7 min) indicated >99.5% ee.

Example 131 trans-N-(4-Dimethylaminophenyl)-3-phenylpropenamide

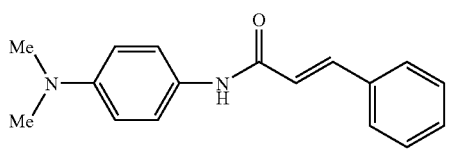 [SMILES: CN(C)c1ccc(NC(=O)/C=C/c2ccccc2)cc1]

A 15 mL resealable Schlenk tube was charged with CuI (9.6 mg, 0.0504 mmol, 5.0 mol %), 4-dimethylamino-1-bromobenzene (201 mg, 1.00 mmol), trans-cinnamamide (178 mg, 1.21 mmol), K$_2$CO$_3$ (280 mg, 2.03 mmol), evacuated and backfilled with argon. trans-N,N'-Dimethyl-1,2-cyclohexanediamine (16 μL, 0.102 mmol, 10 mol %) and toluene (1.0 mL) were added under argon. The Schlenk tube was sealed with a Teflon valve and the reaction mixture was stirred at 110° C. for 23 h. The resulting bright yellow suspension was allowed to reach room temperature and then filtered through a 0.5×1 cm pad of silica gel eluting with 10 mL of ethyl acetate-dichloromethane 1:1. The filtrate was concentrated, the residue was dissolved in 10 mL of dichloromethane and purified by flash chromatography on silica gel (2×20 cm, ethyl acetate-dichloromethane 1:4, 15 mL fractions). Fractions 10-20 provided 261 mg (98% yield) of the desired product as a bright yellow solid.

Example 132

Preparation of N-phenylacetamide at 60° C. for 4 h

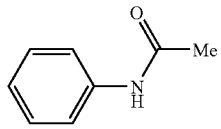

A 15 mL resealable Schlenk tube was charged with CuI (10 mg, 0.0525 mmol, 5.0 mol %), acetamide (170 mg, 2.88 mmol), $K_3PO_4$ (450 mg, 2.12 mmol), evacuated and backfilled with argon. trans-N,N'-Dimethyl-1,2-cyclohexanediamine (17 μL, 0.108 mmol, 10 mol %), iodobenzene (115 μL, 1.03 mmol) and toluene (1.0 mL) were added under argon. The Schlenk tube was sealed with a Teflon valve and the reaction mixture was stirred at 60° C. for 4 h. After the resulting suspension was allowed to reach room temperature, ethyl acetate (1 mL) and dodecane (235 μL, internal GC standard) were added. GC analysis indicated 100% yield of the desired product.

Example 133

Preparation of N,N-diphenylformamide using ethylenediamine as the ligand at 80° C. for 4 h

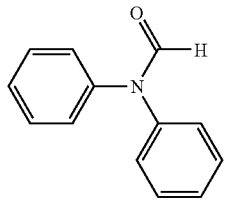 [SMILES: O=CN(c1ccccc1)c1ccccc1]

A 15 mL resealable Schlenk tube was charged with CuI (9.8 mg, 0.0515 mmol, 5.0 mol %), N-phenylformamide (150 mg, 1.24 mmol), $K_3PO_4$ (450 mg, 2.12 mmol), evacuated and backfilled with argon. Ethylenediamine (7.0 μL, 0.105 mmol, 10 mol %), iodobenzene (115 μL, 1.03 mmol) and toluene (1.0 mL) were added under argon. The Schlenk tube was sealed with a Teflon valve and the reaction mixture was stirred at 80° C. for 4 h. The resulting suspension was allowed to reach room temperature and then filtered through a 0.5×1 cm pad of silica gel eluting with 10 mL of ethyl acetate. The filtrate was concentrated and the residue was purified by flash chromatography on silica gel (2×15 cm, hexane-ethyl acetate 2:1, 15 mL fractions). Fractions 10-18 provided 188 mg (93% yield) of the desired product as a white solid.

Example 134

Preparation of N,N-diphenylformamide using 1,2-diaminopropane as the ligand at 80° C. for 4 h A 15 mL resealable Schlenk tube was charged with CuI (9.8 mg, 0.0515 mmol, 5.0 mol %), N-phenylformamide (150 mg, 1.24 mmol), $K_3PO_4$ (450 mg, 2.12 mmol), evacuated and backfilled with argon. 1,2-Diaminopropane (9.0 μL, 0.106 mmol, 10 mol %), iodobenzene (115 μL, 1.03 mmol) and toluene (1.0 mL) were added under argon. The Schlenk tube was sealed with a Teflon valve and the reaction mixture was stirred at 80° C. for 4 h. After the resulting suspension was allowed to reach room temperature, ethyl acetate (1 mL) and dodecane (235 μL, internal GC standard) were added. GC analysis indicated 91% yield of the desired product.

Example 135

N-Formylindoline

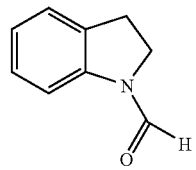 [SMILES: O=CN1CCc2ccccc21]

A 15 mL resealable Schlenk tube was charged with CuI (9.6 mg, 0.0504 mmol, 5.0 mol %), N-formyl-2-(2-bromophenyl)ethylamine (229 mg, 1.00 mmol), $K_2CO_3$ (280 mg, 2.03 mmol), evacuated and backfilled with argon. trans-N,N'-Dimethyl-1,2-cyclohexanediamine (16 μL, 0.102 mmol, 10 mol %) and toluene (1.0 mL) were added under argon. The Schlenk tube was sealed with a Teflon valve and the reaction mixture was stirred at 80° C. for 23 h. The resulting suspension was allowed to reach room temperature and then filtered through a 0.5×1 cm pad of silica gel eluting with 10 mL of ethyl acetate. The filtrate was concentrated and the residue was purified by flash chromatography on silica gel (2×10 cm, hexane-ethyl acetate 3:2, 15 mL fractions). Fractions 13-23 provided 145 mg (99% yield) of the desired product as a light yellow solid.

Example 136

Preparation of N-Formylindoline from an Aryl Bromide at Room Temperature

The procedure above was followed exactly except that the reaction was performed at 25° C. for 24 h. The resulting suspension was filtered through a 0.5×1 cm pad of silica gel eluting with 10 mL of ethyl acetate. The filtrate was concentrated and the residue was purified by flash chromatography on silica gel (2×15 cm, hexane-ethyl acetate 1:1, 15 mL fractions). Fractions 12-21 provided 107 mg (73% yield) of the desired product as a light yellow solid.

Example 137

Preparation of N-formylindoline from an Aryl Chloride at 80° C.

A 15 mL resealable Schlenk tube was charged with CuI (9.6 mg, 0.0504 mmol, 5.0 mol %), N-formyl-2-(2-chlorophenyl)ethylamine (184 mg, 1.00 mmol), $K_2CO_3$ (280 mg, 2.03 mmol), evacuated and backfilled with argon. trans-N,N'-Dimethyl-1,2-cyclohexanediamine (16 μL, 0.102 mmol, 10 mol %) and toluene (1.0 mL) were added under argon. The Schlenk tube was sealed with a Teflon valve and the reaction mixture was stirred at 80° C. for 22 h. The resulting suspension was allowed to reach room temperature and then filtered through a 0.5×1 cm pad of silica gel eluting with 10 mL of ethyl acetate. The filtrate was concentrated and the residue was purified by flash chromatography on silica gel (2×15 cm, hexane-ethyl acetate 1:1, 15 mL fractions). Fractions 13-20 provided 105 mg (71% yield) of the desired product as a white solid.

Example 138

Preparation of N-(3,5-dimethylphenyl)-2-pyrrolidinone using 2,6-dimethylphenol as the ligand

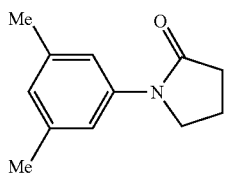

A 15 mL resealable Schlenk tube was charged with CuI (9.5 mg, 0.0499 mmol, 5.0 mol %), 2,6-dimethylphenol (25 mg, 0.205 mmol, 20 mol %), K$_3$PO$_4$ (440 mg, 2.07 mmol), evacuated and backfilled with argon. 5-Iodo-m-xylene (145 µL, 1.00 mmol), 2-pyrrolidinone (95 µL, 1.25 mmol) and toluene (1.0 mL) were added under argon. The Schlenk tube was sealed with a Teflon valve and the reaction mixture was stirred at 110° C. for 21 h. The resulting suspension was allowed to reach room temperature and then filtered through a 0.5×1 cm pad of silica gel eluting with 10 mL of ethyl acetate. The filtrate was concentrated and the residue was purified by flash chromatography on silica gel (2×20 cm, hexane-ethyl acetate 2:3, 15 mL fractions). Fractions 13-24 provided 180 mg (95% yield) of the desired product as a white solid.

Example 139

Preparation of N-(3,5-dimethylphenyl)-2-pyrrolidinone using n-hexylamine as the ligand/solvent at 80° C.

A 15 mL resealable Schlenk tube was charged with CuI (9.5 mg, 0.0499 mmol, 5.0 mol %), K$_3$PO$_4$ (440 mg, 2.07 mmol), evacuated and backfilled with argon. 5-Iodo-m-xylene (145 µL, 1.00 mmol), 2-pyrrolidinone (95 µL, 1.25 mmol) and n-hexylamine (0.94 mL, 7.12 mmol) were added under argon. The Schlenk tube was sealed with a Teflon valve and the reaction mixture was stirred at 80° C. for 23 h. The resulting brown suspension was allowed to reach room temperature and then filtered through a 0.5×1 cm pad of silica gel eluting with 10 mL of ethyl acetate. The filtrate was concentrated and the residue was purified by flash chromatography on silica gel (2×10 cm, hexane-ethyl acetate 2:3, 10 mL fractions). Fractions 9-19 provided 185 mg (98% yield) of the desired product as a pale tan solid.

Example 140

Preparation of N-(3,5-dimethylphenyl)-N-phenylacetamide using 2,6-dimethyl-phenol as the ligand

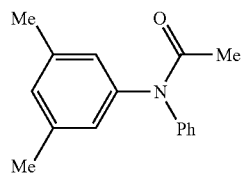

A 15 mL resealable Schlenk tube was charged with CuI (9.5 mg, 0.0499 mmol, 5.0 mol %), 2,6-dimethylphenol (25 mg, 0.205 mmol, 20 mol %), acetanilide (165 mg, 1.22 mmol), K$_3$PO$_4$ (440 mg, 2.07 mmol), evacuated and backfilled with argon. 5-Iodo-m-xylene (145 µL, 1.00 mmol) and toluene (1.0 mL) were added under argon. The Schlenk tube was sealed with a Teflon valve and the reaction mixture was stirred at 110° C. for 21 h. The resulting suspension was allowed to reach room temperature and then filtered through a 0.5×1 cm pad of silica gel eluting with 10 mL of ethyl acetate. The filtrate was concentrated and the residue was purified by flash chromatography on silica gel (2×15 cm, hexane-ethyl acetate 2:1, 15 mL fractions). Fractions 12-20 provided 133 mg (56% yield) of the desired product as a yellow solid.

Example 141

Preparation of N-(3,5-dimethylphenyl)-N-phenylacetamide using n-hexylamine as the ligand and solvent A 15 mL resealable Schlenk tube was charged with CuI (9.5 mg, 0.0499 mmol, 5.0 mol %), acetanilide (165 mg, 1.22 mmol), K$_3$PO$_4$ (440 mg, 2.07 mmol), evacuated and backfilled with argon. 5-Iodo-m-xylene (145 µL, 1.00 mmol) and n-hexylamine (0.94 mL, 7.12 mmol) were added under argon. The Schlenk tube was sealed with a Teflon valve and the reaction mixture was stirred at 100° C. for 21 h. The resulting pale yellow suspension was allowed to reach room temperature and then filtered through a 0.5×1 cm pad of silica gel eluting with 10 mL of ethyl acetate. The filtrate was concentrated and the residue was purified by flash chromatography on silica gel (2×15 cm, hexane-ethyl acetate 2:1, 15 mL fractions). Fractions 12-20 provided 205 mg (86% yield) of the desired product as a pale yellow solid.

Example 142

Preparation of N-methyl-N-phenylacetamide using n-hexylamine as the ligand

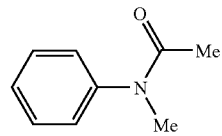 [SMILES: CC(=O)N(C)c1ccccc1]

A 15 mL resealable Schlenk tube was charged with CuI (9.5 mg, 0.0499 mmol, 5.0 mol %) and K$_3$PO$_4$ (430 mg, 2.03 mmol), evacuated and backfilled with argon. Iodobenzene (112 μL, 1.00 mmol), N-methylacetamide (0.46 mL, 6.00 mmol) and n-hexylamine (0.53 mL, 4.01 mmol) were added under argon. The Schlenk tube was sealed with a Teflon valve and the reaction mixture was stirred at 110° C. for 21 h. The resulting white suspension was allowed to reach room temperature and then filtered through a 0.5×1 cm pad of silica gel eluting with 10 mL of ethyl acetate. The filtrate was concentrated and the residue was purified by flash chromatography on silica gel (2×15 cm, hexane-ethyl acetate 2:3, 15 mL fractions). Fractions 12-20 provided 136 mg (91% yield) of the desired product as a pale tan solid.

Example 143

Preparation of N-(3,5-dimethylphenyl)-2-pyrrolidinone using tert-butylimino-tris(pyrrolidino)-phosphorane as the base

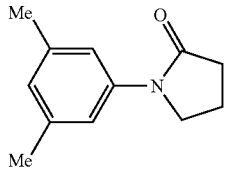

A 15 mL resealable Schlenk tube was charged with CuI (9.5 mg, 0.0499 mmol, 5.0 mol %), evacuated and backfilled with argon. trans-N,N'-Dimethyl-1,2-cyclohexanediamine (16 μL, 0.102 mmol, 10 mol %), 5-iodo-m-xylene (145 μL, 1.00 mmol), 2-pyrrolidinone (95 μL, 1.25 mmol), tert-butylimino-tris(pyrrolidino)phosphorane (0.62 mL, 2.03 mmol), and toluene (1.0 mL) were added under argon. The Schlenk tube was sealed with a Teflon valve and the reaction mixture was stirred at 90° C. for 21 h. The resulting clear, dark brown solution was allowed to reach room temperature and then filtered through a 0.5×2 cm pad of silica gel eluting with 10 mL of ethyl acetate. The filtrate was concentrated and the residue was purified by flash chromatography on silica gel (2×15 cm, hexane-ethyl acetate 2:3, 15 mL fractions). Fractions 10-19 provided 180 mg (95% yield) of the desired product as a white solid.

Example 144

Preparation of N,N-diphenylformamide using 1,8-diazabicyclo[5.4.0]undec-7-ene (DBU) as the base

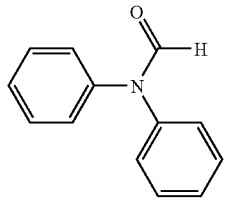

A 15 mL resealable Schlenk tube was charged with CuI (9.6 mg, 0.0504 mmol, 5.0 mol %), N-phenylformamide (146 mg, 1.21 mmol), evacuated and backfilled with argon. trans-N,N'-Dimethyl-1,2-cyclohexanediamine (16 μL, 0.102 mmol, 10 mol %), iodobenzene (112 μL, 1.00 mmol), toluene (1.0 mL) and 1,8-diazabicyclo[5.4.0]undec-7-ene (DBU, 0.45 mL, 3.01 mmol) were added under argon. The Schlenk tube was sealed with a Teflon valve and the reaction mixture was stirred at 100° C. for 22 h. After the resulting clear solution was allowed to reach room temperature, ethyl acetate (2 mL), saturated aq NH₄Cl (2 mL) and dodecane (235 μL, internal GC standard) were added. GC analysis of the top layer indicated 12% yield of the desired product, confirmed by GC-MS analysis (M⁺ signal at 197 m/z).

Example 145

Preparation of N-(2-methyl-1-propenyl)-2-pyrrolidinone from a vinyl bromide

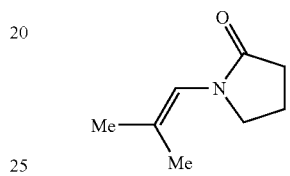

A 15 mL resealable Schlenk tube was charged with CuI (9.5 mg, 0.0499 mmol, 5.0 mol %), K₂CO₃ (280 mg, 2.03 mmol), evacuated and backfilled with argon. trans-N,N'-Dimethyl-1,2-cyclohexanediamine (16 μL, 0.102 mmol, 10 mol %), 1-bromo-2-methylpropene (145 μL, 1.42 mmol), 2-pyrrolidinone (76 μL, 1.00 mmol), and toluene (1.0 mL) were added under argon. The Schlenk tube was sealed with a Teflon valve and the reaction mixture was stirred at 90° C. for 21 h. The resulting light blue suspension was allowed to reach room temperature and then filtered through a 0.5×1 cm pad of silica gel eluting with 10 mL of ethyl acetate. The filtrate was concentrated and the residue was purified by flash chromatography on silica gel (2×10 cm, ethyl acetate, 10 mL fractions). Fractions 10-24 provided 134 mg (96% yield) of the desired product as a colorless liquid.

Example 146

Preparation of trans-N-(1-hexenyl benzamide at room temperature

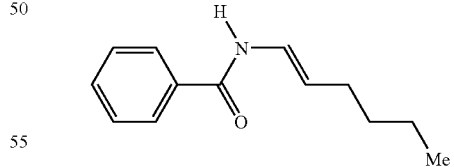

A 15 mL resealable Schlenk tube was charged with CuI (9.6 mg, 0.0504 mmol, 5.0 mol %), benzamide (145 mg, 1.20 mmol), K₃PO₄ (430 mg, 2.03 mmol), evacuated and backfilled with argon. trans-N,N'-Dimethyl-1,2-cyclohexanediamine (16 μL, 0.102 mmol, 10 mol %), trans-1-iodo-1-hexene (143 μL, 1.00 mmol), and toluene (1.0 mL) were added under argon. The Schlenk tube was sealed with a Teflon valve and the reaction mixture was stirred at 25° C. for 24 h. The resulting light blue suspension was allowed to reach room temperature and then filtered through a 0.5×1 cm pad of silica gel eluting with 10 mL of ethyl acetate. The filtrate was concentrated, the residue was dissolved in 5 mL of dichloromethane and purified by flash chromatography on silica gel (2×15 cm, hexane-ethyl acetate, 15 mL fractions). Fractions 12-19 provided 140 mg (69% yield) of the desired product as white needles.

Example 147

N-(4-Methylphenyl)-p-toluenesulfonamide

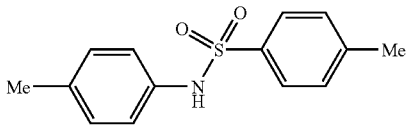

A 15 mL resealable Schlenk tube was charged with CuI (9.5 mg, 0.0499 mmol, 5.0 mol %), 4-iodotoluene (218 mg, 1.00 mmol), p-toluenesulfonamide (205 mg, 1.20 mmol), $K_2CO_3$ (280 mg, 2.03 mmol), evacuated and backfilled with argon. trans-N,N'-Dimethyl-1,2-cyclohexanediamine (16 µL, 0.102 mmol, 10 mol %) and N,N-dimethylformamide (1 mL) were added under argon. The Schlenk tube was sealed with a Teflon valve and the reaction mixture was stirred at 100° C. for 19 h. The resulting pale brown suspension was allowed to reach room temperature, poured into 20 mL of a diluted aq $NH_4Cl$ solution, and extracted with 3×15 mL of dichloromethane. The colorless organic phase was dried ($Na_2SO_4$), concentrated, and the residue was purified by flash chromatography on silica gel (2×15 cm, hexane-ethyl acetate 2:1, 15 mL fractions). Fractions 9-16 provided 251 mg (96% yield) of the desired product as white crystals.

Example 148

N-Ethyl-N-phenyl-p-toluenesulfonamide

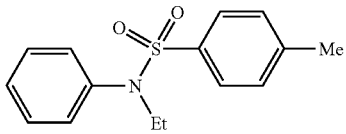

A 15 mL resealable Schlenk tube was charged with CuI (9.6 mg, 0.0504 mmol, 5.0 mol %), N-ethyl-p-toluenesulfonamide (240 mg, 1.20 mmol), $K_2CO_3$ (280 mg, 2.03 mmol), evacuated and backfilled with argon. trans-N,N'-Dimethyl-1,2-cyclohexanediamine (16 µL, 0.102 mmol, 10 mol %), iodobenzene (112 µL, 1.00 mmol) and toluene (1 mL) were added under argon. The Schlenk tube was sealed with a Teflon valve and the reaction mixture was stirred at 110° C. for 23 h. The resulting pale brown suspension was allowed to reach room temperature and then filtered through a 0.5×1 cm pad of silica gel eluting with 10 mL of ethyl acetate. The filtrate was concentrated and the residue was purified by flash-chromatography on silica gel (2×15 cm, hexane-ethyl acetate 4:1, 15 mL fractions). Fractions 10-17 provided 244 mg (89% yield) of the desired product.

Example 149

Preparation of N-phenyl-p-toluenesulfonamide using 1,8-diazabicyclo[5.4.0]undec-7-ene (DBU) as the base

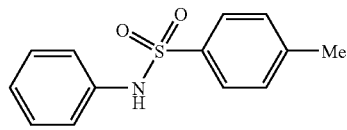 [SMILES: Cc1ccc(S(=O)(=O)Nc2ccccc2)cc1]

A 15 mL resealable Schlenk tube was charged with CuI (9.6 mg, 0.0504 mmol, 5.0 mol %), p-toluenesulfonamide (205 mg, 1.20 mmol), evacuated and backfilled with argon. trans-N,N'-Dimethyl-1,2-cyclohexanediamine (16 µL, 0.102 mmol, 10 mol %), iodobenzene (112 µL, 1.00 mmol), toluene (1.0 mL) and 1,8-diazabicyclo[5.4.0]undec-7-ene (DBU, 0.45 mL, 3.01 mmol) were added under argon. The Schlenk tube was sealed with a Teflon valve and the reaction mixture was stirred at 100° C. for 22 h. The resulting clear solution was allowed to cool to room temperature, poured into aq $NH_4Cl$ solution and extracted with 3×15 mL of $CH_2Cl_2$. The combined organic phases were dried ($Na_2SO_4$), concentrated, and the residue was purified by flash chromatography on silica gel (2×15 cm, hexane-ethyl acetate 3:1, 15 mL fractions). Fractions 9-15 provided 60 mg (24% yield) of the desired product as a white solid.

Example 150

General procedure for the arylation of N—H heterocycles using trans-N,N'-dimethyl-1,2-cyclohexanediamine as ligand To a flame-dried resealable Schlenk tube, or alternatively a reselable test tube, was added CuI (5 mol %), the heterocycle (1.0 mmol) and base (2.1 mmol). The Schlenk tube was fixed with a rubber septum, evacuated twice and back-filled with argon. Dodecane (45 µL, 0.20 mmol), the aryl halide (1.2 mmol), trans-N,N'-dimethyl-1,2-cyclohexanediamine (10-20 mol %) and the respective solvent (1 mL) were then added successively under argon. The reaction tube was sealed and the contents were stirred with heating via an oil bath at 110° C. for 24 hours. The reaction mixture was cooled to ambient temperature, diluted with 2-3 mL ethyl acetate, and filtered through a plug of silica gel eluting with 10-20 mL of ethyl acetate. The filtrate was concentrated and the resulting residue was purified by column chromatography to provide the desired product.

1-(2-Aminophenyl)indole

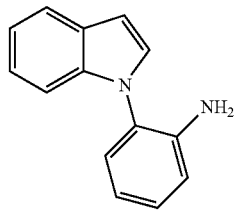 [SMILES: Nc1ccccc1-n1ccc2ccccc21]

Using the general procedure, indole (0.117 g, 1.00 mmol) was coupled with 2-bromoaniline (0.206 g, 1.20 mmol) using CuI (9.5 mg, 0.050 mmol, 5.0 mol %), K$_3$PO$_4$ (2.1 mmol), trans-N,N'-dimethyl-1,2-cyclohexanediamine (16 μL, 0.10 mmol, 10 mol %) and toluene (1.0 mL) to give the crude product. Column chromatography (2×15 cm, hexane:ethyl acetate 5:1) provided 0.148 g (71% yield) of the product as a colorless oil. $^1$H NMR (400 MHz, CDCl$_3$): δ 7.64 (m, 1H), 7.18 (m, 6H), 6.82 (m, 2H), 6.64 (m, 1H), 3.52 (bs, 2H).

Preparation of 1-(2-aminophenyl)indole at 80° C.

Using the general procedure, indole (0.117 g, 1.00 mmol) was coupled at 80° C. with 2-iodoaniline (0.263 g, 1.20 mmol) using CuI (9.5 mg, 0.050 mmol, 5.0 mol %), K$_3$PO$_4$ (2.1 mmol), trans-N,N'-dimethyl-1,2-cyclohexanediamine (32 μL, 0.20 mmol, 20 mol %) and toluene (1.0 mL) to give the crude product. The above product was identified by comparison (GC) to a previously prepared sample and the GC yield was determined to be 92%.

1-Phenyltryptamine

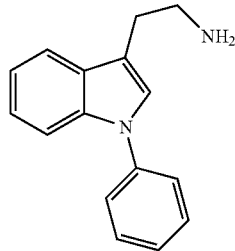 [SMILES: NCCc1cn(-c2ccccc2)c2ccccc12]

Using the general procedure, tryptamine (0.160 g, 1.00 mmol) was coupled with iodobenzene (134 μL, 1.20 mmol) using CuI (9.5 mg, 0.050 mmol, 5.0 mol %), K$_3$PO$_4$ (2.1 mmol), trans-N,N'-dimethyl-1,2-cyclohexanediamine (32 μL, 0.20 mmol, 20 mol %) and toluene (1.0 mL) to give the crude product. Column chromatography (2×15 cm, methylene chloride (saturated with ammonia):methanol 50:1) provided 0.206 g (87% yield) of the product as a yellow oil. $^1$H NMR (400 MHz, CDCl$_3$): δ 7.65 (m, 1H), 7.55 (m, 1H), 7.47 (m, 4H), 7.31 (m, 1H), 7.1-8 (m, 3H), 3.06 (t, J=7 Hz, 2H), 2.94 (t, J=7 Hz, 2H), 1.40 (bs, 2H).

Preparation of 1-(4-ethoxycarbonylphenyl)indole at 80° C.

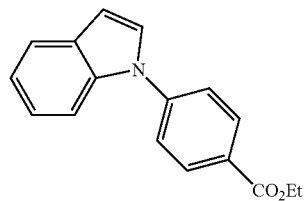 [SMILES: CCOC(=O)c1ccc(-n2ccc3ccccc32)cc1]

Using the general procedure, indole (0.117 g, 1.00 mmol) was coupled at 80° C. with ethyl-4-iodobenzoate (0.331 g, 1.20 mmol) using CuI (9.5 mg, 0.050 mmol, 5.0 mol %), K$_3$PO$_4$ (2.1 mmol), trans-N,N'-dimethyl-1,2-cyclohexanediamine (32 μL, 0.20 mmol, 20 mol %) and toluene (1.0 mL) to give the crude product. The above product was identified by comparison (GC) to a previously prepared sample and the GC yield was determined to be 96%.

Preparation of 1-(2-pyridyl)indole from 2-chloropyridine

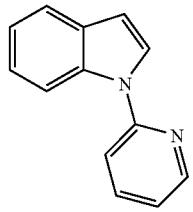 [SMILES: c1ccc(-n2ccc3ccccc32)nc1]

Using the general procedure, indole (0.117 g, 1.00 mmol) was coupled with 2-chloropyridine (113 μL, 1.20 mmol) using CuI (9.5 mg, 0.050 mmol, 5.0 mol %), K$_3$PO$_4$ (2.1 mmol), trans-N,N'-dimethyl-1,2-cyclohexanediamine (32 μL, 0.20 mmol, 20 mol %) and toluene (1.0 mL) to give the crude product. Column chromatography (2×15 cm, hexane: ethyl acetate 9:1) provided 0.194 g (100% yield) of the product as a yellow oil. $^1$H NMR (400 MHz, CDCl$_3$): δ 9.24 (s, 1H), 9.05 (s, 1H), 8.41 (s, 1H), 7.75 (m, 2H), 7.60 (m, 2H), 7.48 (m, 1H).

1-Phenylpurine

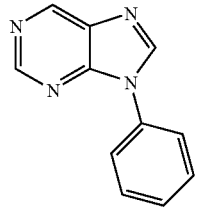 [SMILES: c1ccc(-n2cnc3cncnc32)cc1]

Using the general procedure, purine (0.120 g, 1.00 mmol) was coupled with iodobenzene (225 μL, 2.00 mmol) using CuI (9.5 mg, 0.050 mmol, 5.0 mol %), Cs$_2$CO$_3$ (2.1 mmol), trans-N,N'-dimethyl-1,2-cyclohexanediamine (32 μL, 0.20 mmol, 20 mol %) and dimethylformamide (1.0 mL) to give the crude product. Column chromatography (2×15 cm, hexane:ethyl acetate 1:2) provided 0.136 g (69% yield) of the product as a white solid. $^1$H NMR (400 MHz, CDCl$_3$): δ 8.00 (d, J=0.9 Hz, 1H), 7.52 (m, 3H), 7.42 (m, 5H), 6.73 (dd, J=0.6 Hz and J=3.3 Hz, 1H), 7.60 (m, 2H), 7.48 (m, 1H).

1-(4-Methylphenyl)-3-chloroindazole

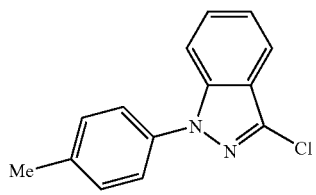 [SMILES: Cc1ccc(-n2nc(Cl)c3ccccc32)cc1]

Using the general procedure, 3-chloroindazole (0.153 g, 1.00 mmol) was coupled with 4-bromotoluene, (148 μL, 1.20 mmol) using CuI (9.5 mg, 0.050 mmol, 5.0 mol %), K$_3$PO$_4$ (2.1 mmol), trans-N,N'-dimethyl-1,2-cyclohexanediamine (32 μL, 0.20 mmol, 20 mol %) and toluene (1.0 mL) to give the crude product. Column chromatography (2×15 cm, hexane:ethyl acetate 50:1) provided 0.211 g (87% yield) of the product as a colorless oil. $^1$H NMR (400 MHz, CDCl$_3$): δ 7.70

(d, J=8.2 Hz, 1H), 7.63 (d, J=8.5 Hz, 1H), 7.52 (m, 2H), 7.43 (m, 1H), 7.24 (d, J=8.2 Hz, 2H), 7.22 (m, 1H), 2.38 (s, 3H).

1-Phenyl-1,2,4-triazole

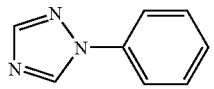

Using the general procedure, 1,2,4-triazole (0.069 g, 1.00 mmol) was coupled with iodobenzene (134 μL, 1.20 mmol) using CuI (9.5 mg, 0.050 mmol, 5.0 mol %), $K_3PO_4$ (2.1 mmol), trans-N,N'-dimethyl-1,2-cyclohexanediamine (16 μL, 0.10 mmol, 10 mol %) and dimethylformamide (1.0 mL) to give the crude product. Column chromatography (2×15 cm, hexane:ethyl acetate 3:1) provided 0.135 g (93% yield) of the product as a white solid. $^1$H NMR (400 MHz, $CDCl_3$): δ 8.58 (s, 1H), 8.10 (s, 1H), 7.66 (m, 2H), 7.47 (m, 2H), 7.37 (m, 1H).

1-Phenylbenzotriazole

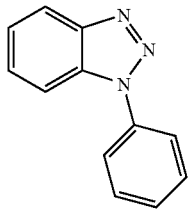 [SMILES: c1ccc(-n2nnc3ccccc32)cc1]

Using the general procedure, benzotriazole (0.119 g, 1.00 mmol) was coupled with iodobenzene (134 μL, 1.20 mmol) using CuI (9.5 mg, 0.050 mmol, 5.0 mol %), $K_3PO_4$ (2.1 mmol), trans-N,N'-dimethyl-1,2-cyclohexanediamine (16 μL, 0.10 mmol, 10 mol %) and dimethylformamide (1.0 mL) to give the crude product. Column chromatography (2×15 cm, hexane:ethyl acetate 9:1) provided 0.186 g (95% yield) of the product as a white solid. $^1$H NMR (400 MHz, $CDCl_3$): δ 8.17 (m, 1H), 7.78 (m, 3H), 7.62 (m, 2H), 7.55 (m, 2H), 7.42 (m, 1H).

Example 151

Preparation of 1-(4-methylphenyl)indole using N,N'-dimethylethylenediamine as ligand

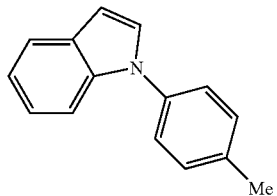 [SMILES: Cc1ccc(-n2ccc3ccccc32)cc1]

To a flame-dried resealable Schlenk tube was added CuI (0.002 g, 0.01 mmol), indole (0.141 g, 1.20 mmol) and $K_3PO_4$ (0.446 g, 2.1 mmol), the Schlenk tube was evacuated twice and back-filled with argon. Dodecane (45 μL, 0.20 mmol), 4-bromotoluene (123 μL, 1.00 mmol), N,N'-dimethylethylenediamine (11 μL, 0.10 mmol) and toluene (1 mL) were then added successively under argon. The reaction tube was sealed and the contents were stirred with heating via an oil bath at 110° C. for 24 hours. The reaction mixture was cooled to ambient temperature, diluted with 2-3 mL ethyl acetate, and filtered through a plug of silica gel eluting with 10-20 mL of ethyl acetate. Comparison to authentic material showed that the product was formed in a 92% GC yield.

Example 152

Preparation of 1-(4-methylphenyl)indole using N-methylethylenediamine as ligand

To a flame-dried resealable Schlenk tube was added CuI (0.002 g, 0.01 mmol), indole (0.141 g, 1.20 mmol) and $K_3PO_4$ (0.446 g, 2.1 mmol), the Schlenk tube was evacuated twice and back-filled with argon. Dodecane (45 μL, 0.20 mmol), 4-bromotoluene (123 μL, 1.00 mmol), N-methylethylenediamine (9 μL, 0.10 mmol) and toluene (1 mL) were then added successively under argon. The reaction tube was sealed and the contents were stirred with heating via an oil bath at 110° C. for 24 hours. The reaction mixture was cooled to ambient temperature, diluted with 2-3 mL ethyl acetate, and filtered through a plug of silica gel eluting with 10-20 mL of ethyl acetate. Comparison to authentic material showed that the product was formed in a 99% GC yield.

Example 153

Preparation of 1-phenylindole in Air

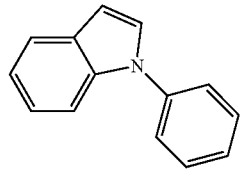 [SMILES: c1ccc(-n2ccc3ccccc32)cc1]

To a flame-dried resealable test tube was added CuI (0.002 g, 0.01 mmol), indole (0.117 g, 1.00 mmol) and $K_3PO_4$ (0.446 g, 2.1 mmol). A rubber septum was fitted and dodecane (45 μL, 0.20 mmol), iodobenzene (134 μL, 1.20 mmol), trans-N,N'-dimethyl-1,2-cyclohexanediamine (16 μL, 0.10 mmol) and toluene (1 mL) were added successively in air. The reaction tube was sealed and the contents were stirred with heating via an oil bath at 110° C. for 24 hours. The reaction mixture was cooled to ambient temperature, diluted with 2-3 mL ethyl acetate, and filtered through a plug of silica gel eluting with 10-20 mL of ethyl acetate. Comparison to authentic material showed that the product was formed in an 82% GC yield.

Example 154

Preparation of 1-phenylindole Using Various Copper Sources

To a flame-dried resealable test tube was added the copper source (0.050 mmol), indole (0.117 g, 1.00 mmol) and $K_3PO_4$ (0.446 g, 2.1 mmol) under an atmosphere of argon. A rubber septum was fitted and dodecane (45 μL, 0.20 mmol), iodobenzene (134 μL, 1.20 mmol), trans-N,N'-dimethyl-1,2-cyclohexanediamine (16 μL, 0.10 mmol) and toluene (1 mL) were added successively under a stream of argon. The reaction tube was sealed and the contents were stirred with heating via an oil bath at 110° C. for 24 hours. The reaction mixture was cooled to ambient temperature, diluted with 2-3 mL ethyl acetate, and filtered through a plug of silica gel eluting with 10-20 mL of ethyl acetate. The GC yields of the desired product are tabulated below.

| Copper source | GC yield 1-phenylindole |
|---|---|
| Cu (copper bronze) | 99% |
| CuI | 100% |
| $CuCl_2$ | 100% |
| $Cu(OAc)_2$ | 100% |
| $Cu(OMe)_2$ | 98% |

Example 155

General Procedure for Malonate Arylation Using Aryl Iodides

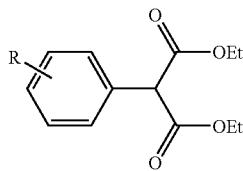

An oven-dried Schlenk tube equipped with a magnetic stirbar and a Teflon stopcock was evacuated while hot and allowed to cool under argon. The tube was charged with CuI (9.6 mg, 5.0 mol %), 2-hydroxybiphenyl (17.1 mg, 10.0 mol %), $Cs_2CO_3$ (0.490 mg, 1.50 mmol), and the aryl iodide (if a solid, 1.0 mmol). The tube was evacuated and backfilled with argon (3 times), and the Teflon stopcock was replaced with a rubber septum. The aryl iodide (if liquid) was added volumetrically (1.0 mmol), followed by diethyl malonate (304 μL, 2.00 mmol) and anhydrous THF (1.0 mL). The septum was replaced by the Teflon stopcock under a positive pressure of argon, and the sealed tube was placed in an oil bath preheated to 70° C. After the designated time period, the reaction was allowed to cool to room temperature and was then partitioned between 20 mL ethyl acetate and 10 mL saturated $NH_4Cl$ (aq). The organic portion was dried ($Na_2SO_4$), filtered through Celite, and concentrated on a rotary evaporator. The oil thus obtained was purified by silica gel chromatography to give the product α-aryl malonate.

Phenyl Diethyl Malonate

Obtained as a colorless oil (217 mg, 92%); reaction time 24 h.

4-Methoxyphenyl diethyl malonate

Obtained as a colorless oil (227 mg, 87%); reaction time 30 h.

4-Chlorophenyl diethyl malonate

Obtained as a colorless oil (265 mg, 97%); reaction time 24 h.

1-Napthyl diethyl malonate

Obtained as a pale yellow solid (280 mg, 98%); reaction time 30 h.

3-Trifluoromethylphenyl diethyl malonate

Obtained as a colorless oil (267 mg, 88%); reaction time 24 h.

2-Isopropylphenyl diethyl malonate

Obtained as a pale yellow oil (238 mg, 86%); reaction time 31 h (10 mol % CuI used in reaction).

2,4-Dimethoxyphenyl diethyl malonate

Obtained as a tan solid (269 mg, 91%); reaction time 30 h.

3-Ethoxycarbonylphenyl diethyl malonate

Obtained as a colorless oil (265 mg, 86%) reaction time 24 h.

4-Aminophenyl diethyl malonate

Obtained as a yellow oil (200 mg, 79%); reaction time 30 h.

4-Hydroxyphenyl diethyl malonate

Obtained as a colorless solid (191 mg, 73%); reaction time 30 h (2.5 equiv $Cs_2CO_3$ used in reaction).

4-N-Acetyl aminophenyl diethyl malonate

Obtained as a colorless solid (214 mg, 72%); reaction time 30 h (10 mol % CuI used in reaction).

3-Nitrophenyl diethyl malonate

Obtained as a yellow oil (240 mg, 85%); reaction time 24 h.

3-Cyanophenyl diethyl malonate

Obtained as a colorless oil (194 mg, 73%); reaction time 24 h.

Example 156

General Procedure for Malonate Arylation Using Aryl Bromides

An oven-dried Schlenk tube equipped with a magnetic stirbar and a Teflon stopcock was evacuated while hot and allowed to cool under argon. The tube was charged with CuI (9.6 mg, 5.0 mol %), 8-hydroxyquinoline (14.5 mg, 10.0 mol %), and $Cs_2CO_3$ (0.490 mg, 1.50 mmol). The tube was evacuated and backfilled with argon (3 times), and the Teflon stopcock was replaced with a rubber septum. The aryl bromide was added volumetrically (1.0 mmol), followed by the malonate (2.00 mmol) and anhydrous dioxane (1.0 mL). The septum was replaced by the Teflon stopcock under a positive pressure of argon, and the sealed tube was placed in an oil bath preheated to 110° C. After the designated time period, the reaction was allowed to cool to room temperature and was treated with n-undecane (105.6 μL, 0.50 mmol) prior to partitioning between 20 mL ethyl acetate and 10 mL saturated $NH_4Cl$ (aq). The organic portion was analyzed by GC and/or GC-MS. GC yield of product was determined using response factors obtained from previously isolated product.

4-Methoxyphenyl dimethyl malonate

After 19.5 hours, a GC yield of 43% was obtained.

4-Trifluoromethylphenyl diethyl malonate

After 20.5 hours, GC-MS indicated complete conversion of the aryl bromide to the title compound in addition to the decarboxylated malonate product, 4-trifluoromethylphenyl ethyl acetate.

Example 157

Synthesis of α-Aryl Acetates

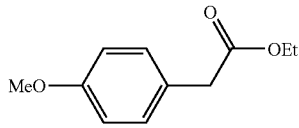

An oven-dried Schlenk tube equipped with a magnetic stirbar and a Teflon stopcock was evacuated while hot and allowed to cool under argon. The tube was charged with CuI (9.6 mg, 5.0 mol %); 1,10-phenanthroline (10.9 mg, 5.5 mol %), Cs$_2$CO$_3$ (0.490 mg, 1.50 mmol), and 4-iodoanisole (0.226 g, 0.97 mmol). The tube was evacuated and backfilled with argon (3 times), and the Teflon stopcock was replaced with a rubber septum. Ethyl acetoacetate was added (0.15 mL, 1.18 mmol), followed by anhydrous dioxane (1.0 mL). The septum was replaced by the Teflon stopcock under a positive pressure of argon, and the sealed tube was placed in an oil bath preheated to 110° C. After 24 h, the reaction was allowed to cool to room temperature, and was then partitioned between 20 mL ethyl acetate and 10 mL saturated NH$_4$Cl (aq). The organic portion was dried (Na$_2$SO$_4$), filtered through Celite, and concentrated on a rotary evaporator. The oil thus obtained was purified by silica gel chromatography to give the product 4-methoxyphenyl ethyl acetate as a. colorless oil (106 mg, 56%).

Example 158

Arylation of Ethyl Cyanoacetate

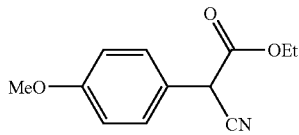

An oven-dried Schlenk tube equipped with a magnetic stirbar and a Teflon stopcock was evacuated while hot and allowed to cool under argon. The tube was charged with CuI (9.6 mg, 5.0 mol %), 1,10-phenanthroline (10.9 mg, 5.5 mol %), Cs$_2$CO$_3$ (0.490 mg, 1.50 mmol), and 4-iodoanisole (0.230 g, 0.98 mmol). The tube was evacuated and backfilled with argon (3 times), and the Teflon stopcock was replaced with a rubber septum. Ethyl cyanoacetate (0.13 mL, 1.22 mmol) was added, followed by anhydrous dioxane (1.0 mL). The septum was replaced by the Teflon stopcock under a positive pressure of argon, and the sealed tube was placed in an oil bath preheated to 110° C. After the designated time, the reaction was allowed to cool to room temperature, and was then partitioned between 20 mL ethyl acetate and 10 mL saturated NH$_4$Cl (aq). The organic portion was dried (Na$_2$SO$_4$), filtered through Celite, and concentrated on a rotary evaporator. The oil thus obtained was purified by silica gel chromatography to give the product 4-methoxyphenyl ethyl cyanoacetate as a yellow oil (132 mg, 61%).

Example 159

Vinylation of indole using trans-N,N'-dimethyl-1,2-cyclohexanediamine as the ligand General Procedure To a resealable test tube was added a stir bar, CuI (5 mol %), indole (1.00 mmol) and base (2.1 mmol). The tube was then fixed with a rubber septum, and evacuated and back-filled with argon twice. Dodecane (45 µL, 0.20 mmol), the vinyl halide (1.2 mmol), trans-N,N'-dimethyl-1,2-cyclohexanediamine (10 mol %) and toluene (1 mL) were then added successively under argon. The septum was replaced with a screw cap and the contents were stirred at the desired temperature (oil bath, if needed) for 24 hours. The reaction mixture was allowed to reach ambient temperature, diluted with 2-3 mL ethyl acetate, shaken, and allowed to settle for a few min before the top layer was sampled for GC and GC/MS analysis.

1-(2-Methylpropenyl)indole

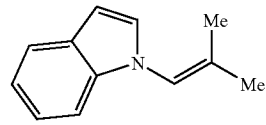 [SMILES: CC(C)=Cn1ccc2ccccc21]

Using the general procedure described above, indole (0.117 g, 1.00 mmol) was coupled with 1-bromo-2-methylpropene (123 µL, 1.20 mmol) using CuI (9.5 mg, 0.050 mmol, 5.0 mol %), K$_3$PO$_4$ (2.1 mmol), trans-N,N'-dimethyl-1,2-cyclohexanediamine (16 µL, 0.10 mmol, 10 mol %) and toluene (1.0 mL) at 80° C. to give 45-50% conversion of indole (GC); the structure of the product was assigned using GC/MS analysis.

1-(1-Hexenyl)indole

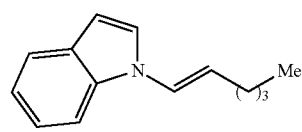

Using the general procedure described above, indole (0.117 g, 1.00 mmol) was coupled with 1-iodo-1-hexene (171 µL, 1.20 mmol) using CuI (9.5 mg, 0.050 mmol, 5.0 mol %), K$_3$PO$_4$ (2.1 mmol), trans-N,N'-dimethyl-1,2-cyclohexanediamine (16 µL, 0.10 mmol, 10 mol %) and toluene (1.0 mL) at ambient temperature to give 42% conversion of indole (GC); the structure of the product was assigned by GC/MS analysis.

Example 160

Arylation of indole using 2-(aminomethyl)pyridine or N,N-diethylsalicylamide as the ligand To a resealable test tube was added a stir bar, CuI (5 mol %), indole (1.00 mmol) and K$_3$PO$_4$ (2.1 mmol). The tube was then fixed with a rubber septum, and evacuated and back-filled with argon twice. Dodecane (45 μL, 0.20 mmol), the vinyl halide (1.2 mmol), ligand (20 mol %) and toluene (1 mL) were then added successively under argon. The septum was replaced with a screw cap and the contents were stirred at 110° C. (oil bath) for 24 hours. The reaction mixture was allowed to reach ambient temperature, diluted with 2-3 mL ethyl acetate, shaken, and allowed to settle for a few minutes. The top layer was then analyzed by GC and GC/MS.

1-(2-Methylphenyl)indole

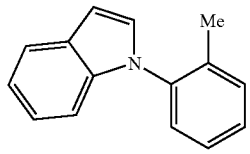 [SMILES: Cc1ccccc1-n1ccc2ccccc21]

Using the general procedure described above, indole (0.117 g, 1.00 mmol) was coupled with 2-bromotoluene (144 μL, 1.20 mmol) using CuI (9.5 mg, 0.050 mmol, 5.0 mol %), K$_3$PO$_4$ (2.1 mmol), 2-(aminomethyl)pyridine (21 μL, 0.20 mmol, 20 mol %) and toluene (1.0 mL) to give 38% conversion of indole (GC). The structure of the product (35% GC yield) was assigned by comparison of the GC to authentic material.

1-(2-Methylphenyl)indole

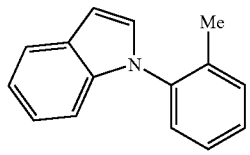 [SMILES: Cc1ccccc1-n1ccc2ccccc21]

Using the general procedure described above, indole (0.117 g, 1.00 mmol) was coupled with 2-bromotoluene (144 μL, 1.20 mmol) using CuI (9.5 mg, 0.050 mmol, 5.0 mol %), K$_3$PO$_4$ (2.1 mmol), N,N-diethylsalicylamide (0.039 g, 0.20 mmol, 20 mol %) and toluene (1.0 mL) to give 42% conversion of indole (GC). The structure of the product (40% GC yield) was assigned comparison of the GC to authentic material.

Example 161

E-1-Benzyloxyhex-1-ene from benzyl alcohol and E-1-iodohexene

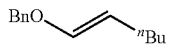

A screw cap test tube was charged with benzyl alcohol (207 μL, 2.00 mmol), E-1-iodohexene (210 mg, 1.00 mmol), CuI (19.0 mg, 0.100 mmol), 1,10-phenanthroline (36.0 mg, 0.200 mmol), Cs$_2$CO$_3$ (489 mg, 1.50 mmol) and toluene (500 μL). The test tube was sealed with a screw cap. The reaction mixture was stirred magnetically and heated at 80° C. for 14 hours. The resulting suspension was allowed to reach room temperature and filtered through a 0.5×1 cm pad of silica gel eluting with dichloromethane. The filtrate was concentrated. Purification of the residue by flash chromatography on silica gel (2×20 cm; pentane/CH$_2$Cl$_2$ 10:1) provided 136 mg (72% yield) of the title compound as a colorless liquid.

Example 162

1-Benzyloxy-2-methylpropene from benzyl alcohol and 1-bromo-2-methylpropene

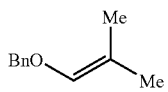

A screw cap test tube was charged with benzyl alcohol (207 μL, 2.00 mmol), 1-bromo-2-methylpropene (103 μL, 1.00 mmol), CuI (19.0 mg, 0.100 mmol), 1,10-phenanthroline (36.0 mg, 0.200 mmol), Cs$_2$CO$_3$ (489 mg, 1.50 mmol) and toluene (500 μL). The test tube was sealed with a screw cap. The reaction mixture was stirred magnetically and heated at 80° C. for 48 hours. The resulting suspension was allowed to reach room temperature and filtered through a 0.5×1 cm pad of silica gel eluting with dichloromethane. The filtrate was concentrated. Purification of the residue by flash chromatography on silica gel (2×20 cm; pentane/CH$_2$Cl$_2$ 10:1) provided 81 mg (50% yield) of the title compound as a colorless oil.

Example 163

E-1-Undecyloxy-hex-1-ene from n-undecanol and E-1-iodohexene

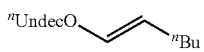

A screw cap test tube was charged with n-undecanol (415 μL, 2.00 mmol), E-1-iodohexene (210 mg, 1.00 mmol), CuI (19.0 mg, 0.100 mmol), 1,10-phenanthroline (36.0 mg, 0.200 mmol), Cs$_2$CO$_3$ (489 mg, 1.50 mmol) and toluene (500 μL). The test tube was sealed with a screw cap. The reaction mixture was stirred magnetically and heated at 100° C. for 36 hours. The resulting suspension was allowed to reach room temperature and filtered through a 0.5×1 cm pad of silica gel eluting with dichloromethane. The filtrate was concentrated. Purification of the residue by flash chromatography on silica gel (2×20 cm; pentane/CH$_2$Cl$_2$ 20:1) provided 141 mg (55% yield) of the title compound as a colorless liquid.

Example 164

1E,2E-1-Dec-1-enyloxyundec-2-ene from E-2-undecene-1-ol and E-1-iododecene

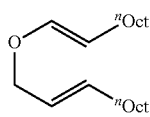

A screw cap test tube was charged with E-2-undecene-1-ol (401 µL, 2.00 mmol), E-1-iododecene (266 mg, 1.00 mmol), CuI (19.0 mg, 0.100 mmol), 3,4,7,8-tetramethyl-1,10-phenanthroline (47.3 mg, 0.200 mmol), Cs₂CO₃ (489 mg, 1.50 mmol) and toluene (500 µL). The test tube was sealed with a screw cap. The reaction mixture was stirred magnetically and heated at 80° C. for 24 hours. The resulting suspension was allowed to reach room temperature and filtered through a 0.5×1 cm pad of silica gel eluting with dichloromethane. The filtrate was concentrated. Purification of the residue by flash chromatography on silica gel (2×20 cm; pentane/CH₂Cl₂ 100:1) provided 141 mg (199 mg, 68% yield) of the title compound as a colorless oil.

Example 165

1E,2Z-1-Hex-2-enyloxydec-1-ene from Z-2-hexen-1-ol and E-1-iododecene

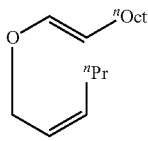

A screw cap test tube was charged with Z-2-hexene-1-ol (237 µL, 2.00 mmol), E-1-iododecene (266 mg, 1.00 mmol), CuI (19.0 mg, 0.100 mmol), 3,4,7,8-tetramethyl-1,10-phenanthroline (47.3 mg, 0.200 mmol), Cs₂CO₃ (489 mg, 1.50 mmol) and toluene (500 µL). The test tube was sealed with a screw cap; The reaction mixture was stirred magnetically and heated at 90° C. for 22 hours. The resulting suspension was allowed to reach room temperature and filtered through a 0.5×1 cm pad of silica gel eluting with dichloromethane. The filtrate was concentrated. Purification of the residue by flash chromatography on silica gel (2×20 cm; pentane/CH₂Cl₂ 100:1) provided 135 mg (57% yield) of the title compound as a colorless oil.

Example 166

2,3-Dioctyl-pent-4-enal from E-2-undecene-1-ol and E-1-iododecene

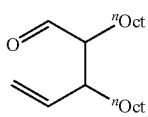

An oven dried screw cap test tube was charged with E-2-undecene-1-ol (401 µL, 2.00 mmol), E-1-iododecene (266 mg, 1.00 mmol), CuI (19.0 mg, 0.100 mmol), 1,10-phenanthroline (36.0 mg, 0.200 mmol), Cs₂CO₃ (489 mg, 1.50 mmol) and o-xylene (500 µL). The test tube was evacuated and backfilled with argon (flushed for 10 min). The test tube was sealed with a screw cap. The reaction mixture was stirred magnetically and heated at 140° C. for 19 hours. The resulting suspension was allowed to reach room temperature and filtered through a 0.5×1 cm pad of silica gel eluting with dichloromethane. The filtrate was concentrated. Purification of the residue by flash chromatography on silica gel (2×20 cm; pentane/CH₂Cl₂ 3:1) provided 188 mg (64% yield) of the title compound as a yellow oil.

Example 167

E-1,3-Dimethyl-5-undec-2-enyloxy-benzene from E-2-undecene-1-ol and 3,5-dimethylbromobenzene

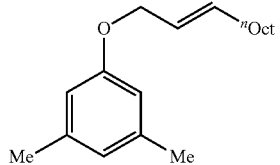

A screw cap test tube was charged with E-2-undecene-1-ol (401 µL, 2.00 mmol), 3,5-dimethylbromobenzene (136 µL, 1.00 mmol), CuI (19.0 mg, 0.100 mmol), 3,4,7,8-tetramethyl-1,10-phenanthroline (47.3 mg, 0.200 mmol), Cs₂CO₃ (489 mg, 1.50 mmol) and o-xylene (500 µL). The test tube was sealed with a screw cap. The reaction mixture was stirred magnetically and heated at 120° C. for 48 hours. The resulting suspension was allowed to reach room temperature and filtered through a 0.5×1 cm pad of silica gel eluting with dichloromethane. The filtrate was concentrated. Purification of the residue by flash chromatography on silica gel (2×20 cm; pentane/CH₂Cl₂ 10:1) provided 128 mg (47% yield) of the title compound as a colorless oil.

Example 168

1-Heptoxy-3,5-methylbenzene from the corresponding arylbromide

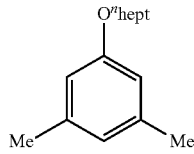

A screw cap test tube was charged with n-heptanol (1.0 mL), 3,5-dimethylbromobenzene (136 µL, 1.00 mmol), CuI (19.0 mg, 0.100 mmol), 3,4,7,8-tetramethyl-1,10-phenanthroline (47.3 mg, 0.200 mmol) and Cs₂CO₃ (977 mg, 3.00 mmol). The test tube was sealed with a screw cap. The reaction mixture was stirred magnetically and heated at 110° C. for 28 hours. The reaction mixture was allowed to reach room temperature. Dodecane (227 µL, 1.00 mmol; internal standard) was added and a GC sample was filtered through Celite and eluted with CH₂Cl₂. GC analysis revealed 51% yield of the desired product.

Example 169

1-Benzyloxy-3,5-dimethylbenzene from benzyl alcohol and 3,5-dimethylbromobenzene

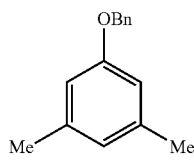

A screw cap test tube was charged with benzyl alcohol (207 μL, 2.00 mmol), 3,5-dimethylbromobenzene (136 μL, 1.00 mmol), CuI (19.0 mg, 0.100 mmol), 3,4,7,8-tetramethyl-1,10-phenanthroline (47.3 mg, 0.200 mmol), Cs$_2$CO$_3$ (489 mg, 1.50 mmol) and o-xylene (500 μL). The test tube was sealed with a screw cap. The reaction mixture was stirred magnetically and heated at 120° C. for 48 hours. The resulting suspension was allowed to reach room temperature and filtered through a 0.5×1 cm pad of silica gel eluting with dichloromethane. The filtrate was concentrated. Purification of the residue by flash chromatography on silica gel (2×20 cm; pentane/CH$_2$Cl$_2$ 10:1) provided 135 mg (64% yield) of the title compound as a colorless oil.

Example 170

3-Methoxyaniline

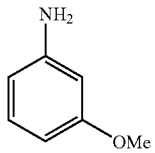

A test tube was charged with CuI (20 mg, 0.10 mmol, 0.10 equiv), 1,10-phenanthroline (36 mg, 0.20 mmol, 0.20 equiv), Cs$_2$CO$_3$ (456 mg, 1.4 mmol, 1.4 equiv), 3-iodoaniline (120 μL, 1.0 mmol, 1.0 equiv) and methanol (1.0 mL, 25 mmol, 25 equiv). The test tube was sealed and the reaction mixture was stirred at 110° C. for 21 h. The resulting suspension was cooled to room temperature and filtered through a 0.5×1 cm pad of silica gel, eluting with diethyl ether. The filtrate was concentrated in vacuo. Purification of the residue by flash chromatography on silica gel (2×20 cm; pentane:diethyl ether 2:1) provided 96 mg (78% yield) of the known title compound as a yellow oil.

Example 171

3-Isopropyloxypyridine

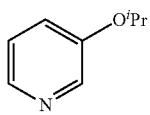

A test tube was charged with CuI (20 mg, 0.10 mmol, 0.10 equiv), 1,10-phenanthroline (36 mg, 0.20 mmol, 0.20 equiv), Cs$_2$CO$_3$ (652 mg, 2.0 mmol, 2.0 equiv), 3-iodopyridine (205 mg, 1.0 mmol, 1.0 equiv) and iso-propanol (1.0 mL, 13 mmol, 13 equiv). The test tube was sealed and the reaction mixture was stirred at 110° C. for 21 h. The resulting suspension was cooled to room temperature and filtered through a 0.5×1 cm pad of silica gel, eluting with diethyl ether. The filtrate was concentrated in vacuo. Purification of the residue by flash chromatography on silica gel (2×20 cm; pentane:diethyl ether 4:1) provided 126 mg (92% yield) of the title compound as a colorless oil.

Example 172

4-(trans-But-2-enyloxy)anisole

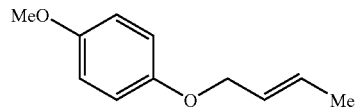 [SMILES: C/C=C/COc1ccc(OC)cc1]

A test tube was charged with CuI (20 mg, 0.10 mmol, 0.10 equiv), 1,10-phenanthroline (36 mg, 0.20 mmol, 0.20 equiv), Cs$_2$CO$_3$ (652 mg, 2.0 mmol, 2.0 equiv), 4-iodoanisole (234 mg, 1.0 mmol, 1.0 equiv), trans-2-buten-1-ol (171 μL, 2.0 mmol, 2.0 equiv) and toluene (0.5 mL). The test tube was sealed and the reaction mixture was stirred at 110° C. for 22 h. The resulting suspension was cooled to room temperature and filtered through a 0.5×1 cm pad of silica gel, eluting with diethyl ether. The filtrate was concentrated in vacuo. Purification of the residue by flash chromatography on silica gel (2×20 cm; pentane:diethyl ether 30:1) provided 153 mg (86% yield) of the title compound as a light yellow oil.

Example 173

4-(2-Methylallyloxy)anisole

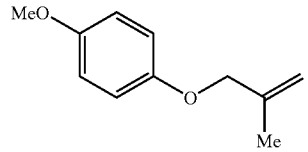

A test tube was charged with CuI (20 mg, 0.10 mmol, 0.10 equiv), 1,10-phenanthroline (36 mg, 0.20 mmol, 0.20 equiv), Cs$_2$CO$_3$ (652 mg, 2.0 mmol, 2.0 equiv), 4-iodoanisole (234 mg, 1.0 mmol, 1.0 equiv), 2-methyl-2-propen-1-ol (168 μL, 2.0 mmol, 2.0 equiv) and toluene (0.5 mL). The test tube was sealed and the reaction mixture was stirred at 110° C. for 28 h. The resulting suspension was cooled to room temperature and filtered through a 0.5×1 cm pad of silica gel, eluting with diethyl ether. The filtrate was concentrated in vacuo. Purification of the residue by flash chromatography on silica gel (2×20 cm; pentane:diethyl ether 30:1) provided 139 mg (78% yield) of the title compound as a colorless solid.

Example 174

4-(1-Methylallyloxy)anisole

A test tube was charged with CuI (20 mg, 0.10 mmol, 0.10 equiv), 1,10-phenanthroline (36 mg, 0.20 mmol, 0.20 equiv), Cs$_2$CO$_3$ (652 mg, 2.0 mmol, 2.0 equiv), 4-iodoanisole (234 mg, 1.0 mmol, 1.0 equiv), 3-buten-2-ol (180 μL, 2.0 mmol, 2.0 equiv) and toluene (0.5 mL). The test tube was sealed and the reaction mixture was stirred at 110° C. for 38 h. The resulting suspension was cooled to room temperature and filtered through a 0.5×1 cm pad of silica gel, eluting with diethyl ether. The filtrate was concentrated in vacuo. Purification of the residue by flash chromatography on silica gel (2×20 cm; pentane:diethyl ether 30:1) provided 96 mg (54% yield) of the known title compound as a colorless oil.

Example 175

2-[(4-Methoxyphenoxy)methyl]pyridine

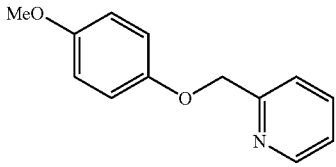 [SMILES: COc1ccc(OCc2ccccn2)cc1]

A test tube was charged with CuI (20 mg, 0.10 mmol, 0.10 equiv), 1,10-phenanthroline (36 mg, 0.20 mmol, 0.20 equiv), Cs$_2$CO$_3$ (652 mg, 2.0 mmol, 2.0 equiv), 4-iodoanisole (234 mg, 1.0 mmol, 1.0 equiv), 2-pyridylcarbinol (193 μL, 2.0 mmol, 2.0 equiv) and toluene (0.5 mL). The test tube was sealed and the reaction mixture was stirred at 110° C. for 22 h. The resulting suspension was cooled to room temperature and filtered through a 0.5×1 cm pad of silica gel, eluting with diethyl ether. The filtrate was concentrated in vacuo. Purification of the residue by flash chromatography on silica gel (2×20 cm; pentane:diethyl ether 1:1) provided 120 mg (56% yield) of the title compound as a light yellow solid.

Example 176

1-Bromo-2-benzyloxybenzene

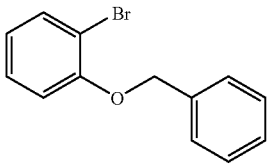 [SMILES: Brc1ccccc1OCc1ccccc1]

A test tube was charged with CuI (20 mg, 0.10 mmol, 0.10 equiv), 1,10-phenanthroline (36 mg, 0.20 mmol, 0.20 equiv), Cs$_2$CO$_3$ (456 mg, 1.4 mmol, 1.4 equiv), benzyl alcohol (207 μL, 2.0 mmol, 2.0 equiv), 2-bromo-iodobenzene (128 μL, 1.0 mmol, 1.0 equiv) and toluene (0.5 mL). The test tube was sealed and the reaction mixture was stirred at 110° C. for 36 h. The resulting suspension was cooled to room temperature and filtered through a 1×1 cm pad of silica gel, eluting with dichloromethane. The filtrate was concentrated in vacuo. Purification of the residue by flash chromatography on silica gel (2×20 cm; pentane:dichloromethane 2:1) provided 187 mg (71% yield) of the title compound as a colorless oil.

Example 177

N-(3,5-Dimethylphenyl)-2-pyrrolidinone using potassium 4-cyano-2,6-di-tert-butylphenoxide as the base

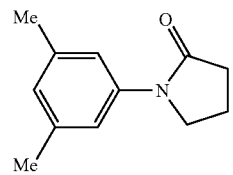 [SMILES: Cc1cc(C)cc(N2CCCC2=O)c1]

A 15 mL resealable Schlenk tube was charged with CuI (9.6 mg, 0.0504 mmol, 5.0 mol %), potassium 4-cyano-2,6-di-tert-butylphenoxide (325 mg, 1.21 mmol), evacuated and backfilled with argon. 5-Iodo-m-xylene (145 μL, 1.00 mmol), 2-pyrrolidinone (94 μL, 1.24 mmol) and toluene (1.0 mL) were added under argon. The Schlenk tube was sealed with a Teflon valve and the reaction mixture was stirred at 100° C. for 23 h. The resulting suspension was allowed to reach room temperature. Dodecane (internal GC standard, 230 μL) and ethyl acetate (2 mL) were added. A 0.1 mL sample of the supernatant solution was diluted with ethyl acetate (1 mL) and analyzed by GC to provide 95% yield of the desired product.

Example 178

N-(3,5-Dimethylphenyl)-N-ethylacetamide using 4-dimethylaminopyridine as ligand, sodium tert-butoxide as base and N-methyl-2-pyrrolidinone as solvent

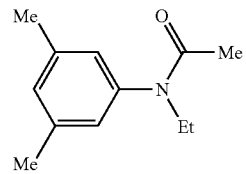 [SMILES: CCN(C(C)=O)c1cc(C)cc(C)c1]

A Schlenk tube was charged with CuI (190 mg, 1.00 mmol), 4-dimethylaminopyridine (245 mg, 2.01 mmol), sodium tert-butoxide (115 mg, 1.20 mmol), evacuated and backfilled with argon. 5-Iodo-m-xylene (145 μL, 1.00 mmol), N-ethylacetamide (142 μL, 1.51 mmol), and N-methyl-2-pyrrolidinone (1.0 mL) were added under argon. The Schlenk tube was sealed with a Teflon valve and the reaction mixture was stirred at 110° C. for 25 h. The resulting brown suspension was allowed to reach room temperature, poured into a solution of 30% aq ammonia (2 mL) in water (20 mL), and extracted with CH$_2$Cl$_2$ (3×15 mL). The combined organic phases were dried (Na$_2$SO$_4$) and concentrated by rotary evaporation. The residue was purified by flash chromatography on silica gel (2×15 cm; hexane-ethyl acetate 3:2; 15 mL fractions). Fractions 8-16 provided 164 mg (86% yield) of the product as a white solid.

Example 179

N-(3,5-Dimethylphenyl)-N-methylformamide using bis(1-methylimidazol-2-yl)ketone as ligand A 15 mL resealable Schlenk tube was charged with CuI (9.6 mg, 0.0504 mmol, 5.0 mol %), bis(1-methylimidazol-2-yl)ketone (19 mg, 0.100 mmol, 10 mol %), $K_3PO_4$ (430 mg, 2.03 mmol), evacuated and backfilled with argon. 5-Iodo-m-xylene (145 µL, 1.00 mmol), N-methylformamide (72 µL, 1.23 mmol) and toluene (1.0 mL) were added under argon. The Schlenk tube was sealed with a Teflon valve and the reaction mixture was stirred at 110° C. for 24 h. The resulting suspension was allowed to reach room temperature. Dodecane (internal GC standard, 230 µL) and ethyl acetate (2 mL) were added. A 0.1 mL sample of the supernatant solution was diluted with ethyl acetate (1 mL) and analyzed by GC to provide 95% yield of the desired product.

Example 180

N-Formylindoline from the Corresponding Aryl Bromide at Room Temperature in 4 h Using 1 Equiv of Water

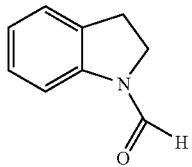 [SMILES: O=CN1CCc2ccccc21]

A Schlenk tube was charged with CuI (9.6 mg, 0.050 mmol, 5.0 mol %), N-[2-(2-bromophenyl)ethyl]formamide (229 mg, 1.00 mmol), $Cs_2CO_3$ (500 mg, 1.53 mmol), evacuated and backfilled with argon. N,N'-Dimethylethylenediamine (11 µL, 0.10 mmol, 10 mol %), THF (1 mL), and finally water (18 µL, 1.0 mmol) were added under argon. The Schlenk tube was sealed with a Teflon valve and the reaction mixture was stirred at 25±5° C. for 4 h. The resulting pale blue-green suspension was filtered through a 0.5×1 cm pad of silica gel eluting with ethyl acetate (20 mL). The filtrate was concentrated and the residue was purified by flash chromatography on silica gel (2×10 cm; hexane-ethyl acetate 2:3; 15 mL fractions). Fractions 8-17 provided 147 mg (100% yield) of the product as a pale yellow solid.

Example 181

Preparation of N-(3,5-dimethylphenyl)benzamide at room temperature for 7 h using 1 equiv of water

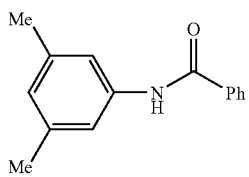

A Schlenk tube was charged with CuI (9.6 mg, 0.050 mmol, 5.0 mol %), benzamide (146 mg, 1.21 mmol), $Cs_2CO_3$ (500 mg, 1.53 mmol), evacuated and backfilled with argon. N,N'-Dimethylethylenediamine (11 µL, 0.10 mmol, 10 mol %), 5-iodo-m-xylene (145 µL, 1.00 mmol), THF (1.0 mL), and finally water (18 µL, 1.0 mmol) were added under argon. The Schlenk tube was sealed with a Teflon valve and the reaction mixture was stirred at 25±5° C. for 7 h. The resulting white suspension was filtered through a 0.5×1 cm pad of silica gel eluting with ethyl acetate (20 mL). The filtrate was concentrated and the residue was purified by flash chromatography on silica gel (2×20 cm; hexane-ethyl acetate 3:1; 15 mL fractions; the sample was solubilized with 1 mL of $CH_2Cl_2$). Fractions 9-15 provided 223 mg (99% yield) of the product as white crystals.

Example 182

2,3,5,6-Tetrahydro-1H-benzo[b]-1,5-diazocin-4-one using tandem aryl amidation-ring expansion reaction

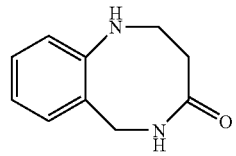 [SMILES: O=C1CCNc2ccccc2CN1]

A Schlenk tube was charged with CuI (9.6 mg, 0.050 mmol, 5.0 mol %), 2-azetidinone (86 mg, 1.21 mmol), $K_3PO_4$ (430 mg, 2.03 mmol), evacuated, and backfilled with Ar. N,N'-Dimethylethylenediamine (11 µL, 0.103 mmol, 10 mol %), 2-iodobenzylamine (132 µL, 1.00 mmol), and toluene (1 mL) were added under Ar. The Schlenk tube was sealed and the reaction mixture was stirred at 100° C. for 22 h. The resulting suspension was allowed to reach room temperature, poured into a solution of 30% aq ammonia (1 mL) in water (20 mL), and extracted with 3×20 mL $CH_2Cl_2$. The combined organic layers were dried ($Na_2SO_4$), concentrated, and the residue was purified by flash chromatography on silica gel (2×15 cm, ethyl acetate-methanol 10:1, 15 mL fractions). Fractions 10-20 provided 144 mg of the desired product (82% yield) as a white solid.

Example 183

N-Benzyl-N-(4-thiomethylphenyl)formamide

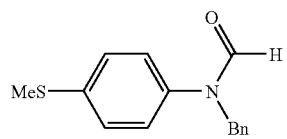 [SMILES: CSc1ccc(N(C=O)Cc2ccccc2)cc1]

A Schlenk tube was charged with CuI (9.6 mg, 0.050 mmol, 5.0 mol %), 4-bromothioanisole (204 mg, 1.00 mmol), N-benzylformamide (163 mg, 1.21 mmol), $K_2CO_3$ (280 mg, 2.12 mmol), briefly evacuated and backfilled with argon. N,N'-Dimethylethylenediamine (11 µL, 0.10 mmol, 10 mol %) and toluene (1.0 mL) were added under argon. The Schlenk tube was sealed with a Teflon valve and the reaction mixture was stirred at 110° C. for 23 h. The resulting pale brown suspension was allowed to reach room temperature and filtered through a 0.5×1 cm pad of silica gel eluting with ethyl acetate (10 mL). The filtrate was concentrated and the residue was purified by flash chromatography on silica gel (2×15 cm; hexane-ethyl acetate 2:1; 15 mL fractions). Fractions 9-19 provided 243 mg (94% yield) of the product as a white solid. Mp: 73-74° C.

Example 184

2-Hydroxy-N-phenylpropionamide using DMF as solvent

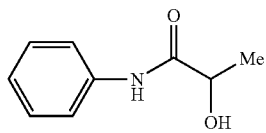 [SMILES: CC(O)C(=O)Nc1ccccc1]

A Schlenk tube was charged with CuI (9.6 mg, 0.050 mmol, 5.0 mol %), racemic lactamide (107 mg, 1.20 mmol), K₃PO₄ (430 mg, 2.03 mmol), evacuated and backfilled with argon. N,N'-Dimethylethylenediamine (11 µL, 0.10 mmol, 10 mol %), iodobenzene (112 µL, 1.00 mmol) and dimethylformamide (1.0 mL) were added under argon. The Schlenk tube was sealed with a Teflon valve and the reaction mixture was stirred at 60° C. for 23 h. The resulting purple-blue suspension was allowed to reach room temperature and filtered through a 0.5×1 cm pad of silica gel eluting with 10:1 dichloromethane-methanol (20 mL). The filtrate was concentrated using a rotary evaporation followed by evacuation at 0.1 mm Hg to remove dimethylformamide. The residue was purified by flash chromatography on silica gel (2×20 cm; dichloromethane-methanol 25:1; 15 mL fractions). Fractions 10-16 provided 146 mg (88% yield) of the product as a pale tan solid.

Example 185

N-tert-Butoxycarbonyl-4-chloroaniline

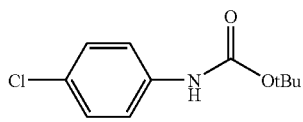 [SMILES: CC(C)(C)OC(=O)Nc1ccc(Cl)cc1]

A Schlenk tube was charged with CuI (9.6 mg, 0.050 mmol, 5.0 mol %), 4-bromo-1-chlorobenzene (192 mg, 1.00 mmol), tert-butyl carbamate (142 mg, 1.21 mmol), K₂CO₃ (280 mg, 2.03 mmol), briefly evacuated and backfilled with argon. N,N'-Dimethylethylenediamine (11 µL, 0.10 mmol, 10 mol %) and toluene (1.0 mL) were added under argon. The Schlenk tube was sealed with a Teflon valve and the reaction mixture was stirred at 110° C. for 23 h. The resulting pale blue suspension was allowed to reach room temperature and filtered through a 0.5×1 cm pad of silica gel eluting with ethyl acetate (10 mL). The filtrate was concentrated and the residue was purified by flash chromatography on silica gel (2×20 cm; hexane-ethyl acetate 9:1; 15 mL fractions). Fractions 12-22 provided 178 mg (78% yield) of the product as white crystals.

Example 186

N-(3-Aminomethylphenyl)-2-piperidone

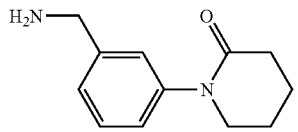

A Schlenk tube was charged with CuI (9.6 mg, 0.050 mmol, 5.0 mol %), δ-valerolactam (120 mg, 1.21 mmol), K₃PO₄ (430 mg, 2.03 mmol), briefly evacuated and backfilled with argon. N,N'-Dimethylethylenediamine (11 µL, 0.10 mmol, 10 mol %), 3-iodobenzylamine (134 µL, 1.01 mmol), and toluene (1.0 mL) were added under argon. The Schlenk tube was sealed with a Teflon valve and the reaction mixture was stirred at 100° C. for 18 h. The resulting pale yellow suspension was allowed to reach room temperature, and then 30% aq ammonia (1 mL) and water (10 mL) were added. The biphasic mixture was extracted with CH₂Cl₂ (3×15 mL). The combined organic phases were dried (Na₂SO₄), concentrated, and the residue was purified by flash chromatography on silica gel (2×15 cm; CH₂Cl₂ (saturated with 30% aq ammonia)-CH₂Cl₂—MeOH 10:10:1; 15 mL fractions). Fractions 14-19 provided 199 mg (96% yield) of the product as a pale yellow oil.

Example 187

N-(3-Hydroxymethylphenyl)-2-pyrrolidinone

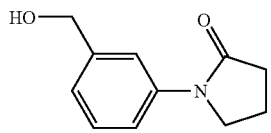

A Schlenk tube was charged with CuI (9.6 mg, 0.050 mmol, 5.0 mol %) and K₃PO₄ (430 mg, 2.03 mmol), evacuated and backfilled with argon. N,N'-Dimethylethylenediamine (11 µL, 0.10 mmol, 10 mol %), 3-iodobenzyl alcohol (128 µL, 1.01 mmol), 2-pyrrolidinone (94 µL, 1.24 mmol) and toluene (1.0 mL) were added under argon. The Schlenk tube was sealed with a Teflon valve and the reaction mixture was stirred at 80° C. for 3 h. The resulting white suspension was allowed to reach room temperature and filtered through a 0.5×1 cm pad of silica gel eluting with 5:1 ether-methanol (10 mL). The filtrate was concentrated and the residue was purified by flash chromatography on silica gel (2×20 cm; dichloromethane-methanol 25:1; 15 mL fractions). Fractions 14-19 provided 180 mg (93% yield) of the product as a white solid. Mp: 120-121° C.

Example 188

N-(3-Methyl-2-butenyl)-2-pyrrolidinone from a vinyl bromide

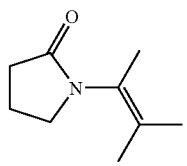

A 15 mL screw top test tube fitted with a PTFE septum cap was charged with CuI (10.0 mg, 0.05 mmol, 5 mol %) and K$_2$CO$_3$ (276 mg, 2.00 mmol). 2-Pyrrolidinone (76 μL, 1.00 mmol), 2-bromo-3-methyl-2-butene (116 μL, 1.00 mmol), N,N'-dimethyl ethylenediamine (11 μL, 0.10 mmol, 10 mol %), and 1,4-dioxane (1 mL) were added, via syringe, while purging with nitrogen. The septum cap was replaced with a solid, Teflon-lined cap and the reaction was stirred magnetically at 100° C. for 38 h. The resulting heterogeneous solution was allowed to cool before dilution with 5 mL ethyl acetate. The reaction mixture was filtered and the solution obtained was concentrated to a yellow oil. The crude material was purified by silica gel chromatography using methylene chloride:ethyl acetate (80:20); the product was isolated, as a yellow oil, in 69% yield (105.3 mg). $^1$H NMR (300 MHz, CDCl$_3$): a 1.60 (d, J=1.4 Hz, 3H), 1.74 (s, 3H), 1.79 (dd, J=1.3, 1.1 Hz, 3H), 2.14 (m, 2H), 2.42 (t, J=8.1 Hz, 2H), 3.44 (t, J=6.8 Hz, 2H). $^{13}$C NMR (75.5 MHz, CDCl$_3$): 14.9, 18.5, 19.4, 19.5, 30.9, 47.5, 124.9, 129.0, 173.2.

Example 189

N-(3-methyl-2-butenyl)benzamide from a vinyl bromide

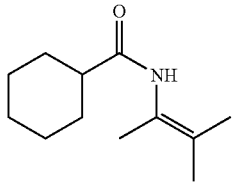

A 15 mL screw top test tube fitted with a PTFE septum cap was charged with CuI (10.0 mg, 0.05 mmol, 5 mol %), K$_2$CO$_3$ (276 mg, 2.00 mmol), and cylohexane carboxamide (127 mg, 1.00 mmol). 2-Bromo-3-methyl-2-butene (116 μL, 1.00 mmol), N,N'-dimethyl ethylenediamine (11 μL, 0.10 mmol, 10.0 mol %), and 1,4-dioxane (1 mL) were added, via syringe, while purging with nitrogen. The septum cap was replaced with a solid, Teflon-lined cap and the reaction was stirred magnetically at 100° C. for 38 h. The resulting heterogeneous solution was allowed to cool before dilution with 5 mL ethyl acetate. The reaction mixture was filtered and the solvent was removed to yield a white solid. The crude material was purified by recrystallization from ethyl acetate:hexanes (1:1); the product was obtained as white, fibrous crystals in 62% yield (121.7 mg) $^1$H NMR (300 MHz, CDCl$_3$): ∂ 1.55 (m, 10H), 1.60 (s, 3H), 1.68 (s, 3H), 1.87 (s, 3H), 2.12 (m, 1H), 6.40 (broad s, 1H). $^{13}$C NMR (75.5 MHz, CDCl$_3$): 17.5, 19.5, 19.7, 25.8, 29.7, 29.9, 45.7, 124.0, 124.4, 174.1.

Example 190

N'-(3,5-dimethylphenyl)benzhydrazide from an aryl bromide

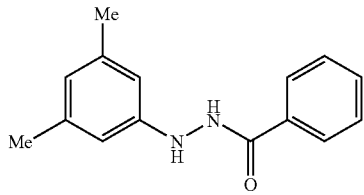 [SMILES: Cc1cc(C)cc(NNC(=O)c2ccccc2)c1]

CuOAc (6 mg, 0.05 mmol), N,N-diethylsalicylamide (39 mg, 0.20 mmol), benzhydrazide (207 mg, 1.5 mmol) and K$_3$PO$_4$ (425 mg, 2.0 mmol) were put into a screw-capped test tube with a Teflon-lined septum. The tube was then evacuated and backfilled with argon (3 cycles). 5-Bromo-m-xylene (136 μL, 1.0 mmol) and DMF (0.5 mL) were added by syringes. The reaction was heated at 90° C. for 22 hours. The reaction was allowed to reach room temperature. Ethyl acetate (~2 mL), water (~10 mL), ammonium hydroxide (~0.5 mL) and dodecane (227 μL) were added. The organic phase was analyzed by GC or GC-MS. The reaction was further extracted by ethyl acetate (4×10 mL). The combined organic phases were washed with brine and dried over Na$_2$SO$_4$. Solvent was removed in vacuo and the yellow residue was purified by column chromatography on silica gel using dichloromethane/ethyl acetate (20:1) as eluent to afford the desired product as a white solid (107 mg, 46% yield). R$_f$=0.5 (dichloromethane/ethyl acetate=20:1).

Example 191

N-Butyl-N'-(3-methoxyphenyl)urea

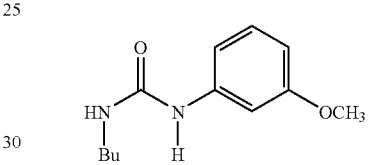

A test tube was charged with CuI (10 mg, 0.05 mmol, 0.05 equiv), K$_3$PO$_4$ (425 mg, 2.0 mmol, 2.0 equiv), butylurea (232 mg, 2.0 mmol, 2.0 equiv), filled with argon. 3-Iodoanisole (119 μL, 1.0 mmol, 1.0 equiv), N,N'-dimethylethylendiamine (11 μL, 0.10 mmol, 0.10 equiv) and dry toluene (1.0 mL) were added under argon. The test tube was sealed and the reaction mixture was stirred at 110° C. for 24 h. The resulting suspension was cooled to room temperature and filtered through a 0.5×1 cm pad of silica gel, eluting with diethyl ether. The filtrate was concentrated in vacuo. Purification of the residue by flash chromatography on silica gel (2×20 cm; pentane:diethyl ether 1:2) provided 188 mg (85% yield) of the title compound as a light yellow oil.

Example 192

N-(3-Methoxyphenyl)-2-imidazolidone

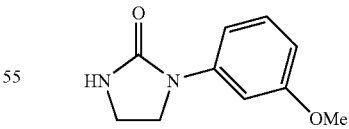

A test tube was charged with CuI (40 mg, 0.20 mmol, 0.10 equiv), K$_3$PO$_4$ (850 mg, 2.0 mmol, 2.0 equiv), 2-imidazolidone (2.58 g, 30.0 mmol, 15.0 equiv), 3-iodoanisole (238 μL, 2.0 mmol, 1.0 equiv), N,N'-dimethylethylendiamine (44 μL, 0.40 mmol, 0.20 equiv) and dry DMF (4.0 mL), filled with argon. The test tube was sealed and the reaction mixture was stirred at 120° C. for 7 h. The resulting suspension was cooled to room temperature and filtered through a 0.5×1 cm pad of silica gel, eluting with ethyl acetate. The filtrate was concentrated in vacuo. Purification of the residue by flash chromatography on silica gel (2×20 cm; hexane:ethyl acetate 1:2) provided 288 mg (75% yield) of the title compound as a light yellow solid.

Example 193

Preparation of N-(3-methoxyphenyl)-2-imidazolidone using microwave irradiation

A microwave test tube was charged with CuI (20 mg, 0.10 mmol, 0.10 equiv), K$_3$PO$_4$ (425 mg, 2.0 mmol, 2.0 equiv), 2-imidazolidone (1.29 g, 15.0 mmol, 15.0 equiv), 3-iodoanisole (119 µL, 1.0 mmol, 1.0 equiv), N,N'-dimethylethylenediamine (22 µL, 0.20 mmol, 0.20 equiv) and dry DMF (2.0 mL), filled with argon. The test tube was sealed and the reaction mixture was stirred at 130° C. for 15 h in the microwave. The resulting suspension was cooled to room temperature and filtered through a 0.5×1 cm pad of silica gel, eluting with ethyl acetate. The filtrate was concentrated in vacuo. Purification of the residue by flash chromatography on silica gel (2×20 cm; hexane:ethyl acetate 1:2) provided 128 mg (67% yield) of the title compound as a white solid.

Example 194

N-(3-Methoxyphenyl)-N'-(3,5-dimethylphenyl)-2-imidazolidone

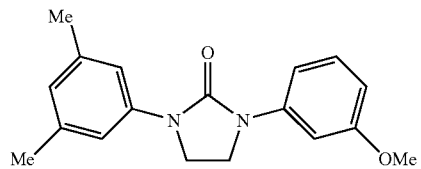 [SMILES: COc1cccc(N2CCN(c3cc(C)cc(C)c3)C2=O)c1]

A microwave test tube was charged with CuI (20 mg, 0.10 mmol, 0.20 equiv), K$_3$PO$_4$ (212 mg, 1.0 mmol, 2.0 equiv), N-(3-methoxyphenyl)-2-imidazolidone (96 mg, 0.5 mmol, 1.0 equiv), 3,5-dimethyliodobenzene (144 µL, 1.0 mmol, 2.0 equiv), N,N'-dimethylethylendiamine (22 µL, 0.20 mmol, 0.40 equiv) and dry DMF (2.0 mL), filled with argon. The test tube was sealed and the reaction mixture was stirred at 130° C. for 15 h and at 160° C. for further 15 h in the microwave. The resulting suspension was cooled to room temperature and filtered through a 0.5×1 cm pad of silica gel, eluting with ethyl acetate. The filtrate was concentrated in vacuo. Purification of the residue by flash chromatography on silica gel (2×20 cm; hexane:ethyl acetate 4:1) provided 134 mg (91% yield) of the title compound as a white solid.

Example 195

N-Benzyl-N'-phenyl-urea

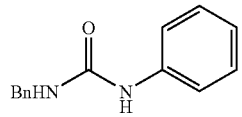

A test tube was charged with CuI (20 mg, 0.10 mmol, 0.10 equiv), K$_3$PO$_4$ (425 mg, 2.0 mmol, 2.0 equiv), benzylurea (225 mg, 1.5 mmol, 1.5 equiv), filled with argon. Bromobenzene (105 µL, 1.0 mmol, 1.0 equiv), N,N'-dimethylethylendiamine (22 µL, 0.20 mmol, 0.20 equiv) and dry dioxane (1.0 mL) were added under argon. The test tube was sealed and the reaction mixture was stirred at 80° C. for 25 h. The resulting suspension was cooled to room temperature and filtered through a 0.5×1 cm pad of silica gel, eluting with ethyl acetate. The filtrate was concentrated in vacuo. The solid residue was dissolved in 2 mL DMF. Purification of the residue by flash chromatography on silica gel (2×20 cm; hexane:ethyl acetate 3:1) provided 179 mg (79% yield) of the title compound as a white solid.

Example 196

N-Benzyl-N'-(3-aminophenyl)urea

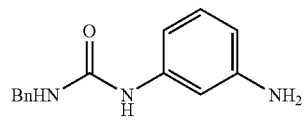

A test tube was charged with CuI (20 mg, 0.10 mmol, 0.10 equiv), K$_3$PO$_4$ (425 mg, 2.0 mmol, 2.0 equiv), benzylurea (225 mg, 1.5 mmol, 1.5 equiv), 3-bromoaniline (109 µL, 1.0 mmol, 1.0 equiv), N,N'-dimethylethylendiamine (22 µL, 0.20 mmol, 0.20 equiv) and dry dioxane (1.0 mL), filled with nitrogen. The test tube was sealed and the reaction mixture was stirred at 80° C. for 24 h. The resulting suspension was cooled to room temperature and filtered through a 0.5×1 cm pad of silica gel, eluting with ethyl acetate. The filtrate was concentrated in vacuo. The solid residue was dissolved in 2 mL DMF. Purification of the residue by flash chromatography on silica gel (2×20 cm; hexane:ethyl acetate 1:2) provided 185 mg (77% yield) of the title compound as a light yellow solid.

Example 197

N-Benzyl-N'-(2-methoxyphenyl)urea

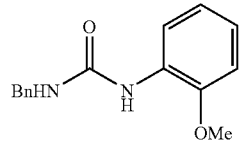

A test tube was charged with CuI (20 mg, 0.10 mmol, 0.10 equiv), K$_3$PO$_4$ (425 mg, 2.0 mmol, 2.0 equiv), benzylurea (225 mg, 1.5 mmol, 1.5 equiv), 2-bromoanisole (125 µL, 1.0 mmol, 1.0 equiv), N,N'-dimethylethylendiamine (22 µL, 0.20 mmol, 0.20 equiv) and dry dioxane (1.0 mL), filled with nitrogen. The test tube was sealed and the reaction mixture was stirred at 80° C. for 26 h. The resulting suspension was cooled to room temperature and filtered through a 0.5×1 cm pad of silica gel, eluting with ethyl acetate. The filtrate was concentrated in vacuo. The solid residue was dissolved in ~2 mL DMF. Purification of the residue by flash chromatography on silica gel (2×20 cm; hexane:ethyl acetate 2:1) provided 172 mg (67% yield) of the title compound as a white solid.

Example 198

(R)—N-(3,5-dimethylphenyl)-α-methylbenzylamine

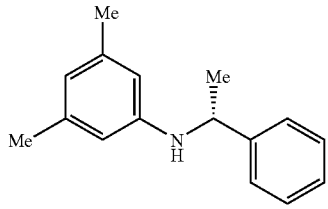 [SMILES: Cc1cc(C)cc(N[C@H](C)c2ccccc2)c1]

CuOAc (6 mg, 0.05 mmol), N,N-diethylsalicylamide (39 mg, 0.20 mmol) and K$_3$PO$_4$ (425 mg, 2.0 mmol) were put into a screw-capped test tube with a Teflon-lined septum. The tube was then evacuated and backfilled with argon (3 cycles). 5-Bromo-m-xylene (136 μL, 1.0 mmol), (R)-α-methylbenzylamine (193 μL, 1.5 mmol) and DMF (0.5 mL) were added by syringes. The reaction mixture was stirred at 100° C. for 30 h. The reaction mixture was allowed to reach room temperature. Ethyl acetate (~2 mL), water (~10 mL), ammonium hydroxide (~0.5 mL) and dodecane (227 μL) were added. The organic phase was analyzed by GC or GC-MS. The reaction mixture was further extracted by ethyl acetate (4×10 mL). The combined organic phases were washed with brine and dried over Na$_2$SO$_4$. Solvent was removed in vacuo and the yellow residue was purified by column chromatography on silica gel using hexane/ethyl acetate (20:1) as eluent to afford the desired product as a colorless oil (160 mg, 71% yield, 98% ee). R$_f$=0.4 (hexane/ethyl acetate=20:1). HPLC conditions: (column: Daciel OD; flow rate: 0.7 mL/min; UV lamp: 254 nm; solvent system: hexane/2-propanol (9:1); retention time: 7.80 min).

Example 199

3-Methoxy-N-hexylaniline from 3-chloroanisole

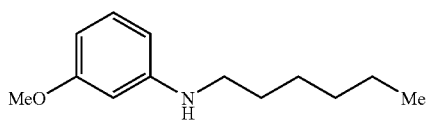 [SMILES: CCCCCCNc1cccc(OC)c1]

CuOAc (6 mg, 0.05 mmol), N,N-diethylsalicylamide (39 mg, 0.20 mmol) and K$_3$PO$_4$ (425 mg, 2.0 mmol) were put into a screw-capped test tube with a Teflon-lined septum. The tube was then evacuated and backfilled with argon (3 cycles). 3-Chloroanisole (122 μL, 1.0 mmol) and n-hexylamine (0.5 mL, as solvent) were added by syringes. The reaction mixture was stirred at 130° C. for 24 h. The reaction mixture was allowed to reach room temperature. Ethyl acetate (~2 mL), water (~10 mL), ammonium hydroxide (~0.5 mL) and dodecane (227 μL) were added. The organic phase was analyzed by GC which afforded 64% conversion of 3-chloroanisole and 40% GC yield of the desired product.

Example 200

4-Nitro-N-hexylaniline from 1-chloro-4-nitrobenzene

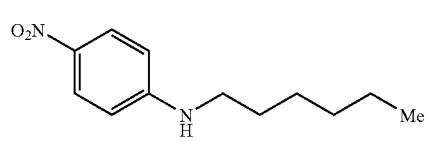 [SMILES: CCCCCCNc1ccc([N+](=O)[O-])cc1]

CuOAc (6 mg, 0.05 mmol), N,N-diethylsalicylamide (39 mg, 0.20 mmol), 1-chloro-4-nitrobenzene (158 mg, 1.0 mmol) and K$_3$PO$_4$ (425 mg, 2.0 mmol) were put into a screw-capped test tube with a Teflon-lined septum. The tube was then evacuated and backfilled with argon (3 cycles). n-Hexylamine (198 μL, 1.5 mmol) and DMF (0.5 mL) were added by syringes. The reaction mixture was stirred at 120° C. for 22 h. The reaction mixture was allowed to reach room temperature. Ethyl acetate (~2 mL), water (~10 mL), ammonium hydroxide (~0.5 mL) and dodecane (227 μL) were added. The organic phase was analyzed by GC and GC-MS. The reaction mixture was further extracted by ethyl acetate (4×10 mL). The combined organic phases were washed with brine and dried over Na$_2$SO$_4$. Solvent was removed in vacuo and the orange residue was purified by column chromatography on silica gel using hexane/ethyl acetate (10:1) as eluent to afford the desired product as a yellow solid (199 mg, 90% yield). R$_f$=0.2 (hexane/ethyl acetate=10:1).

Example 201

N-(3,5-Dimethylphenyl)pyrrolidine with DMF as solvent

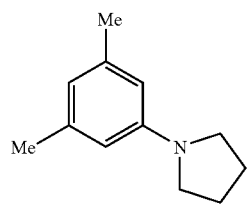 [SMILES: Cc1cc(C)cc(N2CCCC2)c1]

CuI (10 mg, 0.05 mmol), N,N-diethylsalicylamide (39 mg, 0.20 mmol) and K$_3$PO$_4$ (425 mg, 2.0 mmol) were put into a screw-capped test tube with a Teflon-lined septum. The tube was then evacuated and backfilled with argon (3 cycles). 5-Bromo-m-xylene (136 μL, 1.0 mmol), pyrrolidine (333 μL, 4.0 mmol) and DMF (0.5 mL) were added by syringes. The reaction mixture was stirred at 100° C. for 20 h. The reaction mixture was allowed to reach room temperature. Ethyl acetate (~2 mL), water (~10 mL), ammonium hydroxide (~0.5 mL) and dodecane (227 μL) were added. The organic phase was analyzed by GC and GC-MS. A 99% conversion of 5-bromo-m-xylene and 74% calibrated GC yield was obtained.

Example 202

N-(3,5-Dimethylphenyl)pyrrolidine in neat pyrrolidine

CuI (10 mg, 0.05 mmol), N,N-diethylsalicylamide (39 mg, 0.20 mmol) and $K_3PO_4$ (425 mg, 2.0 mmol) were put into a screw-capped test tube with a Teflon-lined septum. The tube was then evacuated and backfilled with argon (3 cycles). 5-Bromo-m-xylene (136 μL, 1.0 mmol) and pyrrolidine (250 μL, 3.0 mmol) were added by syringes. The reaction mixture was stirred at 100° C. for 20 h. The reaction mixture was allowed to reach room temperature. Ethyl acetate (~2 mL), water (~10 mL), ammonium hydroxide (~0.5 mL) and dodecane (227 μL) were added. The organic phase was analyzed by GC and GC-MS. A 86% conversion of 5-bromo-m-xylene and 65% calibrated GC yield was obtained.

Example 203

N-(4-Chlorophenyl)piperidine

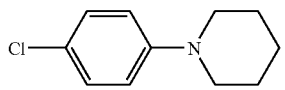 [SMILES: Clc1ccc(N2CCCCC2)cc1]

CuI (10 mg, 0.05 mmol), N,N-diethylsalicylamide (39 mg, 0.20 mmol), 4-bromochlorobenzene (191 mg, 1.0 mmol) and $K_3PO_4$ (425 mg, 2.0 mmol) were put into a screw-capped test tube with a Teflon-lined septum. The tube was then evacuated and backfilled with argon (3 cycles). Piperidine (148 μL, 1.5 mmol) and DMF (0.5 mL) were added by syringes. The reaction mixture was stirred at 90° C. for 20 h. The reaction mixture was allowed to reach room temperature. Ethyl acetate (~2 mL), water (~10 mL), ammonium hydroxide (~0.5 mL) and dodecane (227 μL) were added. The organic phase was analyzed by GC and GC-MS. A 75% conversion of 4-bromochlorobenzene and 29% calibrated GC yield was obtained.

Example 204

4-tert-Butyl-N-hexylaniline from 4-tert-butylphenyl trifluoromethanesulfonate

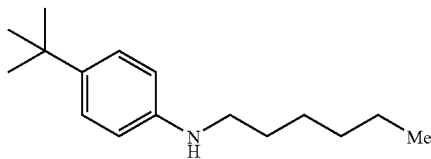 [SMILES: CCCCCCNc1ccc(C(C)(C)C)cc1]

CuI (10 mg, 0.05 mmol), N,N-diethylsalicylamide (39 mg, 0.20 mmol) and $Na_2CO_3$ (127 mg, 1.2 mmol) were put into a screw-capped test tube with a Teflon-lined septum. The tube was then evacuated and backfilled with argon (3 cycles). 4-tert-Butylphenyl trifluoromethanesulfonate (282 mg, 1.0 mmol), n-hexylamine (198 μL, 1.5 mmol) and DMF (0.5 mL) were added by syringes. The reaction mixture was stirred at 90° C. for 18 h. The reaction mixture was allowed to reach room temperature. Ethyl acetate (~2 mL), water (~10 mL), ammonium hydroxide (~0.5 mL) and dodecane (227 μL) were added. The organic phase was analyzed by GC and GC-MS. A 3% calibrated GC yield was obtained.

Example 205

Figure 5:
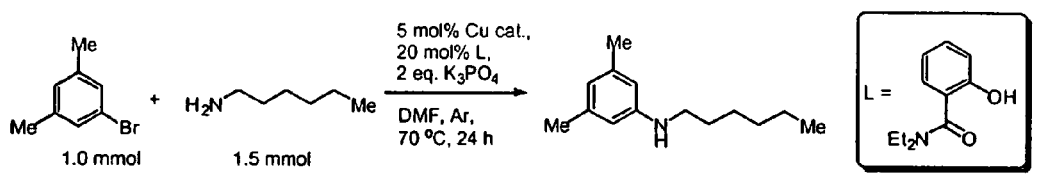
FIG. 5 tabulates copper-catalyzed aminations of 1-bromo-3,5-dimethylbenzene using n-hexyl amine and various copper complexes.

Evaluation of Various Copper Catalysts in the Cu-Catalyzed Amination of an Aryl Bromide in DMF (See FIG. 5)

Copper complex (0.05 mmol), N,N-diethylsalicylamide (39 mg, 0.2 mmol) and $K_3PO_4$ (425 mg, 2.0 mmol) were put into a screw-capped test tube with a Teflon-lined septum. The tube was then evacuated and backfilled with argon (3 cycles). 5-Bromo-m-xylene (136 μL, 1.0 mmol), n-hexylamine (198 μL, 1.5 mmol) and DMF (0.5 mL) were added by syringes. The reaction mixture was stirred at 70° C. for 24 h. The reaction mixture was allowed to reach room temperature. Ethyl acetate (~2 mL), water (~10 mL), ammonium hydroxide (~0.5 mL) and dodecane (227 μL) were added. The organic phase was analyzed by GC or GC-MS. The results are presented in FIG. 5.

Example 206

Figure 6:
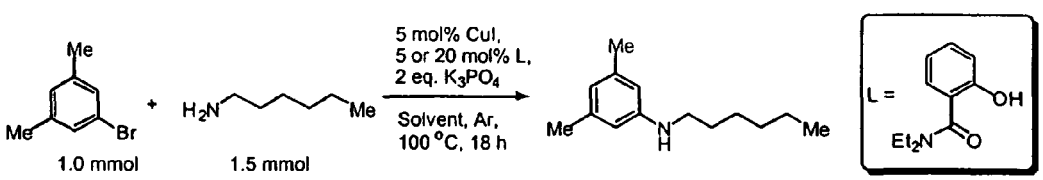
FIG. 6 tabulates copper-catalyzed aminations of 1-bromo-3,5-dimethylbenzene using n-hexyl amine in various solvents.

Evaluation of Various Solvents in the Cu-Catalyzed Amination of an Aryl Bromide (See FIG. 6)

Copper(I) iodide (10 mg, 0.05 mmol), N,N-diethylsalicylamide (39 mg, 0.2 mmol) and $K_3PO_4$ (425 mg, 2.0 mmol) were put into a screw-capped test tube with a Teflon-lined septum. The tube was then evacuated and backfilled with argon (3 cycles). 5-Bromo-m-xylene (136 μL, 1.0 mmol), n-hexylamine (198 μL, 1.5 mmol) and solvent (0.5 mL) were added by syringes. The reaction mixture was stirred at 100° C. for 18 h. The reaction mixture was allowed to reach room temperature. Ethyl acetate (~2 mL), water (~10 mL), ammonium hydroxide (~0.5 mL) and dodecane (227 μL) were added. The organic phase was analyzed by GC or GC-MS. The results are presented in FIG. 6.

Example 207

Figure 7:
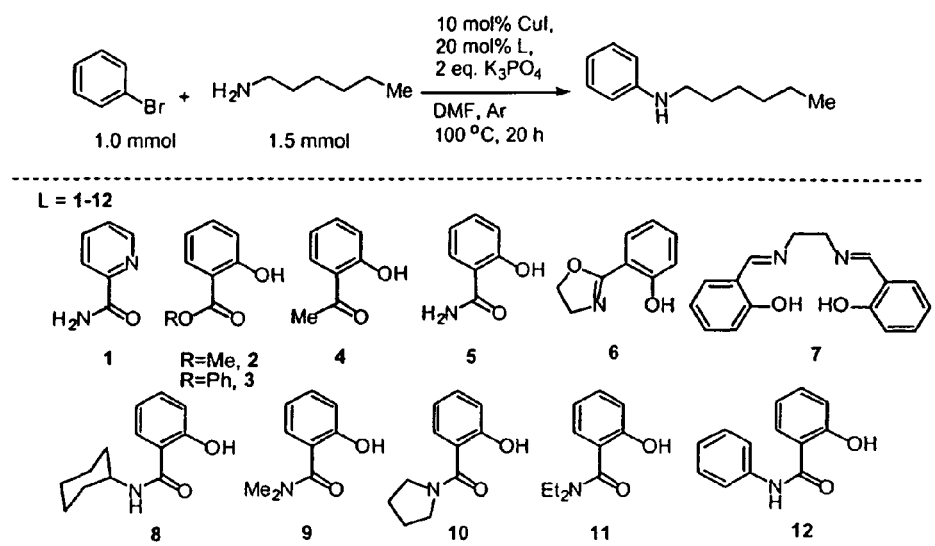
FIG. 7 tabulates copper-catalyzed aminations of bromobenzene using n-hexyl amine and various ligands.

Evaluation of Various Ligands in the Cu-Catalyzed Amination of Aryl Bromides in DMF (See FIG. 7)

CuI (10-19 mg, 0.05-0.10 mmol), ligand (0.2 mmol) and $K_3PO_4$ (425 mg, 2.0 mmol) were put into a screw-capped test tube with a Teflon-lined septum. The tube was then evacuated and backfilled with argon (3 cycles). Aryl bromide (1.0 mmol), n-hexylamine (198 μL, 1.5 mmol) and DMF (0.5 mL) were added by syringes. The reaction mixture was stirred at 100° C. for 20 h. The reaction mixture was allowed to reach room temperature. Ethyl acetate (~2 mL), water (~10 mL), ammonium hydroxide (~0.5 mL) and dodecane (227 μL) were added. The organic phase was analyzed by GC or GC-MS. The results are presented in FIG. 7.

Example 208

Figure 8:
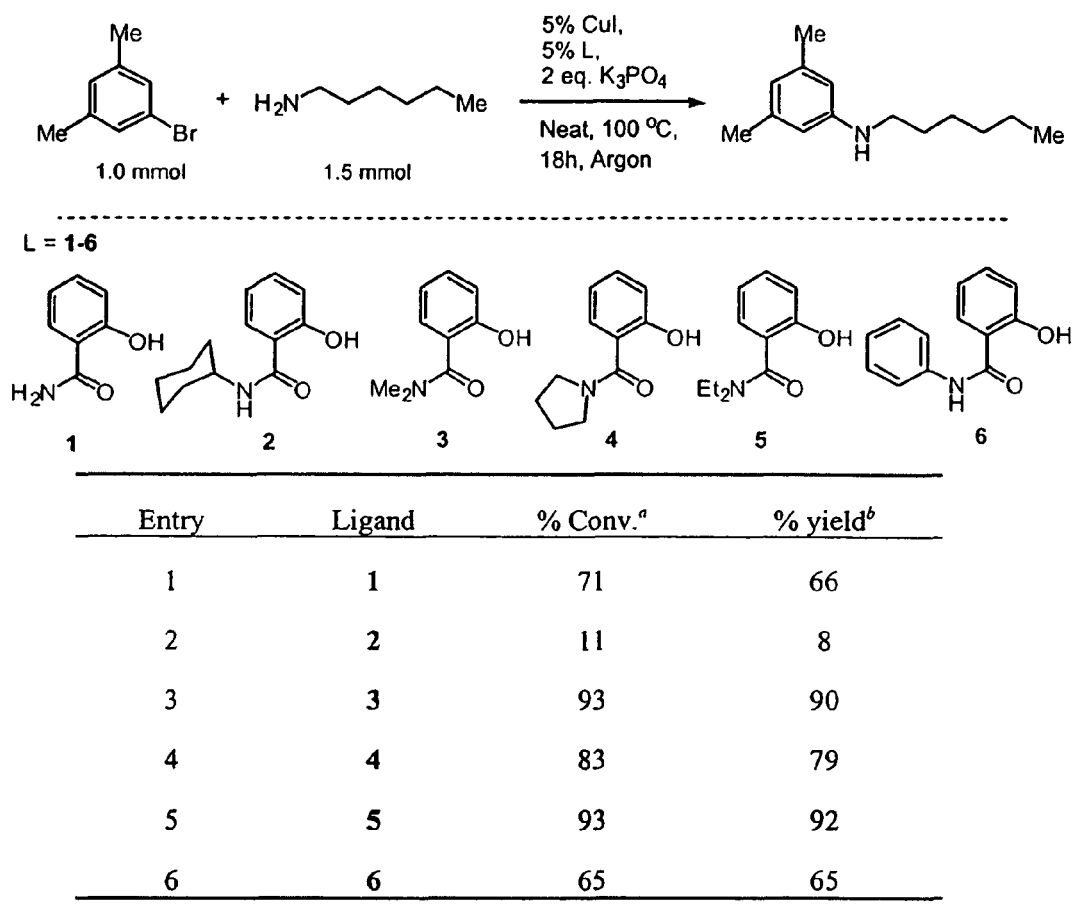
FIG. 8 tabulates copper-catalyzed aminations of 1-bromo-3,5-dimethylbenzene using n-hexyl amine and various ligands without solvent.

Evaluation of Various Ligands in the Cu-Catalyzed Amination of an Aryl Bromide without Solvent (See FIG. 8)

CuI (10 mg, 0.05 mmol), ligand (0.2 mmol) and $K_3PO_4$ (425 mg, 2.0 mmol) were put into a screw-capped test tube with a Teflon-lined septum. The tube was then evacuated and backfilled with argon (3 cycles). 5-Bromo-m-xylene (136 μL, 1.0 mmol), n-hexylamine (198 µL, 1.5 mmol) were added by syringes. The resulting mixture was stirred at 100° C. for 18 h. The reaction mixture was allowed to reach room temperature. Ethyl acetate (~2 mL), water (~10 mL), ammonium hydroxide (~0.5 mL) and dodecane (227 µL) were added. The organic phase was analyzed by GC or GC-MS. The results are presented in FIG. 8.

Example 209

Figure 9:
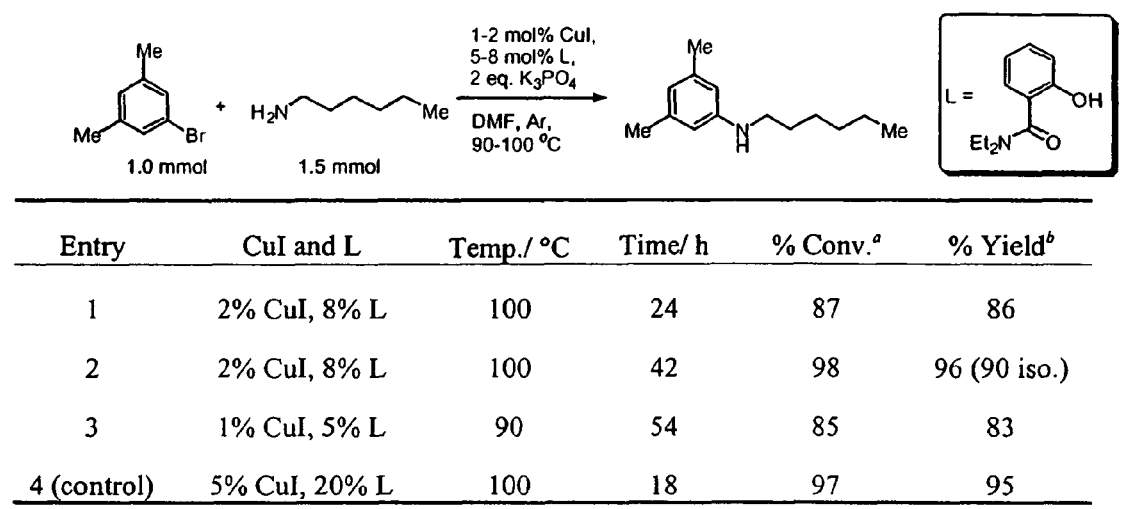
FIG. 9 tabulates copper-catalyzed aminations of 1-bromo-3,5-dimethylbenzene using n-hexyl amine with low catalyst loading.

Evaluation of the Cu-Catalyzed Amination of an Aryl Bromide in DMF Using Low Catalyst Loading (See FIG. 9)

CuI (2-10 mg, 0.01-0.05 mmol), N,N-diethylsalicylamide (10-39 mg, 0.05-0.20 mmol) and $K_3PO_4$ (425 mg, 2.0 mmol) were put into a screw-capped test tube with a Teflon-lined septum. The tube was then evacuated and backfilled with argon (3 cycles). 5-Bromo-m-xylene (136 µL, 1.0 mmol), n-hexylamine (198 µL, 1.5 mmol) and DMF (0.5 mL) were added by syringes. The resulting mixture was stirred at 90-100° C. for 18-54 h. The reaction mixture was allowed to reach room temperature. Ethyl acetate (~2 mL), water (~10 mL), ammonium hydroxide (~0.5 mL) and dodecane (227 µL) were added. The organic phase was analyzed by GC or GC-MS. The results are presented in FIG. 9.

Example 210

Figure 10:
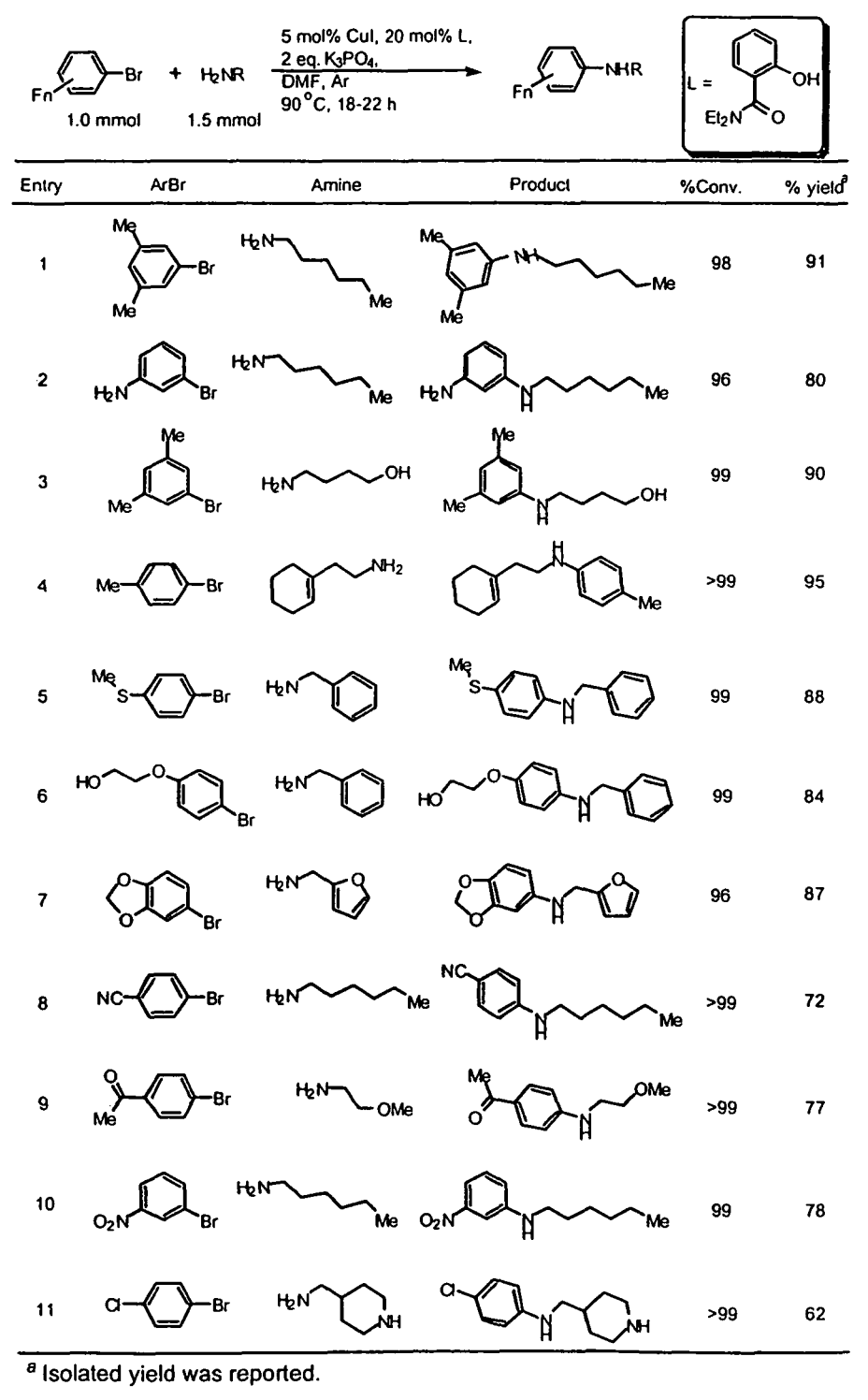

Cu-Catalyzed Amination of Functionalized Aryl Bromides (See FIG. 10)

CuI (10 mg, 0.05 mmol), N,N-diethylsalicylamide (39 mg, 0.20 mmol), aryl bromide (if solid; 1.0 mmol), and $K_3PO_4$ (425 mg, 2.0 mmol) were put into a screw-capped test tube with a Teflon-lined septum. The tube was then evacuated and backfilled with argon (3 cycles). Aryl bromide (if liquid; 1.0 mmol), amine (1.5 mmol), and DMF (0.5 mL) were added by syringes. The reaction mixture was stirred at 90° C. for 18-22 h. The reaction mixture was allowed to reach room temperature. Ethyl acetate (~2 mL), water (~10 mL), ammonium hydroxide (~0.5 mL) and dodecane (227 µL) were added. The organic phase was analyzed by GC or GC-MS. The reaction mixture was further extracted by ethyl acetate (4×10 mL). The combined organic phases were washed with brine and dried over $Na_2SO_4$. Solvent was removed in vacuo and the residue was purified by column chromatography on silica gel to afford the desired product.

N-Hexyl-3,5-dimethylaniline (FIG. 10, Entry 1)

Using the general procedure, 5-bromo-m-xylene (136 µL, 1.0 mmol) was coupled with n-hexylamine (198 µL, 1.5 mmol). Purification of the crude product by column chromatography on silica gel using hexane/ethyl acetate (20:1) as eluent afforded the desired product as a colorless oil (187 mg, 91% yield).

3-Amino-N-hexylaniline (FIG. 10, Entry 2)

Using the general procedure, 3-bromoaniline (172 mg, 1.0 mmol) was coupled with n-hexylamine (198 µL, 1.5 mmol). Purification of the crude product by column chromatography on silica gel using hexane/ethyl acetate (2:1) as eluent afforded the desired product as a colorless oil (154 mg, 80% yield). $R_f$=0.4 (hexane/ethyl acetate=2:1).

4-(N-(3,5-Dimethylphenyl)amino)butanol (FIG. 10, Entry 3)

Using the general procedure, 5-bromo-m-xylene (136 µL, 1.0 mmol) was coupled with 4-aminobutanol (138 µL, 1.5 mmol). Purification of the crude product by column chromatography on silica gel using hexane/ethyl acetate (2:1) as eluent afforded the desired product as a colorless oil (174 mg, 90% yield). $R_f$=0.4 (hexane/ethyl acetate=1:1).

4-Methyl-N-(2-(1-cyclohexenyl)ethyl)aniline (FIG. 10, Entry 4)

Using the general procedure, 4-bromotoluene (172 mg, 1.0 mmol) was coupled with 2-(1-cyclohexenyl)ethylamine (209 µL, 1.5 mmol). Purification of the crude product by column chromatography on silica gel using hexane/ethyl acetate (20:1) as eluent afforded the desired product as a colorless oil (205 mg, 95% yield). $R_f$=0.6 (hexane/ethyl acetate=10:1).

4-(N-Benzyl)aminothioanisole (FIG. 10, Entry 5)

Using the general procedure, 4-bromothioanisole (203 mg, 1.0 mmol) was coupled with benzylamine (164 µL, 1.5 mmol). Purification of the crude product by column chromatography on silica gel using hexane/ethyl acetate (15:1) as eluent afforded the desired product as a white solid (201 mg, 88% yield). $R_f$=0.4 (hexane/ethyl acetate=10:1).

2-(4-(N-Benzyl)amino)phenoxy)ethanol (FIG. 10, Entry 6)

Using the general procedure, 2-(4-bromophenoxy)ethanol (217 mg, 1.0 mmol) was coupled with benzylamine (164 µL, 1.5 mmol). Purification of the crude product by column chromatography on silica gel using hexane/ethyl acetate (2:1) as eluent afforded the desired product as a colorless oil (201 mg, 84% yield). $R_f$=0.5 (hexane/ethyl acetate=1:1).

3,4-(Methylenedioxy)-N-furfurylaniline (FIG. 10, Entry 7)

Using the general procedure, 4-bromo-1,2-(methylenedioxy)benzene (120 µL, 1.0 mmol) was coupled with furfurylamine (132 µL, 1.5 mmol). Purification of the crude product by column chromatography on silica gel using hexane/ethyl acetate (8:1) as eluent afforded the desired product as a colorless oil (187 mg, 87% yield). $R_f$=0.5 (hexane/ethyl acetate=5:1).

4-(N-Hexyl)aminobenzonitrile (FIG. 10, Entry 8)

Using the general procedure, 4-bromobenzonitrile (182 mg, 1.0 mmol) was coupled with n-hexylamine (198 µL, 1.5 mmol). Purification of the crude product by column chromatography on silica gel using hexane/ethyl acetate (6:1) as eluent afforded the desired product as a light yellow solid (145 mg, 72% yield). $R_f$=0.6 (hexane/ethyl acetate=3:1).

4-(N-(2-Methoxy)ethyl)aminoacetophenone (FIG. 10, Entry 9)

Using the general procedure, 4-bromoacetophenone (199 mg, 1.0 mmol) was coupled with 2-methoxyethylamine (130 µL, 1.5 mmol). Purification of the crude product by column chromatography on silica gel using hexane/ethyl acetate (1:1)

as eluent afforded the desired product as a light yellow solid (148 mg, 77% yield). $R_f$=0.6 (hexane/ethyl acetate=2:3).

3-Nitro-N-hexylaniline (FIG. 10, Entry 10)

Using the general procedure, 3-bromonitrobenzene (202 mg, 1.0 mmol) was coupled with n-hexylamine (198 μL, 1.5 mmol). Purification of the crude product by column chromatography on silica gel using hexane/ethyl acetate (6:1) as eluent afforded the desired product as a light yellow solid (174 mg, 78% yield). $R_f$=0.5 (hexane/ethyl acetate=5:1).

4-(N-(4-Chlorophenyl))aminomethylpiperidine (FIG. 10, Entry 11)

Using the general procedure, 4-bromochlorobenzene (192 mg, 1.0 mmol) was coupled with 4-aminomethylpiperidine (171 mg, 1.5 mmol). Purification of the crude product by column chromatography on silica gel using methanol/dichloromethane (saturated with ammonia) (1:20) as eluent afforded the desired product as a light yellow solid (138 mg, 62% yield). $R_f$=0.3 (methanol/dichloromethane (saturated with ammonia) (1:20)).

Example 211

Cu-Catalyzed Amination of Ortho-Substituted, Dibromo-Substituted and Heterocyclic Aryl Bromides (See FIG. 11)

CuI (10 mg, 0.05 mmol), N,N-diethylsalicylamide (39 mg, 0.20 mmol), aryl bromide (if solid; 1.0 mmol)) and $K_3PO_4$ (425 mg, 2.0 mmol) were put into a screw-capped test tube with a Teflon-lined septum. The tube was then evacuated and backfilled with argon (3 cycles). Aryl bromide (if liquid; 1.0 mmol), amine (1.2-4.0 mmol) and DMF (0.5 mL) were added by syringes. The reaction mixture was stirred at 90-100° C. for 18-24 h. The reaction mixture was allowed to reach room temperature. Ethyl acetate (~2 mL), water (~10 mL), ammonium hydroxide (~0.5 mL) and dodecane (227 μL) were added. The organic phase was analyzed by GC or GC-MS. The reaction mixture was further extracted by ethyl acetate (4×10 mL). The combined organic phases were washed with brine and dried over $Na_2SO_4$. Solvent was removed in vacuo and the yellow residue was purified by column chromatography on silica gel to afford the desired product.

2-Methoxy-N-hexylaniline (FIG. 11, Entry 1)

Using the general procedure, 2-bromoanisole (125 μL, 1.0 mmol) was coupled with n-hexylamine (198 μL, 1.5 mmol) at 100° C. for 22 h. Purification of the crude product by column chromatography on silica gel using hexane/ethyl acetate (30:1) as eluent afforded the desired product as a colorless liquid (184 mg, 89% yield). $R_f$=0.4 (hexane/ethyl acetate=20:1).

2-(N-Hexylamino)benzylalcohol (FIG. 11, Entry 2)

Using the general procedure, 2-bromobenzyl alcohol (187 mg, 1.0 mmol) was coupled with n-hexylamine (198 μL, 1.5 mmol) at 90° C. for 22 h. Purification of the crude product by column chromatography on silica gel using hexane/ethyl acetate (6:1) as eluent afforded the desired product as a colorless liquid (168 mg, 81% yield). $R_f$=0.7 (hexane/ethyl acetate=2:1).

2-(N-2-(1-Cyclohexenyl)ethyl)amino-para-xylene (FIG. 11, Entry 3)

Using the general procedure, 2-bromo-p-xylene (138 μL, 1.0 mmol) was coupled with 2-(1-cyclohexenyl)ethylamine (209 μL, 1.5 mmol) at 100° C. for 24 h. Purification of the crude product by column chromatography on silica gel using hexane/ethyl acetate (30:1) as eluent afforded the desired product as a colorless oil (180 mg, 79% yield). $R_f$=0.5 (hexane/ethyl acetate=20:1).

4-Bromo-N-hexylaniline (FIG. 11, Entry 4)

Using the general procedure, 1,4-dibromobenzene (236 mg, 1.0 mmol) was coupled with n-hexylamine (158 μL, 1.2 mmol) at 90° C. for 20 h. Purification of the crude product by column chromatography on silica gel using hexane/ethyl acetate (20:1) as eluent afforded the desired product as a colorless oil (212 mg, 83% yield). $R_f$=0.6 (hexane/ethyl acetate=10:1).

N,N'-(Dihexyl)-4-aminoaniline (FIG. 11, Entry 5)

CuI (10 mg, 0.05 mmol), N,N-diethylsalicylamide (39 mg, 0.20 mmol), 1,4-dibromobenzene (236 mg, 1.0 mmol) and $K_3PO_4$ (636 mg, 3.0 mmol) were put into a screw-capped test tube with a Teflon-lined septum. The tube was then evacuated and backfilled with argon (3 cycles). n-Hexylamine (527 μL, 4.0 mmol) and DMF (0.5 mL) were added by syringes. The reaction mixture was stirred at 100° C. for 42 h. The reaction mixture was allowed to reach room temperature. Ethyl acetate (~2 mL), water (~10 mL), ammonium hydroxide (~0.5 mL) and dodecane (227 μL) were added. The organic phase was analyzed by GC or GC-MS. The reaction mixture was further extracted by ethyl acetate (4×10 mL). The combined organic phases were washed with brine and dried over $Na_2SO_4$. Solvent was removed in vacuo and the brown residue was purified by column chromatography on silica gel using hexane/ethyl acetate (5:1) as eluent to afford the desired product as a brown solid (224 mg, 81% yield). $R_f$=0.3 (hexane/ethyl acetate=5:1).

3-(N-(3-Pyridyl)aminomethyl)pyridine (FIG. 11, Entry 6)

Using the general procedure, 3-bromopyridine (96 μL, 1.0 mmol) was coupled with 3-(aminomethyl)pyridine (153 μL, 1.5 mmol) at 90° C. for 20 h. Purification of the crude product by column chromatography on silica gel using dichloromethane(saturated with ammonia)/methanol (15:1) as eluent afforded the desired product as a light yellow liquid (153 mg, 83% yield). $R_f$=0.4 (dichloromethane(saturated with ammonia)/methanol=10:1).

3-(N-(2-(1-Cyclohexenyl)ethyl))aminothianaphthene (FIG. 11, Entry 7)

Using the general procedure, 3-bromothianaphthene (131 μL, 1.0 mmol) was coupled with 2-(1-cyclohexenyl)ethylamine (209 μL, 1.5 mmol) at 90° C. for 20 h. Purification of the crude product by column chromatography on silica gel using hexane/ethyl acetate (20:1) as eluent afforded the desired product as a deep yellow liquid (211 mg, 82% yield). $R_f$=0.4 (hexane/ethyl acetate=20:1).

5-(N-(4-Methoxybenzyl))aminopyrimidine (FIG. 11, Entry 8)

Using the general procedure, 5-bromopyrimidine (159 mg, 1.0 mmol) was coupled with 4-methoxybenzylamine (196

µL, 1.5 mmol) at 90° C. for 22 h. Purification of the crude product by column chromatography on silica gel using dichloromethane(saturated with ammonia)/ethyl acetate (1:1) as eluent afforded the desired product as a white solid (183 mg, 85% yield). $R_f$=0.2 (dichloromethane(saturated with ammonia)/ethyl acetate=1:1).

Example 212

Cu-Catalyzed Amination of Functionalized Aryl Bromides without Solvent (See FIG. 12)

CuI (10 mg, 0.05 mmol), N,N-diethylsalicylamide (10 mg, 0.05 mmol) and $K_3PO_4$ (425 mg, 2.0 mmol) were put into a screw-capped test tube with a Teflon-lined septum. The tube was then evacuated and backfilled with argon (3 cycles). Aryl bromide (1.0 mmol) and amine (1.5 mmol) were added by syringes. The mixture was stirred at 90-100° C. for 18-22 h. The reaction mixture was allowed to reach room temperature. Ethyl acetate (~2 mL), water (~10 mL), ammonium hydroxide (~0.5 mL) and dodecane (227 µL) were added. The organic phase was analyzed by GC or GC-MS. The reaction mixture was further extracted by ethyl acetate (4×10 mL). The combined organic phases were washed with brine and dried over $Na_2SO_4$. Solvent was removed in vacuo and the residue was purified by column chromatography on silica gel to afford the desired product.

N-Hexyl-3,5-dimethylaniline (FIG. 12, Entry 1)

Using the general procedure, 5-bromo-m-xylene (136 µL, 1.0 mmol) was coupled with n-hexylamine (198 µL, 1.5 mmol). Purification of the crude product by column chromatography on silica gel using hexane/ethyl acetate (20:1) as eluent afforded the desired product as a colorless oil (185 mg, 90% yield).

N-(4-Methylphenyl)-3,5-dimethylaniline (FIG. 12, Entry 2)

CuI (10 mg, 0.05 mmol), N,N-diethylsalicylamide (10 mg, 0.05 mmol), 4-toluidine (161, 1.5 mmol) and $K_3PO_4$ (425 mg, 2.0 mmol) were put into a screw-capped test tube with a Teflon-lined septum. The tube was then evacuated and backfilled with argon (3 cycles). 5-Bromo-m-xylene (136 µL, 1.0 mmol) was added by a syringe. The reaction mixture was stirred at 100° C. for 20 h. The reaction mixture was allowed to reach room temperature. Ethyl acetate (~2 mL), water (~10 mL), ammonium hydroxide (~0.5 mL) and dodecane (227 µL) were added. The organic phase was analyzed by GC and 22% conversion of 5-bromo-m-xylene and 9% GC yield of the desired product was obtained.

N-(3,5-Dimethylphenyl)indole (FIG. 12, Entry 3)

CuI (10 mg, 0.05 mmol), N,N-diethylsalicylamide (10 mg, 0.05 mmol), indole (176 mg, 1.5 mmol) and $K_3PO_4$ (425 mg, 2.0 mmol) were put into a screw-capped test tube with a Teflon-lined septum. The tube was then evacuated and backfilled with argon (3 cycles). 5-Bromo-m-xylene (136 µL, 1.0 mmol) was added by a syringe. The reaction mixture was stirred at 100° C. for 20 h. The reaction mixture was allowed to reach room temperature. Ethyl acetate (~2 mL), water (~10 mL), ammonium hydroxide (~0.5 mL) and dodecane (227 µL) were added. The organic phase was analyzed by GC or GC-MS. The reaction mixture was further extracted by ethyl acetate (4×10 mL). The combined organic phases were washed with brine and dried over $Na_2SO_4$. Solvent was removed in vacuo and the yellow residue was purified by column chromatography on silica gel using hexane/ethyl acetate (10:1) as eluent to afford the desired product as a brown solid (196 mg, 89% yield).

3-Nitro-N-hexylaniline (FIG. 12, Entry 4)

Using the general procedure, 3-bromonitrobenzene (202 mg, 1.0 mmol) was coupled with n-hexylamine (198 µL, 1.5 mmol) at 100° C. for 22 h. Purification of the crude product by column chromatography on silica gel using hexane/ethyl acetate (6:1) as eluent afforded the desired product as a light yellow solid (132 mg, 59% yield). $R_f$=0.5 (hexane/ethyl acetate=5:1).

3-Amino-N-hexylaniline (FIG. 12, Entry 5)

Using the general procedure, 3-bromoaniline (172 mg, 1.0 mmol) was coupled with n-hexylamine (198 µL, 1.5 mmol) at 100° C. for 20 h. Purification of the crude product by column chromatography on silica gel using hexane/ethyl acetate (2:1) as eluent afforded the desired product as a colorless oil (137 mg, 71% yield). $R_f$=0.4 (hexane/ethyl acetate=2:1).

4-Methyl-N-(2-(1-cyclohexenyl)ethyl)aniline (FIG. 12, Entry 6)

Using the general procedure, 4-bromotoluene (172 mg, 1.0 mmol) was coupled with 2-(1-cyclohexenyl)ethylamine (209 µL, 1.5 mmol) at 100° C. for 20 h. Purification of the crude product by column chromatography on silica gel using hexane/ethyl acetate (20:1) as eluent afforded the desired product as a colorless oil (198 mg, 92% yield). $R_f$=0.6 (hexane/ethyl acetate=10:1).

4-(N-(4-Chlorophenyl))aminomethylpiperidine (FIG. 12, Entry 7)

Using the general procedure, 4-bromochlorobenzene (192 mg, 1.0 mmol) was coupled with 4-aminomethylpiperidine (171 mg, 1.5 mmol) at 100° C. for 20 h. Purification of the crude product by column chromatography on silica gel using methanol/dichloromethane (saturated with ammonia) (1:20) as eluent afforded the desired product as a light yellow solid (134 mg, 60% yield). $R_f$=0.3 (methanol/dichloromethane (saturated with ammonia)=1:20).

3-(N-Hexyl)aminopyridine (FIG. 12, Entry 8)

Using the general procedure, 3-bromopyridine (96 µL, 1.0 mmol) was coupled with n-hexylamine (198 µL, 1.5 mmol) at 90° C. for 18 h. Purification of the crude product by column chromatography on silica gel using hexane/ethyl acetate (1:1) as eluent afforded the desired product as a colorless oil (146 mg, 82% yield). $R_f$=0.2 (hexane/ethyl acetate=2:1).

Example 213

C-Arylation of Triethyl Phosphonoacetate

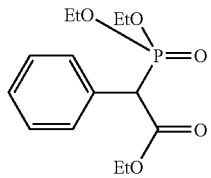

Procedure Using Iodobenzene

An oven dried Schlenk tube equipped with a magnetic stirbar and a Teflon stopcock was evacuated while hot and cooled under argon. The tube was charged with CuI (9.8 mg, 5.1 mol %) and $Cs_2CO_3$ (0.434 g, 1.33 mmol). The tube was evacuated and backfilled with argon (3 times), and the Teflon stopcock was replaced with a rubber septum. Trans-1,2-diaminocyclohexane (12 µL, 10.0 mol %) was added volumetrically, followed by iodobenzene (114 µL, 1.00 mmol), triethyl phosphonoacetate (220 µL, 1.11 mmol), and anhydrous toluene (1.0 mL). The septum was replaced by the Teflon stopcock under a positive pressure of argon, and the sealed tube was placed in an oil bath preheated to 70° C. After 22 h, the reaction was allowed to cool to room temperature, and was partitioned between ethyl acetate (20 mL) and saturated aqueous $NH_4Cl$ (10 mL). The organic portion was dried ($Na_2SO_4$) and filtered through Celite. The solution was then analyzed by gas chromatography, which indicated complete conversion of iodobenzene to the above compound in 93% GC yield.

Procedure Using Bromobenzene

An oven dried Schlenk tube equipped with a magnetic stirbar and a Teflon stopcock was evacuated while hot and cooled under argon. The tube was charged with CuI (9.5 mg, 5.0 mol %) and $Cs_2CO_3$ (0.428 g, 1.31 mmol). The tube was evacuated and backfilled with argon (3 times), and the Teflon stopcock was replaced with a rubber septum. Trans-1,2-diaminocyclohexane (12 µL, 10.0 mol %) was added volumetrically, followed by bromobenzene (109 µL, 1.00 mmol), triethyl phosphonoacetate (220 µL, 1.11 mmol), and anhydrous toluene (1.0 mL). The septum was replaced by the Teflon stopcock under a positive pressure of argon, and the sealed tube was placed in an oil bath preheated to 70° C. After 16.5 h, the reaction was allowed to cool to room temperature, and was partitioned between ethyl acetate (20 mL) and saturated aqueous $NH_4Cl$ (10 mL). The organic portion was dried ($Na_2SO_4$) and filtered through Celite. The solution was then analyzed by gas chromatography, which indicated complete conversion of bromobenzene to the above compound in 2% GC yield.

Example 214

C-Arylation of Deoxybenzoin

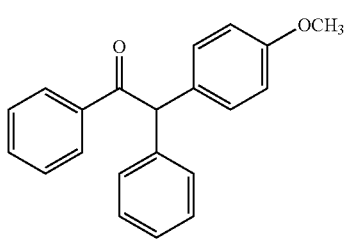 [SMILES: COc1ccc(C(C(=O)c2ccccc2)c2ccccc2)cc1]

An oven dried Schlenk tube equipped with a magnetic stirbar and a Teflon stopcock was evacuated while hot and cooled under argon. The tube was charged with CuI (9.4 mg, 4.9 mol %), $K_3PO_4$ (0.435 g, 2.05 mmol), 4-iodoanisole (0.235 g, 1.00 mmol), and deoxybenzoin (0.295 g, 1.46 mmol). The tube was evacuated and backfilled with argon (3 times), and the Teflon stopcock was replaced with a rubber septum. Trans-1,2-diaminocyclohexane (12 µL, 10.0 mol %) was added volumetrically, followed by anhydrous toluene (1.0 mL). The septum was replaced by the Teflon stopcock under a positive pressure of argon, and the sealed tube was placed in an oil bath preheated to 110° C. After 42 h, the reaction was allowed to cool to room temperature, and was partitioned between ethyl acetate (20 mL) and saturated aqueous $NH_4Cl$ (10 mL). The organic portion was dried ($Na_2SO_4$), filtered through Celite, and concentrated via rotary evaporation. The oil thus obtained was purified by silica gel chromatography to give the product shown as a pale yellow oil (64 mg, 21%).

Example 215

Benzonitrile from Iodobenzene and Copper Cyanide Using N,N'-dimethylethylenediamine as Ligand A Schlenk tube was charged with CuCN (108 mg, 1.21 mmol), evacuated, backfilled with Ar. N,N'-Dimethylethylenediamine (21.5 µL, 0.202 mmol, 20 mol %), iodobenzene (112 µL, 1.00 mmol), and toluene (1.0 mL) were added under Ar. The Schlenk tube was sealed with a Teflon valve and the reaction mixture was stirred at 110° C. for 17 h. Dodecane (internal GC standard, 230 µL) and ethyl acetate (2 mL) were added. A 0.1 mL sample of the supernatant solution was diluted with ethyl acetate (1 mL) and analyzed by GC to provide a 31% yield of benzonitrile.

Example 216

3,5-Dimethylbenzonitrile from 5-bromo-m-xylene and potassium cyanide using N,N'-dimethylethylenediamine as ligand A Schlenk tube was charged with CuI (19.5 mg, 0.102 mmol, 20 mol %), KCN (78 mg, 1.20 mmol), evacuated, backfilled with Ar. N,N'-Dimethylethylenediamine (21.5 µL, 0.202 mmol, 20 mol %), 5-bromo-m-xylene (136 µL, 1.00 mmol), and toluene (1.0 mL) were added under Ar. The Schlenk tube was sealed with a Teflon valve and the reaction mixture was stirred at 110° C. for 24 h. Dodecane (internal GC standard, 230 µL), ethyl acetate (2 mL), and 30% aq ammonia (1 mL) were added. A 0.1 mL sample of the supernatant solution was diluted with ethyl acetate (1 mL) and analyzed by GC to provide a 15% yield of 3,5-dimethylbenzonitrile.

Example 217

Figure 13:
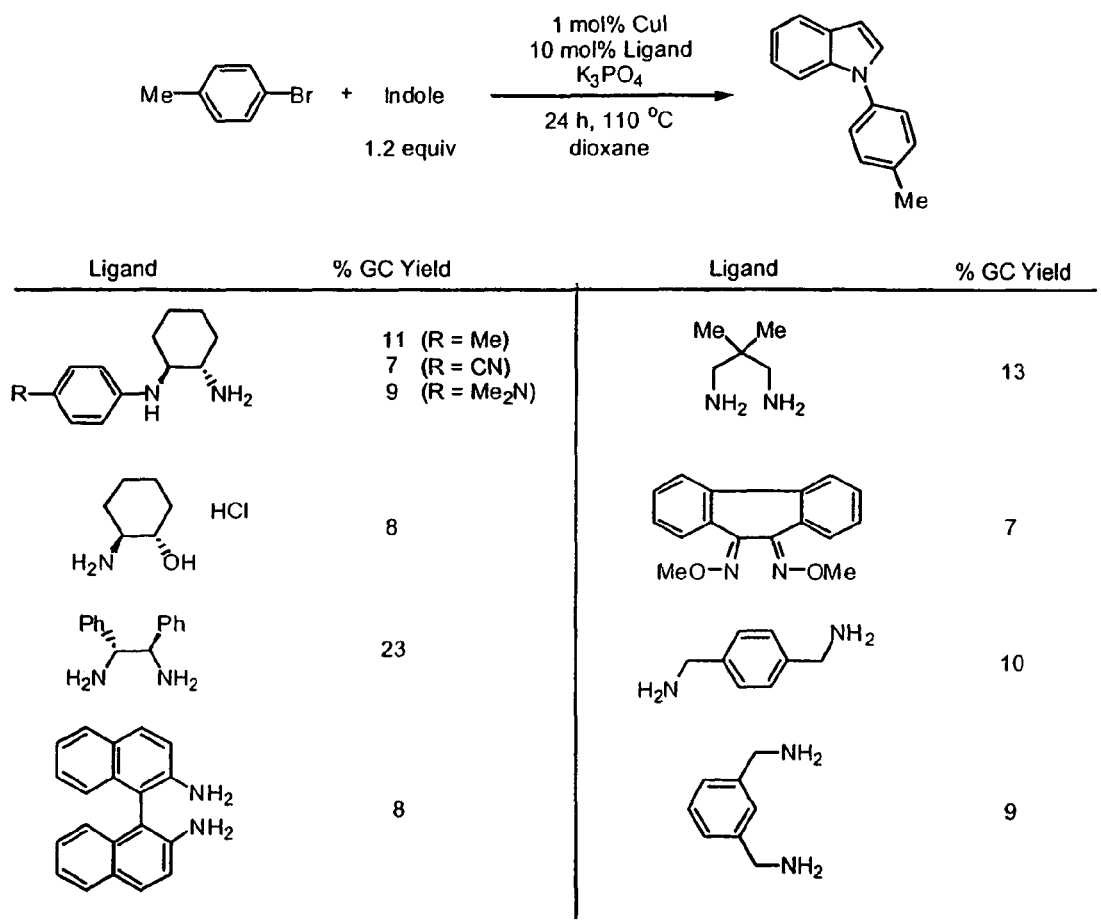
FIG. 13 tabulates copper-catalyzed arylations of indole in dioxane using 4-bromotoluene and various ligands.

Cu-Catalyzed Arylation of Indole in Dioxane with 4-bromotoluene and Various Ligands (FIG. 13)

To a flame-dried resealable test tube was added CuI (1 mol %), indole (1.2 mmol) and $K_3PO_4$ (2.1 mmol). The test tube was fixed with a rubber septum, was evacuated and backfilled with argon, and this evacuation/back-fill procedure was repeated. To this tube 4-bromotoluene (1.0 mmol), the ligand (10 mol %), dodecane (0.20 mmol, internal GC standard) and dioxane (1 mL) were then added successively under argon.

The reaction tube was sealed using a screw cap and the contents were stirred with heating via an oil bath at 110 C for 24 hours. The reaction mixture was cooled to ambient temperature, diluted with 2-3 mL ethyl acetate, and filtered through a plug of silica gel, eluting with 10-20 mL of ethyl acetate. The filtrate was analyzed by GC and compared to a known sample of authentic product to provide a corrected GC yield (FIG. 13).

Example 218

Cu-Catalyzed Arylation of Indole in Toluene with 4-bromotoluene and Various Ligands (FIG. 14)

The procedure outlined in Example 217 was used, with toluene (1 mL) as the solvent. The ligands depicted in FIG. 14 were used. Corrected GC yields are shown in FIG. 14.

Example 219

Figure 15:
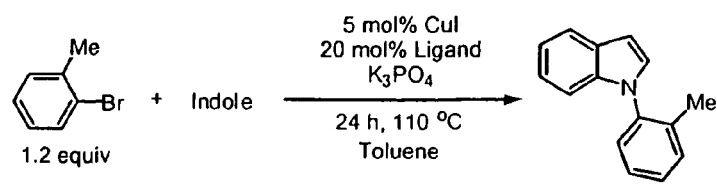
FIG. 15 tabulates copper-catalyzed arylations of indole in toluene using 2-bromotoluene and various ligands.
Figure 16:
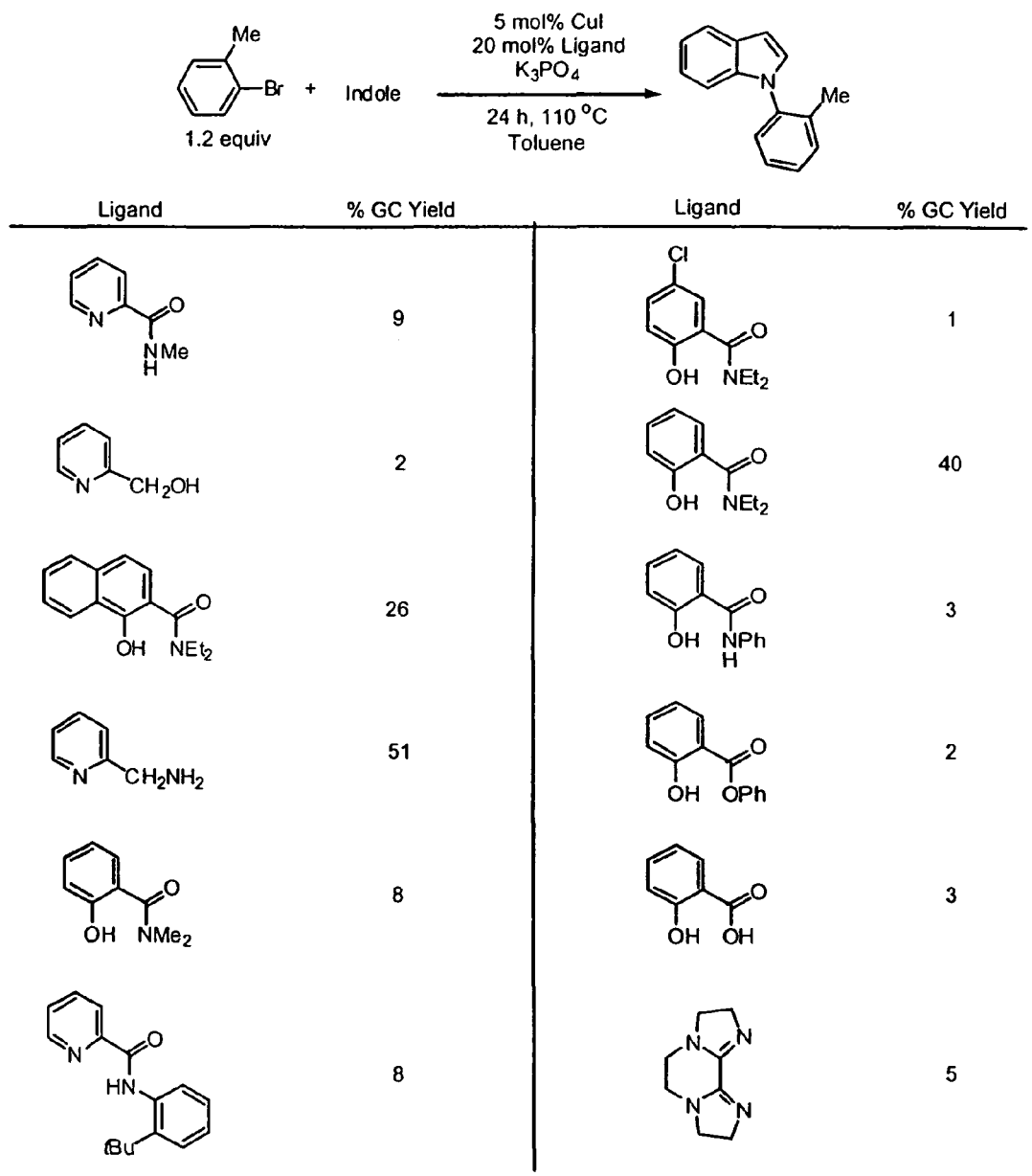
FIG. 16 tabulates copper-catalyzed arylations of indole in toluene using 2-bromotoluene and various ligands.

Cu-Catalyzed Arylation of Indole in Toluene with 2-bromotoluene and Various Ligands (FIGS. 15 and 16)

To a flame-dried resealable test tube was added CuI (1 mol %), indole (1.0 mmol) and $K_3PO_4$ (2.1 mmol). The test tube was fixed with a rubber septum, was evacuated and backfilled with argon, and this evacuation/back-fill procedure was repeated. To this tube 2-bromotoluene (1.0 mmol), the ligand (20 mol %, FIG. 15 or 16), dodecane (0.20 mmol, internal GC standard) and toluene (1 mL) were then added successively under argon. The reaction tube was sealed using a screw cap and the contents were stirred with heating via an oil bath at 110 C for 24 hours. The reaction mixture was cooled to ambient temperature, diluted with 2-3 mL ethyl acetate, and filtered through a plug of silica gel, eluting with 10-20 mL of ethyl acetate. The filtrate was analyzed by GC and compared to a known sample of authentic product to provide a corrected GC yield (shown in FIGS. 15 and 16).

Example 220

Arylation of Acetamide Generated In Situ from N,O-Bis(Trimethylsilyl)Acetamide

A Schlenk tube was charged with CuI (9.6 mg, 0.050 mmol, 5.0 mol %), KF (350 mg, 6.0 mmol), evacuated, backfilled with Ar. N,N'-Dimethylethylenediamine (11 μL, 0.10 mmol, 10 mol %), 2-iodotoluene (128 μL, 1.01 mmol), N,O-bis(trimethylsilyl)acetamide (300 μL, 1.21 mmol), and toluene (1.0 mL) were added under Ar. The Schlenk tube was sealed with a Teflon valve and the reaction mixture was stirred at 110° C. for 16 h. The resulting suspension was allowed to reach room temperature and then filtered through a 0.5×1 cm pad of silica gel eluting with ethyl acetate (20 mL). The filtrate was concentrated and the residue was purified by flash chromatography on silica gel (2×15 cm; hexane-ethyl acetate 1:4; 15 mL fractions). Fractions 10-17 provided 78 mg (52% yield) of N-(2-methylphenyl)acetamide as white needles.

Example 221

Arylation of N-phenyl acetamide using copper(II) acetylacetonate or copper(II) 2,2,6,6-tetramethyl-3,5-heptadienoate as the catalyst A Schlenk tube was charged with Cu(II) acetylacetonate (14 mg, 0.054 mmol, 5.1 mol %), N-phenylacetamide (165 mg, 1.22 mmol), $Cs_2CO_3$ (460 mg, 1.41 mmol), evacuated, backfilled with Ar. In a separate flask, a stock solution of 5-iodo-m-xylene (3.0 mL) and dodecane (internal GC standard, 4.7 mL) in dioxane (20 mL) was prepared. A portion of the stock solution (1.4 mL) containing 1.05 mmol of 5-iodo-m-xylene was added to the Schlenk tube under Ar. The Schlenk tube was sealed with a Teflon valve and the reaction mixture was stirred at 110° C. for 22 h. The resulting white suspension was allowed to reach room temperature. A 0.1 mL sample of the suspension was filtered through a plug of Celite eluting with ethyl acetate (1 mL). The filtrate was analyzed by GC to provide a 58% yield of the desired product.

Use of copper(II) 2,2,6,6-tetramethyl-3,5-heptadienoate (23 mg, 0.054 mmol, 5.1 mol %) in place of Cu(II) acetylacetonate and the reaction was performed at 110° C. for 24 h, GC analysis indicated a 68% yield of N-(3,5-dimethylphenyl)-N-phenylacetamide.

Example 222

Figure 17:
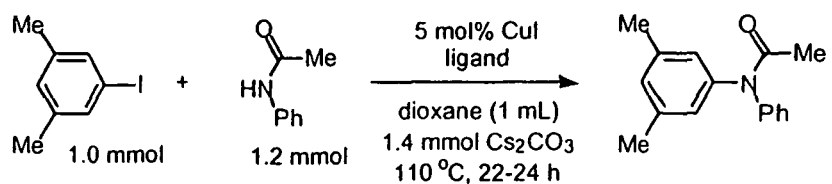
FIG. 17 tabulates copper-catalyzed arylations of N-phenyl acetamide in dioxane using 3,5-dimethylphenyl iodide and various ligands.

Arylation of N-phenylacetamide Using Various Ligands (FIG. 17)

A Schlenk tube was charged with CuI (10 mg, 0.053 mmol, 5.0 mol %), the ligand (in those cases where the ligand was a solid) N-phenylacetamide (165 mg, 1.22 mmol), $Cs_2CO_3$ (460 mg, 1.41 mmol), evacuated, backfilled with Ar. The ligand (in those cases where the ligand was a liquid), 5-iodo-m-xylene (150 μL, 1.04 mmol), dodecane (internal GC standard, 235 μL), and dioxane (1.0 mL) were added under Ar. The Schlenk tube was sealed with a Teflon valve and the reaction mixture was stirred at 110° C. for 23 h. The resulting suspension was allowed to reach room temperature. A 0.1 mL sample of the suspension was filtered through a plug of Celite eluting with ethyl acetate (1 mL), and the filtrate was analyzed by GC. The results are presented in FIG. 17.

Example 223

Figure 18:
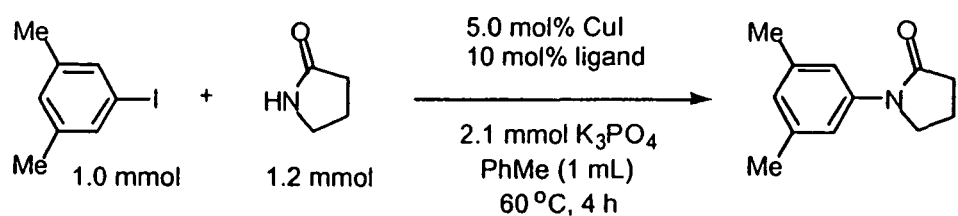
FIG. 18 tabulates copper-catalyzed arylations of 2-pyrrolidinone in toluene using 3,5-dimethylphenyl iodide and various ligands.

Arylation of 2-pyrrolidinone with 5-iodo-m-xylene using various 1,2-diamine ligands (FIG. 18)

A Schlenk tube was charged with CuI (10 mg, 0.052 mmol, 5.0 mol %), $K_3PO_4$ (450 mg, 2.1 mmol), evacuated, backfilled with Ar. Ligand (0.11 mmol, 10 mol %), 5-iodo-m-xylene (150 μL, 1.04 mmol), 2-pyrrolidinone (94 μL, 1.24 mmol), and toluene (1.0 mL) were added under Ar. The Schlenk tube was sealed with a Teflon valve and the reaction mixture was stirred at 60° C. for 4 h. The resulting suspension was allowed to reach room temperature. Dodecane (internal GC standard, 235 μL) and ethyl acetate (1 mL) were added. A 0.1 mL sample of the supernatant solution was diluted with ethyl acetate (1 mL) and analyzed by GC. The results are presented in FIG. 18.

Example 224

Arylation of N-benzylformamide with 5-bromo-m-xylene using various 1,2-diamine ligands (FIG. 19)

Ten 15 mL test tubes with screw threads were equipped with one 10×3 mm Teflon-coated stirring bar each and charged with CuI (9.6 mg, 0.050 mmol, 5.0 mol %) and $K_2CO_3$ (280 mg, 2.03 mmol). Each test tube was closed with an open-top screw cap fitted with a Teflon-lined silicon rubber septum, evacuated through a 21-gauge needle, and then backfilled with argon. Meanwhile, a stock solution of 5-bromo-m-xylene (2.64 mL, 15.0 mmol), N-benzylformamide (2.44 g, 18.1 mmol), and dodecane (internal GC standard, 0.68 mL) in toluene (15 mL) was prepared in a 25 mL pear-shaped flask under argon. To each test tube were added 1.28 mL of the stock solution followed by the ligand using syringes. The reaction mixtures in the test tubes were stirred in a 110±5° C. oil bath for 22 h. The test tubes were then allowed to reach room temperature, the screw caps were removed, and ethyl acetate (2 mL) was added. A 50-100 µL sample of the supernatant solution from each test tube was diluted with ethyl acetate (1 mL) and the resulting solutions were analyzed by GC. The results are presented in FIG. 19.

Example 225

Figure 20:
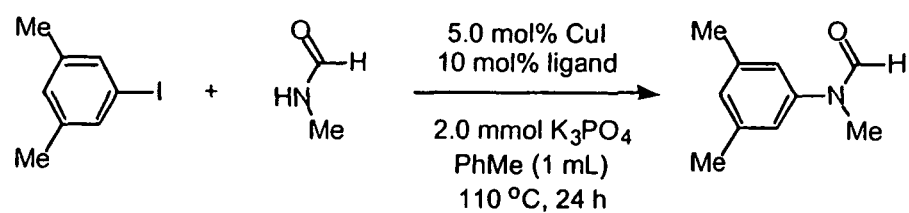
FIG. 20 tabulates copper-catalyzed arylations of N-methyl formamide in toluene using 3,5-dimethylphenyl iodide and various ligands.

Arylation of N-methylformamide Using Various Ligands (FIG. 20)

Six 15 mL test tubes with screw threads were equipped with one 10×3 mm Teflon-coated stirring bar each and charged with CuI (9.6 mg, 0.050 mmol, 5.0 mol %), the ligand (in those cases where the ligand was a solid; 0.10 mmol), and $K_3PO_4$ (430 mg, 2.03 mmol). Each test tube was closed with an open-top screw cap fitted with a Teflon-lined silicon rubber septum, evacuated through a 21-gauge needle, and then backfilled with argon. Meanwhile, a stock solution of 5-iodo-m-xylene (2.16 mL, 15.0 mmol), N-methylformamide (1.06 mL, 18.1 mmol), and dodecane (internal GC standard, 0.68 mL) in toluene (15 mL) was prepared in a 25 mL pear-shaped flask under argon. To each test tube was added 1.28 mL of the stock solution containing 1.0 mmol of 5-iodo-m-xylene and 1.2 mmol of N-methylformamide, using a syringe followed by the ligand (in those cases where the ligand was a liquid; 0.10 mmol). The top of the septum was then covered with a dab of vacuum grease to seal the injection spot. The reaction mixtures in the test tubes were stirred in a 110±5° C. oil bath for 24 h. The test tubes were then allowed to reach room temperature, the screw caps were removed, and ethyl acetate (3 mL) was added. A 50-100 µL sample of the supernatant solution from each test tube was diluted with ethyl acetate (1 mL) and the resulting solutions were analyzed by GC. The results are reported in FIG. 20.

Example 226

Arylation of N-methylformamide Using Di-tert-butylphosphine Oxide as the Ligand

A Schlenk tube was charged with CuI (9.6 mg, 0.050 mmol, 5.0 mol %), di-tert-butylphosphine oxide (16.5 mg, 0.102 mmol), $K_3PO_4$ (430 mg, 2.03 mmol), evacuated, backfilled with Ar. 5-Iodo-m-xylene (145 µL, 1.00 mmol), N-methylformamide (72 µL, 1.23 mmol), and toluene (1.0 mL) were added under Ar. The Schlenk tube was sealed with a Teflon valve and the reaction mixture was stirred at 110° C. for 24 h. The suspension was allowed to reach room temperature. Dodecane (internal GC standard, 230 µL) and ethyl acetate (2 mL) were added. A 0.1 mL sample of the supernatant solution was diluted with ethyl acetate (1 mL) and analyzed by GC to provide a 46% yield of N-(3,5-dimethylphenyl)-N-methylformamide.

Example 227

Arylation of N-methylformamide Using Hexamethylphosphorous Triamide as the Ligand A Schlenk tube was charged with CuI (9.6 mg, 0.050 mmol, 5.0 mol %), $K_3PO_4$ (430 mg, 2.03 mmol), evacuated, backfilled with Ar. Hexamethylphosphorous triamide (18.5 µL, 0.102 mmol, 10 mol %) 5-iodo-m-xylene (145 µL, 1.00 mmol), N-methylformamide (72 µL, 1.23 mmol), and toluene (1.0 mL) were added under Ar. The Schlenk tube was sealed with a Teflon valve and the reaction mixture was stirred at 110° C. for 24 h. The suspension was allowed to reach room temperature. Dodecane (internal GC standard, 230 µL) and ethyl acetate (2 mL) were added. A 0.1 mL sample of the supernatant solution was diluted with ethyl acetate (1 mL) and analyzed by GC to provide 76% yield of N-(3,5-dimethylphenyl)-N-methylformamide.

Example 228

Arylation of N-methylformamide using 3,1'-dimethyl-4,5-dihydro-3H,1'H-[1,2']biimidazolyl-2-one as the ligand A Schlenk tube was charged with CuI (9.6 mg, 0.050 mmol, 5.0 mol %), 3,1'-dimethyl-4,5-dihydro-3H,1'H-[1,2'] biimidazolyl-2-one (18 mg, 0.10 mmol, 10 mol %), $K_3PO_4$ (430 mg, 2.03 mmol), evacuated, backfilled with Ar. 5-Iodo-m-xylene (145 µL, 1.00 mmol), N-methylformamide (72 µL, 1.23 mmol), and toluene (1.0 mL) were added under Ar. The Schlenk tube was sealed with a Teflon valve and the reaction mixture was stirred at 110° C. for 24 h. The suspension was allowed to reach room temperature. Dodecane (internal GC standard, 230 µL) and ethyl acetate (2 mL) were added. A 0.1 mL sample of the supernatant solution was diluted with ethyl acetate (1 mL) and analyzed by GC to provide 54% yield of N-(3,5-dimethylphenyl)-N-methylformamide.

Example 229

Figure 21:
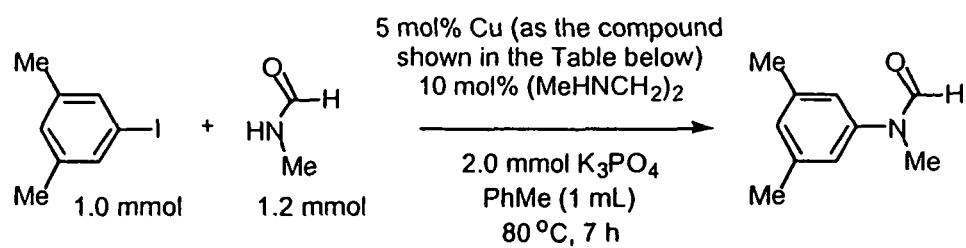
FIG. 21 tabulates copper-catalyzed arylations of N-methyl formamide in toluene using 3,5-dimethylphenyl iodide and various sources of copper.

Arylation of N-methylformamide Using Various Copper Sources (FIG. 21)

Nine 15 mL test tubes with screw threads were equipped with one 10×3 mm Teflon-coated stirring bar each and charged with $K_3PO_4$ (430 mg, 2.03 mmol) and one of the following copper sources: 1) copper powder, bronze (Aldrich, 99%; 3.2 mg, 0.050 mmol); 2) CuI (Strem, 98%; 9.6 mg, 0.050 mmol); 3) CuCl (Strem, 97+%; 5.0 mg, 0.050 mmol); 4) CuSCN (Aldrich, 98+%; 6.1 mg, 0.050 mmol); 5) $CU_2O$ (Alfa Aesar, 99%; 3.6 mg, 0.025 mmol); 6) $CUCl_2$ (Strem, 98%; 6.8 mg, 0.051 mmol); 7) $CuSO_4 5H_2O$ (Aldrich, 98+%; 12.5 mg, 0.0501 mmol); 8) $Cu(OAc)_2$ (Strem, 99%; 9.1 mg, 0.050 mmol); 9) Cu(II) acetylacetonate (Lancaster, 98%; 13.1 mg, 0.0500 mmol). Each test tube was closed with an open-top screw cap fitted with a Teflon-lined silicon rubber septum, evacuated through a 21-gauge needle, and then backfilled with argon. Meanwhile, a stock solution of 5-iodo-m-xylene (2.16 mL, 15.0 mmol), N-methylformamide (1.06 mL, 18.1 mmol), N,N'-dimethylethylenediamine (160 µL, 1.50 mmol) and dodecane (internal GC standard, 0.68 mL) in toluene (15 mL) was prepared in a 25 mL pear-shaped flask under argon. To each test tube was added 1.28 mL of the stock solution containing 1.0 mmol of 5-iodo-m-xylene, 1.2 mmol of N-methylformamide, 0.10 mmol of N,N'-dimethylethylenediamine using a syringe. The top of the septum was then covered with a dab of vacuum grease to seal the injection spot. The reaction mixtures in the test tubes were stirred in a 80±5° C. oil bath for 7 h. The test tubes were then allowed to reach room temperature, the screw caps were removed, and ethyl acetate (2 mL) was added. A 50-100 µL sample of the supernatant solution from each test tube was diluted with ethyl acetate (1 mL) and the resulting solutions were analyzed by GC. The results are reported in FIG. 21.

Example 230

Figure 22:
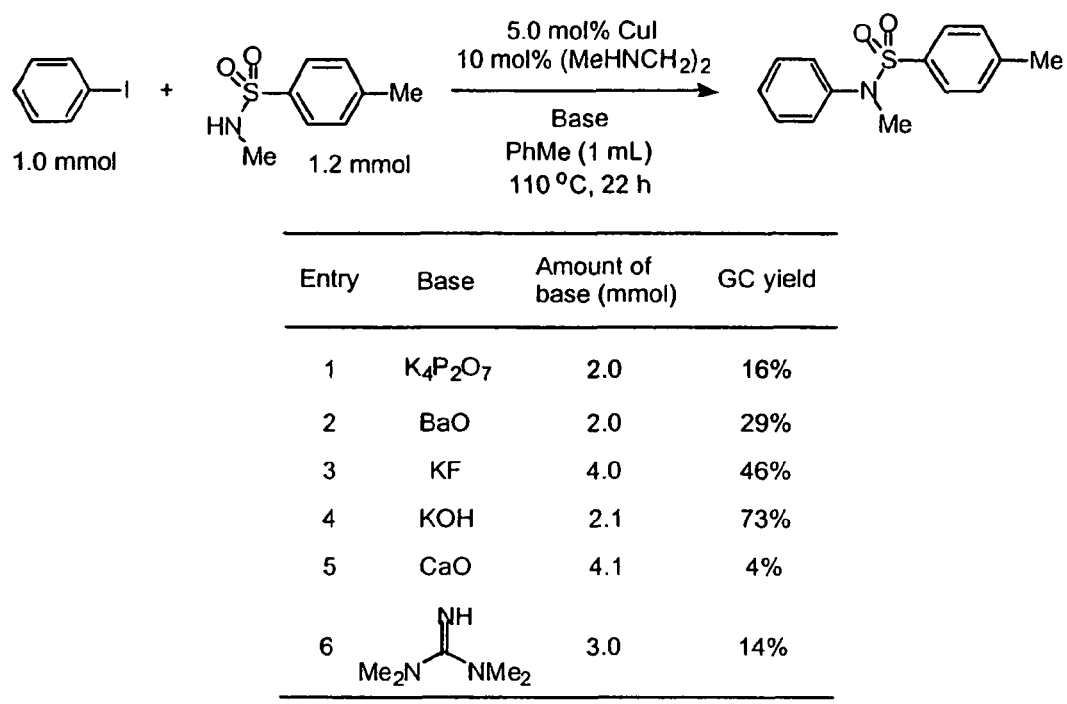
FIG. 22 tabulates copper-catalyzed arylations of N-methyl para-toluenesulfonamide in toluene using iodobenzene and various bases.

Arylation of N-methyl-4-methylbenzenesulfonamide using various bases (FIG. 22)

A Schlenk tube was charged with CuI (9.6 mg, 0.050 mmol, 5.0 mol %), the base (2.0-4.1 mmol), evacuated, backfilled with Ar (in the case of N,N,N',N'-tetramethylguanidine as the base, it was added after the Schlenk tube was backfilled with Ar). N,N'-Dimethylethylenediamine (11 µL, 0.10 mmol, 10 mol %), iodobenzene (112 µL, 1.00 mmol), and toluene (1.0 mL) were added under Ar. The Schlenk tube was sealed with a Teflon valve and the reaction mixture was stirred at 110° C. for 22 h. The resulting suspension was allowed to reach room temperature. Dodecane (internal GC standard, 230 µL) and ethyl acetate (3 mL) were added. A 0.1 mL sample of the supernatant solution was diluted with ethyl acetate (1 mL) and analyzed by GC. The results are presented in FIG. 22.

Example 231

Arylation of 2-pyrrolidinone Using Potassium Triphosphate as the Base

A test tube with a screw thread was equipped with a 10×3 mm Teflon-coated stirring bar and charged with CuI (9.6 mg, 0.050 mmol, 5.0 mmol %) and $K_5P_3O_{10}$ (Strem, finely ground, 430 mg, 0.96 mmol). The test tube was closed with an open-top screw cap fitted with a Teflon-lined silicon rubber septum, evacuated through a 21-gauge needle, and then backfilled with argon. Meanwhile, a stock solution of 5-iodo-m-xylene (2.16 mL), 2-pyrrolidinone (1.40 mL), and dodecane (internal GC standard, 0.68 mL) in toluene (15 mL) was prepared in a 25 mL pear-shaped flask under argon. A portion of the stock solution (1.28 mL) containing 1.0 mmol of 5-iodo-m-xylene and 1.2 mmol of 2-pyrrolidinone was added using a syringe, followed by N-methylethylenediamine (8.9 µL, 1.0 mmol, 10 mol %). The reaction mixture in the test tube was stirred in a 60±5° C. oil bath for 5 h. The test tube was then allowed to reach room temperature, the screw cap was removed, and ethyl acetate (2 mL) was added. A 50-100 µL sample of the supernatant solution from the test tube was diluted with ethyl acetate (1 mL). GC analysis of the resulting solution indicated a 95% yield of N-(3,5-dimethylphenyl)-2-pyrrolidinone.

Use of N,N'-dimethylethylenediamine (11 µL, 1.0 mmol, 10 mol %) in place of N-methylethylenediamine provided a 93% yield of N-(3,5-dimethylphenyl)-2-pyrrolidinone according to GC analysis.

Use of ethylenediamine (6.8 µL, 1.0 mmol, 10 mol %) in place of N-methylethylenediamine provided a 61% yield of N-(3,5-dimethylphenyl)-2-pyrrolidinone according to the GC analysis.

Example 232

Figure 23:
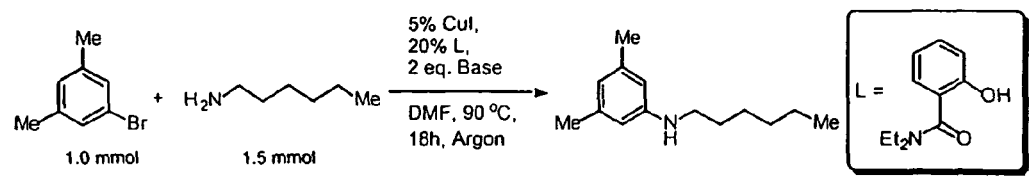
FIG. 23 tabulates copper-catalyzed arylations of n-hexyl amine in DMF using diethyl salicylamide as the ligand and various bases.

Arylation of n-hexyl Amine Using Various Bases (FIG. 23)

CuI (10 mg, 0.05 mmol), base (2.0 mmol) and N,N-diethylsalicylamide (39 mg, 0.2 mmol) were added to a screw-capped test tube equipped with Teflon-lined septum. The tube was then evacuated and backfilled with argon (3 cycles). 5-Bromo-m-xylene (136 µL, 1.0 mmol), n-hexylamine (198 µL, 1.5 mmol) and DMF (0.5 mL) were added by syringes. The reaction mixture was stirred and heated at 90° C. for 18 hours. The test tube was allowed to reach room temperature. Ethyl acetate (~2 mL), water (~10 mL), ammonium hydroxide (~0.5 mL) and dodecane (227 µL) were added. The organic phase was analyzed by GC. The results are presented in FIG. 23.

Example 233

Figure 24:
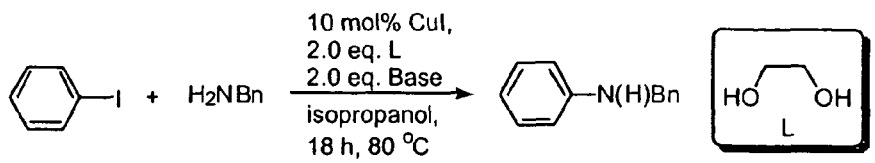
FIG. 24 tabulates copper-catalyzed arylations of benzyl amine in isopropanol using ethylene glycol as the ligand and various bases.

Arylation of Benzylamine Using Various Bases (FIG. 24)

CuI (19 mg, 0.1 mmol) and base (2.0 mmol) were added to a screw-capped test tube equipped with a Teflon-lined septum. The test tube was evacuated and backfilled with argon (3 cycles). 2-Propanol (1.0 mL), ethylene glycol (111 µL, 2.0 mmol), iodobenzene (112 µL, 1.0 mmol) and benzylamine (131 µL, 1.2 mmol) were added by syringes. The reaction mixture was stirred and heated at 80° C. for 18 hours. The reaction mixture was allowed to reach room temperature. Diethyl ether (~2 mL), water (~10 mL) and dodecane (227 µL) were added. The organic phase was analyzed by GC. The results are presented in FIG. 24.

Example 234

Arylation of Benzylamine Using Various Diols as Ligands (FIG. 25)

CuI (19 mg, 0.1 mmol) and anhydrous $K_3PO_4$ (425 mg, 2.0 mmol) were added to a screw-capped test tube equipped with a Teflon-lined septum. The test tube was evacuated and backfilled with argon (3 cycles). 2-Propanol (1.0 mL, not necessary if diol was used as solvent), diol (0.1-2.0 mmol), Iodobenzene (112 µL, 1.0 mmol) and benzylamine (131 µL, 1.2 mmol) were added by syringes. The reaction mixture was stirred and heated at 80° C. for 18 hours. The reaction mixture was allowed to reach room temperature. Diethyl ether (~2 mL), water (~10 mL) and dodecane (227 µL) were added. The organic phase was analyzed by GC. The results are presented in FIG. 25.

Example 235

Arylation of Benzylamine Generated In Situ from N-Benzyl-Trifluoroacetamide

A Schlenk tube was charged with CuI (9.6 mg, 0.050 mmol, 5.0 mol %), N-benzyl-trifluoroacetamide (244 mg, 1.20 mmol), $K_3PO_4$ (640 mg, 3.01 mmol), evacuated, backfilled with Ar. Iodobenzene (112 µL, 1.00 mmol), ethylene glycol (0.11 mL, 2.0 mmol), and isopropanol (1.5 mL) were added under Ar. The Schlenk tube was sealed with a Teflon valve and the reaction mixture was stirred at 80° C. for 24 h. The resulting white suspension was allowed to reach room temperature. Dodecane (internal GC standard, 230 µL), ethyl acetate (2 mL), and 30% aq ammonia (2 mL) were added. A 0.1 mL sample of the top layer was diluted with ethyl acetate (1 mL) and analyzed by GC to provide a 76% yield of N-phenylbenzylamine.

Example 236

Figure 26:
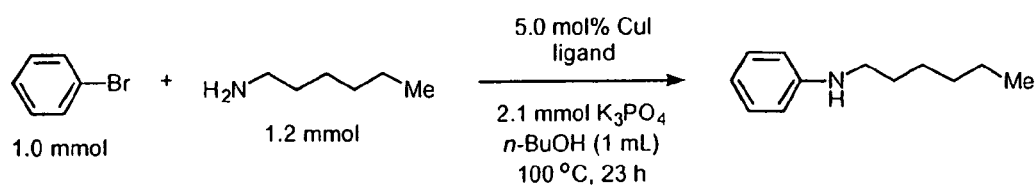
FIG. 26 tabulates copper-catalyzed arylations of n-hexyl amine in n-butanol using various ligands.

Arylation of n-hexyl Amine Using Various Ligands (FIG. 26)

Eight test tubes with screw threads were brought into a nitrogen filled glovebox and capped, then removed from the glovebox. Copper iodide (9.5 mg, 0.050 mmol, 5.0 mol %), the ligand (in those cases where the ligand was a solid), and $K_3PO_4$ (440 mg, 2.07 mmol) were added to the test tubes in the air. The test tubes were immediately capped and brought into a nitrogen-filled glovebox, the caps being removed immediately before the evacuation of the antechamber. Inside the glovebox, the test tubes were capped with open-top screw caps lined with a silicon rubber septum and then removed from the glovebox. In a separate flask, a stock solution of bromobenzene (1.05 mL) and n-hexylamine (1.60 mL) in n-butanol (10 mL) was prepared. The ligand (in those cases where the ligand was a liquid) and a portion of the stock solution (1.3 mL) containing 1.0 mmol of bromobenzene and 1.2 mmol of n-hexylamine were added using syringes. The open-top screw caps were replaced with solid screw caps. The reaction mixtures were stirred at 100° C. for 23 h and then allowed to reach room temperature. Dodecane (internal GC standard, 230 μL), ethyl acetate (2 mL), and water (1 mL) were added. A 0.1 mL sample of the top (organic) layer was diluted with ethyl acetate (1 mL) and analyzed by GC. The results are presented in FIG. 26.

INCORPORATION BY REFERENCE

All of the patents and publications cited in the Specification are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A method comprising the step of reacting Z-X with

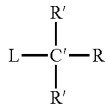

in the presence of a catalyst, a base, and a solvent, thereby forming

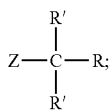

wherein
X represents I, Cl, alkylsulfonate, or arylsulfonate;
Z represents optionally substituted aryl, heteroaryl or alkenyl;
L represents H or a negative charge;
catalyst comprises a copper atom or ion, and a chelating ligand, wherein the chelating ligand is an optionally substituted aryl alcohol, alkyl amine, 1,2-diamine, 1,2-aminoalcohol, or 1,10-phenanthroline; and the chelating ligand is not the solvent;
base is a carbonate, phosphate, oxide, hydroxide, alkoxide, aryloxide, amine, metal amide, fluoride, or guanidine;
R represents H, optionally substituted alkyl, cycloalkyl, aralkyl, aryl, or heteroaryl;

R' represents independently for each occurrence H, alkyl, cycloalkyl, aralkyl, aryl, or heteroaryl, formyl, acyl, —$CO_2R''$, —$C(O)N(R)_2$, sulfonyl, —$P(O)(OR'')_2$, —CN, or —$NO_2$, provided that at least one occurrence of R' represents formyl, acyl, —$CO_2R''$, —$C(O)N(R)_2$, sulfonyl, —$P(O)(OR'')_2$, —CN, or —$NO_2$;
R" represents independently for each occurrence optionally substituted alkyl, cycloalkyl, aralkyl, aryl, or heteroaryl; and
$C(R')_2(R)$ taken together may represent nitrile.
2. The method of claim 1, wherein X represents I.
3. The method of claim 1, wherein the chelating ligand is selected from the group consisting of 8-hydroxyquinoline, 2-(dimethylamino)ethanol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, (methylimino)diacetic acid, and trans-1,2-cyclohexanediamine.
4. The method of claim 1, wherein the chelating ligand is an optionally substituted 1,2-diaminocyclohexane, 1,10-phenanthroline, 2-hydroxyethyl amine, or 1,2-diaminoethane.
5. The method of claim 1, wherein the base is potassium phosphate, potassium carbonate, cesium carbonate, sodium tert-butoxide, or sodium hydroxide.
6. The method of claim 1, wherein the catalyst is present in less than or equal to about 5 mol % relative to Z-X.
7. The method of claim 1, wherein the method is conducted at a temperature less than about 150 C.
8. The method of claim 1, wherein the method is conducted at a temperature less than about 140 C.
9. The method of claim 1, wherein the method is conducted at a temperature less than about 110 C.
10. The method of claim 1, wherein Z represents optionally substituted aryl.
11. The method of claim 1, wherein Z represents optionally substituted phenyl.
12. The method of claim 1, wherein R represents H.
13. The method of claim 1, wherein R' represents independently for each occurrence acyl, or —$CO_2R''$.
14. The method of claim 1, wherein R" represents independently for each occurrence alkyl, cycloalkyl, or aralkyl.
15. The method of claim 1, wherein X represents I; and the chelating ligand is selected from the group consisting of 8-hydroxyquinoline, 2-(dimethylamino)ethanol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, (methylimino)diacetic acid, and trans-1,2-cyclohexanediamine.
16. The method of claim 1, wherein X represents I; and the chelating ligand is an optionally substituted 1,2-diaminocyclohexane, 1,10-phenanthroline, 2-hydroxyethyl amine, or 1,2-diaminoethane.
17. The method of claim 1, wherein X represents I.
18. The method of claim 1, wherein X represents I; and the chelating ligand is selected from the group consisting of 8-hydroxyquinoline, 2-(dimethylamino)ethanol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1, 10-phenanthroline, 5-nitro-1,10-phenanthroline, (methylimino)diacetic acid, and trans-1,2-cyclohexanediamine.

19. The method of claim 1, wherein X represents I; and the chelating ligand is an optionally substituted 1,2-diaminocyclohexane, 1,10-phenanthroline, 2-hydroxyethyl amine, or 1,2-diaminoethane.

20. The method of claim 1, wherein X represents I; and the base is potassium phosphate, potassium carbonate, cesium carbonate, sodium tert-butoxide, or sodium hydroxide.

21. The method of claim 1, wherein X represents I; the chelating ligand is selected from the group consisting of 8-hydroxyquinoline, 2-(dimethylamino)ethanol, N,N-diethylsalicylamide, 2-(dimethylamino)glycine, N,N,N',N'-tetramethyl-1,2-diaminoethane, 1,10-phenanthroline, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, (methylimino)diacetic acid, and trans-1,2-cyclohexanediamine; and the base is potassium phosphate, potassium carbonate, cesium carbonate, sodium tert-butoxide, or sodium hydroxide.

\* \* \* \* \*

UNITED STATES PATENT AND TRADEMARK OFFICE
CERTIFICATE OF CORRECTION

PATENT NO.        : 9,067,955 B2                                  Page 1 of 1
APPLICATION NO.   : 11/431154
DATED             : June 30, 2015
INVENTOR(S)       : Stephen L. Buchwald et al.

It is certified that error appears in the above-identified patent and that said Letters Patent is hereby corrected as shown below:

ON THE TITLE PAGE

Item (62), Related U.S. Application Data, line 5, replace:

"Apr. 24, 2001" with

--Apr. 24, 2002--.

Signed and Sealed this
Third Day of November, 2015

Michelle K. Lee
*Director of the United States Patent and Trademark Office*